(12) United States Patent
Patel et al.

(10) Patent No.: US 7,897,330 B2
(45) Date of Patent: Mar. 1, 2011

(54) METHODS FOR CHARACTERIZING ENZYME INHIBITORS

(75) Inventors: Mehul Patel, Ambler, PA (US); Dawn M. Schmidt, Durham, NC (US); Sara H. Thrall, Collegeville, PA (US); David G. Tew, Harlow Essex (GB)

(73) Assignee: AB Sciex, LLC, Framingham, MA (US)

( * ) Notice: Subject to any disclaimer, the term of this patent is extended or adjusted under 35 U.S.C. 154(b) by 519 days.

(21) Appl. No.: 11/719,528

(22) PCT Filed: Aug. 10, 2006

(86) PCT No.: PCT/US2006/031055

§ 371 (c)(1),
(2), (4) Date: May 16, 2007

(87) PCT Pub. No.: WO2007/021756

PCT Pub. Date: Feb. 22, 2007

(65) Prior Publication Data

US 2009/0148858 A1    Jun. 11, 2009

Related U.S. Application Data

(60) Provisional application No. 60/707,328, filed on Aug. 11, 2005.

(51) Int. Cl.
*C12Q 1/00* (2006.01)

(52) U.S. Cl. .......................... 435/4; 435/69.2

(58) Field of Classification Search ................ 435/4, 435/7.1, 69.2, 288.7
See application file for complete search history.

(56) References Cited

U.S. PATENT DOCUMENTS

| | | | |
|---|---|---|---|
| 2005/0221410 A1 | 10/2005 | Seethala et al. | |
| 2006/0134696 A1 | 6/2006 | Chiem et al. | |
| 2007/0095407 A1* | 5/2007 | Chen et al. | 137/597 |
| 2007/0134739 A1* | 6/2007 | Holmquist et al. | 435/7.9 |

OTHER PUBLICATIONS

Liu, Y. et al., "Use of a Fluorescence Plate Reader for Measuring Kinetic Parameters with Inner Filter Effect Correction," Analytical Biochemistry, 1999, vol. 267, pp. 331-335.

Perdickakis, B. et al., "Analysis of slow-binding enzyme inhibitors at elevated enzyme concentrations," Analytical Biochemistry, 2005, vol. 337, pp. 221-223.

Peter, M.G., et al., "Apparent cooperativity in multivalent verotoxin-globotriaosyl ceramide binding: kinetic and saturation binding studies with [125I]verotoxin," Biochimica et Biophysica Acta, 2000, vol. 1501, pp. 116-124.

International Search Report and Written Opinion of the International Searching Authority, for PCT/US06/31055, dated Mar. 31, 2008, 8 pages.

Gautier, S.M. et al., "Dehydrogenase activity monitoring by flow-injection analysis combined with luminescense-based fibre-optics sensors," Analytica Chimica Acta, 1992, vol. 266, pp. 331-338.

Girotti, S. et al., "Bioluminescent Flow Sensors: L-Lactate Dehydrogenase Activity Determination in Serum," Journal of Bioluminescence and Chemiluminescence, 1989, vol. 3, No. 2, pp. 41-45.

Holden, M.A. et al., "Microfluidic Tools For Studying The Specific Binding, Adsorption, and Displacement Of Proteins At Interfaces," Annu. Rev. Phys. Chem., 2005, vol. 56, pp. 369-387.

Schulz, C.M. et al., "Real-time monitoring of lactate extrusion and glucose consumption of cultured cells using a lab-on-valve system," The Analyst, 2002, vol. 127, No. 12, pp. 1583-1588.

Supplementary European Search Report for European Patent App. No. 06801046.1, dated Oct. 7, 2009, 8 pages.

Wang, J., "On-chip enzymatic assays," Electrophoresis, 2002, vol. 23, No. 5, pp. 713-718.

Huang, C.Y., "Determination of Binding Stoichiometry by the Continuous Variation Method: The Job Plot," Methods in Enzymology, 1982, vol. 87, pp. 509-525.

* cited by examiner

*Primary Examiner* — Ralph Gitomer
(74) *Attorney, Agent, or Firm* — Laura M. Lloyd; Jeffrey G. Sheldon; Sheldon Mak & Anderson PC

(57) ABSTRACT

Methods for characterizing a biochemical reaction and analysis of reaction products by establishing continuously variable concentration gradients of one or more reagents of the biochemical reaction are provided. Methods for determining mechanism of inhibition or activation, potency of inhibition or activation, or both of an enzyme inhibitor or activator, respectively, are also provided. The continuously variable concentration gradients can be established in a microfluidic chip.

17 Claims, 65 Drawing Sheets

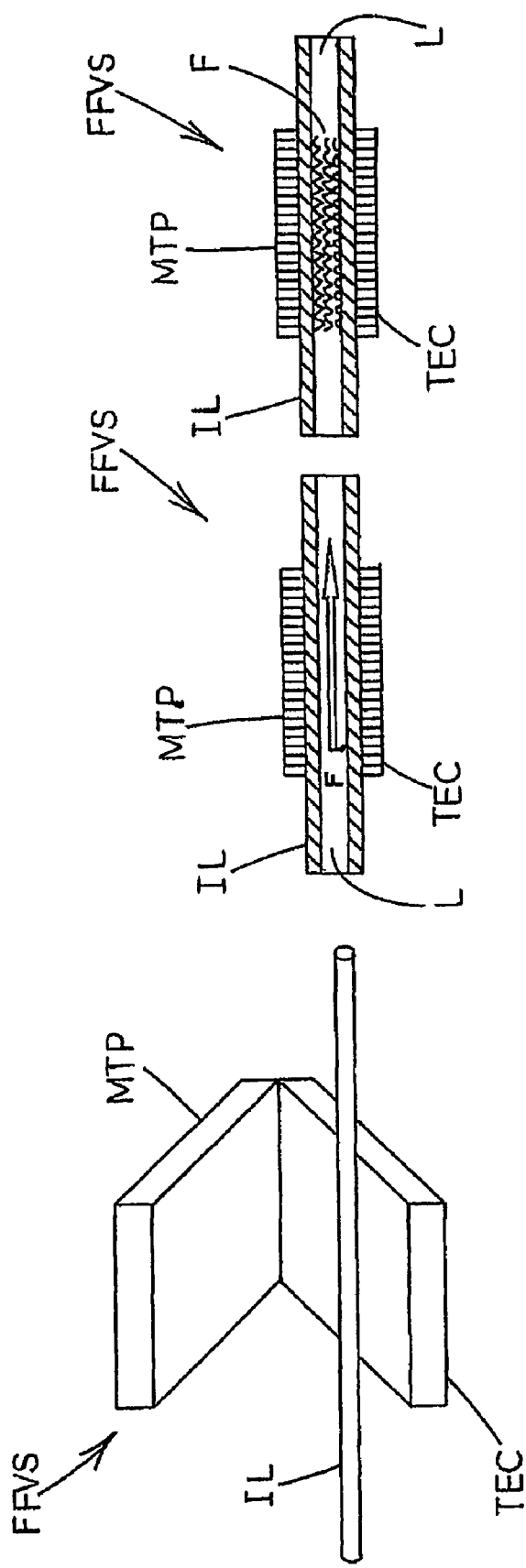

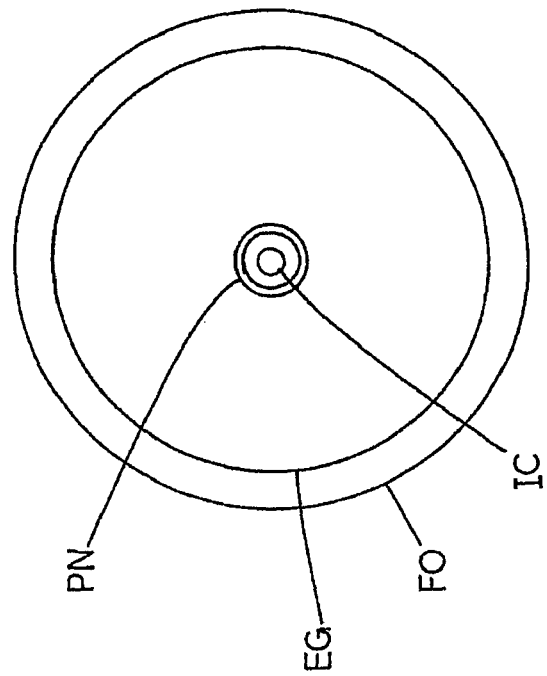
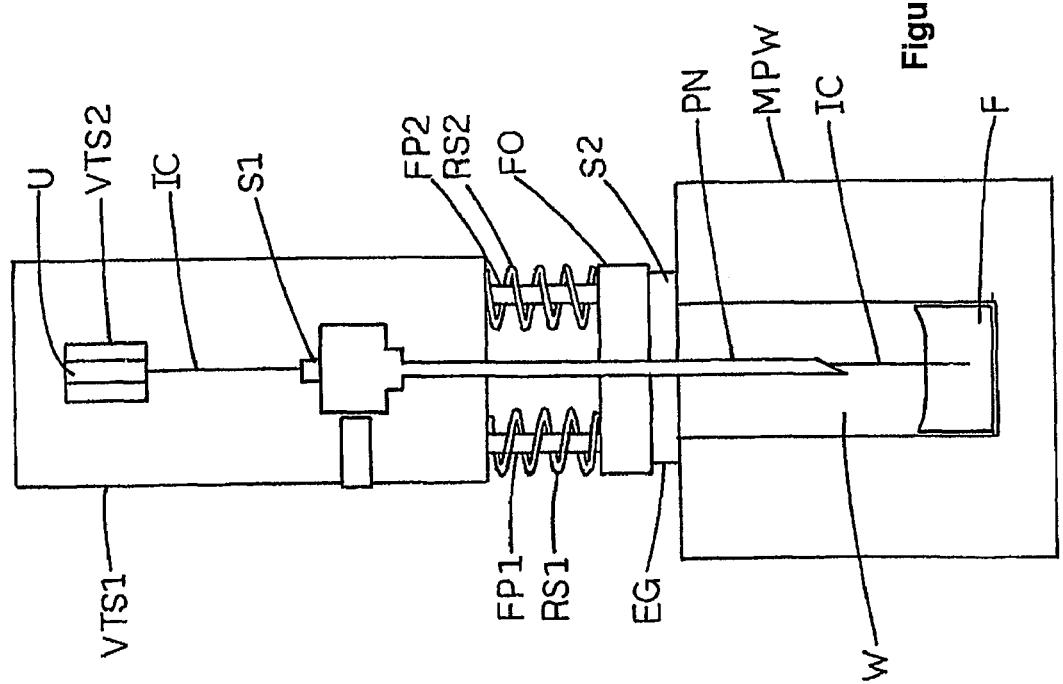

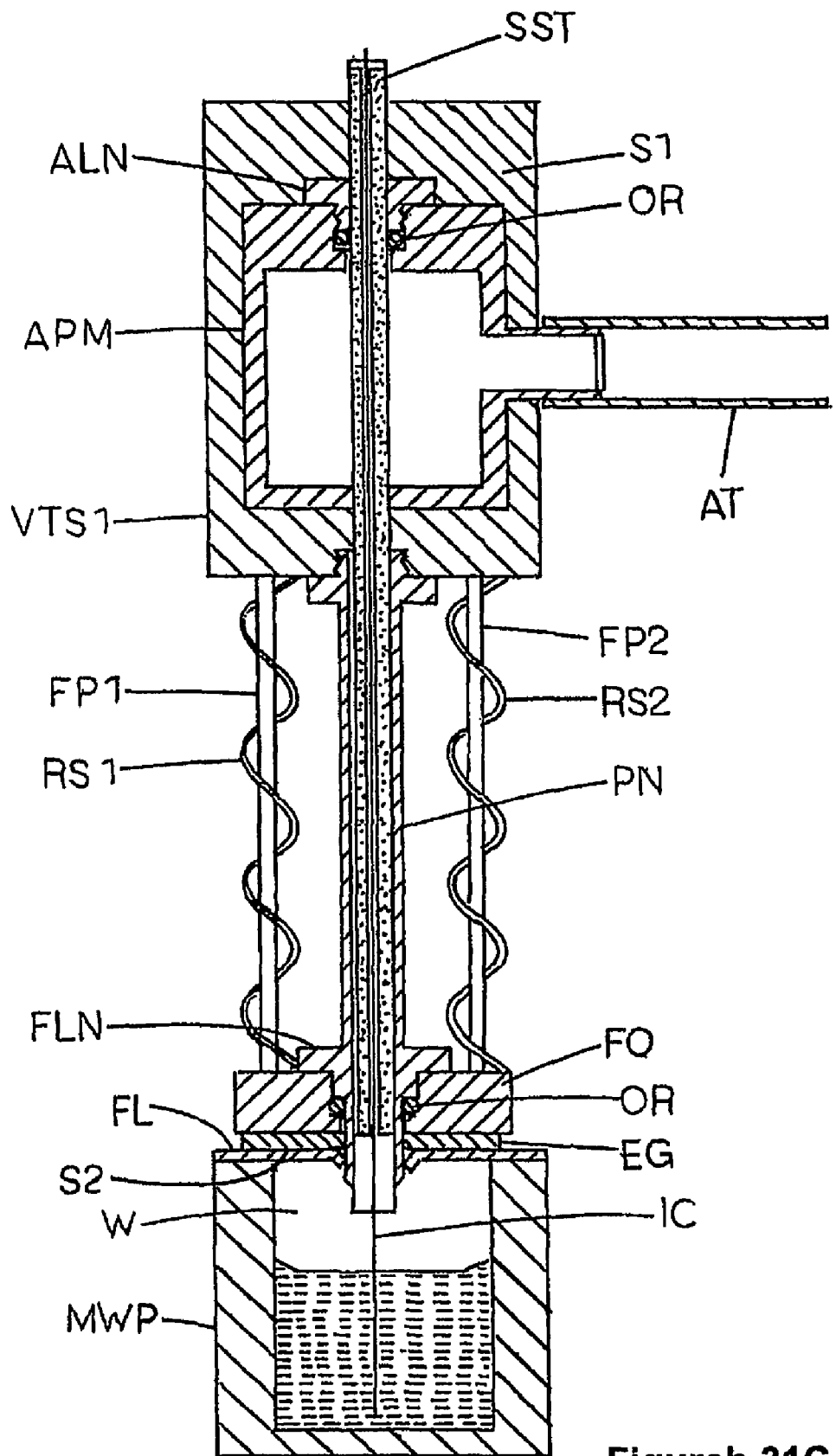
Figureb 31C

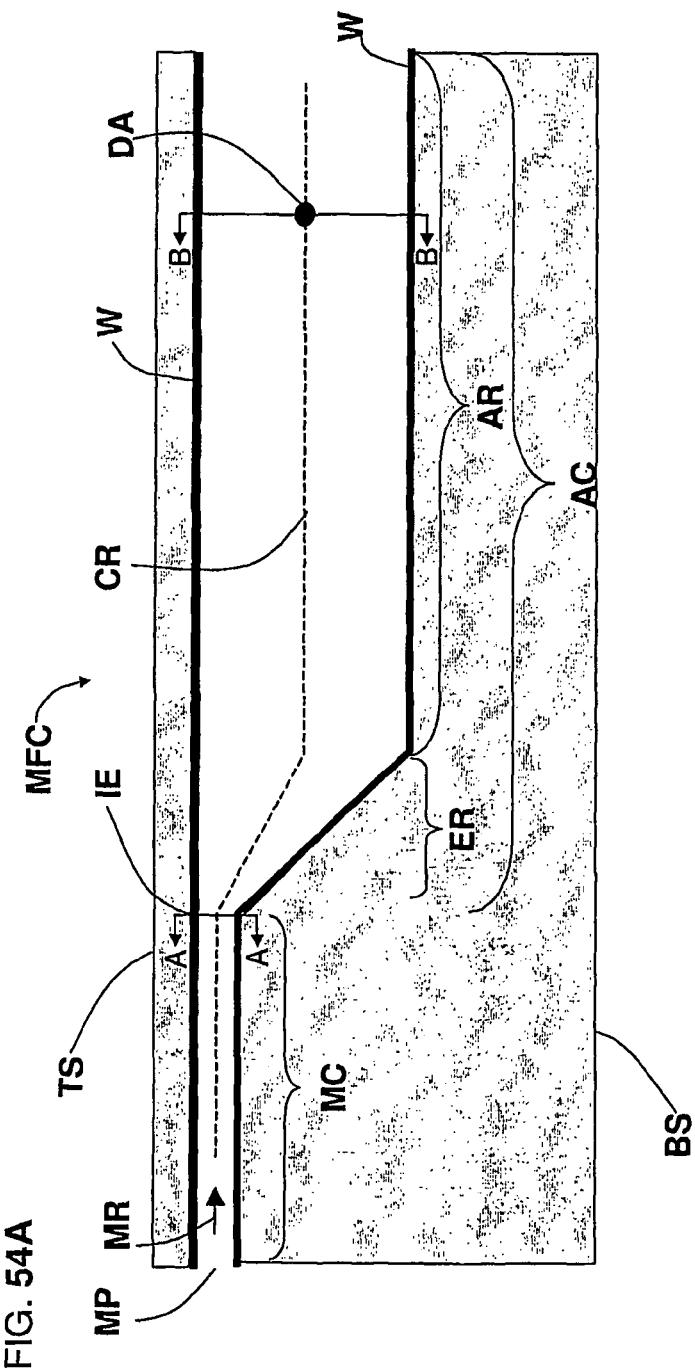
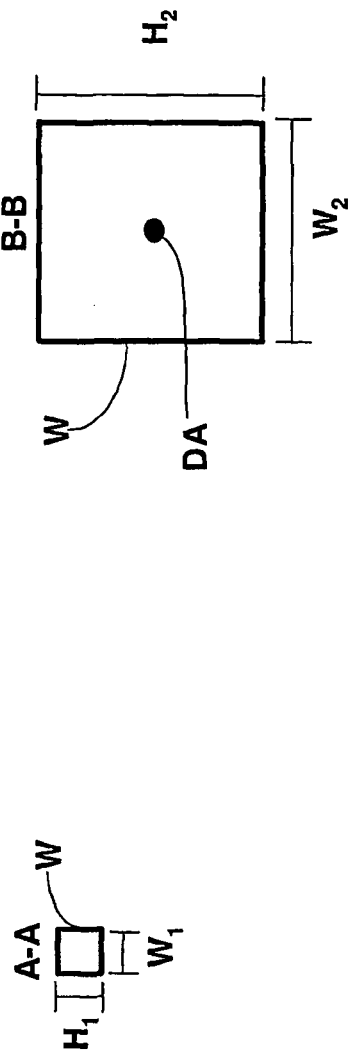
FIG. 54A
FIG. 54B

METHODS FOR CHARACTERIZING ENZYME INHIBITORS

CROSS-REFERENCE TO RELATED APPLICATIONS

This application is the U.S. national stage of International Application No. PCT/US2006/31055, filed Aug. 10, 2006 and entitled METHODS FOR CHARACTERIZING BIOLOGICAL MOLECULE MODULATORS, which claims the benefit of U.S. Patent Application Ser. No. 60/707,328, filed Aug. 11, 2005, the disclosure of which is incorporated herein by reference in its entirety. The disclosures of the following U.S. Provisional Applications, commonly owned and simultaneously filed Aug. 11, 2005, are all incorporated by reference in their entirety: U.S. Provisional Application entitled APPARATUS AND METHOD FOR HANDLING FLUIDS AT NANO-SCALE RATES, U.S. Provisional Application No. 60/707,421; U.S. Provisional Application entitled MICROFLUIDIC BASED APPARATUS AND METHOD FOR THERMAL REGULATION AND NOISE REDUCTION, U.S. Provisional Application No. 60/707,330; U.S. Provisional Application entitled MICROFLUIDIC METHODS AND APPARATUSES FOR FLUID MIXING AND VALVING, U.S. Provisional Application No. 60/707,329; U.S. Provisional Application entitled METHODS AND APPARATUSES FOR GENERATING A SEAL BETWEEN A CONDUIT AND A RESERVOIR WELL, U.S. Provisional Application No. 60/707,286; U.S. Provisional Application entitled MICROFLUIDIC SYSTEMS, DEVICES AND METHODS FOR REDUCING DIFFUSION AND COMPLIANCE EFFECTS AT A FLUID MIXING REGION, U.S. Provisional Application No. 60/707,220; U.S. Provisional Application entitled MICROFLUIDIC SYSTEMS, DEVICES AND METHODS FOR REDUCING NOISE GENERATED BY MECHANICAL INSTABILITIES, U.S. Provisional Application No. 60/707,245; U.S. Provisional Application entitled MICROFLUIDIC SYSTEMS, DEVICES AND METHODS FOR REDUCING BACKGROUND AUTOFLUORESCENCE AND THE EFFECTS THEREOF, U.S. Provisional Application No. 60/707,386; U.S. Provisional Application entitled MICROFLUIDIC CHIP APPARATUSES, SYSTEMS, AND METHODS HAVING FLUIDIC AND FIBER OPTIC INTERCONNECTIONS, U.S. Provisional Application No. 60/707,246; U.S. Provisional Application entitled METHODS FOR CHARACTERIZING BIOLOGICAL MOLECULE MODULATORS, U.S. Provisional Application No. 60/707,328; U.S. Provisional Application entitled METHODS FOR MEASURING BIOCHEMICAL REACTIONS, U.S. Provisional Application No. 60/707,370; U.S. Provisional Application entitled METHODS AND APPARATUSES FOR REDUCING EFFECTS OF MOLECULE ADSORPTION WITHIN MICROFLUIDIC CHANNELS, U.S. Provisional Application No. 60/707,366; U.S. Provisional Application entitled PLASTIC SURFACES AND APPARATUSES FOR REDUCED ADSORPTION OF SOLUTES AND METHODS OF PREPARING THE SAME, U.S. Provisional Application No. 60/707,288; U.S. Provisional Application entitled BIOCHEMICAL ASSAY METHODS, U.S. Provisional Application No. 60/707,374; U.S. Provisional Application entitled FLOW REACTOR METHOD AND APPARATUS, U.S. Provisional Application No. 60/707,233; and U.S. Provisional Application entitled MICROFLUIDIC SYSTEM AND METHODS, U.S. Provisional Application No. 60/707,384.

TECHNICAL FIELD

The present disclosure generally relates to methods for characterizing biochemical reactions and analysis of reaction products. More specifically, the present disclosure relates to methods for characterizing a biochemical reaction and analysis of reaction products by establishing continuously variable concentration gradients of one or more of the reagents of the biochemical reaction.

BACKGROUND ART

Biochemical and biological assays are a primary tool utilized in many aspects of drug discovery, including but not limited to (1) fundamental research in biochemistry and biology to describe novel phenomena, (2) analysis of large numbers of compounds, (3) screening of compounds, (4) clinical tests applied during clinical trials, and (5) even diagnostic tests during administration of drugs. Many biological and biochemical assays require measurement of the response of a biological or biochemical system to different concentrations of one reagent, such as an inhibitor, an activator, a substrate, or an enzyme. Typically, discrete steps of biochemical concentration are mixed within a prescribed range. The number of concentrations measured is limited by the number of dilution steps, which are limited in practice by the time and effort required to make the discrete dilutions, by the time and effort to process the resulting individual reactions, by reagent consumption as the number of reactions increases, and more strictly by pipetting errors that limit the resolution of discrete steps.

As technology advances in drug development, miniaturization and automation are active areas of innovation, with primary drivers being decreased cost (through decreased reagent use and decreased manpower) and improved data quality (through finer process control and increased process reliability). Improvements in data quality and automation frequently convey additional advantages that permit new scientific approaches to questions. Automation, if sufficiently extensive, can include software that permits automatic work scheduling to improve efficiency or statistical process control for process improvement. Again, these improvements achieve greater reliability, use less manpower, and improve throughput.

Microfluidic systems, including labs-on-a-chip (LoCs) and micro-total analysis systems (μ-TAS), are currently being explored as an alternative to conventional approaches that use microtiter plates. The miniaturization afforded by microfluidic systems has the potential to greatly reduce the amount of reagent needed to conduct high-throughput screening. Thus far, commercial microfluidic systems have shown some promise in performing point measurements, but have not been employed to mix concentration gradients and particularly continuous gradients due to technologic limitations. In particular, several challenges remain in the design of industry-acceptable microfluidic systems. Apart from cost and manufacture related issues, many sources of such challenges relate to the fact that, in a micro-scale or sub-micro-scale environment, certain fluid characteristics such as viscosity, surface tension, shear resistance, thermal conductivity, electrical conductivity, molecular diffusivity, and the like, take on a much more dominant role than other, more easily manageable factors such as weight and gravity. In addition, controlling the signal-to-noise ratio becomes much more challenging when working with nano-scale volumes and flow rates, as certain sources of noise that typically are inconsequential in macroscopic applications now become more noticeable and thus deleterious to the accuracy of data acquisition instruments.

Thus, it would be desirable to analyze biochemical and biological systems using assays that employ continuous gradients so as to achieve higher quality data in a shorter time frame and using fewer reagents than present methods. It would further be desirable to utilize continuous concentration gradients within a microfluidic system.

SUMMARY

According to one embodiment, a method for determining one of a mechanism of inhibition, potency of an inhibitor, and both a mechanism of inhibition and potency of an inhibitor of a biological molecule are provided. The method comprises contacting at least one inhibitor, a biological molecule, and at least one ligand for the biological molecule under conditions where concentrations of at least two of the at least one inhibitor, the biological molecule and the at least one ligand are simultaneously varied and determining an outcome of the contacting of the at least one inhibitor, the at least one ligand, and the biological molecule to determine one of the mechanism of inhibition, potency of the inhibitor, and both the mechanism of inhibition and potency of the inhibitor. The concentrations of the at least one inhibitor and the at least one ligand can be simultaneously varied. Further, the concentrations of the inhibitor and the at least one ligand can be simultaneously varied such that a ratio of the concentrations is constant.

In some embodiments of the method, the at least one inhibitor comprises two inhibitors. The two inhibitors can in some embodiments both inhibit the biological molecule. The concentrations of the two inhibitors and the at least one ligand can be simultaneously varied. Further, in some embodiments, the concentrations of the two inhibitors and the at least one ligand can be simultaneously varied such that a ratio of the concentrations is constant.

In some embodiments of the method, the biological molecule comprises an enzyme and the at least one ligand comprises a substrate of the enzyme. In other embodiments of the method, the biological molecule comprises a receptor and the at least one ligand comprises a ligand of the receptor.

In some embodiments of the method the concentrations are simultaneously varied with discrete concentration gradients. Further, in some embodiments, each of the discrete concentrations can be contained in discrete containers. The discrete containers can be wells in a microtiter plate. In other embodiments, the concentrations are simultaneously varied with continuous concentration gradients, and in some embodiments the continuous concentration gradients are in a microfluidic chip.

In some embodiments of the method, determining the outcome comprises determining an inhibition constant of the at least one inhibitor. In some embodiments, the at least one inhibitor comprises two inhibitors and the inhibition constant is determined for each of the two inhibitors. Further, the determined inhibition constant for each of the two inhibitors can provide for determining whether the two inhibitors are synergistic, antagonistic or neutral with respect to each other. The determined inhibition constant for each of the two inhibitors can further provide for determination of an interaction factor ($\alpha$) between the two inhibitors.

The inhibition constant determined can be selected from the group consisting of an inhibition constant of the inhibitor with the biological molecule, an inhibition constant of the at least one inhibitor with the biological molecule-ligand complex, and both the inhibition constant of the inhibitor with the biological molecule and the inhibition constant of the at least one inhibitor with the biological molecule-ligand complex. Further, the inhibition constant determined can provide for determination of one of the mechanism of inhibition, potency of the inhibitor and both the mechanism of inhibition and potency of the inhibitor.

In some embodiments of the method, the mechanism of action determined for the inhibitor can be selected from the group consisting of competitive, non-competitive, uncompetitive, and mixed. In some embodiments, determining the potency of the inhibitor comprises determining the $IC_{50}$ of the inhibitor.

According to a second embodiment, a method for determining one of a mechanism of activation, potency of an activator, and both a mechanism of activation and potency of an activator of a biological molecule is provided. The method comprises contacting at least one activator, a biological molecule, and at least one ligand for the biological molecule under conditions where concentrations of at least two of the at least one activator, the biological molecule and the at least one ligand are simultaneously varied and determining an outcome of the contacting of the at least one activator, the at least one ligand, and the biological molecule to determine one of the mechanism of activation, potency of the activator, and both the mechanism of activation and potency of the activator. The concentrations of the at least one activator and the at least one ligand can be simultaneously varied. Further, the concentrations of the activator and the at least one ligand can be simultaneously varied such that a ratio of the concentrations is constant.

In some embodiments of the method, the biological molecule comprises an enzyme and the at least one ligand comprises a substrate of the enzyme. In other embodiments, the biological molecule comprises a receptor and the at least one ligand comprises a ligand of the receptor.

In some embodiments of the method the concentrations are simultaneously varied with discrete concentration gradients. Further, in some embodiments, each of the discrete concentrations can be contained in discrete containers. The discrete containers can be wells in a microtiter plate. In other embodiments, the concentrations are simultaneously varied with continuous concentration gradients and the continuous concentration gradients can be in a microfluidic chip.

In some embodiments of the method, determining the mechanism of action of the activator comprises determining an activation constant for the activator ($K_{act}$). Further, in some embodiments, determining the potency of the activator comprises determining at least one activator interaction factor affecting a Michaelis constant for the ligand ($K_m$), a maximal velocity ($V_{max}$), or both $K_m$ and $V_{max}$. The at least one activator interaction factor can comprise a first activator interaction factor ($\alpha$) and a second activator interaction factor ($\beta$).

According to a third embodiment, a method for determining one of a mechanism of reaction, kinetic constants of ligands, and both a mechanism of reaction and kinetic constants of ligands of a bireactant biological molecule system is provided. The method comprises contacting a biological molecule and a plurality of ligands for the biological molecule under conditions where concentrations of at least two of the biological molecule and plurality of ligands are simultaneously varied and determining an outcome of the contacting of the biological molecule and the plurality of ligands to determine one of the mechanism of reaction, the kinetic constants of the ligands, or both the mechanism of reaction and the kinetic constants of the ligands of the bireactant biological molecule system. In some embodiments, the concentrations of the plurality of ligands are each simultaneously varied. Further, in some embodiments, the concentrations of the plurality of ligands are each simultaneously varied such that a ratio of the concentrations is constant.

In some embodiments of the method, the biological molecule can comprise an enzyme and the plurality of ligands can each comprise a substrate of the enzyme. Further, determining the kinetics constants of the enzyme substrates in these embodiments can comprise determining the Michaelis constant ($K_m$) for at least one of the enzyme substrates. In other embodiments, the biological molecule can comprise a receptor and the plurality of ligands can each comprise a ligand of the receptor. Further, determining the kinetics constants of the receptor ligands in these embodiments can comprise determining the dissociation constant for at least one of the receptor ligands.

In some embodiments of the method, the concentrations are simultaneously varied with discrete concentration gradients. Further, in some embodiments, each of the discrete concentrations can be contained in discrete containers. The discrete containers can be wells in a microtiter plate. In other embodiments, the concentrations are simultaneously varied with continuous concentration gradients and the continuous concentration gradients are in a microfluidic chip.

Therefore, it is an object to provide methods for characterizing biological molecule substrates and modulator molecules.

An object having been stated hereinabove, and which is achieved in whole or in part by the present disclosure, other objects will become evident as the description proceeds when taken in connection with the accompanying drawings as best described hereinbelow.

BRIEF DESCRIPTION OF THE DRAWINGS

FIG. 24A is a top perspective view of a fluid freeze valve;

FIG. 24B is a side cross-sectional view of a movable top plate, thermo-electric cooler, and capillary of the fluid freeze valve shown in, FIG. 24A wherein the thermo-electric cooler is not energized such that a fluid can flow through lumen of capillary in the "on" state;

FIG. 24C is a side cross-sectional view of a movable top plate, thermo-electric cooler, and capillary of the fluid freeze valve shown in FIGS. 24A and 24B wherein thermo-electric cooler is energized for reducing the temperature of capillary such that fluid reaches a solid or nearly solid state to stop fluid flow through lumen of capillary in the "off" state;

FIG. 31A is a cross-sectional view of a configuration for forming a seal in an automated liquid handling system;

FIG. 31B is a cross-sectional view of a configuration for forming another seal in an automated liquid handling system;

FIG. 31C is a cross-sectional view of another configuration for forming a seal in an automated liquid handling system;

FIG. 54A is a schematic cross-sectional side view of an embodiment of analysis channel disclosed herein and upstream fluidly communicating microscale channel; and FIG. 54B shows schematic cross-sectional cuts at A-A and B-B of the analysis channel of FIG. 54A.

DETAILED DESCRIPTION

I. General Considerations

Figure 1A:
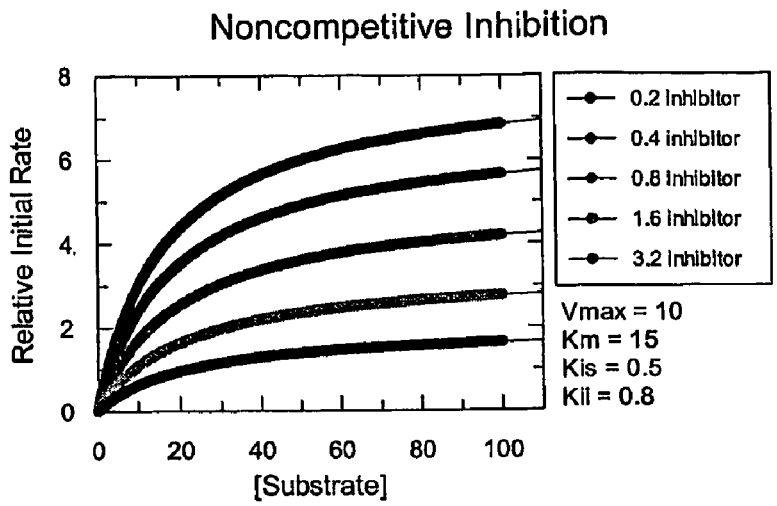
FIG. 1A is a graph showing simulations using the rate equation of rate vs. substrate concentration patterns that would indicate a strictly noncompetitive inhibitor.

I.A. Enzyme Inhibitor Potency and Mechanism of Inhibition

Inhibitors of enzyme targets are often sought as part of the drug development process. The understanding of potency and mechanism of inhibition provides desirable information for progressing inhibitors into drugs. Enzyme reaction and inhibition kinetics are conventionally studied with the assumption that equilibria are achieved rapidly and thus the kinetics can be described by rate equations that assume a steady-state concentration of enzyme, substrate(s) and any other added ligand effectors (if their concentrations are greater than 10 fold higher than enzyme concentration). A comprehensive review of enzyme kinetics theory and enzyme inhibition mechanisms can be found in *Enzyme Kinetics: Behavior and Analysis of Rapid Equilibrium and Steady-State Enzyme Systems*; Segel, Irwin (1975) Wiley Interscience (ISBN: 0-471-30309-7), incorporated herein by reference.

Characterization of enzyme inhibition is generally discussed in terms of the three Michaelis-Menten reaction schemes shown below. A rate equation can be derived for each inhibition mechanism, which describes how the rate of product formation is decreased with increasing amounts of inhibitor.

An enzyme inhibition reaction in which an inhibitor (I) binds to an enzyme (E), to the exclusion of a substrate of the enzyme (S) is termed a "competitive" inhibition reaction and is illustrated by the reaction formula below. The competitive inhibition can be overcome by an excess concentration of substrate.

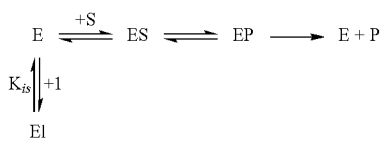

An enzyme inhibition reaction in which an inhibitor binds to an enzyme-substrate (ES), but not the enzyme alone is termed an "uncompetitive" inhibition reaction and is illustrated by the reaction formula below. In an uncompetitive inhibition reaction, the reaction rate is decreased by inhibitor binding to a site distant or separate from the substrate-binding site. The inhibition increases with increasing substrate concentration, as the concentration of ES is increased.

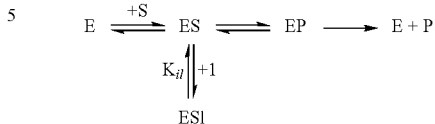

An enzyme inhibition reaction in which an inhibitor binds to both the free enzyme (E) and an enzyme-substrate complex (ES) is termed a "mixed" or "noncompetitive" inhibition reaction and is illustrated by the reaction formula below. The inhibitor binds to the free enzyme and to the enzyme-substrate complex with equal (noncompetitive inhibition) or unequal (mixed inhibition) affinities. Substrate binding may (mixed inhibition) or may not (noncompetitive inhibition) enhance the affinity of the inhibitor (i.e. $K_{ii} \neq K_{is}$ or $K_{ii} = K_{is}$, see term definitions below).

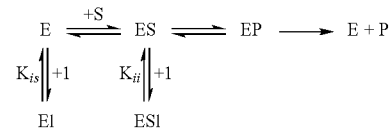

Figure 1B:
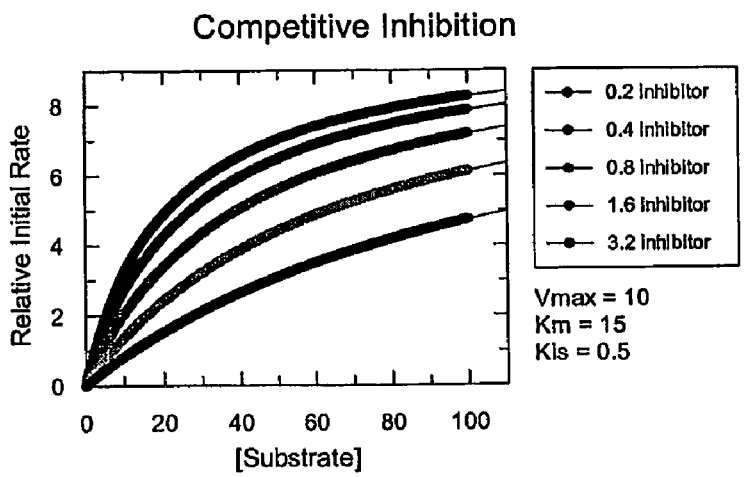
FIG. 1B is a graph showing simulations using the rate equation of rate vs. substrate concentration patterns that would indicate a strictly competitive inhibitor.
Figure 1C:
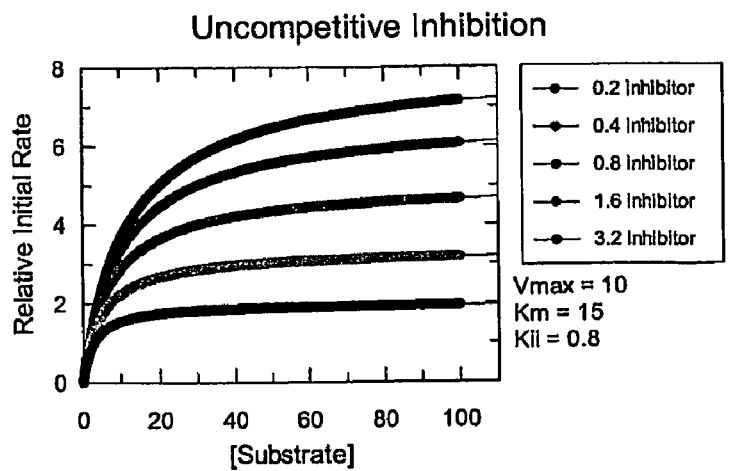
FIG. 1C is a graph showing simulations using the rate equation of rate vs. substrate concentration patterns that would indicate a strictly uncompetitive inhibitor.

In conventional experimental and data fitting methods, inhibition mechanisms are identified by measuring the initial rate of the enzymatic reaction while independently and iteratively varying inhibitor and substrate concentrations, with every substrate and inhibitor concentration condition contained in a separate reaction solution (discontinuous data generation). The data from these orthogonal experiments are then fitted to Michaelis-Menten rate equations that describes one of the three inhibition mechanisms outlined above. More often, the data are fitted to the mixed inhibition rate equation (see the mixed/noncompetitive inhibition reaction formula above), shown below in Equation 1, which can discriminate between the mechanisms by the relative values of $K_{ii}$ and $K_{is}$ yielded from the data fitting, which determine the relative affinities of inhibitor to E or ES or both. For a strictly competitive inhibitor, data fitting to this model would yield a reasonable number for $K_{is}$ (competitive component), but an unreasonable value of $K_{ii}$ (uncompetitive component), while an uncompetitive inhibitor would yield the reverse: a reasonable $K_{ii}$ term (for binding to ES), but unreasonable $K_{is}$ (no binding to free enzyme). Mixed or noncompetitive binding would yield values of $K_{ii}$ and $K_{is}$ that are equal, or unequal but significant.

$$v = V_{max} * S/K_m * (1 + I/K_{is}) + S * (1 + I/K_{ii}) \quad \text{(Equation 1)}$$

where:
v=initial velocity of the reaction;
$V_{max}$=maximal velocity;
S=concentration of interrogated substrate;
I=concentration of inhibitor;
$K_m$=Michaelis constant for substrate;
$K_{is}$=slope inhibition constant; and
$K_{ii}$=intercept inhibition constant For example, the graphs in FIGS. 1A-1C show simulations (using Equation 1) of rate vs. substrate concentration patterns that would predict either a strictly noncompetitive inhibitor (FIG. 1A), a strictly competitive inhibitor (FIG. 1B), or a strictly uncompetitive inhibitor (FIG. 1C).

As discussed above, in a conventional experiment (using microtiter plates) the substrate and inhibitor concentrations are varied independently, or orthogonally, such that each curve would require at least ten independent reaction solutions to fit unambiguously. Since all five curves are minimally required to pinpoint the mechanism and obtain $K_{ii}/K_{is}$ values, each inhibitor would require at least 50 independent reactions from which to obtain reaction rates, and ultimately the potency and mechanism of the inhibitor. A single enzyme drug discovery program normally requires the mechanism and potencies of 10 s, 100 s and even 1000 s of inhibitors at a time, representing up to 50,000 individual reaction wells to measure and analyze. Thus, using known methods discussed above to analyze potential modulators of enzymes (including enzyme inhibitors and activators) in a new drug-screening program creates issues related to amounts of reagents required and time needed to develop useful data.

I.B. Kinetic Mechanism of Bireactant Enzyme Systems

Inhibitors of enzyme targets can be identified from an analysis and understanding of the enzyme's chemical and kinetic mechanisms. Characterization of the enzyme mechanism often sheds light on how to best inhibit (or activate) the enzyme activity, which is then connected to the desired biological response in other studies. As discussed herein above, enzyme reaction and Inhibition kinetics are conventionally studied with the assumption that equilibria are achieved rapidly. Thus, the kinetics can be described by rate equations that assume a steady-state concentration of enzyme, substrate(s) and any other added ligand effectors. The rate equation derived in Equation 1 is based on the uni-reactant kinetic mechanism presented for all three main types of inhibition. However, many enzyme targets have more than one substrate and product, and therefore have net rate equations that describe the additional binding and release steps.

Bireactant enzyme systems comprise two general kinetic mechanisms, ternary and ping-pong. A ternary mechanism describes a mechanism in which the enzyme and the two substrates form a unit complex before chemistry occurs, and a ping-pong mechanism is one in which a product forms and dissociates before the addition of the second substrate and release of the second product. A comprehensive review of enzyme kinetics theory describing bireactant mechanisms can be found in *Enzyme Kinetics: Behavior and Analysis of Rapid Equilibrium and Steady-State Enzyme Systems*; Segel, Irwin; (1975) Wiley Interscience; ISBN: 0-471-30309-7).

A classical ternary kinetic mechanism includes random or ordered addition of the multiple substrates to the enzyme to form an enzyme-substrate A-substrate B complex (EAB).

The formula below illustrates a kinetic scheme for a random ternary bireactant mechanism.

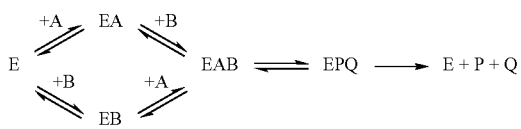

In contrast, the formula below illustrates a kinetic scheme for an ordered ternary bireactant mechanism.

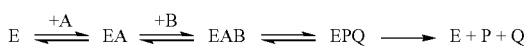

Although mechanistically different, both types of ternary mechanisms can be described by Equation 2:

$$v = V_{max}*A*B/(K_{ia}*K_b + K_b*A + K_a*B + A*B) \quad \text{(Equation 2)}$$

where: f
v=initial velocity of the reaction;
$V_{max}$=maximal velocity;
A=concentration of substrate A;
B=concentration of substrate B;
$K_a$=Michaelis constant for substrate A;
$K_b$=Michaelis constant for substrate B; and
$K_{ia}$=dissociation constant of substrate A.

Figure 2:
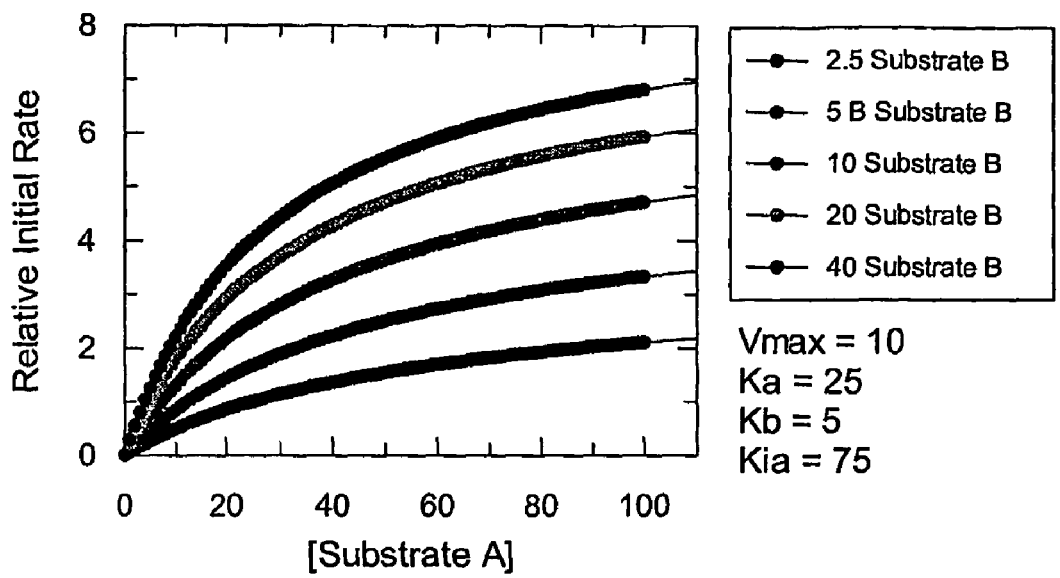
FIG. 2 is a graph showing a classical diagnostic model of a ternary bireactant mechanism from an orthogonal dataset.

FIG. 2 shows a classical diagnostic model of a ternary bireactant mechanism from an orthogonal dataset utilizing Equation 2.

A key feature of a classical ping-pong bireactant mechanism is that the enzyme (E) assumes an intermediate modified form (F) after binding a first substrate (A), distinct from the starting enzyme form. After releasing a first product (P), the modified enzyme form binds a second substrate (B), which results in the formation of a second product (Q) and the return of the enzyme to its starting form.

The formula below illustrates a kinetic scheme for a ping-pong bireactant mechanism.

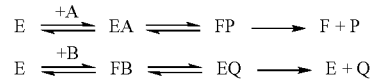

The Ping Pong mechanism can be described by Equation 3:

$$v = V_{max}*A*B/(K_b*A + K_a*B + A*B) \quad \text{(Equation 3)}$$

where:
$V_{max}$=maximal velocity;
A=concentration of substrate A;
B=concentration of substrate B;
$K_a$=Michaelis constant for substrate A; and
$K_b$=Michaelis constant for substrate B.

Figure 3:
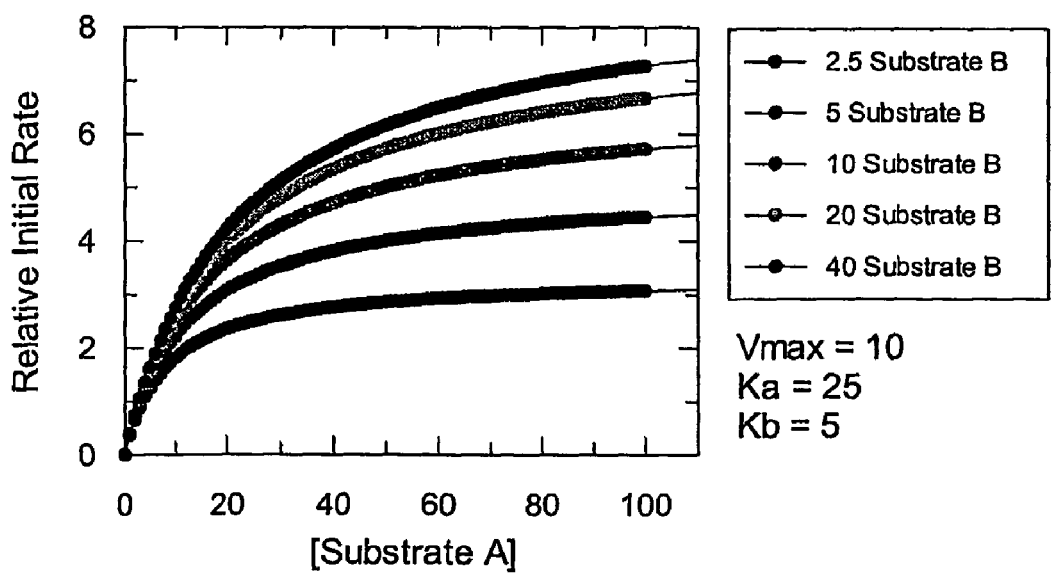
FIG. 3 is a graph showing a classical diagnostic model of a ping-pong bireactant mechanism from an orthogonal dataset.

FIG. 3 shows a classical diagnostic model of a ping-pong bireactant mechanism from an orthogonal dataset utilizing Equation 3.

As discussed above, the conventional discontinuous method of substrate concentration variation and data analysis requires a multitude of data sets to obtain enough data to unambiguously determine mechanism. Therefore, using prior art discontinuous methods to analyze kinetic mechanisms a bireactant enzyme system creates issues related to amounts of reagents required and time needed to develop useful data.

II. Determination of Enzyme Inhibitor Potency and Mechanism of Action

The presently disclosed subject matter provides methods for determining a mechanism of inhibition and/or potency of one or more inhibitors of a biological molecule. The known models and equations discussed in the General Considerations section herein above with respect to enzyme inhibitors are modified as disclosed herein below to provide applicable equations for interpreting data obtained by simultaneous and continuous variation of at least two components of the reaction system, including one or more inhibitors of the biological molecule and/or a substrate of the biological molecule.

Further, the presently disclosed novel methods of continuous variation of multiple variables can be extended to other enzymological/pharmacological methods including the Job plot method of determining binding stoichiometry and inhibitor synergy (see Huang, C. Y. (1982) *Methods Enzymol.* 87; 509-25 for review).

II.A. Single Inhibitor Systems

The methods of the presently disclosed subject matter described herein provide for determining the mechanism of inhibition and/or potency of an inhibitor of a biological molecule, such as for example an enzyme or receptor, by simultaneously and continuously varying the concentrations of at least one substrate of the biological molecule and an inhibitor of the biological molecule to obtain a far greater density of data than is possible using present methods utilizing discrete concentration gradients.

The mixed inhibition model (Equation 1) can be recast into one in which the interrogated substrate and inhibitor are co-varied around a constant ratio to one another (Equation 4). The model can be used universally to discriminate the three mechanisms of inhibitor action (competitive, noncompetitive and uncompetitive). The fractional gradient that describes this constant ratio of S relative to I concentration is introduced as a new independent variable, B, which in effect modifies each concentration term by this factor.

$$v = V_{max} * S * B / K_m * (1 + I * B / K_{is}) + S * B * (1 + I * B / K_{ii}) \quad \text{(Equation 4)}$$

where:
- $v$ = initial velocity of the reaction;
- $V_{max}$ = maximal velocity;
- $S$ = concentration of interrogated substrate;
- $I$ = concentration of inhibitor;
- $K_m$ = Michaelis constant for substrate;
- $K_{is}$ = slope inhibition constant; and
- $K_{ii}$ = intercept inhibition constant.

Figure 4:
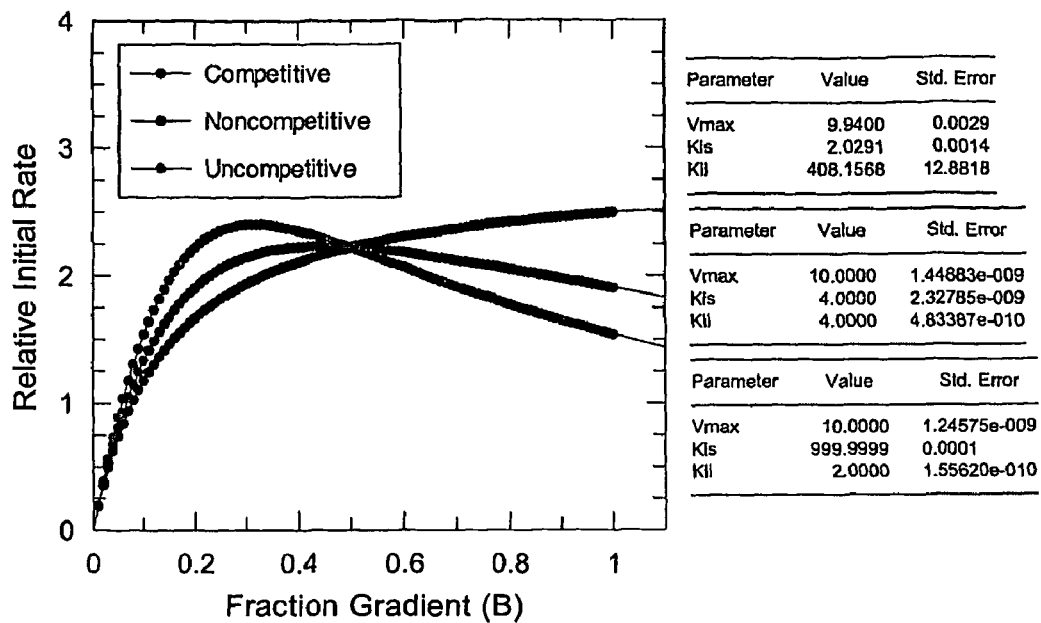
FIG. 4 is a graph showing a simulation of velocity verses fraction gradient (B) of inhibitor and substrate using an equation for calculation of noncompetitive, competitive and uncompetitive inhibition mechanisms.

FIG. 4 illustrates a simulation of velocity verses the fraction gradient (B) using Equation 4 for noncompetitive, competitive and uncompetitive inhibition mechanisms. From the graph shown in FIG. 4, it can be seen that each inhibition type has a unique shape that can be examined to identify the mechanism of inhibition. For example, a competitive inhibitor yields a hyperbolic curve; noncompetitive (or mixed) inhibitors give a peak, or a maximum between B=0 and B=1, followed by a decline; and an uncompetitive inhibitor yields a sharper peak and decline than a noncompetitive inhibitor.

As discussed in the General Considerations section herein above, the conventional method of data generation and analysis data fitted to the model can yield $K_{ii}$ and $K_{is}$ values, which reveal potency and mechanism of the inhibitor, it can also yield ambiguous results. A critical control experiment is the condition in which inhibitor is lacking to obtain the $V_{max}$ and $K_m$ values. These values are used as fixed constraints in Equation 4.

Some representative advantages of the continuous method of S and I variation, over the conventional orthogonal method using independent reaction wells with discrete concentrations of S and I to determine inhibitor potency and mechanism are:

1) A single curve with a high level of data density in the continuous variation method represents potency and mechanism for an inhibitor, whereas the conventional method requires at least 5 curves (25 orthogonally spaced reactions) with discrete mixtures of S and I, to unambiguously determine potency and mechanism; and
2) The conventional discontinuous method of evaluating proportional mixtures of S and I is incapable of generating data which is precise enough to discriminate between the uncompetitive and noncompetitive (or mixed) mechanisms. This is, in large part, due to coefficient of variance values in the 5-20% range caused by limitations in the precision of liquid handling.

The definitive discrimination between the two mechanisms that produce a peak and decline curve (uncompetitive and noncompetitive inhibitors) is difficult from a low-density, limited precision, discontinuous dataset. This point is demonstrated in the Examples presented herein below, which compares data collection via a microtiter plate vs. a microfluidics system disclosed herein providing continuously variable concentration gradients for the same enzyme system, using the methodology described by the presently disclosed subject matter and data analysis available using Equation 4.

The method for determining a mechanism of inhibition and/or potency of an inhibitor of a biological molecule comprises contacting at least one inhibitor, a biological molecule, and at least one ligand for the biological molecule under conditions where concentrations of at least two of the at least one inhibitor, the biological molecule and the at least one ligand are simultaneously varied; and determining an outcome of the contacting of the at least one inhibitor, the at least one ligand, and the biological molecule to determine one of the mechanism of inhibition, potency of the inhibitor, and both the mechanism of inhibition and potency of the inhibitor.

In some embodiments, the biological molecule comprises an enzyme, such as for example lactate dehydrogenase, and the at least one ligand comprises a substrate of the enzyme, such as for example an enzyme inhibitor. In other embodiments, the biological molecule comprises a receptor and the at least one ligand comprises a receptor ligand. As a non-limiting example, 7-transmembrane receptors in general could be acceptable receptors for use with the methods of the presently disclosed subject matter.

In some embodiments, the concentrations of the at least one inhibitor and the at least one ligand are simultaneously varied, and further, in some embodiments, the concentrations are simultaneously varied such that a ratio of the concentrations is held constant. That is, for example, in some embodiments as the concentration of either the ligand or inhibitor is increased, the concentration of the other component is proportionately decreased. Thus, in embodiments where the concentrations of components are varied by varying the flow rates of the fluid streams through which the components flow, the total flow rate of the combined fluid streams remains the same, even as the flow rate of each stream varies proportionately with the other fluid stream. Examples 3 and 4 herein below further illustrate this embodiment in detail.

In some embodiments of the presently disclosed subject matter, the concentrations are simultaneously varied with discrete concentration gradients. The discrete concentration gradients can in some embodiments be contained within discrete containers, which can be for example, wells in a microtiter plate. In other embodiments, the concentrations are simultaneously varied with continuous concentration gradients. The continuous concentration gradients can be formed in some embodiments, for example, using a microfluidic system comprising a microfluidic chip. In some preferred embodiments, the microfluidic system comprises a system as described herein below.

Further, in some embodiments, determining the outcome of contacting together at least one inhibitor, at least one ligand and the biological molecule, which can for example be an enzyme or receptor, comprises an inhibition constant of the at least one inhibitor. The determined inhibition constant can be the inhibition constant of the at least one inhibitor with regard to biological molecule and/or the inhibition constant of the at least one inhibitor with the biological molecule-ligand complex. For example with regard to enzyme inhibitors, a slope inhibition constant ($K_{is}$) and/or an intercept inhibition constant ($K_{ii}$) can be determined as the outcome of contacting at least one inhibitor, at least one ligand, and a biological molecule. The inhibition constants can be determined using Equation 4, for example, as described above. These calculations are further of value in determining the mechanism of inhibition and/or the potency of the inhibitor. For example, the mechanism of inhibition determined can be a determination of whether the inhibitor acts by a competitive, non-competitive, uncompetitive or mixed mechanism of inhibition. Further, determining the potency of the inhibitor can, for example, comprise determining the $IC_{50}$ of the inhibitor with regard to the particular biological molecule and ligand.

II.B. Dual Inhibitor Systems

The methods of the presently disclosed subject matter described herein provide for determining the interaction with each other of two inhibitors of the same biological molecule, by simultaneously and continuously varying the concentrations of the inhibitors of the biological molecule with regard to each other to obtain a far greater density of data than is possible using present discrete concentration gradients.

Figure 5:
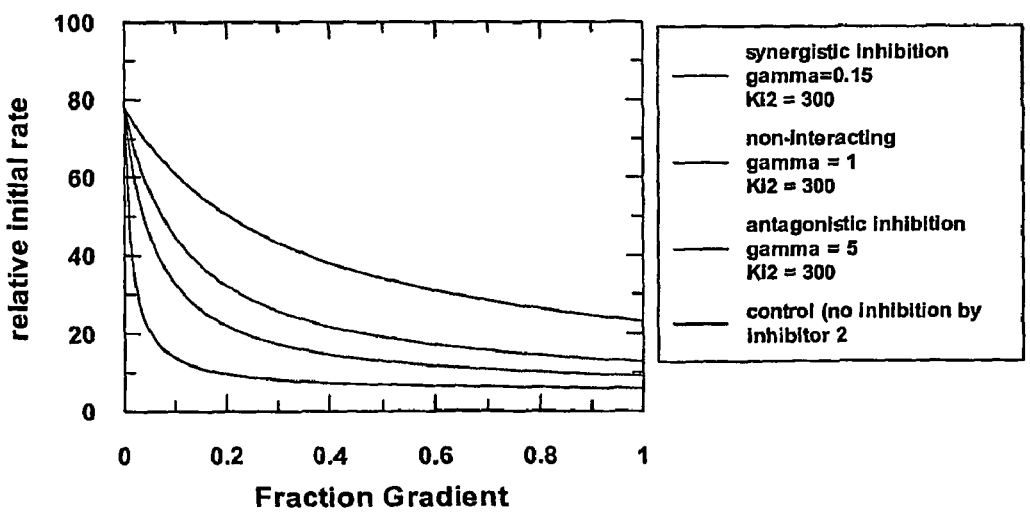
FIG. 5 is a graph showing a simulation of velocity verses fraction gradient (B) of two inhibitors using an equation for calculation of the interaction factor of two inhibitors with varying α values.

A general equation describing dual inhibition can be reformulated into one in which the two inhibitors are co-varied around a constant ratio to one another (Equation 5). The methods described herein can be used to identify whether inhibitors are synergistic, antagonistic, or neutral with respect to each other. The fractional gradient describing this constant ratio of inhibitor 1 relative to inhibitor 2 is introduced as the independent variable, B, which in effect modifies each concentration term by this factor.

$$v = V_{max}*S/(K_m*(1+I_1*B/K_{i2}+I_2*B/K_{i2}+(I_1*I_2*B)/(\alpha*K_{i1}*K_{i2}))+S*(1+I_1*B/K_{i1}+I_2*B/K_{i2}+(I_1*I_2*B)/(\alpha*K_{i1}*K_{i2})))$$ (Equation 5)

where:
v=initial velocity of the reaction
$V_{max}$=maximal velocity
S=concentration of interrogated substrate
$I_1$=concentration of inhibitor 1
$I_2$=concentration of inhibitor 2
$K_m$=Michaelis constant for substrate
$K_{i1}$=Inhibition constant for inhibitor 1
$K_{i2}$=Inhibition constant for inhibitor 2
α=interaction factor FIG. 5 illustrates a simulation of velocity verses the fraction gradient (B) using Equation 5 for two inhibitors with varying α values. From the graph shown in FIG. 5, it can be seen that each inhibitor interaction type (e.g. synergistic, neutral (non-interacting), and antagonistic inhibition) creates a unique line useful in characterizing the type of interaction.

The representative advantages provided by the novel methods disclosed herein for determining potency and mechanism of action for a single inhibitor system apply as well to the novel continuous method of dual inhibitor variation, over the conventional orthogonal method using independent reaction wells with discrete concentrations. The precise high density data provided by the methods of the presently disclosed subject matter provide greater accuracy in determining type of inhibitor interaction using fewer reagents, over a shorter period of time, and permitting greater automation than conventional techniques.

As with reactions having a single inhibitor analyzed using the presently disclosed subject matter, reactions comprising two inhibitors suspected to inhibit the same biological molecule can be analyzed using methods disclosed herein. In some embodiments, the methods comprise contacting a biological molecule, at least one ligand of the biological molecule, and two inhibitors suspected of being capable of inhibiting the biological molecule, under condition wherein concentrations of at least two of the biological molecule, the at least one ligand, and the two suspected inhibitors are simultaneously varied, and determining an outcome of the contact.

In some embodiments, the concentrations of the two inhibitors and/or the at least one ligand are simultaneously varied, and further, in some embodiments, the two inhibitors and/or the at least one ligand are simultaneously varied such that a ratio of the concentrations is constant.

In some embodiments, determining an outcome of the contact between a biological molecule, at least one ligand of the biological molecule, and two inhibitors suspected of being capable of inhibiting the biological molecule comprises determining an interaction factor (α) of the interaction between the two inhibitors. The interaction factor can be calculated, for example, utilizing Equation 5. Determining the interaction factor permits for determination of whether the two inhibitors are synergistic, antagonistic or neutral with respect to each other.

III. Determination of Enzyme Activator Potency and Mechanism of Action

The presently disclosed subject matter provides methods for determining a mechanism of activation and/or potency of an activator of a biological molecule. The methods of the presently disclosed subject matter described herein provide for determining the mechanism of activation and/or potency of an activator of a biological molecule, such as for example an enzyme or receptor, by simultaneously and continuously varying the concentrations of at least one substrate of the biological molecule and at least one activator of the biological molecule to obtain-far greater data density than is possible using present discrete concentration gradients. The known models and equations discussed in General Considerations and Section II herein above with respect to enzyme inhibitors are further modified as disclosed herein below to provide applicable equations for interpreting data obtained by simultaneous and continuous variation of at least two components of the reaction system.

The model presented above in Section II for inhibitors (Equation 4) can be extended for use in reactions comprising biological molecule activators in which substrate and activator are simultaneously and continuously varied. The formula below illustrates a general kinetic scheme describing a nonessential activation mechanism.

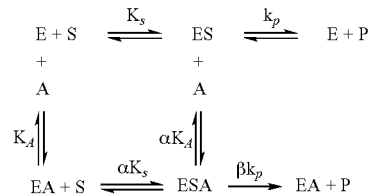

Figure 6:
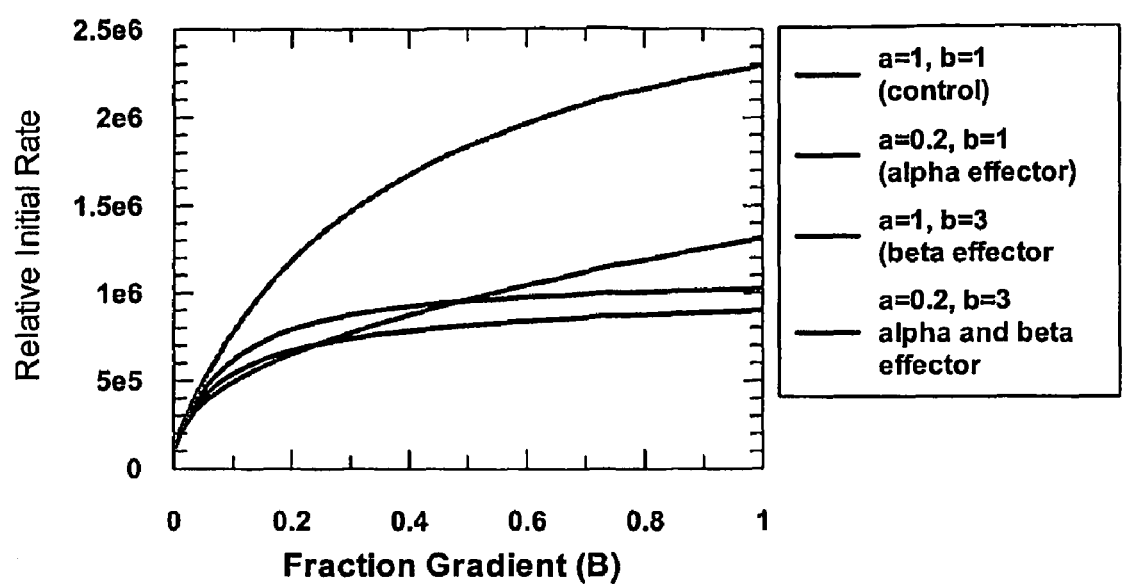
FIG. 6 is a graph showing a simulation of velocity verses fraction gradient (B) of two activators using an equation for calculation of the interaction of two activators affecting α only, β only, and both α and β.

A general equation describing nonessential activation was recast into one in which the interrogated substrate and activator are co-varied around a constant ratio to one another for use with methods of the presently disclosed subject matter (Equation 6). This model can also be used universally to discriminate between activators that are effectors of $V_{max}$, $K_m$, or both. The fractional gradient that describes this constant ratio of concentration S relative to concentration A is introduced as the independent variable, B, which in effect modifies each concentration term by this factor.

$$v = V_{max}*S*B/(K_m*(1+\beta(A*B/K_{act})/(1+\beta(A*B/\alpha*K_{act}))+(S*B*(1+(A*B/\alpha*K_{act}))/(1+\beta(A*B/\alpha*K_{act}))))$$ (Equation 6)

where:
v=initial velocity of the reaction
$V_{max}$=maximal velocity
S=concentration of interrogated substrate A=concentration of activator $K_m$=Michaelis constant for substrate $K_{act}$=Activation constant for activator $\alpha$ and $\beta$=activator interaction factors on $K_m$, $K_{act}$, and $V_{max}$ FIG. 6 illustrates a simulation of velocity verses the fraction gradient (B) using Equation 6 for activators affecting $\alpha$ only, $\beta$ only, and both $\alpha$ and $\beta$. From the graph shown in FIG. 6, it can be seen that each activator type creates a unique line useful in characterizing the type of activation.

As with methods disclosed herein for use in determining mechanism of action and/or potency of inhibitors, similar representative advantages exist over conventional methodology when using the novel methods, of the presently disclosed subject matter as applied to characterizing reactions comprising activators of biological molecules.

In some embodiments, methods described herein for determining a mechanism of activation and/or potency of an activator of a biological molecule comprises contacting at least one activator, a biological molecule, and at least one ligand for the biological molecule under conditions where concentrations of at least two of the at least one activator, the biological molecule and the at least one ligand are simultaneously varied; and determining an outcome of the contacting of the at least one activator, the at least one ligand, and the biological molecule to determine the mechanism of activation, potency of the activator, or both the mechanism of activation and potency of the activator.

In some embodiments, the biological molecule comprises an enzyme and the at least one ligand comprises a substrate of the enzyme, such as for example an enzyme activator. In other embodiments, the biological molecule comprises a receptor and the at least one ligand comprises a receptor ligand.

In some embodiments, the concentrations of the at least one inhibitor and the at least one ligand are simultaneously varied, and further, in some embodiments, the concentrations are simultaneously varied such that a ratio of the concentrations is held constant. That is, for example, in some embodiments as the concentration of either the ligand or inhibitor is increased, the concentration of the other component is proportionately decreased. Thus, in embodiments where the concentrations of components are varied by varying the flow rates of the fluid streams through which the components flow, the total flow rate of the combined fluid streams remains the same, even as the flow rate of each stream varies proportionately with the other fluid stream. Examples 3 and 4 herein below further illustrate this embodiment in detail.

In some embodiments of the presently disclosed subject matter, the concentrations are simultaneously varied with discrete concentration gradients. The discrete concentration gradients can in some embodiments be contained within discrete containers, which can be for example, wells in a microtiter plate. In other embodiments, the concentrations are simultaneously varied with continuous concentration gradients. The continuous concentration gradients can be formed in some embodiments, for example, using a microfluidic system comprising a microfluidic chip. In some preferred embodiments, the microfluidic system comprises a system as described herein below.

Further, in some embodiments, determining the mechanism of activation of an activator comprises determining an activation constant for the activator ($K_{act}$), which is described in detail above and can be calculated, for example, utilizing Equation 6. Further, in some embodiments, determining the potency of the activator comprise determining at least one activator interaction factor affecting a Michaelis constant for the ligand ($K_m$) and/or a maximal velocity ($V_{max}$). Equation 6 can further be utilized, as described above, to calculate $K_m$ and $V_{max}$ to determine activator potency.

IV. Determination of Bisubstrate Enzyme System Kinetic Mechanism

The presently disclosed subject matter provides methods for determining a mechanism of reaction and/or kinetic constants of ligands of a bireactant biological molecule system. The methods of the presently disclosed subject matter described herein provide for determining mechanism of reaction and/or kinetic constants of ligands of a bireactant biological molecule system by simultaneously and continuously varying the concentrations of at least two of a biological molecule, such as for example an enzyme or receptor molecule, and a plurality of ligands of the biological molecule, thereby obtaining far greater data density than is possible using present discrete concentration gradients.

The known mechanism models and equations discussed in Section I herein above with respect to bireactant enzyme systems (Equations 2 and 3) are further modified by the presently disclosed subject matter methods as disclosed herein below to provide applicable equations for interpreting data obtained by simultaneous and continuous variation of at least two components of a bireactant substrate/ligand reaction system. The models discussed in Section I (Equations 2 and 3) for all types of bireactant kinetic mechanisms described above can be collated into one of two equations, for use with a planar dataset with simultaneous continuous variation of two substrates.

The novel methods disclosed herein provide at least two methods of presenting the modified model.

Method 1 presents data as a concentration of substrate A and introduces a ratio constant of concentration of substrate B/concentration of substrate A, as demonstrated by Equation 7a:

$$v = V_{max} * x * A^2 / (K_{ia} * K_b + K_b * A + K_a * x * A + x * A^2) \quad \text{Equation 7a}$$

where:

$V_{max}$=maximal velocity;

A=concentration of substrate A;

B=concentration of substrate B;

$K_a$=Michaelis constant for substrate A;

$K_b$=Michaelis constant for substrate B;

$K_{ia}$=dissociation constant of substrate A; and x=ratio constant where x=[B]/[A].

Figure 7A:
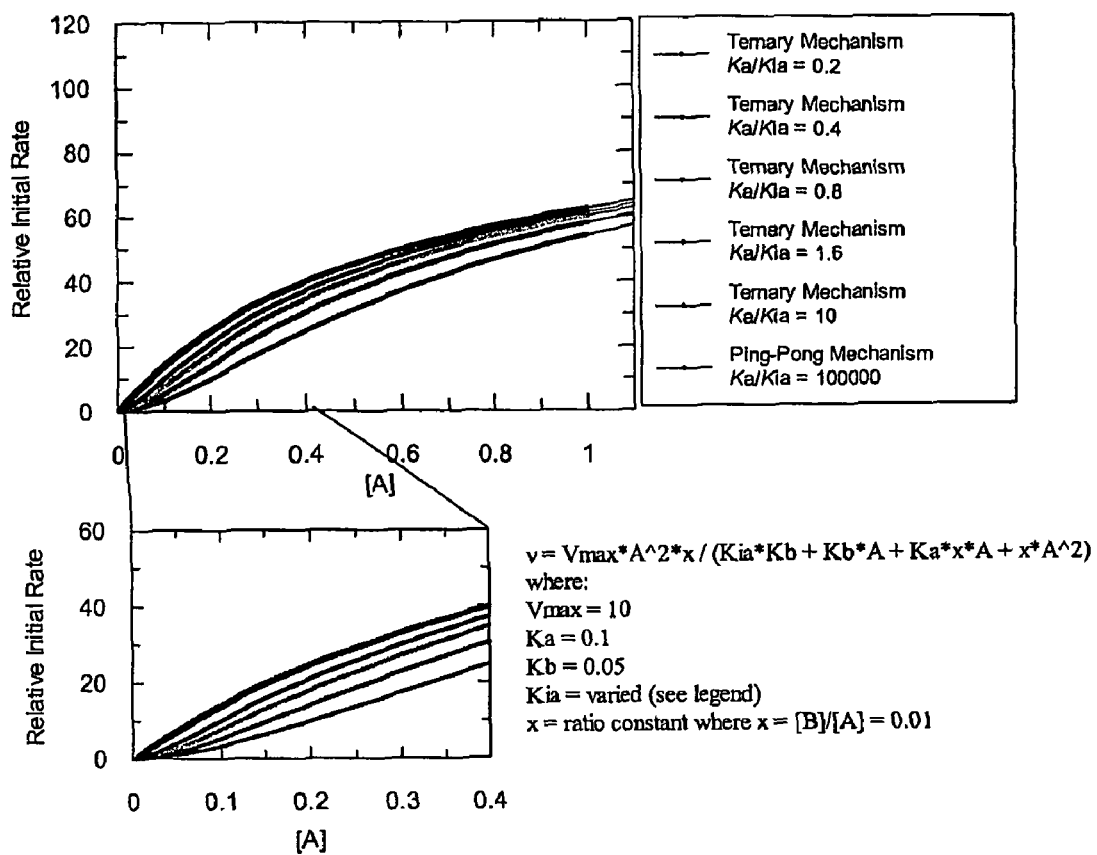
FIG. 7A is a graph showing a simulation for characterization of bisubstrate kinetic mechanisms using a first method and equation.

FIG. 7A is a graph showing simulations of the model presented in Equation 7a. A sigmoidal profile suggests a ping-pong mechanism when the $K_a/K_{ia}$ ratio is significantly greater than 10, whereas a more hyperbolic profile indicates a ternary mechanism. Note that each curve is generated in one experimental run, providing the advantage over known methods of identifying the mechanism in one single run of continuous variation of substrates around a set ratio of [B]/[A].

Method 2 presents data as a fraction gradient of a constant ratio of substrates A and B, as demonstrated by Equation 7b:

$$v = V_{max} * A * B * G / (K_{ia} * K_b + K_b * A * G + K_a * A * G + A * B * G) \quad \text{Equation 7b}$$

where:

$V_{max}$=maximal velocity;

A=concentration of substrate A;

B=concentration of substrate B;

$K_a$=Michaelis constant for substrate A;

$K_b$=Michaelis constant for substrate B;

$K_{ia}$=dissociation constant of substrate A; and

G=fraction gradient of constant ratio of A and B.

Figure 7B:
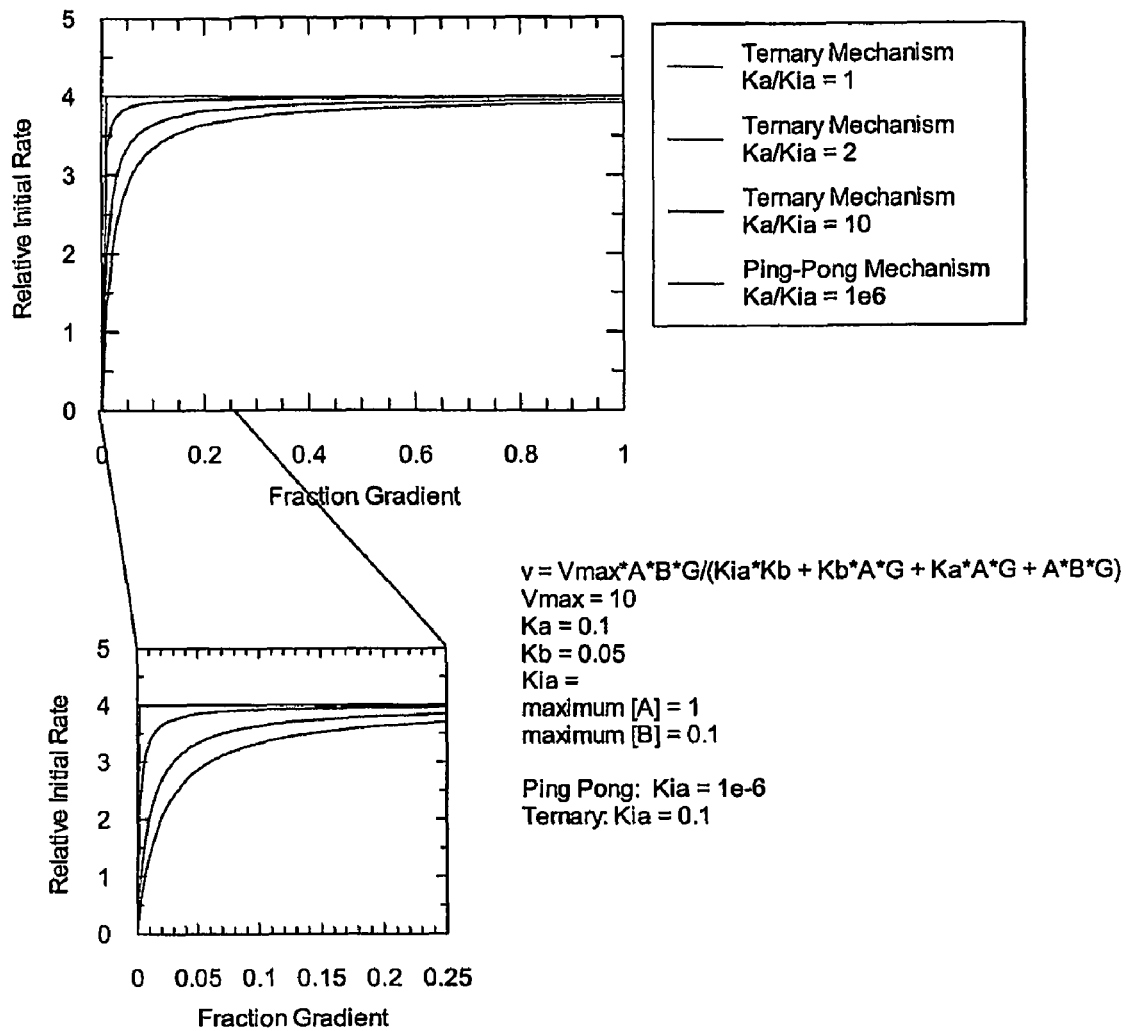
FIG. 7B is a graph showing a simulation for characterization of bisubstrate kinetic mechanisms using a second method and equation.

FIG. 7B is a graph showing simulations of the model presented in Equation 7b. A "square" profile suggests a ping-pong mechanism when the Ka/Kia ratio is significantly greater than 10, whereas a more hyperbolic profile indicates a ternary mechanism. Again, note that each curve is generated in one experimental run, providing an advantage over known methods of identifying the mechanism in one single run of continuous variation of substrates.

In some embodiments, methods for determining one of a mechanism of reaction, kinetic constants of ligands, and both a mechanism of reaction and kinetic constants of ligands of a bireactant biological molecule system are provided. The methods comprise in some embodiments, contacting a biological molecule and a plurality of ligands for the biological molecule under conditions where concentrations of at least two of the biological molecule and plurality of ligands are simultaneously varied and determining an outcome of the contacting of the biological molecule and the plurality of ligands to determine one of the mechanism of reaction, the kinetic constants of the ligands, or both the mechanism of reaction and the kinetic constants of the ligands of the bireactant biological molecule system.

In some embodiments, the concentrations of the plurality of ligands are each simultaneously varied. Further, in some embodiments, the concentrations of the plurality of ligands are each simultaneously varied such that a ratio of the concentrations is constant. That is, for example, as the concentration of either the ligand or inhibitor is increased, the concentration of the other component is proportionately decreased. Thus, in embodiments where the concentrations of components are varied by varying the flow rates of the fluid streams through which the components flow, the total flow rate of the combined fluid streams remains the same, even as the flow rate of each stream varies proportionately with the other fluid stream.

In some embodiments of the methods, the biological molecule can comprise an enzyme and the plurality of ligands can each comprise a substrate of the enzyme. Further, determining the kinetics constants of the enzyme substrates in these embodiments can comprise determining the Michaelis constant ($K_m$) for at least one of the enzyme substrates. The $K_m$ for at least one of the enzyme substrates can be determined by application of the experimental data to either Equation 7a or 7b, as described above. Further, in some embodiments, the $K_m$ can be determined for both substrates. For example, the $K_m$ for a first substrate A ($K_a$) can be determined and the Km for a second substrate B ($K_b$) can be determined simultaneously utilizing either Equation 7a or 7b.

In other embodiments, the biological molecule can comprise a receptor and the plurality of ligands can each comprise a ligand of the receptor. Further, determining the kinetics constants of the receptor ligands in these embodiments can comprise determining the dissociation constant for at least one of the receptor ligands utilizing either Equation 7a or 7b.

In some embodiments of the method, the concentrations are simultaneously varied with discrete concentration gradients. Further, in some embodiments, each of the discrete concentrations can be contained in discrete containers. The discrete containers can be wells in a microtiter plate. In other embodiments, the concentrations are simultaneously varied with continuous concentration gradients. The continuous concentration gradients can be in a microfluidic chip. In some preferred embodiments, the microfluidic system comprises a system as described herein below.

V. Microfluidic Systems for Generating Continuous Concentration Gradients

Exemplary microfluidic chips, systems, and related methods are described herein below for generating continuous concentration gradients of reagents for use with the presently disclosed novel methods. In some embodiments, the microfluidic systems described herein incorporate improvements for reducing or eliminating noise in the fluid mix concentration and for improving rapid diffusion and dispersion or reagents in the fluid stream. These microfluidic chips, systems, and methods are described with regard to the accompanying drawings. It should be appreciated that the drawings pertaining to particular embodiments do not constitute limitations on the scope of the disclosed microfluidic chips, systems, and methods.

As used herein, the term "microfluidic chip," "microfluidic system," or "microfluidic device" generally refers to a chip, system, or device which can incorporate a plurality of interconnected channels or chambers, through which materials, and particularly fluid borne materials can be transported to effect one or more preparative or analytical manipulations on those materials. A microfluidic chip is typically a device comprising structural or functional features dimensioned on the order of mm-scale or less, and which is capable of manipulating a fluid at a flow rate on the order of μl/min or less. Typically, such channels or chambers include at least one cross-sectional dimension that is in a range of from about 1 μm to about 500 μm. The use of dimensions on this order allows the incorporation of a greater number of channels or chambers in a smaller area, and utilizes smaller volumes of reagents, samples, and other fluids for performing the preparative or analytical manipulation of the sample that is desired.

Microfluidic systems are capable of broad application and can generally be used in the performance of biological and biochemical analysis and detection methods. The systems described herein can be employed in research, diagnosis, environmental assessment and the like. In particular, these systems, with their micron scales, nanoliter volumetric fluid control systems, and integratability, can generally be designed to perform a variety of fluidic operations where these traits are desirable or even required. In addition, these systems can be used in performing a large number of specific assays that are routinely performed at a much larger scale and at a much greater cost.

A microfluidic device or chip can exist alone or may be a part of a microfluidic system which, for example and without limitation, can include: pumps for introducing fluids, e.g., samples, reagents, buffers and the like, into the system and/or through the system; detection equipment or systems; data storage systems; and control systems for controlling fluid transport and/or direction within the device, monitoring and controlling environmental conditions to which fluids in the device are subjected, e.g., temperature, current and the like.

As used herein, the term "channel" or "microfluidic channel" can mean a cavity formed in a material by any suitable material removing technique, or can mean a cavity in combination with any suitable fluid-conducting structure mounted in the cavity such as a tube, capillary, or the like.

As used herein, the term "reagent" generally means any flowable composition or chemistry. The result of two reagents merging or combining together is not limited to any particular response, whether a biological response or biochemical reaction, a dilution, or otherwise.

In referring to the use of a microfluidic chip for handling the containment or movement of fluid, the terms "in", "on", "into", "onto", "through", and "across" the chip generally have equivalent meanings.

As used herein, the term "communicate" (e.g., a first component "communicates with" or "is in communication with" a second component) and grammatical variations thereof are used herein to indicate a structural, functional, mechanical, electrical, optical, or fluidic relationship, or any combination thereof, between two or more components or elements. As such, the fact that one component is said to communicate with a second component is not intended to exclude the possibility that additional components may be present between, and/or operatively associated or engaged with, the first and second components.

As used herein, the terms "measurement", "sensing", and "detection" and grammatical variations thereof have interchangeable meanings; for the purpose of the present disclosure, no particular distinction among these terms is intended.

Embodiments disclosed herein comprise hardware and/or software components for controlling liquid flows in microfluidic devices and measuring the progress of miniaturized biochemical reactions occurring in such microfluidic devices. As the description proceeds, it will become evident that the various embodiments disclosed herein can be combined according to various configurations to create a technologic system or platform for implementing micro-scale or sub-micro-scale analytical functions. One or more of these embodiments can contribute to or attain one or more advantages over prior art technology, including: (1) 1000-fold reduction in the amount of reagent needed for a given assay or experiment; (2) capability of generating continuous concentration gradients between reagents and subsequent elimination of the need for disposable assay plates; (3) fast, serial processing of independent reactions; (4) data readout in real-time; (5) improved data quality; (6) more fully integrated software and hardware, permitting more extensive automation of instrument function, 24/7 operation, automatic quality control and repeat of failed experiments or bad gradients, automatic configuration of new experimental conditions, and automatic testing of multiple hypotheses; (7) fewer moving parts and consequently greater robustness and reliability; and (8) simpler human-instrument interface. As the description proceeds, other advantages may be recognized by persons skilled in the art.

Figure 8:
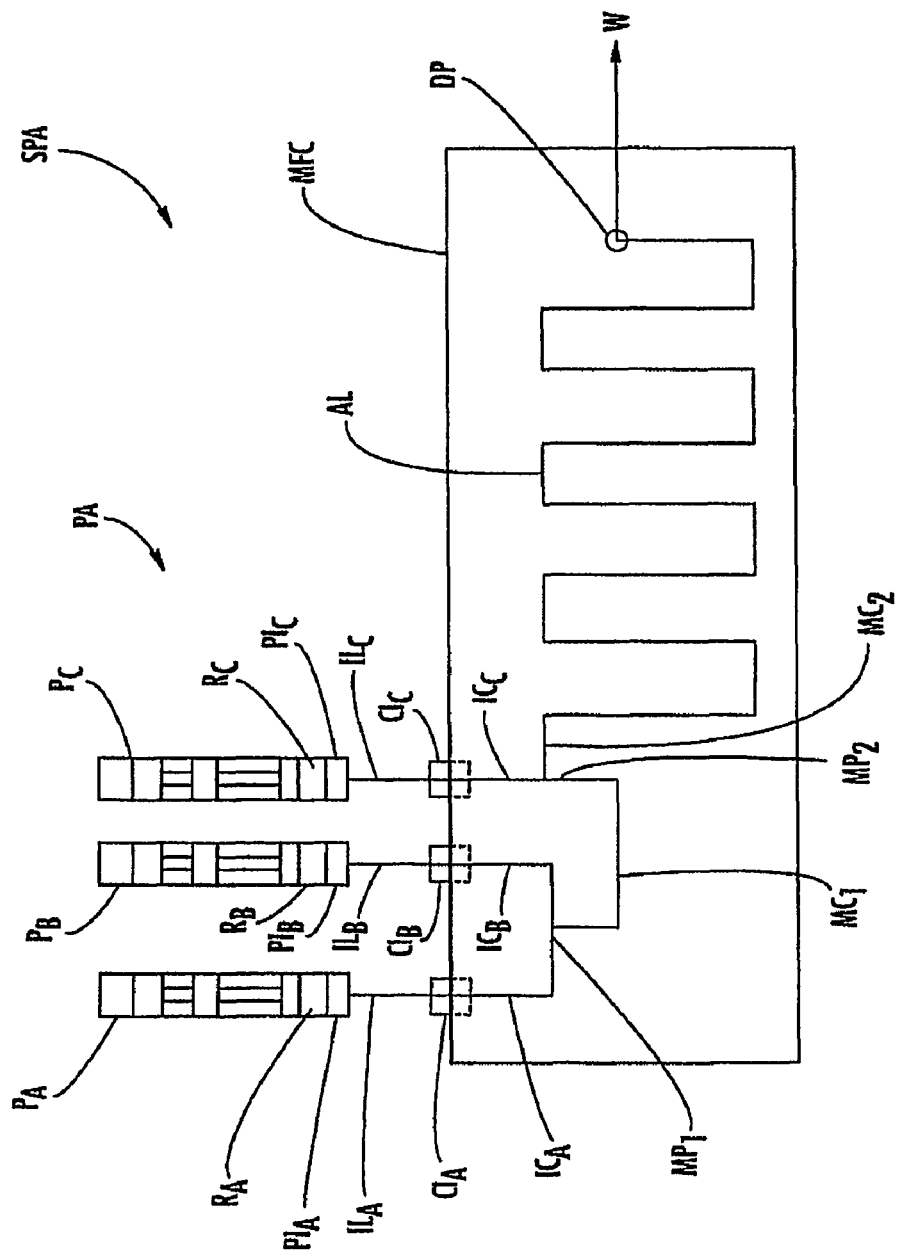
FIG. 8 is a schematic view of a sample processing apparatus including a pump assembly and a microfluidic chip provided in accordance with embodiments disclosed herein.

Referring now to FIG. 8, a sample processing apparatus, generally designated SPA, is illustrated according to certain embodiments. Generally, sample processing apparatus SPA can be utilized for precisely generating and mixing continuous concentration gradients of reagents in the nl/min to µl/min range, particularly for initiating a biological response or biochemical reaction and more particularly, in some embodiments as described herein above, for studying an interaction between at least one inhibitor or activator of a biological molecule and/or a substrate of the biological molecule from which results can be read after a set period of time. Sample processing apparatus SPA generally comprises a reagent introduction device advantageously provided in the form of a pump assembly, generally designated PA, and a microfluidic chip MFC. Pump assembly PA comprises one or more linear displacement pumps such as syringe pumps or the like. For mixing two or more reagents, pump assembly PA comprises at least two or more pumps. In the illustrated embodiment in which three reagents can be processed (e.g., reagent $R_A$, $R_B$, and $R_C$), sample processing apparatus SPA includes a first pump $P_A$, a second pump $P_B$, and a third pump $P_C$. Sample processing apparatus SPA is configured such that pumps $P_A$, $P_B$ and $P_C$ are disposed off-chip but inject their respective reagents $R_A$, $R_B$ and $R_C$ directly into microfluidic chip MFC via separate input lines $IL_A$, $IL_B$ and $IL_C$ such as fused silica capillaries, polyetheretherketone (such as PEEK® available from Upchurch Scientific of Oak Harbor, Wash.) tubing, or the like. In some embodiments, the outside diameter of input lines $IL_A$, $IL_B$ and $IL_C$ can range from approximately 50-650 µm. In some embodiments, each pump $P_A$, $P_B$ and $P_C$ interfaces with its corresponding input line $IL_A$, $IL_B$ and $IL_C$ through a pump interconnect $PI_A$, $PI_B$ and $PI_C$ designed for minimizing dead volume and bubble formation, and with replaceable parts that are prone to degradation or wear. Pump interconnects $PI_A$, $PI_B$ and $PI_C$ according to some embodiments are described in more detail hereinbelow with reference to FIGS. 18A and 18B.

Figure 9:
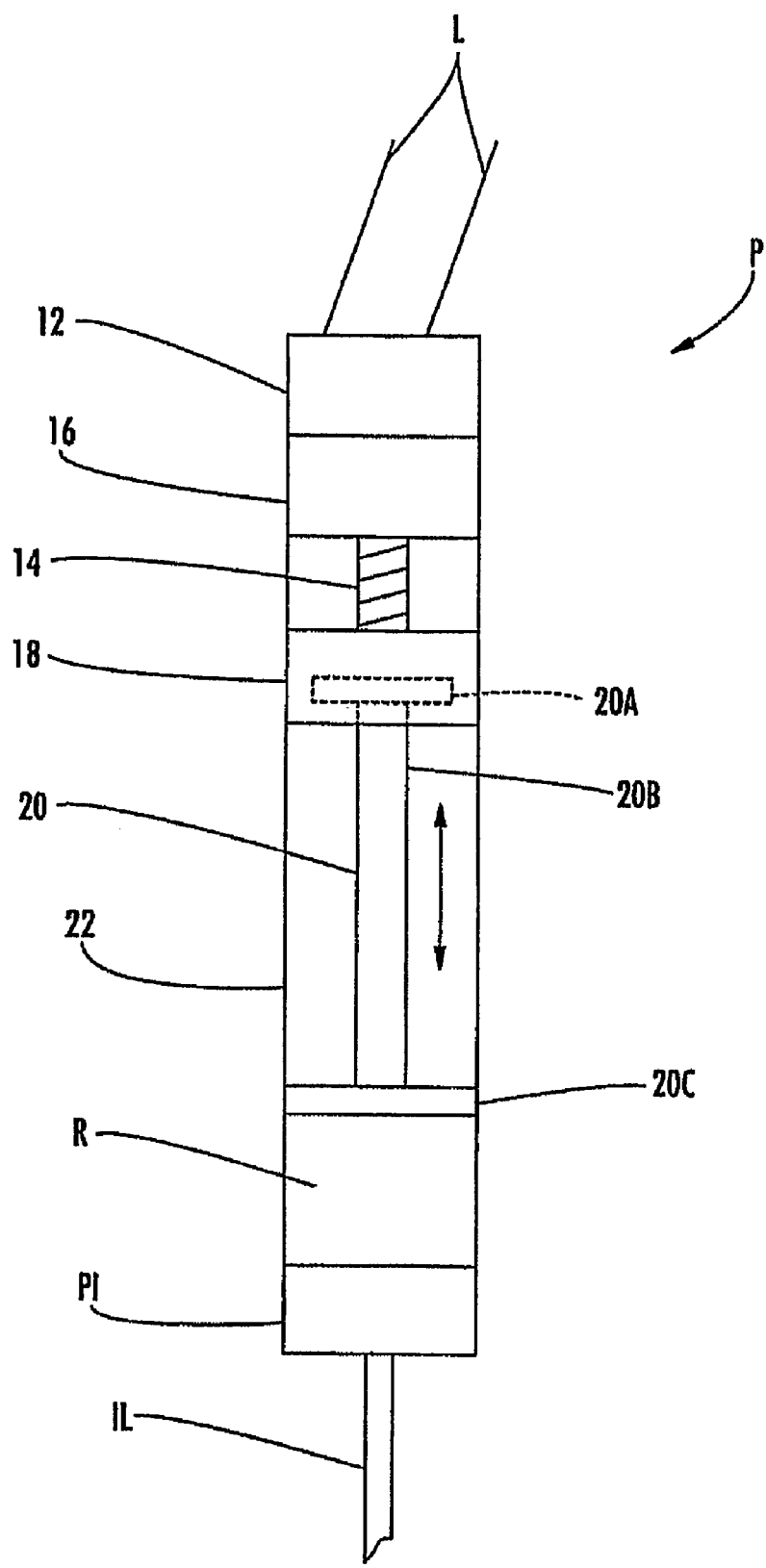
FIG. 9 is a simplified diagram of a linear displacement pump provided in the sample processing apparatus of FIG. 8.

Referring to FIG. 9, an example of a suitable linear displacement pump, generally designated P, is diagrammatically illustrated. Pump P includes a servo motor 12 that is energized and controlled through its connection with any suitable electrical circuitry, which could comprise computer hardware and/or software, via electrical leads L. Alternatively, pump P can include any suitable motor for driving the components of a linear displacement pump. For example, pump P can be a stepper motor. Continuing with FIG. 9, servo motor 12 drives a rotatable lead screw 14 through a gear reduction device 16. Lead screw 14 engages a linearly translatable pump stage 18. A piston or plunger 20 is coupled to pump stage 18 for linear translation within a pump barrel 22 that stores and contains a reagent R to be introduced into microfluidic chip MFC (FIG. 8). Typically, plunger 20 comprises a head portion 20A, an elongate portion or stem 20B, and a distal end or movable boundary 20C. In operation, reagent R is pushed by movable boundary 20C through pump interconnect PI and into input line IL. The structure of each pump P according to advantageous embodiments is further described hereinbelow with reference to FIGS. 14A-16.

In one exemplary yet non-limiting embodiment, pump barrel 22 is a gas-tight micro-syringe type, having a volume ranging from approximately 10-250 µl. The thread pitch of lead screw 14 can be approximately 80 threads per inch. Gear reduction device 16 produces a gear reduction of 1024:1 or thereabouts. Servo motor 12 and gear reduction device 16 can have an outside diameter of 10 mm or thereabouts. Servo motor 12 uses a 10-position magnetic encoder with quadrature encoding that provides forty encoder counts per revolution, and the resolution is such that each encoder count is equivalent to 0.0077 µm of linear displacement. The foregoing specifications for the components of pump P can be changed without departing from the scope of the embodiment.

Figure 10A:
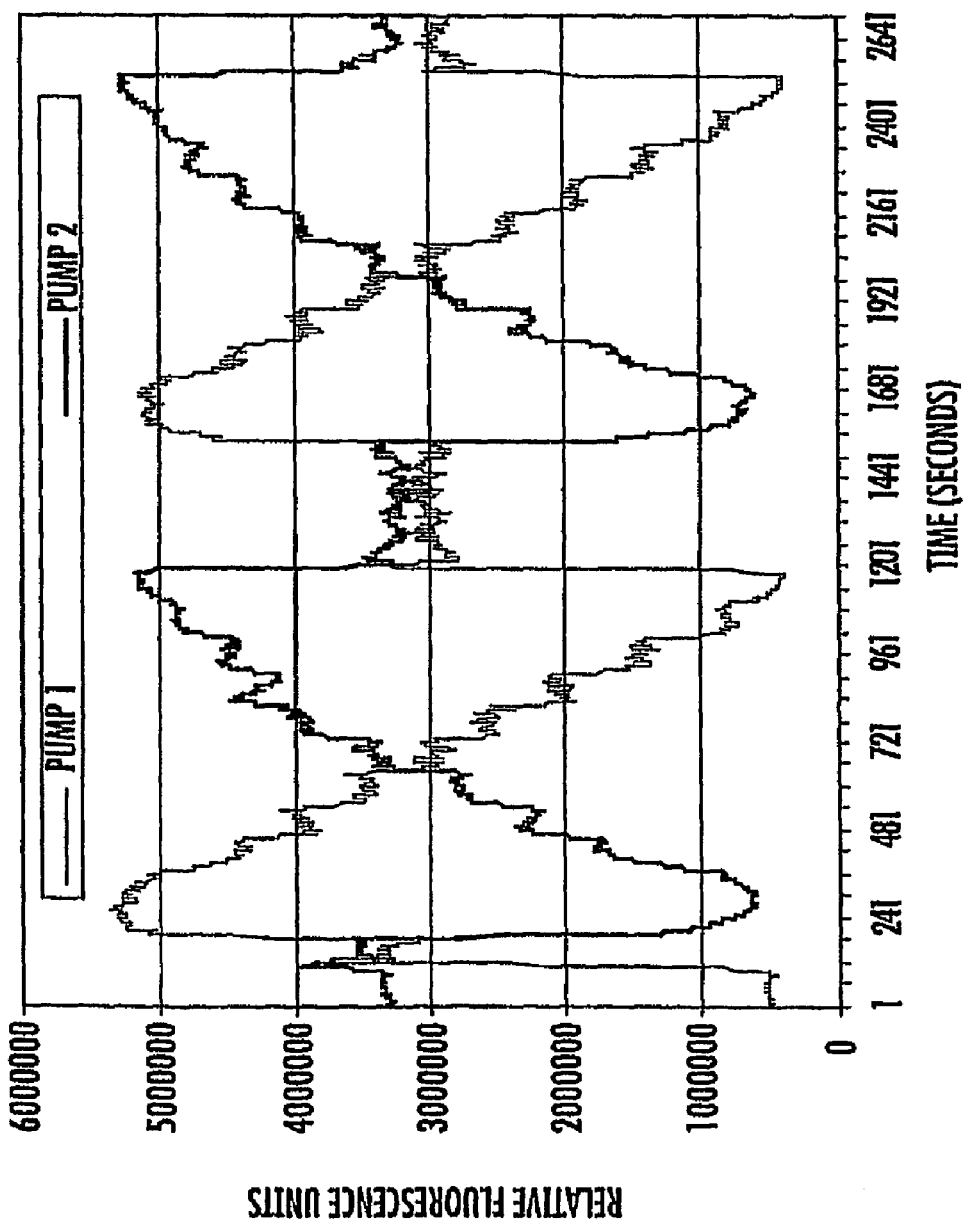
FIG. 10A is a plot of step gradients generated by two pumps, each containing a different fluorophore, and controlled to create steps of 0.1 nl/min ranging from 0.0 to 1.0 nl/min.

In some embodiments for which a plurality of pumps are provided (e.g., pumps $P_A$-$P_C$ in FIG. 8), the respective operations of pumps $P_A$-$P_C$ and thus the volumetric flow rates produced thereby are individually controllable according to individual, pre-programmable fluid velocity profiles. The use of pumps $P_A$-$P_C$ driven by servo motors 12 can be advantageous in that smooth, truly continuous (i.e., non-pulsatile and non-discrete) flows can be processed in a stable manner. In some embodiments, pumps $P_A$-$P_C$ are capable of producing flow rates permitting flow grading between about 0 and 500 nl/min, with a precision of 0.1 nl/min in a stable, controllable manner. Optionally, pumps $P_A$-$P_C$ can produce flow rates permitting flow grading from 0 to as little as 5 nl/min. FIG. 10A is a plot of step gradients generated by two pumps, each containing a different fluorophore, and controlled to create steps of 0.1 nl/min ranging from 0.0 to 1.0 nl/min. The flow in the two pumps were merged in a microfluidic chip and the resulting fluorescence signals were measured to determine the ratio of the mix. The combined flow rate of the two pumps was 1 nl/min, with steps of 0.1 nl/min being made to demonstrate the precision of the flow rate—continuously varying flows also are possible, as described hereinbelow. Moreover, the operation of each servo motor 12 (e.g., the angular velocity of its rotor) can be continuously varied in direct proportion to the magnitude of the electrical control signal applied thereto. In this manner, the ratio of two or more converging streams of reagents (e.g., reagents $R_A$-$R_C$ in FIG. 8) can be continuously varied over time to produce continuous concentration gradients in microfluidic chip MFC. Thus, the number of discrete measurements that can be taken from the resulting concentration gradient is limited only by the sampling rate of the measurement system employed and the noise in the concentration gradient. Moreover, excellent data can be acquired using a minimal amount of reagent. For instance, in the practice of the present embodiment, high-quality data has been obtained from concentration gradients that consumed only 10 nl of reagent (total volume) from three simultaneous flows of reagents $R_A$-$R_C$.

The ability to produce very low flow-rate, stable displacement flows to generate concentration gradients, believed to be 3-4 orders of magnitude slower than that heretofore attainable, provides a number of advantages. Chips can be fabricated from any material, and surface chemistry does not need to be carefully controlled, as with electro-osmotic pumping. Any fluid can be pumped, including fluids that would be problematic for electro-osmotic flows (full range of pH, full range of ionic strength, high protein concentrations) and for pressure driven flows (variable viscosities, non-Newtonian fluids), greatly simplifying the development of new assays. Variations in channel diameters, either from manufacture variability or from clogging, do not affect flow rates, unlike electro-osmotic or pressure flows. Computer control and implementation of control (sensors and actuators) are simpler than for pressure flows, which require sensors and actuators at both ends of the channel. Displacement-driven flows provide the most-straightforward means for implementing variable flows to generate concentration gradients.

The ability to pump at ultra-low flow rates (nl/min) provides a number of advantages in the operation of certain embodiments of microfluidic chip MFC and related methods disclosed herein. These low flow rates enable the use of microfluidic channels with very small cross-sections. Higher, more conventional flow rates require the use of longer channels in order to have equivalent residence times (required to allow many biochemical reactions or biological responses to proceed) or channels with larger cross-sectional areas (which can greatly slow mixing by diffusion and increase dispersion of concentration gradients). In addition, reagent use is decreased because, all other parameters being equal, decreasing the flow rate by half halves the reagent use. Smaller channel dimensions (e.g., 5-30 µm) in the directions required for diffusional mixing of reagents permits even large molecules to rapidly mix in the microfluidic channels.

Referring back to FIG. 8, microfluidic chip MFC comprises a body of material in which channels are formed for conducting, merging, and mixing reagents $R_A$-$R_C$ for reaction, dilution or other purposes. Microfluidic chip MFC can be structured and fabricated according to any suitable techniques, and using any suitable materials, now known or later developed. In advantageous embodiments, the channels of microfluidic chip MFC are formed within its body to prevent evaporation, contamination, or other undesired interaction with or influence from the ambient environment.

Suitable examples of such a microfluidic chip MFC are disclosed in co-pending, commonly owned U.S. Provisional Applications entitled MICROFLUIDIC SYSTEMS, DEVICES AND METHODS FOR REDUCING DIFFUSION AND COMPLIANCE EFFECTS AT A FLUID MIXING REGION, U.S. Provisional Application No. 60/707,220; MICROFLUIDIC SYSTEMS, DEVICES AND METHODS FOR REDUCING NOISE GENERATED BY MECHANICAL INSTABILITIES, U.S. Provisional Application No. 60/707,245; MICROFLUIDIC SYSTEMS, DEVICES AND METHODS FOR REDUCING BACKGROUND AUTOFLUORESCENCE AND THE EFFECTS THEREOF, U.S. Provisional Application No. 60/707,386; and MICROFLUIDIC CHIP APPARATUSES, SYSTEMS, AND METHODS HAVING FLUIDIC AND FIBER OPTIC INTERCONNECTIONS, U.S. Provisional Application No. 60/707,246, the contents of which are incorporated herein in their entireties. As discussed therein, to provide internal channels, microfluidic chip MFC can comprise two body portions such as plates or layers, with one body portion serving as a substrate or base on which features such as channels are formed and the other body portion serving as a cover. The two body portions can be bonded together by any means appropriate for the materials chosen for the body portions. Non-limiting examples of bonding techniques include thermal bonding, anodic bonding, glass frit bonding, adhesive bonding, and the like. Non-limiting examples of materials used for the body portions include various structurally stable polymers such as polystyrene, metal oxides such as sapphire ($Al_2O_3$), silicon, and oxides, nitrides or oxynitrides of silicon (e.g., $Si_xN_y$, glasses such as $SiO_2$, or the like). In advantageous embodiments, the materials are chemically inert and biocompatible relative to the reagents to be processed, or include surfaces, films, coatings or are otherwise treated so as to be rendered inert and/or biocompatible. The body portions can be constructed from the same or different materials. To enable optics-based data encoding of analytes processed by microfluidic chip MFC, one or both body portions can be optically transmissive or include windows at desired locations. The channels can be formed by any suitable micro-fabricating techniques appropriate for the materials used, such as the various etching, masking, photolithography, ablation, and micro-drilling techniques available. The channels can be formed, for example, according to the methods disclosed in a co-pending, commonly owned U.S. Provisional Application entitled MICROFLUIDIC CHIP APPARATUSES, SYSTEMS, AND METHODS HAVING FLUIDIC AND FIBER OPTIC INTERCONNECTIONS, U.S. Provisional Application No. 60/707,246, the content of which is incorporated herein in its entirety. In some embodiments, the size of the channels can range from approximately 5 to 500 µm in cross-sectional area.

As shown in FIG. 8, as one exemplary fluidic architecture, the channels of microfluidic chip MFC include a first input or pre-mixing channel $IC_A$, a second input or pre-mixing channel $IC_B$, and a third input or pre-mixing channel $IC_C$. Input channels $IC_A$, $IC_B$ and $IC_C$ fluidly communicate with corresponding pumps $P_A$, $P_B$, and $P_C$ via input lines $IL_A$, $IL_B$, and $IL_C$. In some embodiments, input channels $IC_A$, $IC_B$ and $IC_C$ interface with input lines $IL_A$, $IL_B$, and $IL_C$ through respective chip interconnects $CI_A$, $CI_B$ and $CI_C$. Chip interconnects $CI_A$, $CI_B$ and $CI_C$ can be provided in accordance with embodiments disclosed in a co-pending, commonly owned U.S. Provisional Application entitled MICROFLUIDIC CHIP APPARATUSES, SYSTEMS, AND METHODS HAVING FLUIDIC AND FIBER OPTIC INTERCONNECTIONS, U.S. Provisional Application No. 60/707,246, the content of which is incorporated herein in its entirety. In addition to introducing separate reagent streams into microfluidic chip MFC, first and second input channels $IC_A$ and $IC_B$ can serve as temperature-equilibrating channels in which their respective reagents $R_A$ and $R_B$ to be mixed are equilibrated to a given surrounding temperature.

First input channel $IC_A$ and second input channel $IC_B$ terminate or meet at a first T-junction or merging point $MP_1$. From first merging point $MP_1$, a first mixing channel $MC_1$ traverses through microfluidic chip MFC over a distance sufficient to enable passive mixing of reagents $R_A$ and $R_B$ introduced by first input channel $IC_A$ and second input channel $IC_B$. In some embodiments, the mechanism for passive mixing is thermal or molecular diffusion that depends on flow velocity (e.g. time of flight) and distance of travel. Accordingly, microfabricated active mixers, which can be a source of noise, complexity, unreliability and cost are not required but could be provided. In the present exemplary embodiment, third input channel $IC_C$ and first mixing channel $MC_1$ terminate or meet at a second T-junction or merging point $MP_2$, from which a second mixing channel $MC_2$ traverses through microfluidic chip MFC over a distance sufficient for mixing.

Second mixing channel $MC_2$ communicates with a process/reaction channel or aging loop AL. Aging loop AL has a length sufficient for prosecuting a reaction or other interaction between reagents after the reagents have been introduced in two or more of first input channel $IC_A$, second input channel $IC_B$ and/or third input channel $IC_C$, merged at first mixing point $MP_1$ and/or second mixing point $MP_2$, and thereafter mixed in first mixing channel $MC_1$ and/or second mixing channel $MC_2$. For a given area of microfluidic chip MFC, the length of aging loop AL can be increased by providing a folded or serpentine configuration as illustrated in FIG. 8. For many processes contemplated herein, the length of aging loop AL and the linear velocity of the fluid flowing therethrough determines the time over which a reaction can proceed. A longer aging loop AL or a slower linear velocity permits longer reactions. The length of aging loop AL can be tailored to a specific reaction or set or reactions, such that the reaction or reactions have time to proceed to completion over the length of aging loop AL. Conversely, a long aging loop AL can be used in conjunction with measuring shorter reaction times by taking measurements closer to second mixing channel $MC_2$.

As further illustrated in FIG. 8, a detection location or point DP is defined in microfluidic chip MFC at an arbitrary point along the flow path of the reagent mixture, e.g., at a desired point along aging loop AL. More than one detection point DP can be defined so as to enable multi-point measurements and thus permit, for example, the measurement of a reaction product at multiple points along aging loop AL and hence analysis of time-dependent phenomena or automatic localization of the optimum measurement point (e.g., finding a point yielding a sufficient yet not saturating analytical signal). In some methods as further described hereinbelow, however, only a single detection point DP is needed. Detection point DP represents a site of microfluidic chip MFC at which any suitable measurement (e.g., concentration) of the reagent mixture can be taken by any suitable encoding and data acquisition technique. As one example, an optical signal can be propagated though microfluidic chip MFC at detection point DP, such as through its thickness (e.g., into or out from the sheet of FIG. 8) or across its plane (e.g., toward a side of the sheet of FIG. 8), to derive an analytical signal for subsequent off-chip processing. Hence, microfluidic chip MFC at detection point DP can serve as a virtual, micro-scale flow cell as part of a sample analysis instrument.

After an experiment has been run and data have been acquired, the reaction products flow from aging loop AL to any suitable off-chip waste site or receptacle W. Additional architectural details and features of microfluidic chip MFC are disclosed in co-pending, commonly owned U.S. Provisional Applications entitled MICROFLUIDIC SYSTEMS, DEVICES AND METHODS FOR REDUCING DIFFUSION AND COMPLIANCE EFFECTS AT A FLUID MIXING REGION, U.S. Provisional Application No. 60/707,220; MICROFLUIDIC SYSTEMS, DEVICES AND METHODS FOR REDUCING NOISE GENERATED BY MECHANICAL INSTABILITIES, U.S. Provisional Application No. 60/707,245; MICROFLUIDIC SYSTEMS, DEVICES AND METHODS FOR REDUCING BACKGROUND AUTOFLUORESCENCE AND THE EFFECTS THEREOF, U.S. Provisional Application No. 60/707,386; and MICROFLUIDIC CHIP APPARATUSES, SYSTEMS, AND METHODS HAVING FLUIDIC AND FIBER OPTIC INTERCONNECTIONS, U.S. Provisional Application No. 60/707,246, the contents of which are incorporated in their entireties.

An example of a method for generating and mixing concentration gradients using sample processing apparatus SPA illustrated in FIG. 8 will now be described. The respective pump barrels 22 (FIG. 9) of two or more of pumps $P_A$-$P_C$ are filled with different reagents $R_A$-$R_C$ and installed in pump assembly PA (FIG. 8). It will be understood, however, that one or more of pumps $P_A$-$P_C$ could be placed in communication with an automated or non-automated liquid handling system to selectively supply reagents $R_A$-$R_C$ as well as buffers, solvents, and the like. Examples of automated liquid handling systems are described hereinbelow with reference to FIGS. 22A-22C. Microfluidic chip MFC, typically with input lines $IL_A$, $IL_B$ and $IL_C$ attached, is mounted to any suitable holder such as a microscope stage as described hereinbelow in conjunction with one particular embodiment. The proximal (upstream) ends of input lines $IL_A$, $IL_B$ and $IL_C$ are attached to the corresponding distal (downstream) ends of pump barrels 22 (FIG. 9), such as by using pump interconnects $PI_A$-$PI_C$ according to certain embodiments disclosed herein. Any suitable method can then be performed to purge the channels of microfluidic chip MFC to remove any contaminants, as well as bubbles or any other compressible fluids affecting flow rates and subsequent concentration gradients. For instance, prior to loading reagents $R_A$-$R_C$ into pump assembly PA, pump assembly PA can be used to run a solvent through microfluidic chip MFC. Any configuration and calibration of the equipment used for detection/measurement can also be performed at this point, including the selection and/or alignment of optical equipment such as the optics described hereinbelow with reference to FIG. 12.

Once sample processing apparatus SPA has been prepared, concentration gradients can be run through microfluidic chip MFC. Two or more of pumps $P_A$, $P_B$ and/or $P_C$ are activated to establish separate flows of different reagents $R_A$, $R_B$ and/or $R_C$ into microfluidic chip MFC for combination, mixing, reaction, and measurement. A variety of combining strategies can be employed, depending on the number of inputs into microfluidic chip MFC and the corresponding number of pumps $P_A$-$P_C$, on their sequence of mixing determined by the geometry of fluidic channels in microfluidic chip MFC, and on the sequence of control commands sent to the pumps $P_A$-$P_C$. Using a microfluidic chip MFC with three inputs as illustrated in FIG. 8, for example, three reagents (reagents $R_A$, $R_B$ and $R_C$) can be input into microfluidic chip MFC, and concentration gradients of reagents $R_A$ versus $R_B$ can then be run against a constant concentration of reagent $R_C$. For another example, by using a four-input microfluidic chip MFC, concentration gradients of reagents $R_A$ and $R_B$ can be run with fixed concentrations of reagent $R_C$ and an additional reagent $R_D$. Due to the small size of the channels of microfluidic chip MFC, reagents $R_A$, $R_B$ and/or $R_C$ mix quickly (e.g., less than one second) in mixing channels $MC_1$ and/or $MC_2$ due to passive diffusion.

In accordance with one embodiment of the method, the total or combined volumetric flow rate established by the active pumps $P_A$, $P_B$ and/or $P_C$ can be maintained at a constant value during the run, in which case the transit time from mixing to measurement is constant and, consequently, the duration of reaction is held constant. In addition, the ratio of the individual flow rates established by respective pumps $P_A$, $P_B$ and/or $P_C$ can be varied over time by individually controlling their respective servo motors 12, thereby causing the resulting concentration gradient of the mixture in aging loop AL to vary with time (i.e. concentration varies with distance along aging loop AL). The concentration gradient of interest is that of the analyte relative to the other components of the mixture. The analyte can be any molecule of interest, and can be any form of reagent or component. Non-limiting examples include inhibitors, substrates, enzymes, fluorophores or other tags, and the like. As the reaction product passes through detection point DP with a varying concentration gradient, the detection equipment samples the reaction product flowing through according to any predetermined interval (e.g., 100 times per second). The measurements taken of the mixture passing through detection point DP can be temporally correlated with the flow ratio produced by pumps $P_A$, $P_B$ and/or $P_C$, and a response can be plotted as a function of time or concentration.

Figure 10B:
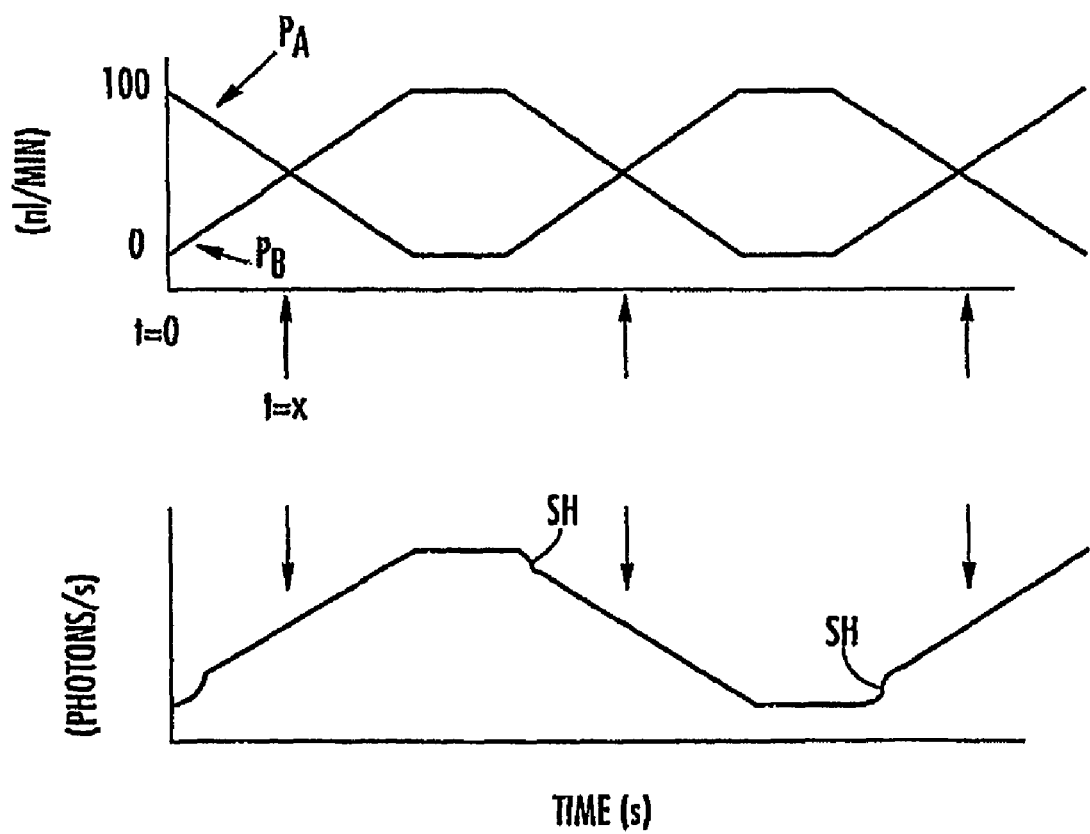
FIG. 10B is a plot of pump-driven flow velocity profiles superimposed over a plot of a measured concentration value resulting from the combination of reagent input streams in accordance with the flow velocity profiles according to embodiments disclosed herein.

Referring to FIG. 10B, an exemplary plot of varying flow velocity profiles programmed for two pumps (e.g., pumps $P_A$ and $P_B$) is given as a function of time, along with the resulting reagent concentration over time. As can be appreciated by persons skilled in the art, the flow velocity profiles can be derived from information generated by encoders typically provided with pumps $P_A$, $P_B$ and $P_C$ that, for example, transduce the angular velocities of their respective servo motors 12 by magnetic coupling or by counting a reflective indicator such as a notch or hash mark. Similarly, a linear encoder can directly measure the movement of plunger 20 or parts that translate with plunger 20. It can be seen that the total volumetric flow rate produced by all of the pumps together can be kept constant even while varying concentration gradients over time, by decreasing the flow rate of pump $P_A$ while increasing the flow rate of pump $P_B$, etc. For instance, at time t=0, the flow rate associated with pump $P_A$ has the relative value of 100% of the total volumetric flow rate, and the flow rate associated with pump $P_B$ has the relative value of 0%. As the flow rate of pump $P_A$ is ramped down and the flow rate of pump $P_B$ is ramped up, their respective profile lines cross at time t=x, where each flow rate is 50%. As shown in FIG. 10B, each flow rate can be oscillated between 0% and 100%. The resulting plot of concentration can be obtained, for example, through the use of a photodetector that counts photons per second, although other suitable detectors could be utilized as described hereinbelow. Similarly, non-linear concentration gradients and more complex concentration gradients of reagents $R_A$, $R_B$ and $R_C$ can be generated through appropriate command of the pumps $P_A$, $P_B$ and $P_C$. The trace of fluorescence in FIG. 10B includes apparent steps of "shoulders" SH at the beginning of each increasing gradient and each decreasing gradient. These can arise from such phenomena as diffusion across mixing point MP1, stiction in the pump or associated parts, inertia of the motor, poor encoder resolution at rotational velocities near zero, or compliance upstream of a merge point. Shoulders SH are systematic errors in the gradient, and means to minimize these errors are disclosed in co-pending, commonly owned U.S. Provisional Applications entitled MICROFLUIDIC SYSTEMS, DEVICES AND METHODS FOR REDUCING DIFFUSION AND COMPLIANCE EFFECTS AT A FLUID MIXING REGION, U.S. Provisional Application No. 60/707,220; and MICROFLUIDIC SYSTEMS, DEVICES AND METHODS FOR REDUCING NOISE GENERATED BY MECHANICAL INSTABILITIES, U.S. Provisional Application No. 60/707,245, the contents of which are incorporated in their entireties.

In addition to the methods previously described in Sections II-IV above, sample processing apparatus SPA is useful for a wide variety of applications, due at least in part to the simplicity of the technique for concentration gradient mixing described hereinabove and the ubiquity of concentration gradients in assays. Non-limiting examples of applications include enzyme kinetics, clinical diagnostics for neo-natal care (e.g., blood enzyme diagnostics with microliter samples), toxicity studies for drug development (e.g., P450 assays or S9 fraction assays), flow cytometry, cell-based assays, and gradient elution for mass spectrometry.

Exemplary enzymological variables and measurements that can be analyzed and prepared include, but are not limited to:

(1) basic steady-state kinetic constants, such as Michaelis constants for substrates ($K_m$), maximum velocity ($V_{max}$), and the resultant specificity constant ($V_{max}/K_m$ or $k_{cat}/K_m$);

(2) binding constants for ligands ($K_d$) and capacity of receptor binding ($B_{max}$);

(3) kinetic mechanism of a bi- or multi-substrate enzyme reaction;

(4) effect of buffer components, such as salts, metals and any inorganic/organic solvents and solutes on enzyme activity and receptor binding;

(5) kinetic isotope effect on enzyme catalyzed reactions;

(6) effect of pH on enzyme catalysis and binding;

(7) dose-response of inhibitor or activator on enzyme or receptor activity ($IC_{50}$ and $EC_{50}$ value);

(8) analysis of mechanism of inhibition of an enzyme catalyzed reaction and associated inhibition constants (slope inhibition constant ($K_{is}$) and intercept inhibition constant ($K_{ii}$));

(9) equilibrium binding experiments to determine binding constants ($K_d$);

(10) determination of binding stoichiometry via a continuous variation method; and

(11) interaction of two inhibitors, two ligands or a ligand and an inhibitor by a method of continuous variation.

In some embodiments of the presently disclosed methods, a first reagent flows within a first fluid stream and the second reagent flows within a second fluid stream. Further, contacting the first and second reagents comprises flowing the first fluid stream into contact with the second fluid stream so as to merge the first and second fluid streams into a merged fluid stream. Further, in some embodiments, continuously varying the concentration of at least one of the first and second reagents comprises varying volumetric flow rates of the first and second fluid streams within a continuous-flow reaction system. Additionally, in some embodiments, varying the volumetric flow rates of the first and second fluid streams comprises controlling speeds of a first pump and a second pump which individually drive first and second fluid streams, respectively. The pumps can be in some embodiments displacement pumps. In some embodiments, the first and second pumps are synchronized to maintain overall constant volumetric flow rate while varying individual volumetric flow rates of the first and second fluid streams. Still further, in some embodiments of the presently disclosed methods, the continuous-flow reaction system is a fluidic system comprising a network of tubing in flow communication.

In some embodiments of the presently disclosed methods, the continuous-flow reaction system is a fluidic system, wherein the first and second fluid streams are merged via a same fluidic input. In some embodiments, the continuous-flow reaction system is a microfluidic device and in some embodiments, the first and second fluid streams flow within channels on a microfluidic chip, such as for example a microfluidic chip as described herein, including a microfluidic chip as encompassed by sample processing apparatus SPA described herein and illustrated in FIGS. 8 and 11, in particular. For example, in some embodiments first fluid stream flows within a first input channel and the second fluid stream flows within a second input channel, and the contacting between the first and second fluid streams to form the merged fluid stream occurs at a merge region where the first and second channels intersect.

In other embodiments of the method, the method further comprises contacting a third reagent with the first and second reagents, wherein the concentration of at least one of the first, second, and third reagents continuously varies with time. In some embodiments, the third reagent is a second substrate or ligand of the first reagent, whereas in other embodiments the third reagent is a proton, and in others, the third reagent is a reaction component varied to determine optimal reaction conditions, such as for example, buffers, co-factors, salts and salt concentrations, pH, etc.

In still further embodiments of the method wherein a third reagent is present, the first reagent flows within a first fluid stream, the second reagent flows within a second fluid stream, and the third reagent flows within a third fluid stream and contacting the first and second reagents comprises flowing the first fluid stream into contact with the second fluid stream so as to merge the first and second fluid streams into a first merged fluid stream and contacting the third reagent with the first and second reagents comprises flowing the third fluid stream into contact with the first merged fluid stream so as to merge the third fluid stream and the first merged fluid stream into a second merged fluid stream.

In some embodiments wherein a third reagent is present, continuously varying the concentration of at least one of the first, second, and third reagents comprises varying volumetric flow rates of the first, second, and third fluid streams within a continuous-flow reaction system. Further, in some embodiments, varying the volumetric flow rates of the first, second, and third fluid streams comprises controlling speeds of a first pump, a second pump, and a third pump which individually drive first, second, and third fluid streams, respectively. The first, second, and third pumps can be in some embodiments displacement pumps. The first and second pumps can be synchronized to maintain an overall constant volumetric flow rate of the first merged fluid stream while varying individual volumetric flow rates of the first and second fluid streams. The third pump can also be synchronized with the first and second pumps to produce an overall constant volumetric flow rate of the second merged fluid stream. In still further embodiments wherein a third reagent is present, the continuous-flow reaction system can be a fluidic system comprising a network of tubing in flow communication.

Figure 11:
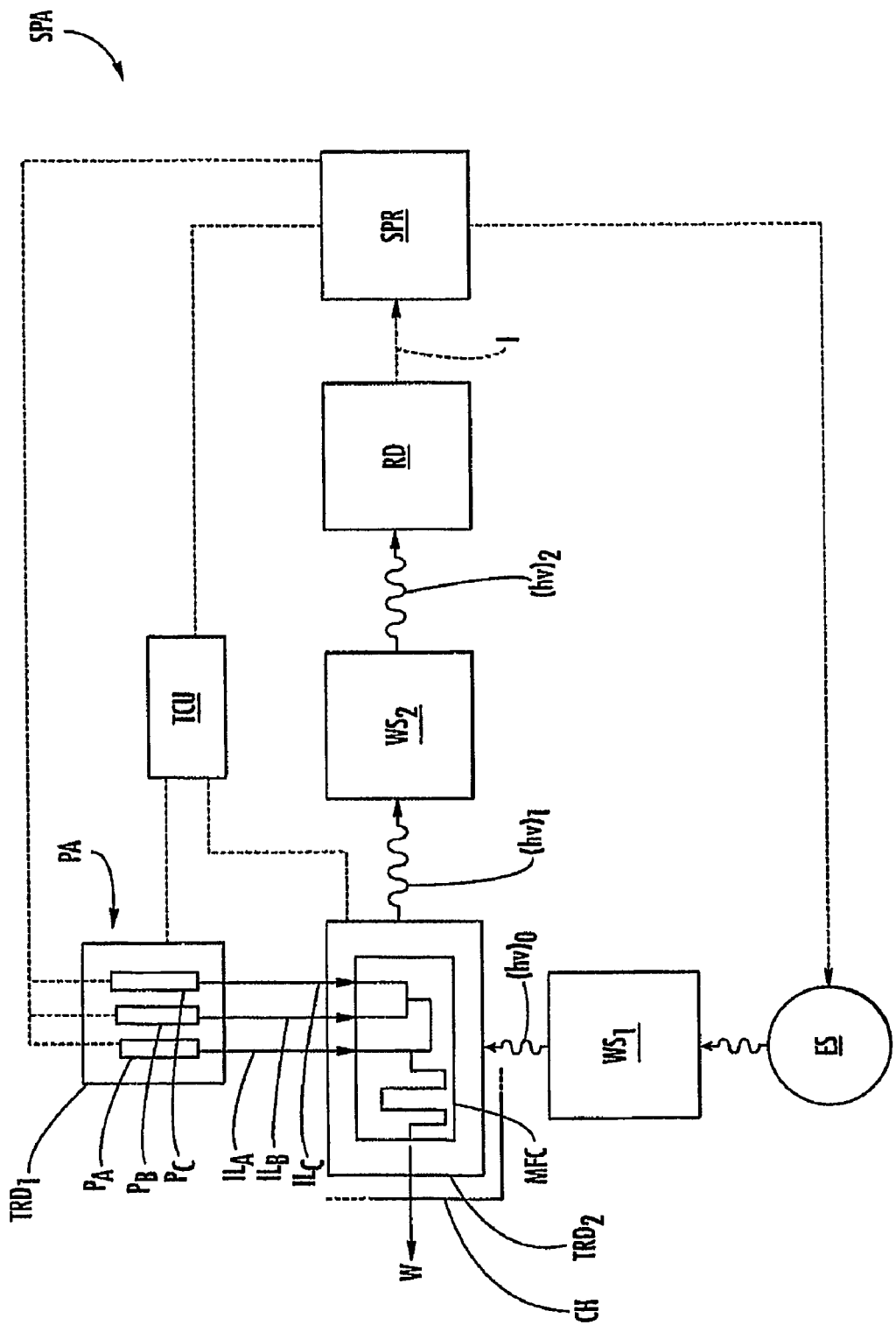
FIG. 11 is a schematic view of a sample processing apparatus with sample measurement components integrated therein according to embodiments disclosed herein.

In some embodiments wherein a third reagent is present, the continuous-flow reaction system is a microfluidic device and the first, second, and third fluid streams flow within channels on a microfluidic chip, including for example, a microfluidic chip as encompassed by sample processing apparatus SPA described herein and illustrated in FIGS. 8 and 11, in particular. For example, in some embodiments, as illustrated in FIGS. 8 and 11, the first fluid stream flows within a first input channel, the second fluid stream flows within a second input channel, and the third fluid stream flows within a third input channel of the microfluidic chip, and the contacting between the first and second fluid streams to form the first merged fluid stream occurs at a first merge region where the first and second channels intersect and the contacting between the third fluid stream and the first merged fluid stream to form the second merged fluid stream occurs at a second merge region where the third channel intersects the second merge region.

The amount of data points and accuracy of collection for the above noted exemplary applications, when performed using the sample processing apparatus SPA described herein, are superior to that observed in any heretofore known data collection techniques. In particular, the sample processing apparatus SPA provides directly measurable continuous concentration gradients by accurately varying the volumetric flow rates of multiple reagent streams simultaneously by a precisely known amount. Therefore, it is known by direct observation what the expected concentration gradients are, rather than having to calculate the gradients indirectly. This allows for more accurate data collection than is possible with previously described devices for the applications listed above and others. The pump mechanisms described herein facilitate the use of continuous concentration gradients, in that in one embodiment, the pump mechanisms operate by flow displacement, which provides more precise volume control.

Referring now to FIG. 11, a generalized schematic of sample processing apparatus SPA is illustrated to show by way of example the integration of other useful components for analytical testing and data acquisition according to spectroscopic, spectrographic, spectrometric, or spectrophotometric techniques, and particularly UV or visible molecular absorption spectroscopy and molecular luminescence spectrometry (including fluorescence, phosphorescence, and chemiluminescence). In addition to pump assembly PA and microfluidic chip MFC, which at detection point DP (FIG. 8) could be considered as serving as a data encoding or analytical signal generating virtual sample cell or cuvette, sample processing apparatus SPA can include an excitation source ES, one or more wavelength selectors $WS_1$ and $WS_2$ or similar devices, a radiation detector RD, and a signal processing and readout device SPR. The particular types of these components and their inclusion with sample processing apparatus SPA can depend on, for example, the type of measurement to be made and the type of analytes to be measured/detected. In some embodiments, sample processing apparatus SPA additionally comprises a thermal control unit or circuitry TCU that communicates with a pump temperature regulating device $TRD_1$ integrated with pump assembly PA for regulating the temperature of the reagents residing in pumps $P_A$-$P_C$, and/or a chip temperature regulating device $TRD_2$ in which microfluidic chip MFC can be enclosed for regulating the temperature of reagents and mixtures flowing therein. Details of these temperature regulating components according to specific embodiments are given hereinbelow. Additionally, a chip holder CH can be provided as a platform for mounting and positioning microfluidic chip MFC, with repeatable precision if desired, especially one that is positionally adjustable to allow the user to view selected regions of microfluidic chip MFC and/or align microfluidic chip MFC (e.g., detection point DP thereof) with associated optics.

Generally, excitation source ES can be any suitable continuum or line source or combination of sources for providing a continuous or pulsed input of initial electromagnetic energy $(hv)_0$ to detection point DP (FIG. 8) of microfluidic chip MFC. Non-limiting examples include lasers, such as visible light lasers including green HeNe lasers, red diode lasers, and frequency-doubled Nd:YAG lasers or diode pumped solid state (DPSS) lasers (532 nm); hollow cathode lamps; deuterium, helium, xenon, mercury and argon arc lamps; xenon flash lamps; quartz halogen filament lamps; and tungsten filament lamps. Broad wavelength emitting light sources can include a wavelength selector $WS_1$ as appropriate for the analytical technique being implemented, which can comprise one or more filters or monochromators that isolate a restricted region of the electromagnetic spectrum. Upon irradiation of the sample at detection point DP, a responsive analytical signal having an attenuated or modulated energy $(hv)_1$ is emitted from microfluidic chip MFC and received by radiation detector RD. Any suitable light-guiding technology can be used to direct the electromagnetic energy from excitation source ES, through microfluidic chip MFC, and to the remaining components of the measurement instrumentation. In some embodiments, optical fibers are employed. The interfacing of optical fibers with microfluidic chip MFC according to advantageous embodiments is disclosed in a co-pending, commonly owned U.S. Provisional Application entitled MICROFLUIDIC CHIP APPARATUSES, SYSTEMS, AND METHODS HAVING FLUIDIC AND FIBER OPTIC INTERCONNECTIONS, U.S. Provisional Application No. 60/707,246, the content of which is incorporated herein in its entirety. In some embodiments, a miniaturized dip probe can be employed at detection point DP, in which both the optical sending and returning fibers enter the same side of microfluidic chip MFC and a reflective element routes the optical signal down the sending fiber back through the microfluidic channel to the returning fiber. Similarly a single fiber can be used both to introduce the light and to collect the optical signal and return it to a detector. For example, the excitation light for a fluorophore can be introduced into the microfluidic chip by an optical fiber, and the fluorescent light emitted by the sample in the microfluidic chip can be collected by that same fiber and transmitted to a photodetector, with appropriate wavelength selectors permitting rejection of excitation light at the photodetector.

Wavelength selector $WS_2$ is utilized as appropriate for the analytical technique being implemented, and can comprise one or more filters or monochromators that isolate a restricted region of the electromagnetic spectrum and provide a filtered signal $(hv)_2$ for subsequent processing. Radiation detector RD can be any appropriate photoelectric transducer that converts the radiant energy of filtered analytical signal $(hv)_2$ into an electrical signal I suitable for use by signal processing and readout device SPR. Non-limiting examples include photocells, photomultiplier tubes (PMTs), avalanche photodiodes (APDs), photodiode arrays (PDAs), and charge-coupled devices (CCDs). In particular, for fluorescence measurements, a PMT or APD can be operated in a photon counting mode to increase sensitivity or yield improved signal-to-noise ratios. Advantageously, radiation detector RD is enclosed in an insulated and opaque box to guard against thermal fluctuations in the ambient environment and keep out light.

Signal processing and readout device SPR can perform a number of different functions as necessary to condition the electrical signal for display in a human-readable form, such as amplification (i.e., multiplication of the signal by a constant greater than unity), phase shifting, logarithmic amplification, ratioing, attenuation (i.e., multiplication of the signal by a constant smaller than unity), integration, differentiation, addition, subtraction, exponential increase, conversion to AC, rectification to DC, comparison of the transduced signal with one from a standard source, and/or transformation of the electrical signal from a current to a voltage (or the converse of this operation). In addition, signal processing and readout device SPR can perform any suitable readout function for displaying the transduced and processed signal, and thus can include a moving-coil meter, a strip-chart recorder, a digital display unit such as a digital voltmeter or CRT terminal, a printer, or a similarly related device. Finally, signal processing and readout device SPR can control one or more other components of sample processing apparatus SPA as necessary to automate the mixing, sampling/measurement, and/or temperature regulation processes of the methods disclosed herein. For instance, signal processing and readout device SPR can be placed in communication with excitation source ES, pumps $P_A$-$P_C$ and thermal control unit TCU via suitable electrical lines to control and synchronize their respective operations, as well as receive feedback from the encoders typically provided with pumps $P_A$-$P_C$.

As appreciated by persons skilled in the art, the signal processing, readout, and system control functions can be implemented in individual devices or integrated into a single device, and can be implemented using hardware (e.g., a PC computer), firmware (e.g., application-specific chips), software, or combinations thereof. The computer can be a general-purpose computer that includes a memory for storing computer program instructions for carrying out processing and control operations. The computer can also include a disk drive, a compact disk drive, or other suitable component for reading instructions contained on a computer-readable medium for carrying out such operations. In addition to output peripherals such as a display and printer, the computer can contain input peripherals such as a mouse, keyboard, barcode scanner, light pen, or other suitable component known to persons skilled in the art for enabling a user to input information into the computer.

Figure 12:
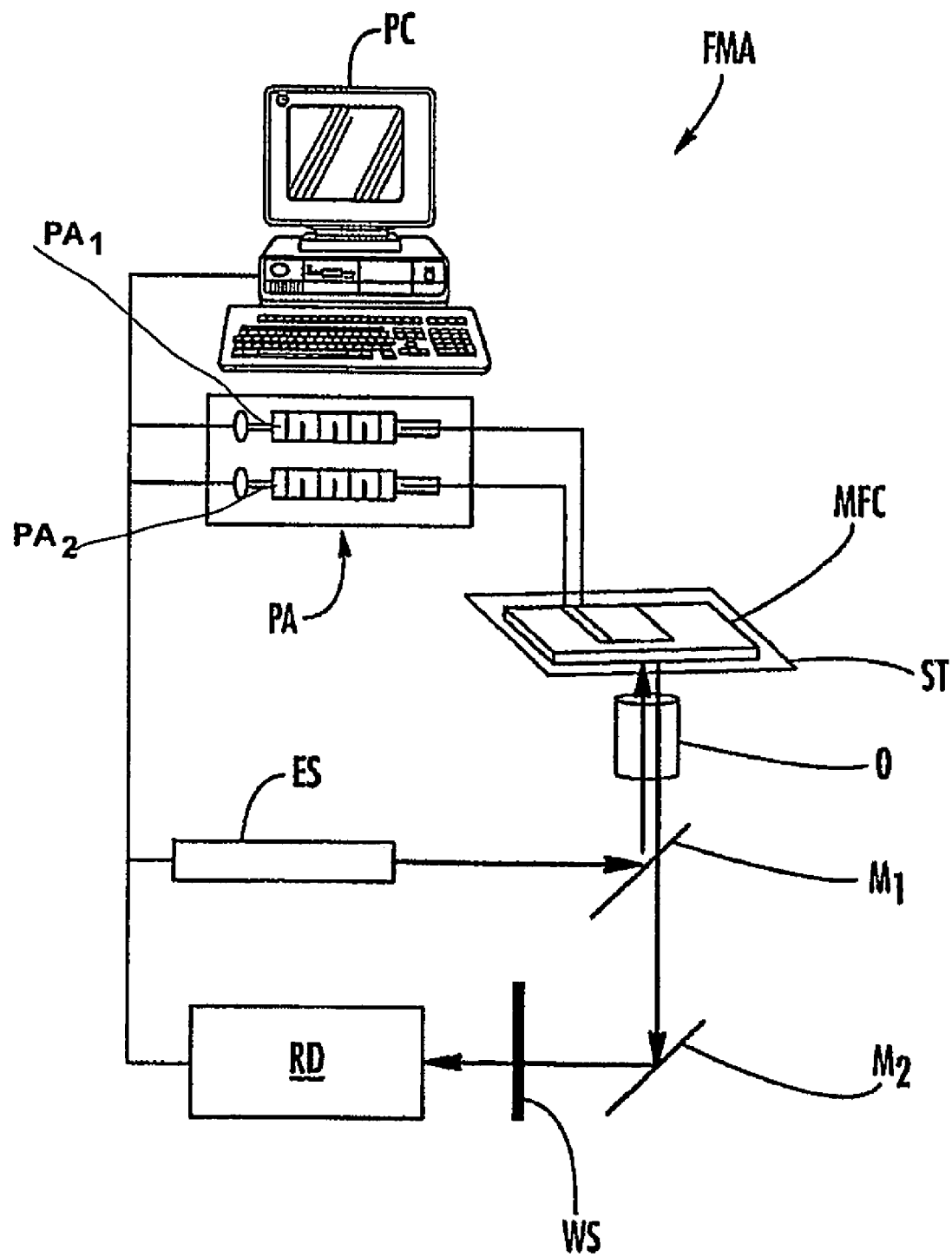
FIG. 12 is a schematic view of a fluorescence measurement apparatus provided in accordance with embodiments disclosed herein.

Referring now to FIG. 12, a specific embodiment of sample processing apparatus SPA is illustrated in the form of a fluorescence measurement apparatus, generally designated FMA, which can be used to measure/detect fluorescence intensity, fluorescence polarization, or time-resolved fluorescence. A microscope, and particularly a fluorescence microscope, can be employed for a number of functions. Microfluidic chip MFC can be mounted on a microscope stage ST typically provided with the microscope. In some embodiments, microscope stage ST can be controllably actuated in X-Y or X-Y-Z space to align microfluidic chip MFC with an objective O of the microscope as well as other associated optics. In addition to enabling a selected area of microfluidic chip MFC to be viewed, objective O can focus or direct incoming light supplied from excitation source ES. Light-guiding optical components can be employed, including a dichroic mirror $M_1$ for reflecting the light from excitation source ES and transmitting the fluorescence signal from microfluidic chip MFC, and an additional mirror $M_2$ if needed for reflecting the attenuated signal to wavelength selector WS.

Fluorescence measuring apparatus FMA can be configured such that multiple excitation wavelengths are simultaneously introduced into a sample containing multiple signal fluorophores inside microfluidic chip MFC. This can be done by using a multiple bandpass filter as a wavelength selector $WS_1$ or by using multiple lasers as excitation light sources. Similarly multiple bandpass dichroic mirrors and multiple wavelength selectors $WS_2$ can be used to transmit the fluorescence from individual fluorophores to multiple signal processing and readout devices SPR.

In the embodiment illustrated in FIG. 12, mirror $M_1$ is a shortpass dichroic reflector that reflects light from excitation source ES and transmits fluorescent light collected from microfluidic chip MFC by objective O back toward radiation detector RD. Wavelength selector WS is a barrier filter appropriate for use in conjunction with a radiation detector RD provided in the form of a photon counter. As further illustrated in FIG. 12, the signal processing and readout device SPR is provided in the form of any suitable computer PC. A suitable computer program, developed for instance using LABVIEW® software, available from National Instruments Corporation, Austin, Tex., can be stored and/or loaded into computer PC to enable computer PC to be specifically programmed to control the operation of fluorescence measurement apparatus FMA.

Figure 13:
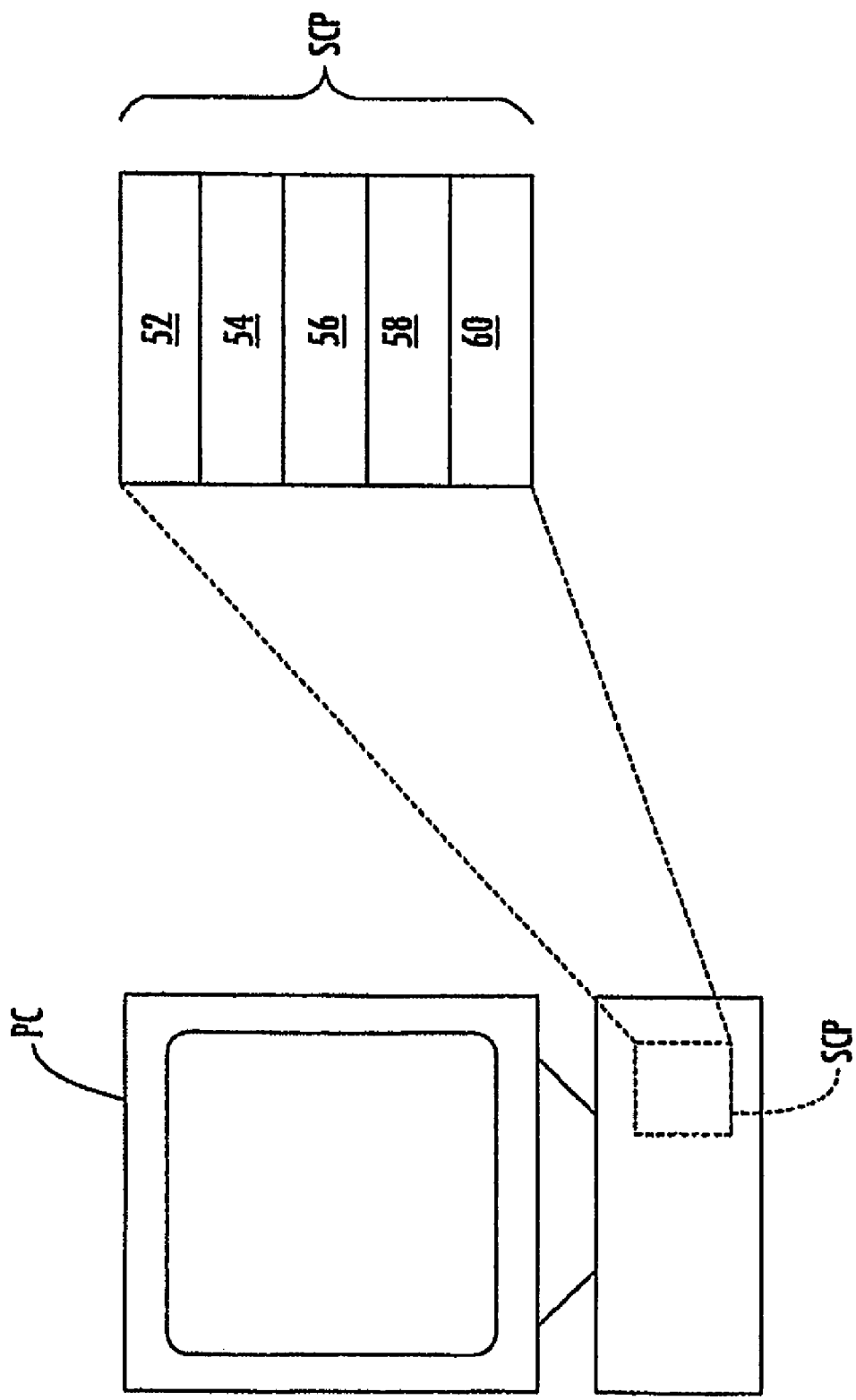
FIG. 13 is a schematic view of system control software provided in accordance with embodiments disclosed herein.

Referring to FIG. 13, an advantageous system control program SCP is depicted for controlling sample processing apparatus SPA generally illustrated in FIG. 11, according to any specific embodiment thereof such as fluorescence measurement apparatus FMA illustrated in FIG. 12. System control program SCP can include five software modules or routines: a configuration module 52, a thermal control module 54, a manual or debug module 56, chip navigating module 58, and a run or data acquisition module 60. As can be appreciated by persons skilled in the art, system control program SCP can be provided as a computer program product, especially one compatible with a graphical user interface (GUI), comprising computer-executable instructions and/or data embodied in a computer-readable medium.

Configuration module 52 enables a user to create individual volumetric flow profiles (see, e.g., FIG. 10B) by which respective pumps $P_A$-$P_C$ of pump assembly PA (see, e.g., FIGS. 8 and 11) are to be controlled for a given experiment. For example, the user can create flow velocity profiles as percentages of a defined total flow rate, as shown in FIG. 10B. Configuration module 52 can include a flag that alerts the user when the individual flow rates do not add up to the total flow rate (i.e., 100%).

Thermal control module 54 controls the operation of thermal control unit TCU (FIG. 11) and thus pump temperature regulating device $TRD_1$ and/or chip temperature regulating device $TRD_2$. Thermal control module 54 can be used, for example, for dictating whether pump temperature regulating device $TRD_1$ and/or chip temperature regulating device $TRD_2$ are to be active during the experiment, providing the set point temperature for pump temperature regulating device $TRD_1$ and/or chip temperature regulating device $TRD_2$, and logging instantaneous temperatures sensed by pump temperature regulating device $TRD_1$ and/or chip temperature regulating device $TRD_2$ to a data file at a user-defined temperature sampling rate.

Manual or debug module 56 can be used to manually control (including, for instance, overriding certain automated functions on an as-needed basis) any aspect of sample processing apparatus SPA. As examples, the user can control the flow rate of each pump $P_A$, $P_B$ and PC individually, adjust the temperature settings of pumps $P_A$-$P_C$ and microfluidic chip MFC, view in real time the values read by radiation detector RD, monitor any peripheral analog input devices such as photodiodes or thermistors, and the like.

Chip navigation module 58 is a tool for controlling the user's view of microfluidic chip MFC and events occurring therein during an experiment. For instance, chip navigation module 58 can allow the user to define an exact point or region of interest on microfluidic chip MFC and repeatably return to that point or region with the click of a button on the user interface, even after microfluidic chip MFC has been removed from and placed back on chip positioning or mounting stage (FIG. 11) such as microscope stage ST (FIG. 12). The user can automatically cycle through different detection spots if desired. As appreciated by persons skilled in the art, the user's view of microfluidic chip MFC can be effected by any suitable means, such as via a peripheral display device (e.g., CRT screen) provided with computer PC and using a CCD camera incorporated with the system for viewing microfluidic chip MFC. The views made by the user during an experiment can be recorded into a data file if desired to add a visual component to the analytical process.

Finally, run or data acquisition module actually executes the experiment according to the various user-defined parameters, including the flow velocity profiles designed using configuration module 52 and set point data inputted using thermal control module 54. Moreover, run or data acquisition module 60 can provide a display of information yielded during the course of the experiment, such as flow velocities and responses as described hereinabove with reference to FIG. 10B. The user can watch in real time as data are collected from radiation detector RD, the encoders provided with pumps $P_A$-$P_C$, pump temperature regulating device $TRD_1$, chip temperature regulating device $TRD_2$, and any other analog or digital data-generating devices provided with sample processing apparatus SPA. It will be understood that some of the data can be acquired according to respective, user-defined sampling rates, while other data can be acquired continuously or on-demand.

Figure 14A:
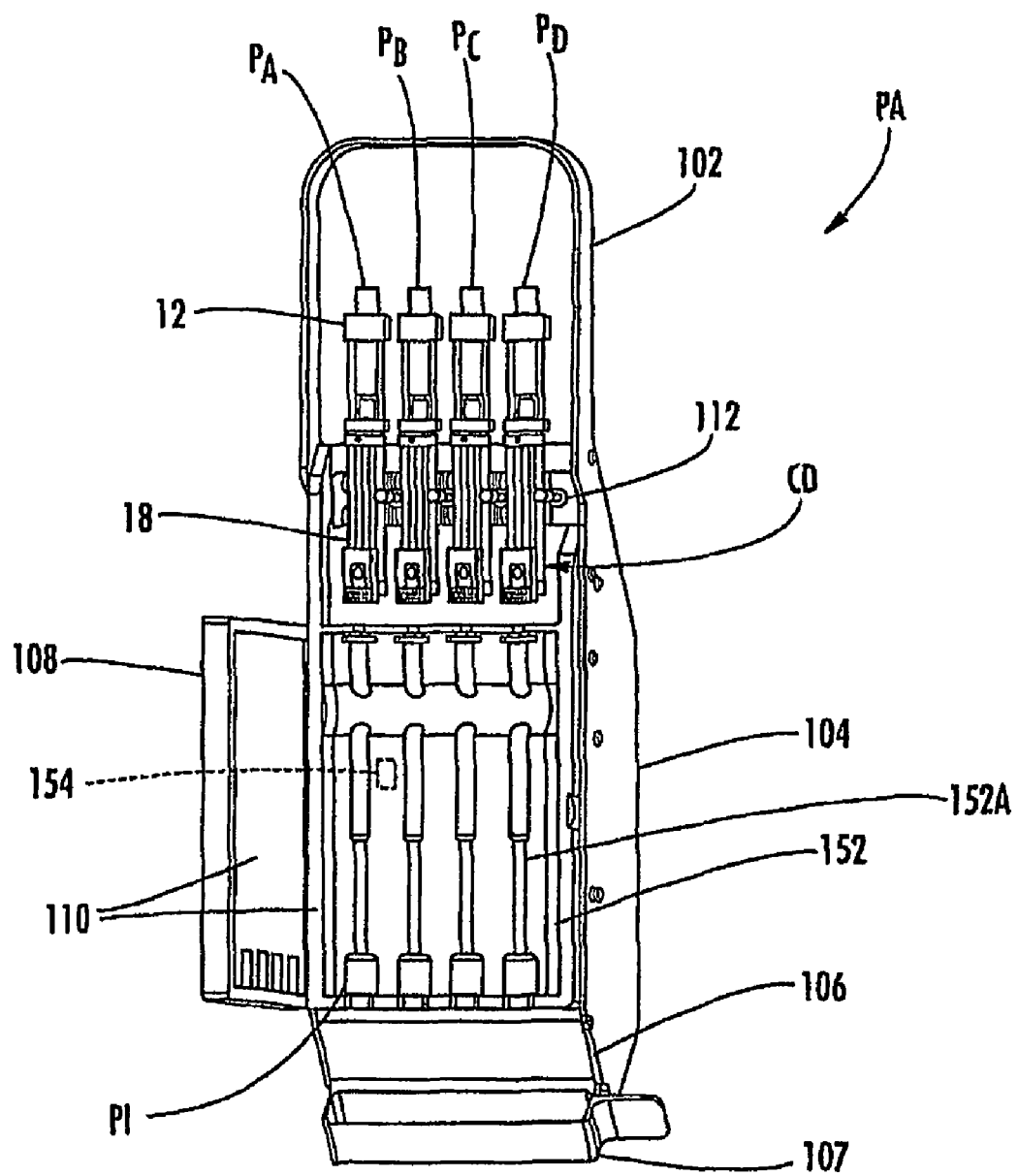
FIGS. 14A and 14B are perspective front and rear views, respectively, of a pump assembly provided in accordance with embodiments disclosed herein.
Figure 14B:
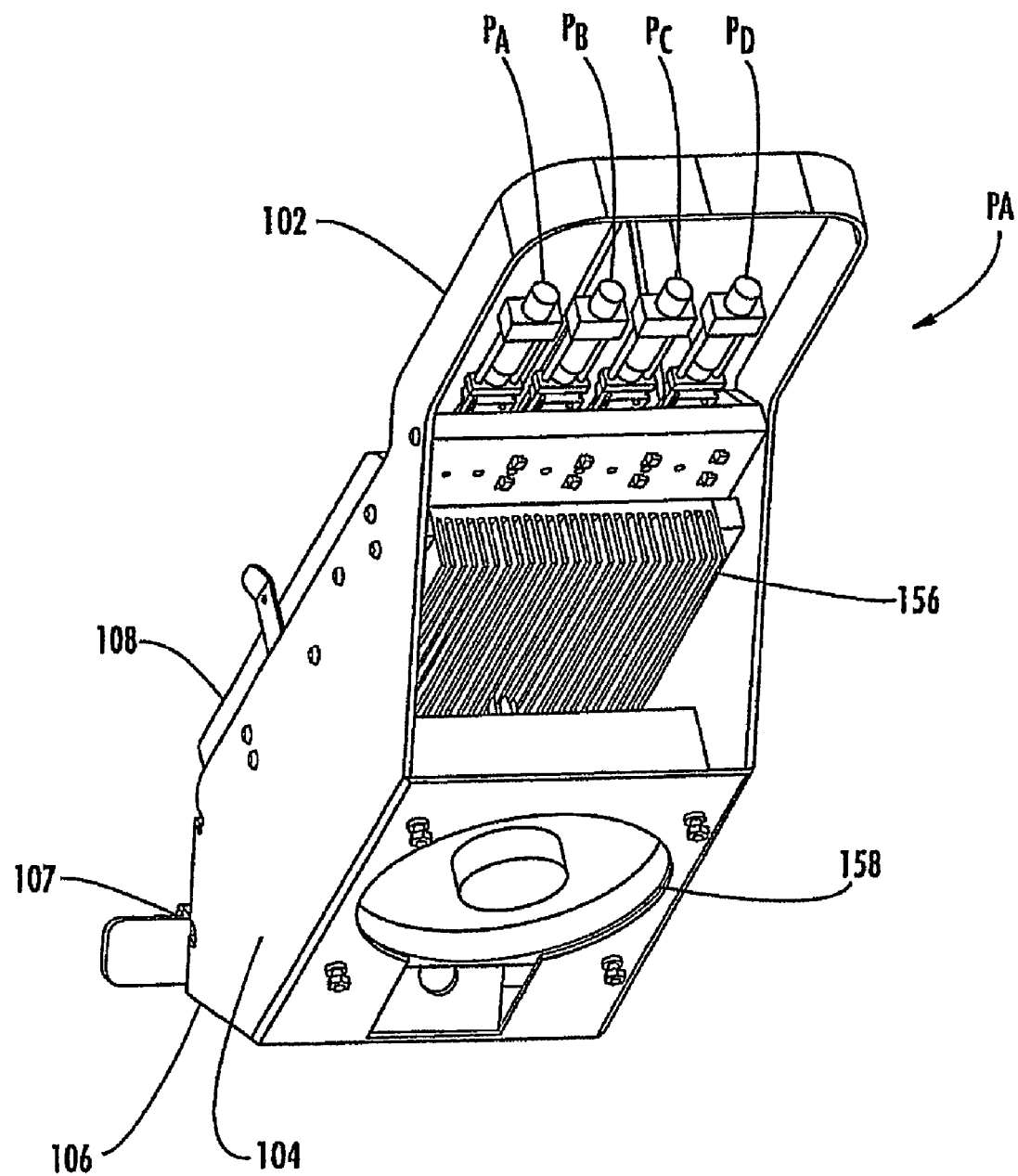
Figure 14C:
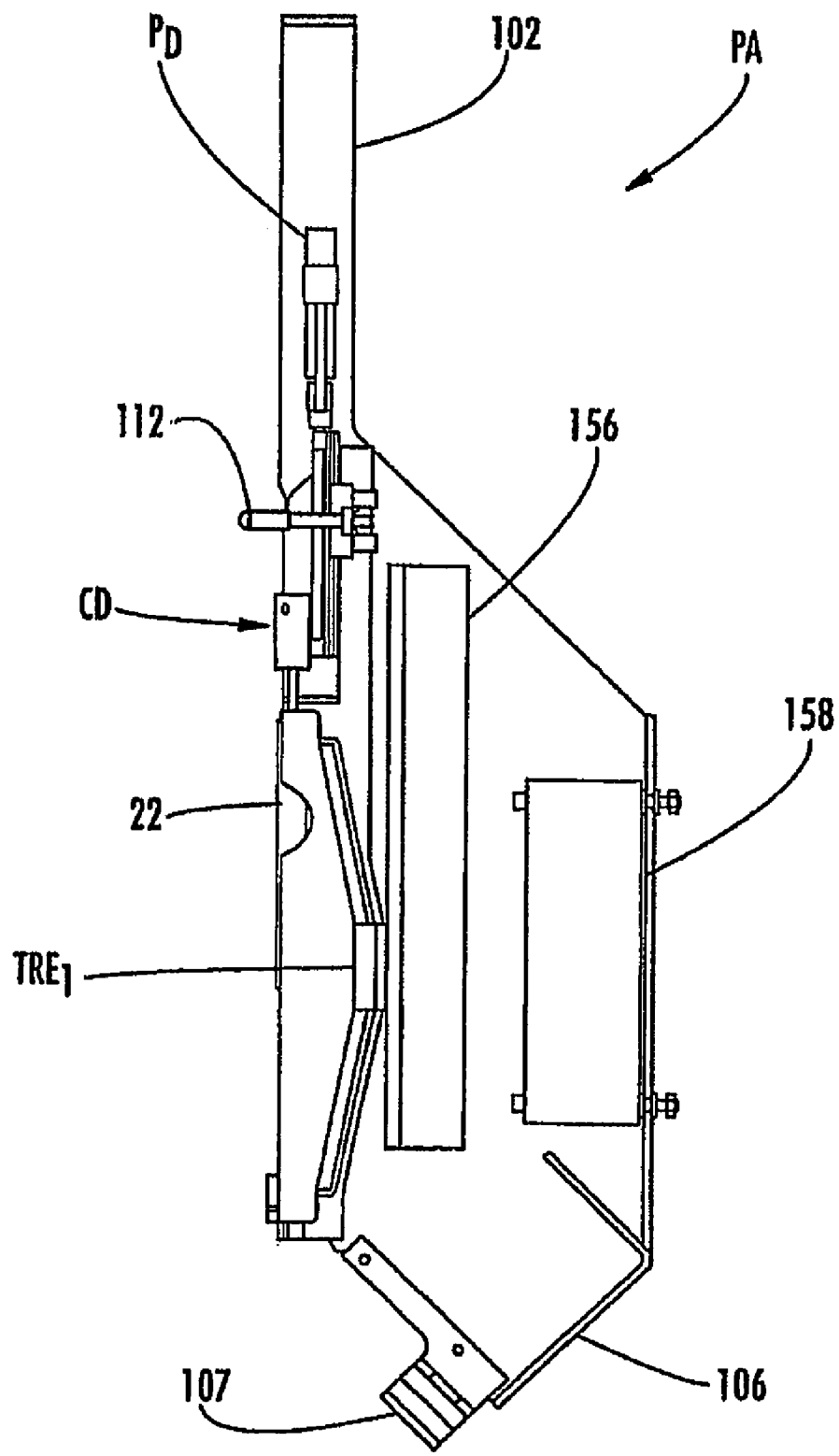
FIG. 14C is a side elevation cut-away view of the pump assembly illustrated in FIGS. 14A and 14B.

Referring now to FIGS. 14A-14C, one exemplary embodiment of pump assembly PA is illustrated that is capable of precisely delivering liquids into microfluidic chip MFC at nl/min-scale, smooth, non-pulsatile flow rates as described hereinabove. Pump assembly PA can include one or more pumps, such as four pumps $P_A$-$P_D$ as illustrated. The various components of each pump $P_A$-$P_D$, described hereinabove and schematically illustrated in FIG. 9, are supported in a pump housing 102 with pump barrels 22 (FIG. 9) being mounted in recesses 152A in a barrel holder 152. Pump housing 102 can be constructed from any suitable material, with non-limiting examples being polyoxymethylene, aluminum, steel, DELRIN® material, or polyvinylchloride. Pump housing 102 can include a stand portion 104 for mounting pump P at a desired angle relative to the vertical to reduce the footprint of pump assembly PA and protect servo motors 12 from condensation resulting from cooling as described hereinbelow. Pump housing 102 can also include a mounting portion 106 such as a bracket for affixing pump assembly PA in place. Preferably, a drip cup 107 is included to catch condensation and serve as a windscreen to prevent input lines IL (see, e.g., FIG. 9) from blowing around, especially when a cooling fan 158 (FIGS. 14B and 14C) is provided to remove heat from a Peltier device or other temperature regulating element $TRE_1$ (see, e.g., FIG. 14C) that cools pump housing 102. Pump housing 102 can include a hinged door 108 to provide access to pump barrels 22 mounted in recesses 152A for replacement or cleaning, or manual loading of reagents therein. The lower portions of pump housing 102 surrounding pump barrels 22, including the inside of door 108 and surrounding barrel holder 152, can be provided with insulation 110 to thermally isolate pump barrels 22 and their contents. To accommodate different positions of plunger 20, the axial positions of pump stages 18 relative to their respective pump barrels 22 (not depicted here, but mounted in recesses 152A in barrel holder 152) can be adjusted through the use of thumb screws 112 or other appropriate fastening or tightening means. Manipulation of thumb screws 112 can release their respective pump stages 18 to allow servo motors 12 to slide up and down while the positions of the pump barrels are fixed by recesses 152A in barrel holder 152.

Figure 15:
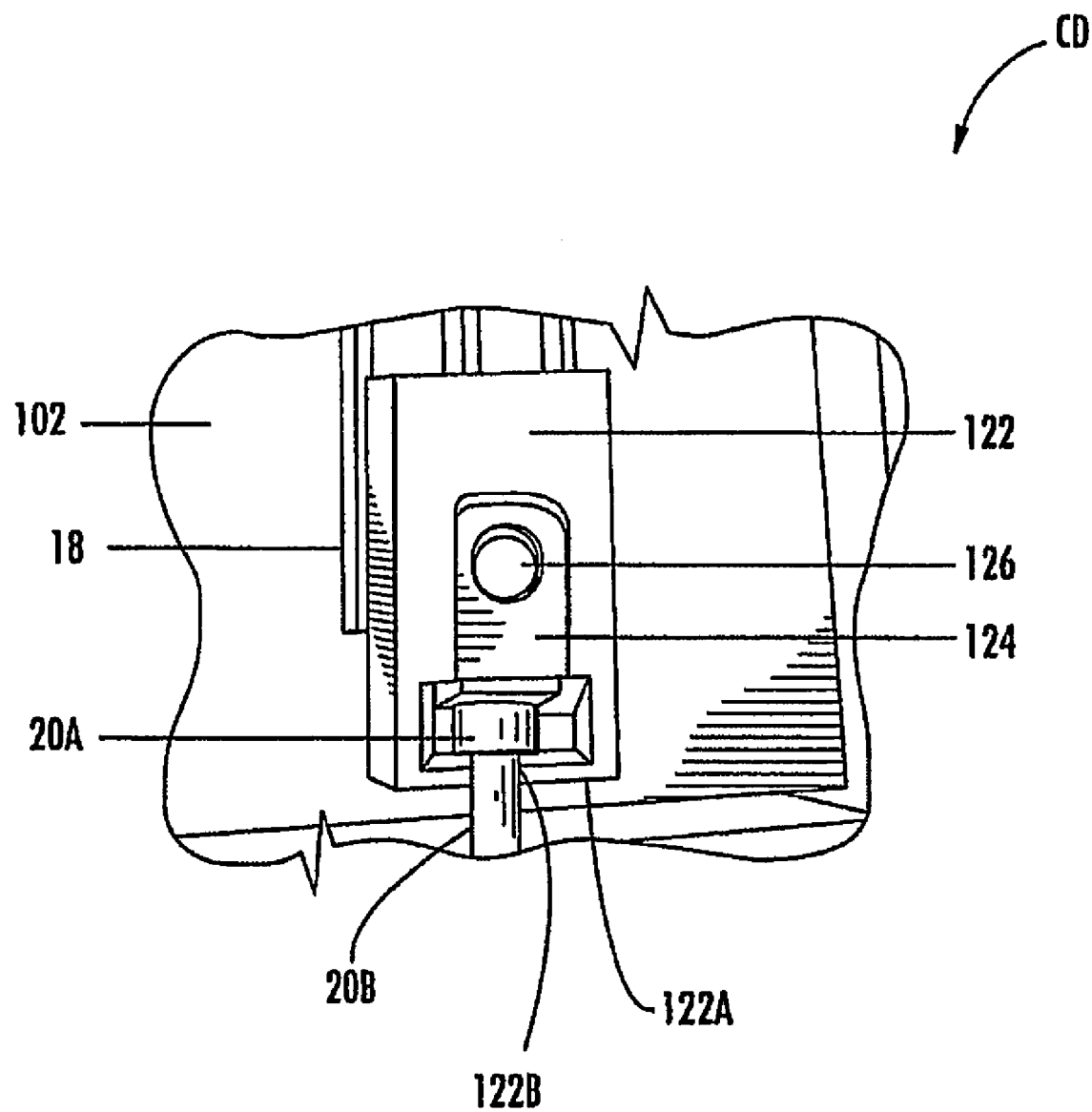
FIG. 15 is a perspective view of a coupling device provided with the pump assembly illustrated in FIGS. 14A, 14B and/or 14C in accordance with embodiments disclosed herein.

Referring to FIG. 15, in one embodiment, each plunger 20 (shown in FIG. 14A) is coupled to its respective pump stage 18 for linear translation therewith by means of a coupling device, generally designated CD. Coupling device CD comprises a plunger clasp 122, a tightening plate 124, and a set screw 126. Plunger clasp 122 is secured to pump stage 18, and includes a cavity 122A and an aperture or recess 122B through which plunger 20 extends. Head portion 20A of plunger 20, which typically has a greater diameter than its stem 20B, is removably disposed in cavity 122A. Set screw 126 extends through a hole of tightening plate 124 and is threaded into pump stage 18. Tightening plate 124 resides in cavity 122A and can be adjusted via set screw 126 to secure head portion 20A of plunger 20 between tightening plate 124 and an inside surface of cavity, thereby effecting a coupling relation between pump stage 18 and plunger 20 with minimal mechanical loss and minimal lateral motion of plunger 20.

In advantageous embodiments, pump assembly PA provides temperature-control functionality. While both heating and cooling can be effected, the ability to cool pump assembly PA is particularly advantageous as it enables thermally labile reagents to be cooled in-situ to prevent their degradation, thereby eliminating the need for ex-situ or on-chip refrigeration. Proteins, for example, can denature at room temperatures in a matter of hours. Thus, cooling is particularly important when lengthy run times are contemplated. For example, if a 10-μl barrel is used, approximately 8 hours of run time is possible at a flow rate of 20 nl/min. In one embodiment, pump assembly PA can maintain a reagent temperature ranging from approximately −4° C. to 70° C. to within 0.05° C. of accuracy. Moreover, thermal control of pump assembly PA provides the flow stability and noise reduction needed when operating at flow rates in the nl/min range. A change in room temperature can cause thermal expansion of the components of pump assembly PA that interact with the liquids being conveyed, thereby causing a thermal pumping effect. For example, when pumping at a low flow rate such as a few nl/min, a 1-nl change in the volume of the system (i.e., 0.01 percent of total volume for a 10 μl syringe pump) over one minute will be noticeable. Similarly, a 1° C. change in the temperature of the stainless steel plunger of some microsyringes causes the plunger to change length by 2 μm, changing the volume inside the microsyringe by 0.3 nl. Because room temperature is a disturbance, thermal pumping appears as noise in the output of the pumps of pump assembly PA. Hence, controlling the temperature of pump assembly PA reduces this noise. Finally, with regard to the multi-pump configuration illustrated in FIGS. 14A-14C, the ability to regulate all pumps $P_A$-$P_D$ at the same temperature reduces any disparity in any temperature gradients respectively existing between each pump $P_A$-$P_D$. Otherwise, the existence of different temperature gradients between pumps $P_A$-$P_D$ can cause pumps $P_A$-$P_D$ to thermally pump out of phase with each other, which can also contribute to signal noise.

As illustrated in FIGS. 14A-14C, pump assembly PA can include a pump temperature regulating device $TRD_1$ (FIG. 11) comprising, in addition to insulated pump housing 102: a barrel holder 152 (FIG. 14A); one or more temperature sensing devices 154 (FIG. 14A); a temperature regulating element, generally designated $TRE_1$ (FIG. 14C); a heat sink 156 (FIGS. 14B and 14C); and a cooling fan 158 (FIGS. 14B and 14C). Barrel holder 152 is mounted within pump housing 102 to support pump barrels 22. To maximize thermal contact between barrel holder 152 and pump barrels 22, elongate recesses 152A are formed in barrel holder 152 that generally conform to the outer profiles of pump barrels 22 for maximum surface contact. Barrel holder 152 can be constructed from any suitably efficient thermally conductive material such as aluminum, copper, or the like. Temperature sensing device 154 is embedded or otherwise placed in thermal contact with barrel holder 152 by any securement means such as thermally conductive epoxy, thermally conducting grease, or simply by direct contact. Temperature sensing device 154 provides real-time temperature feedback for thermal control unit TCU (FIG. 11). Thus, temperature sensing device 154 can be any suitable device such as a thermistor. Heat sink 156 is mounted to pump housing 102 or to barrel holder 152, or is otherwise in thermal contact with the side of barrel holder 152 opposite to pump barrels 22. Heat sink 156 can be employed to dissipate heat during cooling operations, and thus can include cooling fins to maximize the surface area available for heat transfer as appreciated by persons skilled in the art. Additional cooling can be effected through the use of cooling fan 158 if desired or needed. In the illustrated embodiment, cooling fan 158 is mounted at the side of heat sink 156 opposite to barrel holder 152. Similarly, heat can be removed by a water-filled heat exchanger in communication with an external water bath. For instance, heat sink 156 can be configured for circulating water or another suitable heat transfer medium therethrough.

Figure 16:
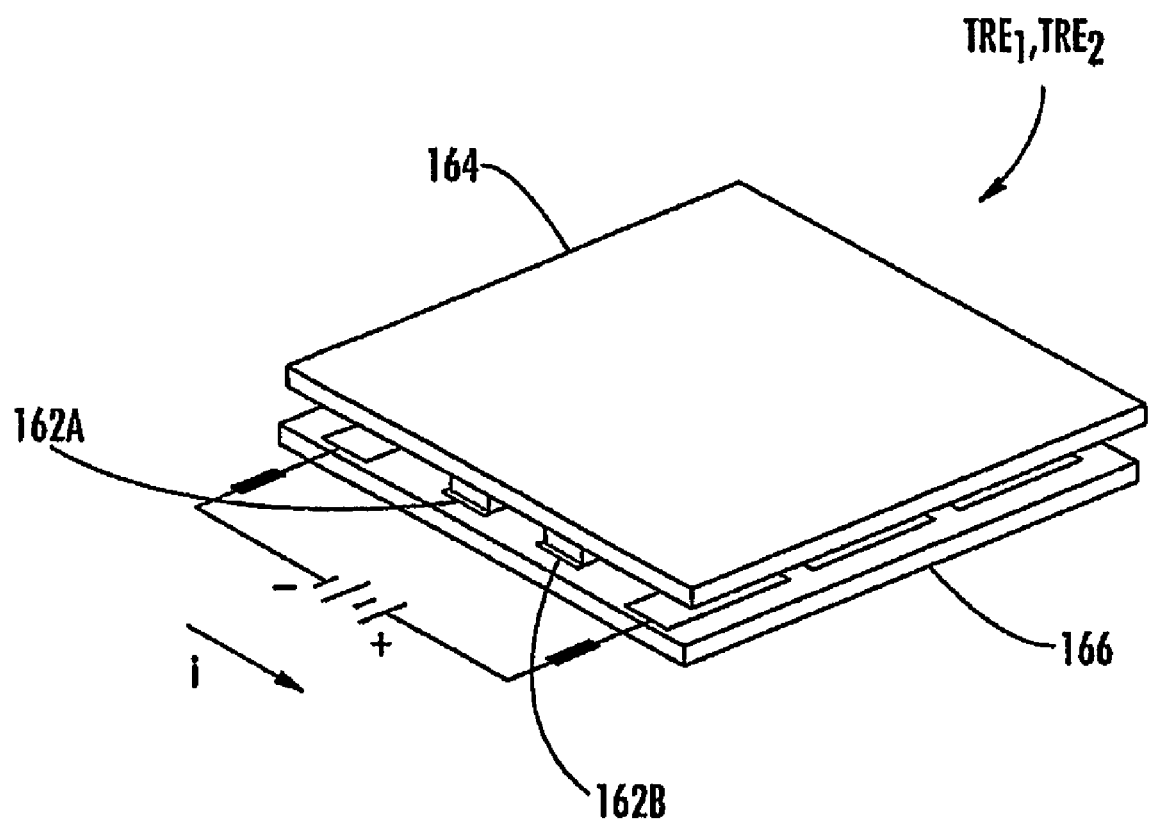
FIG. 16 is a perspective view of a temperature regulating element provided in accordance with embodiments disclosed herein.

Temperature regulating element $TRE_1$ is mounted between barrel holder 152 and heat sink 156 for either transferring heat to barrel holder 152 (and thus barrel and its fluid contents) or transferring heat away from barrel holder 152 to heat sink 156. In advantageous embodiments, temperature regulating element $TRE_1$ is a thermoelectric device such as a Peltier device, as illustrated in FIG. 16, which includes adjoining metals 162A and 162B of different compositions sandwiched between a cold-side plate 164 adjacent to heat sink 156 plate and a hot-side plate 166 adjacent to barrel holder 152. Cold-side plate 164 and hot-side plate 166 are typically of ceramic construction. As appreciated by persons skilled in the art, the passage of current in a reversible direction across the junction of differing metals 162A and 162B, across which a Peltier voltage exists, causes either an evolution or absorption of heat. More specifically, when current is forced across the junction against the direction of the Peltier voltage, active heating occurs. When current is forced in the opposite direction, i.e., in the same direction as the Peltier voltage, active cooling occurs. This current can be controlled by thermal control unit TCU (FIG. 11). Temperature regulating element $TRE_1$ can be employed to regulate the entire interior of pump assembly PA so as to regulate other components such as coupling device CD, pump stage 18, plunger 20, and pump interconnect PI. Thermal expansion of any of these components can generate undesirable thermal pumping.

Figure 17A:
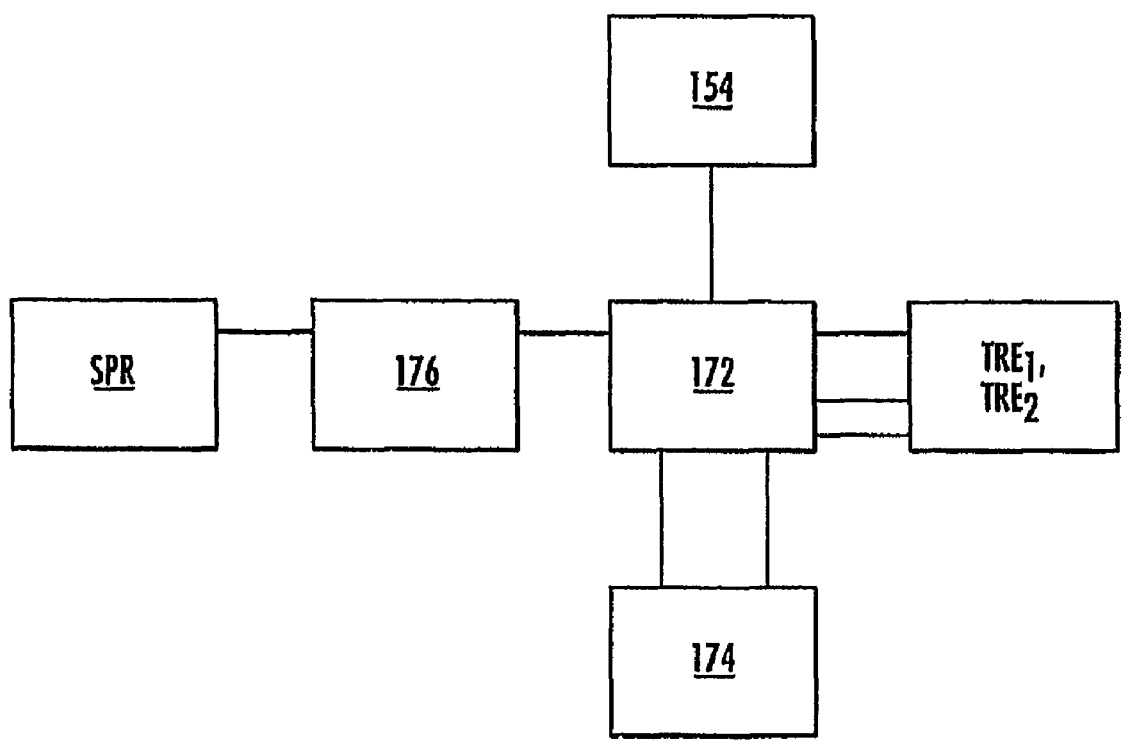
FIG. 17A is a schematic view of temperature regulating circuitry provided in accordance with embodiments disclosed herein.

Referring to FIG. 17A, a general schematic of the temperature control circuitry for implementing temperature regulation of pump assembly PA is illustrated according to an exemplary embodiment. To control the current in temperature regulating element $TRE_1$, the temperature control circuitry can include a proportional-integral-derivative (PID) based thermoelectric module temperature controller 172, such as is commercially available from Oven Industries, Inc., Mechanicsburg, Pa., as Model No. 5 C7-361. Temperature controller 172 communicates with a suitable power supply 174 as well as temperature regulating element $TRE_1$, and receives temperature measurement signals from temperature sensing device 154. In addition, temperature controller 172 communicates with signal processing and readout device SPR (see also FIG. 11 and computer PC in FIG. 12) to provide temperature data thereto and/or receive commands therefrom. If appropriate, temperature controller 172 communicates with signal processing and readout device SPR via a communications module 176 such as an RS-232 to RS-485 converter. Temperature controller 172, power supply 174, and communications module 176 can be integrated as thermal control unit TCU illustrated in FIG. 11. In operation, temperature controller 172 regulates the duty cycle of temperature regulating element $TRE_1$ to maintain a user-selected set point temperature based on the feedback from temperature sensing device 154. According to various embodiments, set point values are either inputted into signal processing and readout device SPR using for example a graphical user interface and sent to temperature controller 172, or directly inputted into temperature controller 172 with user interface hardware (e.g., potentiometers) provided with thermal control unit TCU.

Figure 17B:
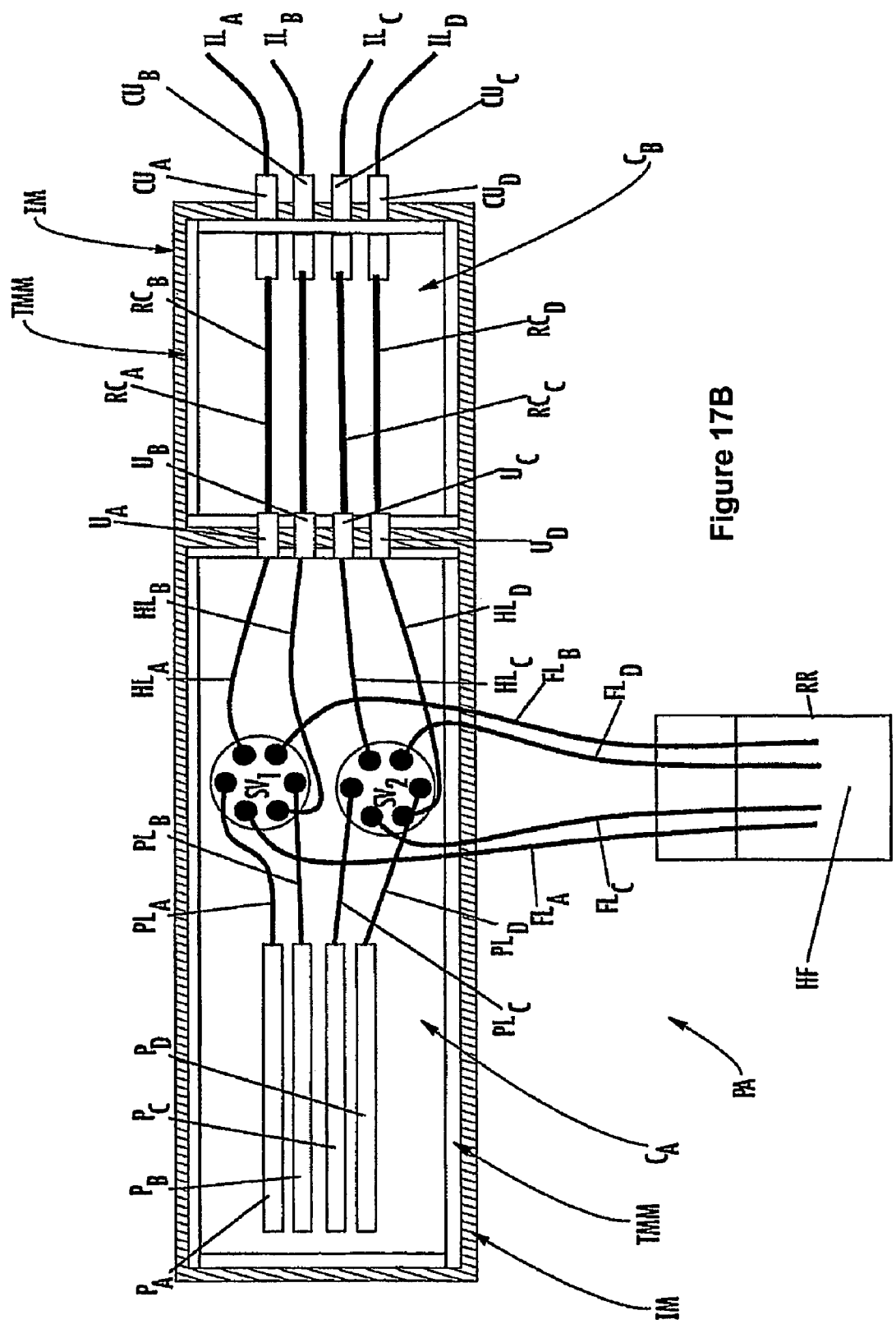
FIG. 17B is a schematic view of a thermally-controlled pump assembly according to embodiments disclosed herein.

FIG. 17B is a schematic view of a thermally-controlled pump assembly, generally designated PA. Two compartments $C_A$ and $C_B$ that house the components of pump assembly PA. Compartments $C_A$ and $C_B$ can be made of thermal mass material TMM comprising the walls, floor, and lid of compartments $C_A$ and $C_B$. Thermal mass material TMM can have large thermal mass, and is typically rigid to provide mechanical integrity to the walls, such as steel, brass, or other metal. Compartments $C_A$ and $C_B$ are insulated with insulating material IM that wraps compartments $C_A$ and $C_B$ and separates compartment $C_A$ from compartment $C_B$. Insulating material IM is a material of low thermal conductivity such as rigid foam. A lid (not shown) made of thermal mass material TMM insulated with insulating material IM encloses compartments $C_A$ and $C_B$. Compartments $C_A$ houses pumps $P_A$-$P_D$ and switching valves $SV_1$ and $SV_2$. Pump lines $PL_A$-$PL_D$ connect, respectively, pumps $P_A$-$P_D$ to switching valves $SV_1$ and $SV_2$. Switching valves $SV_1$ and $SV_2$ thereby switchably connect $PL_A$-$PL_D$ to fill lines $FL_A$-$FL_D$ to or to hydraulic lines $FL_A$-$FL_D$, and pumps $P_A$-$P_D$ can move in reverse to fill with hydraulic fluid HF from refill reservoir RR or switching valves $SV_1$ and $SV_2$ can connect pumps $P_A$-$P_D$ to hydraulic lines $HL_A$-$HL_D$ whereby they pump fluid through unions $U_A$-$U_D$ and into reagent cartridges $RC_A$-$RC_D$, thereby forcing reagent from reagent cartridges $RC_A$-$RC_D$ through chip unions $CU_A$-$CU_D$ and into a microfluidic chip via interconnect lines (such as interconnect lines $IL_A$-$IL_D$ shown in FIG. 8). This embodiment provides several advantages over the embodiment shown in FIG. 14. Reagent cartridges $RC_A$-$RC_D$ can have a volume greater than pumps $P_A$-$P_D$ to extend the life of a pump before reagents have to be replenished. Pumps $P_A$-$P_D$, having smaller volume, should be refilled periodically with hydraulic fluid HF, which can be achieved through switching valves $SV_1$ and $SV_2$, which permit intermittent connection to refill reservoir RR through fill lines $FL_A$-$FL_D$. Hydraulic fluid HF is a chemically inert fluid that will transmit pressure to the solutions in reagent cartridges $RC_A$-$RC_D$ and on through to the microfluidic chip. Compartment $C_A$ housing the pumps can either be thermally controlled by a thermal regulating element TRE (FIG. 11) as described for FIG. 14 or it can be allowed to remain at ambient. The large thermal mass provided by thermal mass material TMM in concert with thermal isolation provided by insulating material IM can prevent contents of compartment $C_A$ from changing appreciably, reducing thermal pumping. Because pumps $P_A$-$P_D$ are entirely enclosed in compartment $C_A$ then thermal pumping caused by thermal expansion of components, such as plungers 20 (FIG. 9), exposed in the pump in FIG. 14 is reduced. Similarly, the contents of reagent cartridges $RC_A$-$RC_D$ can be thermally regulated by regulating the temperature of compartment $C_B$ via thermal regulating element TRE (FIG. 11) as described for FIG. 14. This permits refrigeration of temperature labile reagents, and the large thermal mass provided by thermal mass material TMM in concert with thermal isolation provided by insulating material IM can hold the contents of compartment $C_B$ at constant temperature, reducing thermal pumping.

Referring back to FIG. 11, in embodiments that include pump temperature regulating device $TRD_1$, and where pump temperature regulating device $TRD_1$ is employed for preserving (i.e., cooling) reagents in pump assembly PA, it will be noted that such reagents can be rapidly brought to reaction temperature upon their introduction into microfluidic chip MFC. This facility can be due at least in part to the small volume of the fluid relative to microfluidic chip MFC and the large surface area to volume ratio of the fluid. Additionally, the reaction temperature can be attained through the use of chip temperature regulating device $TRD_2$, described in detail hereinbelow. The provision of pump temperature regulating device $TRD_1$ eliminates the need for on-chip storage of reagents. The thermal conductance on small microfluidic devices (especially those constructed from glass and silicon) does not easily permit different temperature compartments on one chip. Also eliminated is the need for on-chip heat exchangers, which add cost and complexity to the chip design.

Figure 18A:
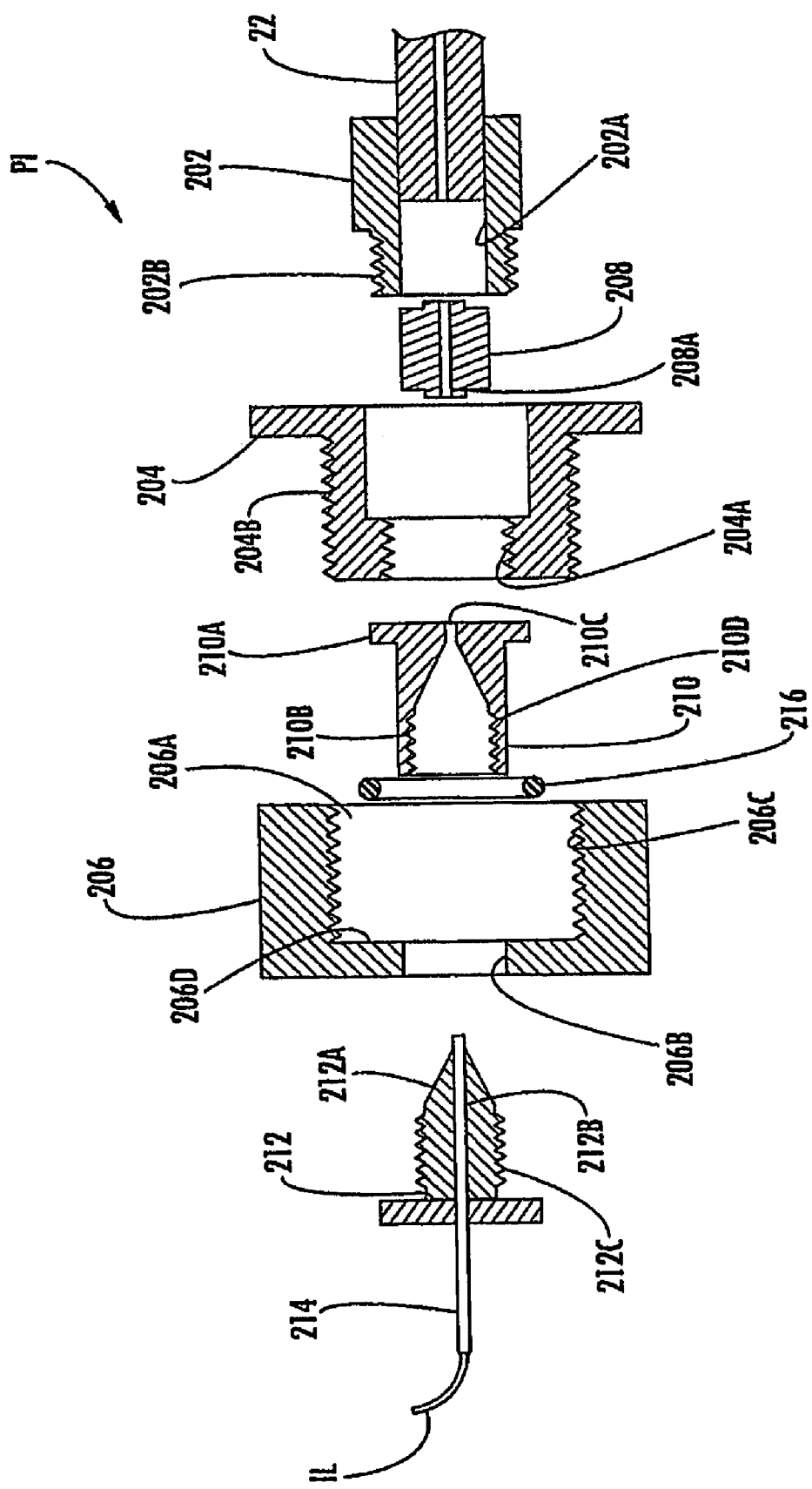
FIGS. 18A and 18B are cross-sectional exploded and assembled views, respectively, of a microfluidic pump interconnect provided in accordance with embodiments disclosed herein.
Figure 18B:
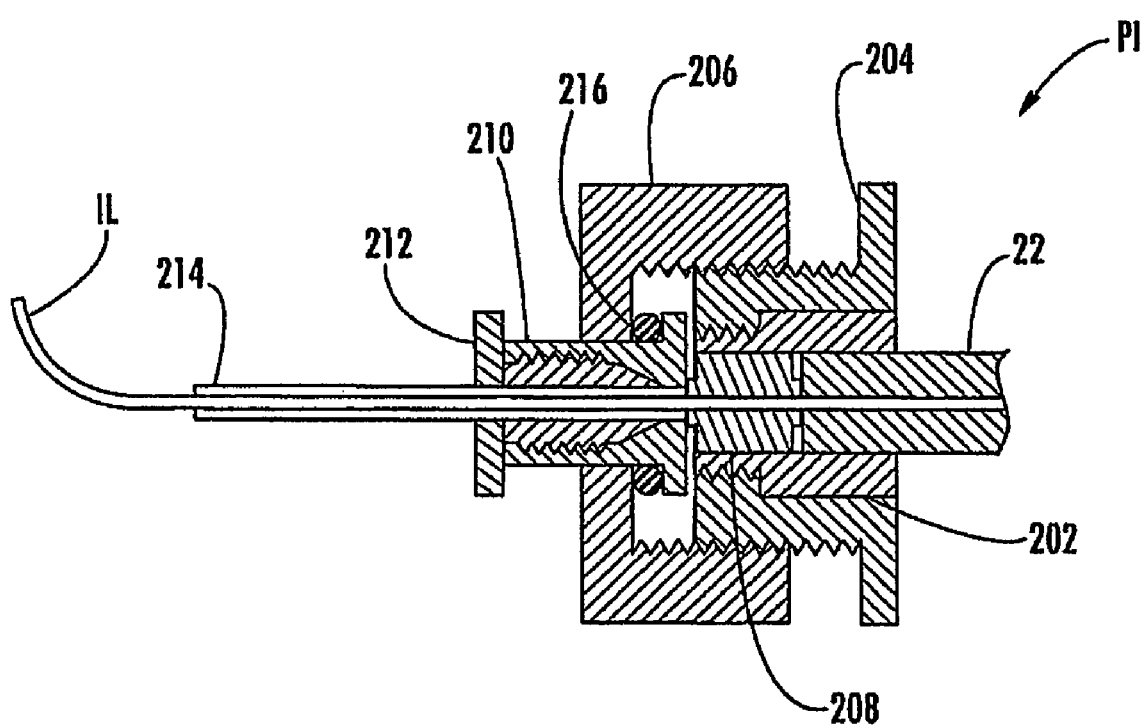

Referring now to the respective exploded and assembly views of FIGS. 18A and 18B, one advantageous embodiment of a pump interconnect, generally designated PI (e.g., pump interconnect $PI_A$, $PI_B$ or $PI_C$ of FIG. 8) is illustrated. Pump interconnect PI can comprise an assembly of collinearly and coaxially interfaced components providing a reliable, fluidly sealed macroscopic-to-microscopic connection with minimal dead volume. In one exemplary embodiment, the dead volume is as low as approximately 70 nl. Moreover, many of the components utilized, particularly those prone to wear or other degradation, are easily removable from the assembly and replaceable. Other components can be bonded to each other by using epoxy adhesive or any other suitable technique.

In the embodiment illustrated in FIGS. 18A and 18B, pump interconnect PI comprises a first annular member 202, a second annular member 204, a third annular member 206, a hollow gasket 208, a female fitting 210, a male fitting 212, and a sleeve 214. These components can be made of any suitable biocompatible, inert material such as stainless steel or various polymers. In some embodiments, female fitting 210, male fitting 212, and sleeve 214 are taken from the NANOPORT™ assembly commercially available from Upchurch Scientific (a division of Scivex), Oak Harbor, Wash. In some embodiments, barrel 22 and first annular member 202 are preassembled pieces belonging to a GASTIGHT microsyringe available from Hamilton Company of Reno, Nev., U.S.A.

First annular member 202 has a bore 202A large enough to receive pump barrel 22. Hollow gasket 208 is sized to effect a fluid seal between pump barrel 22 and female fitting 210 when inserted into bore 202A of first annular member 202. Hollow gasket 208 is inserted far enough to abut the distal end of pump barrel 22, and has a bore 208A fluidly communicating with that of pump barrel 22 and aperture 210C of female fitting 210. In some embodiments, hollow gasket 208 is constructed from polytetrafluoroethylene (PTFE). Second annular member 204 is coaxially disposed about first annular member 202, and is removably secured thereto such as by providing mating threads on an outside surface 202B of first annular member 202 and an inside surface 204A of second annular member 204. Female fitting 210 is disposed within a cavity 206A of third annular member 206 and extends through a bore 206B of third annular member 206. The proximal end of female fitting 210, which can be defined by a flanged portion thereof, abuts the distal end of hollow gasket 208 and may abut the distal ends of first annular member 202 and/or second annular member 204. Female fitting 210 has a bore 210B beginning at a proximal aperture 210C disposed in axial alignment with bore 208A of hollow gasket 208. In the illustrated embodiment, at least a portion of bore 210B of female fitting 210 is tapered, and this tapered profile is complementary to a tapered profile presented by an outside surface 212A of male fitting 212 to effect a removable seal interface.

Third annular member 206 is coaxially disposed about second annular member 204, and is removably secured thereto such as by providing mating threads on an outside surface 204B of second annular member 204 and an inside surface 206C of third annular member 206. This feature enables third annular member 206 to be axially adjustable relative to second annular member 204 so as to bias hollow gasket 208 toward pump barrel 22, thereby improving the sealing interface of hollow gasket 208 between female fitting 210 and pump barrel 22. A sealing member 216, such as an annular gasket or o-ring, can be disposed in cavity 206A of third annular member 206 and is compressed between flanged portion of female fitting 210 and an inside surface 206D of cavity 206A, thereby improving the seal between the inside space of pump interconnect PI and the ambient environment by ensuring that the assembly of female fitting 210 and male fitting 212 sits flat against hollow gasket 208.

Male fitting 212 is inserted into bore 210B of female fitting 210, and has a bore 212B that is axially aligned with proximal aperture 210C of female fitting 210. In some embodiments, male fitting 212 is removably secured to female fitting 210 by providing mating threads on an outside surface 212C of male fitting 212 and an inside surface 210D of bore 210B of female fitting 210. Input line IL, provided for connection with microfluidic chip MFC as described hereinabove with reference to FIG. 8, is inserted through bore 212B of male fitting 212 to extend through proximal aperture 210C in fluid communication with bore 208A of hollow gasket 208. In some embodiments, a sleeve 214 is inserted through bore 212B of male fitting 212 coaxially around input line IL.

Figure 18C:
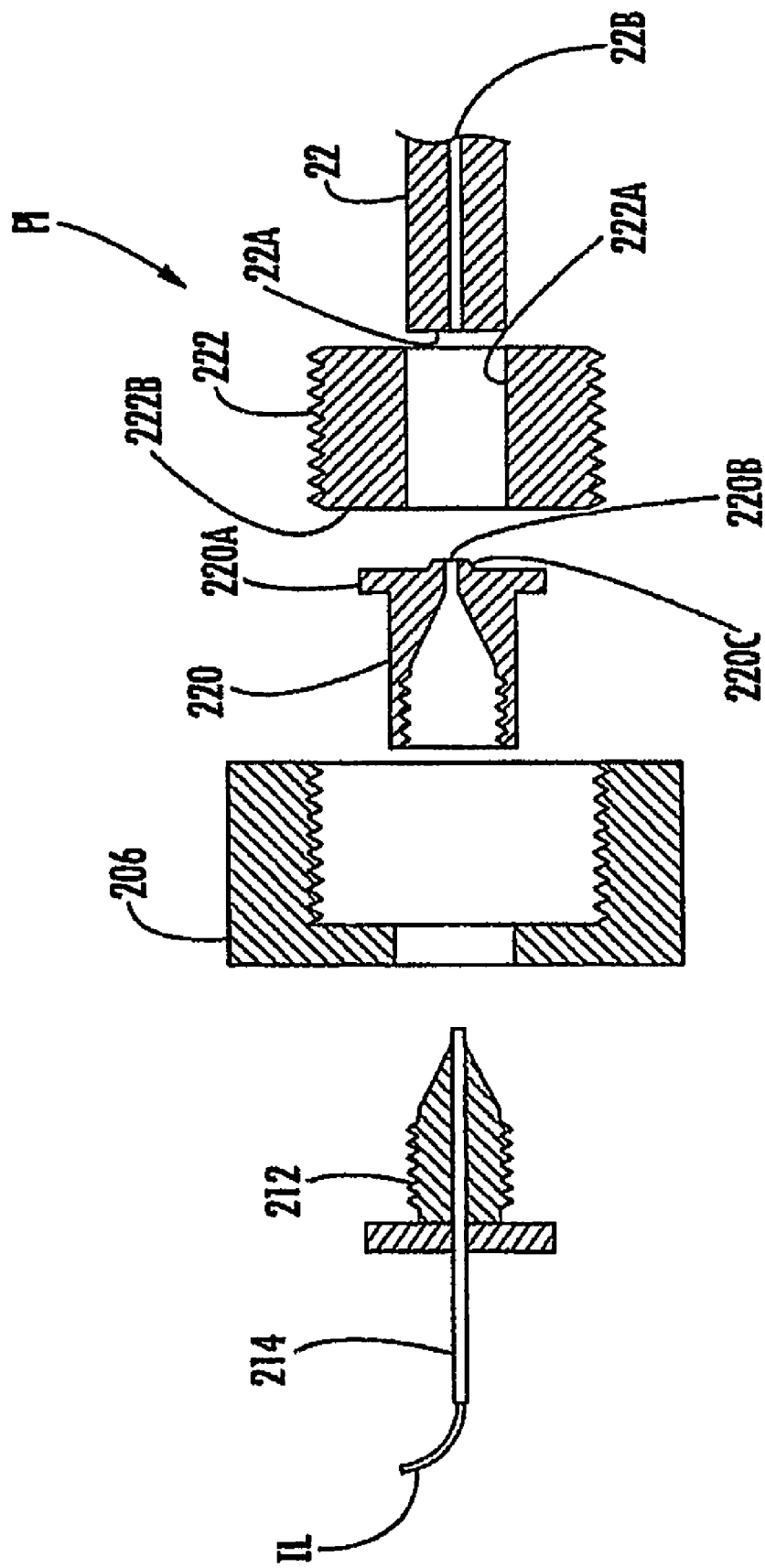
FIG. 18C is a cross-sectional exploded view of a microfluidic pump interconnect provided in accordance with embodiments disclosed herein.

FIG. 18C is a cross-sectional exploded view of a microfluidic pump interconnect, generally designated PI. Pump interconnect PI comprises a first annular member 222, a second annular member 206, a female fitting 220, a male fitting 212, and a sleeve 214. According to one embodiment, female fitting 220, male fitting 212, and sleeve 214 are components of the NANOPORT™ available from Upchurch Scientific. In addition, according to one embodiment, barrel 22 is a GASTIGHT® microsyringe available from Hamilton Company. Female fitting 220 can be identical to female fitting 210 shown in FIG. 18A, however, the side of female fitting 220 containing aperture 220B may be machined back to produce a nipple 220C that directly seals against the glass surface of barrel 22.

Annular member 222 has a bore 222A large enough to receive pump barrel 22, and these two parts are glued together with epoxy such that a front face 22A of barrel 22 extends slightly beyond front face 222B of first annular member 222. Second annular member 206 is then screwed onto first annular member 222 engaging flanges 220A of female fitting 222 and forcing nipple 220C against the front face 22A of barrel 22 such that aperture 220B is in fluid communication with barrel bore 22B, and nipple 220C forms a pressure tight seal against front face 22A of barrel 22.

Figure 19A:
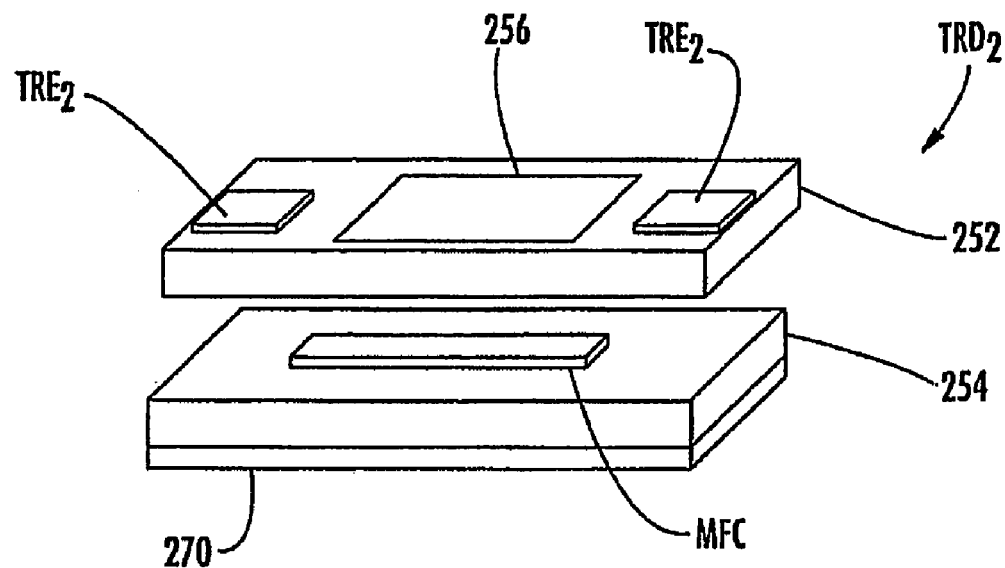
FIGS. 19A and 19B are perspective unassembled and assembled views, respectively, of a microfluidic chip encapsulated within a temperature regulating device in accordance with embodiments disclosed herein.
Figure 19B:
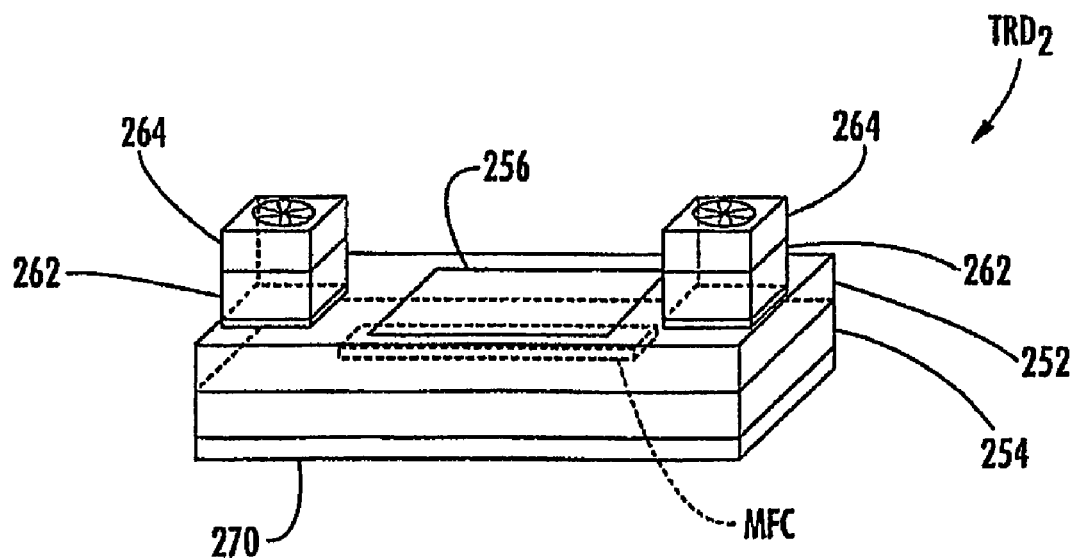

Referring now to FIGS. 19A and 19B, an advantageous embodiment of chip temperature regulating device $TRD_2$ is illustrated. Microfluidic chip MFC can be encapsulated within chip temperature regulating device $TRD_2$ to thermally isolate microfluidic chip MFC from ambient temperature fluctuations, stabilize fluid flow, control the temperature of a biochemical reaction proceeding in or on microfluidic chip MFC, and/or stabilize the position of microfluidic chip MFC and its alignment with other components such as excitation source ES (FIGS. 11 and 12) by minimizing thermally induced motions of one or more components of microfluidic chip MFC, any or all of which can contribute to reducing thermal noise and consequently improving the quality of measurement data acquired during concentration gradient runs. In one specific embodiment, chip temperature regulating device $TRD_2$ can control chip temperature within a range of approximately −4° C. to 70° C. to within 0.1° C. of accuracy. Thus, the temperature of microfluidic chip MFC, and/or one component thereof or associated therewith, and/or the liquid processed by microfluidic chip MFC, can be controlled.

Figure 20:
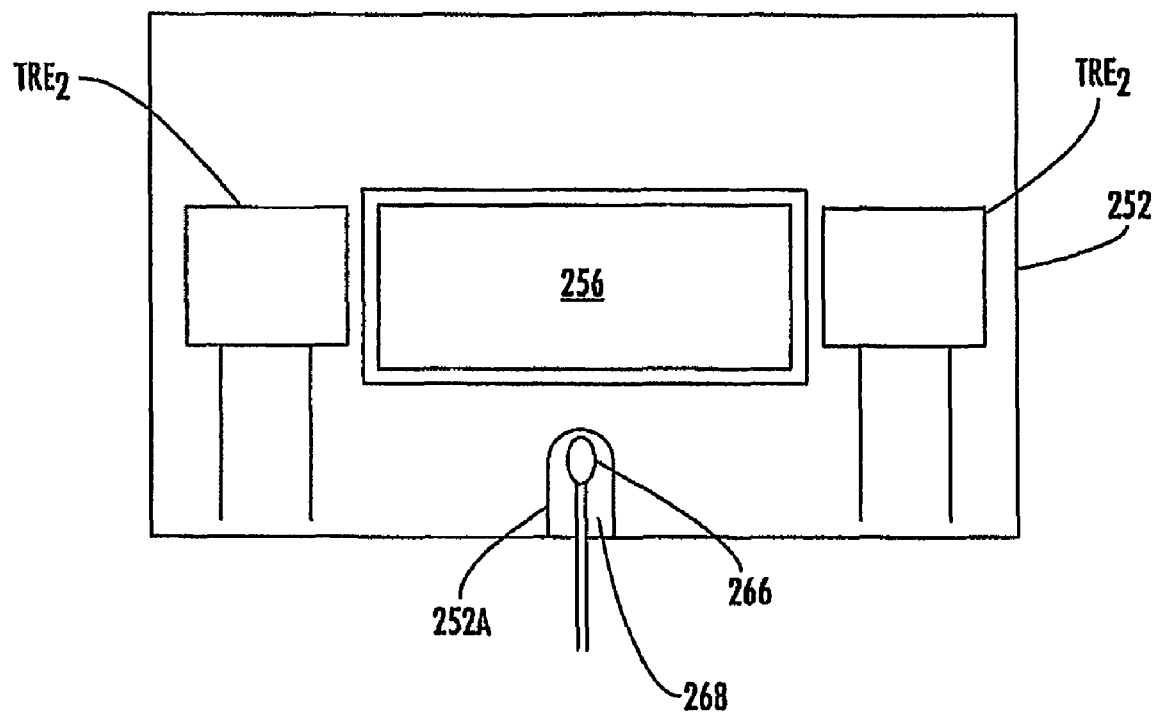
FIG. 20 is a top plan view of an upper portion of the temperature regulating device illustrated in FIGS. 19A and 19B.
Figure 21:
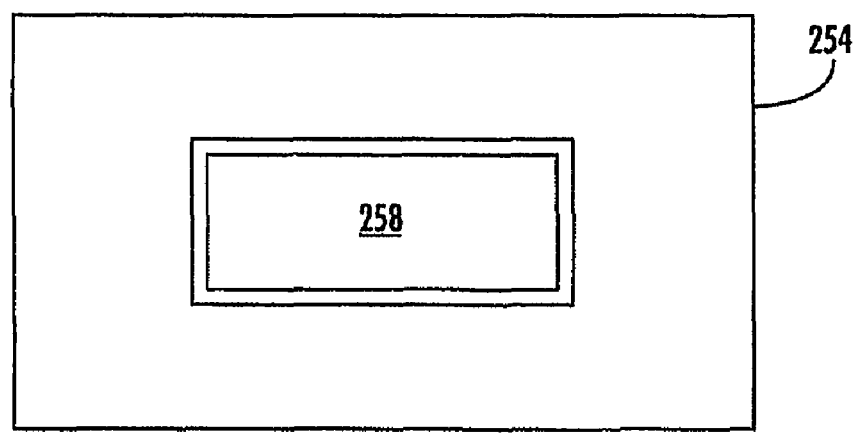
FIG. 21 is a bottom plan view of a lower portion of the temperature regulating device illustrated in FIGS. 19A and 19B.

As illustrated in FIGS. 19A and 19B, microfluidic chip MFC can be encapsulated between a first thermally conductive body or top plate 252 and a second, thermally conductive body or bottom plate 254. First and, second bodies 252 and 254 can be constructed from any suitably efficient thermally conductive material, one non-limiting example being aluminum, and bonded together by any suitable means. As illustrated in FIGS. 20 and 21, first and second bodies 252 and 254, if constructed from a light-scattering and/or an insufficiently light-transmissive material, can each include an optically clear window 256 and 258, respectively, to enable microfluidic chip MFC to be optically interrogated from either the top or the bottom. In one exemplary embodiment, first and second bodies 252 and 254 are each approximately 0.25 inch thick and have a planar area of approximately 3×5 inches, with their respective windows 256 and 258 having an area of approximately 25×50 mm.

Referring specifically to FIG. 20, one or more temperature regulating elements $TRE_2$ are attached to first thermally conductive body 252 by any suitable means to provide active heating and/or cooling. In advantageous embodiments, each temperature regulating element $TRE_2$ is a thermoelectric device such as a Peltier device, which is described hereinabove and illustrated in FIG. 16. To remove heat generated by temperature regulating elements $TRE_2$ during operation, a heat sink 262 can be attached to each temperature regulating element $TRE_2$ as shown in FIG. 19B. Additional cooling means can be provided for cooling heat sink 262 if desired, such as cooling fans 264 shown in FIG. 19B or by circulating a suitable heat transfer medium such as water through heat sinks 262. As shown in FIG. 20, a suitable temperature measuring or sensing device 266 such as a thermistor is embedded or otherwise placed in thermal contact with first body 252 (or, alternatively, second body 254) to provide real-time temperature feedback for thermal control unit TCU (FIG. 11). In the example illustrated in FIG. 20, temperature sensing device 266 is inserted into a cavity 252A formed in first body 252 and secured using a thermally conductive epoxy 268. Alternatively, temperature sensing device 266 can be embedded in, or otherwise placed in thermal contact with, microfluidic chip MFC itself. As a further alternative, temperature sensing device 266 thus built into microfluidic chip MFC can be in contact with the liquid residing or flowing in one or more of the channels of microfluidic chip MFC.

In other advantageous embodiments, if cooling of microfluidic chip MFC is not necessary, temperature regulating element or elements $TRE_2$ comprise resistive heating elements, which are readily commercially available and appreciated by persons skilled in the art. These can eliminate the need for heat sinks 262 and cooling fans 264. In one specific exemplary embodiment, shown in FIG. 21, the resistive heating element can be provided in the form of a transparent, conductive coating that is applied to first body 252 (not shown) and/or second body 254 or portions thereof. In a more specific example, the transparent, conductive coating is composed of a metal oxide such as indium oxide, tin oxide, or indium tin oxide (ITO). Particularly when the resistive heating element is based on a metal oxide, first body 252 and second body 254 can be constructed from a glass-based material, or the metal oxide can be on windows 256 and 258. This has the added advantage of providing a uniform heating source across the plane of microfluidic chip MFC, eliminating thermal gradients from the center of windows 256 and 258 to the edge of the window which are difficult to avoid if heating is from the edge of windows 256 and 258 and especially if windows 256 and 258 should be thin to accommodate optical access.

Second thermally conductive body 254 can serve passively as a large thermal mass to limit temperature fluctuations and isolate microfluidic chip MFC from ambient air currents. The lower periphery of second body 254 can include an insulating layer 270 to thermally isolate second body 254 from any chip holder CH (FIG. 11) such as microscope stage ST (FIG. 12) to which the encapsulated microfluidic chip MFC is to be mounted.

First body 252 is attached directly to second body 254 by any suitable means. Accordingly, thermal management of microfluidic chip MFC can be accomplished by operating temperature regulating devices to create temperature gradients directed either from first body 252 toward second body 254 (i.e., heating) or from second body 254 toward first body 252 (i.e., cooling), but should permit sufficient thermal contact between first body 252 and second body 254 to permit rapid dissipation of thermal gradients between the two, creating a nearly homogenous thermal environment for microfluidic chip MFC. The operation of chip temperature regulating device $TRD_2$ can be controlled as described hereinabove regarding pump temperature regulating device $TRD_1$, using the temperature control circuitry illustrated in FIG. 17A.

An alternate embodiment of the temperature regulating device $TRD_2$ includes only a heat-producing device, comprising, for example, one or more heating elements mounted directly to or otherwise in thermal contact with microfluidic chip MFC, that is used to heat microfluidic chip MFC above ambient temperature. This permits microfluidic chip MFC to operate at the physiological range of many enzymes (e.g. 37° C.) and also accelerates the rate of enzyme action. In this embodiment, the ambient environment removes heat from the temperature regulating device $TRD_2$ obviating any need for specialized heat dissipating components.

Connection of external pumps $P_A$-$P_D$ to microfluidic chip MFC and to external components, such as switching valves and plate handlers as discussed below, requires the use of tubes or other conduits. These should be of minimal internal volume for efficient use of reagents, and their walls should have minimal compliance to avoid their behaving like a pressure "capacitor" in which the walls expand (and thus the internal volume increases) as pressure increases to drive fluid flows. Materials such as fused silica can be readily obtained as microcapillaries with small internal diameters and rigid walls. Additionally, the capillaries should be shielded from thermal fluctuations because thermal expansion of the capillaries will cause them to behave like thermal pumps, and oscillations in temperature will result in noise in the flows through these capillaries. Such shielding can be either an insulative wrap around the capillaries, or all components of the system, including the capillaries, can be housed in a single temperature-controlled enclosure.

Figure 22A:
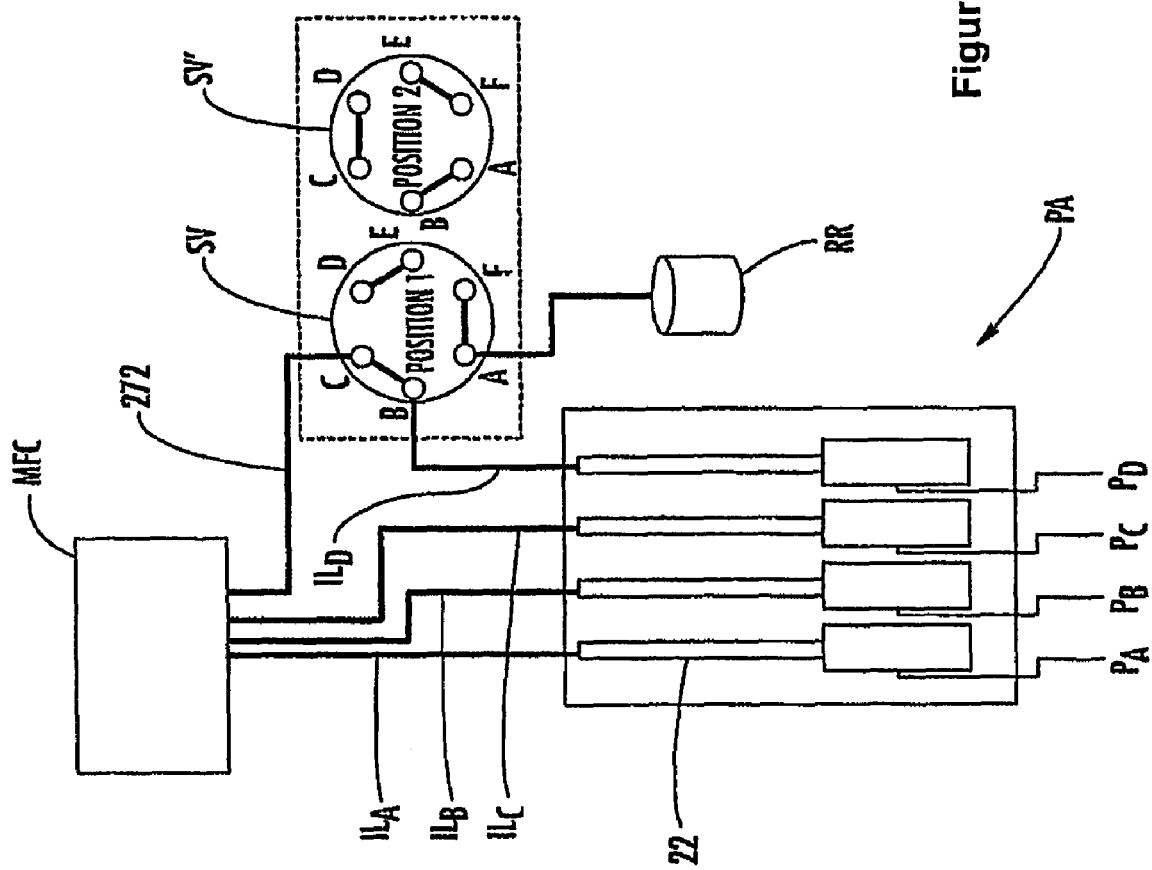
FIGS. 22A, 22B and 22C are respective schematic diagrams of examples of three alternative liquid handling systems that can be integrated with the embodiments of the sample processing apparatus disclosed herein.
Figure 22B:
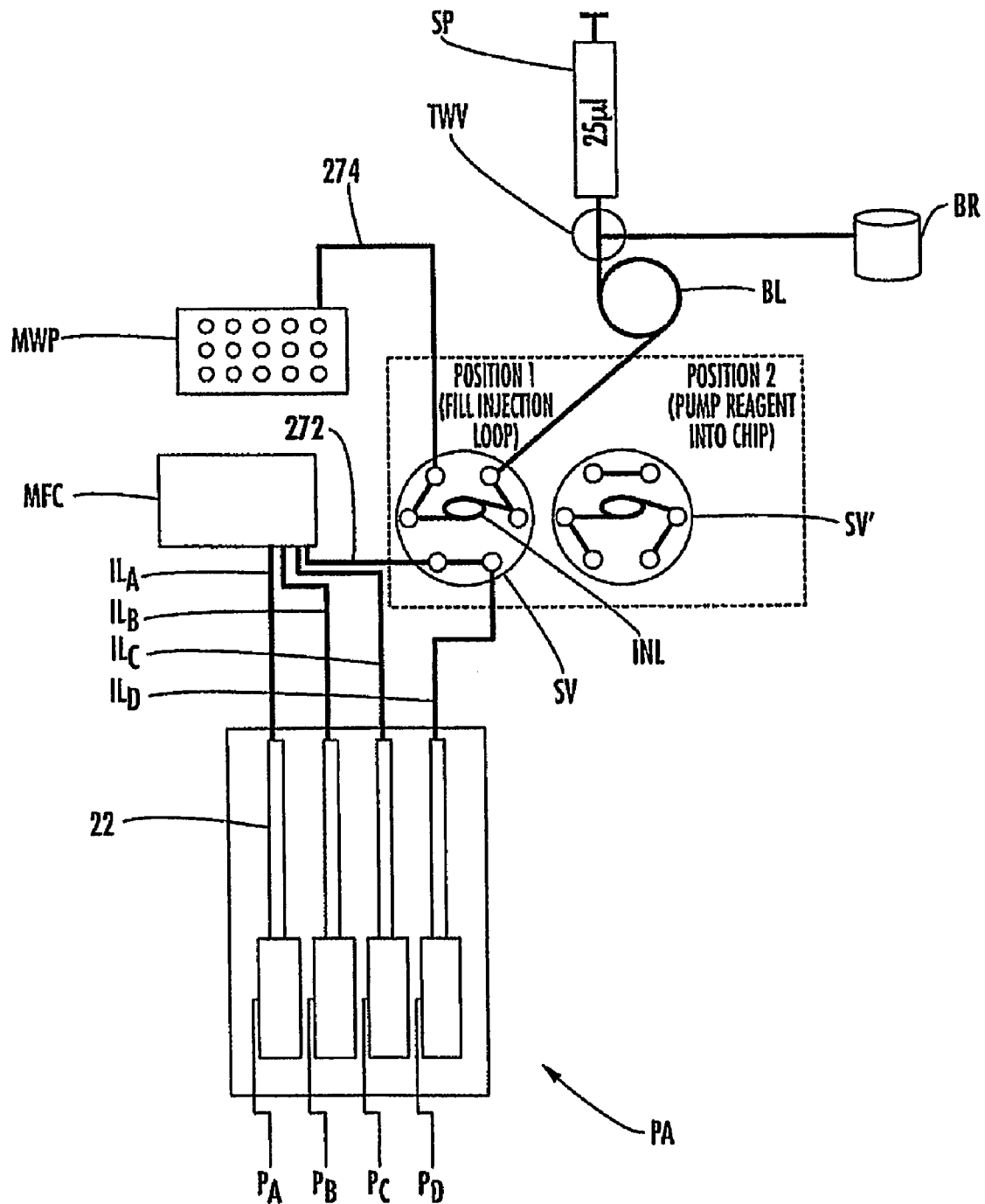
Figure 22C:
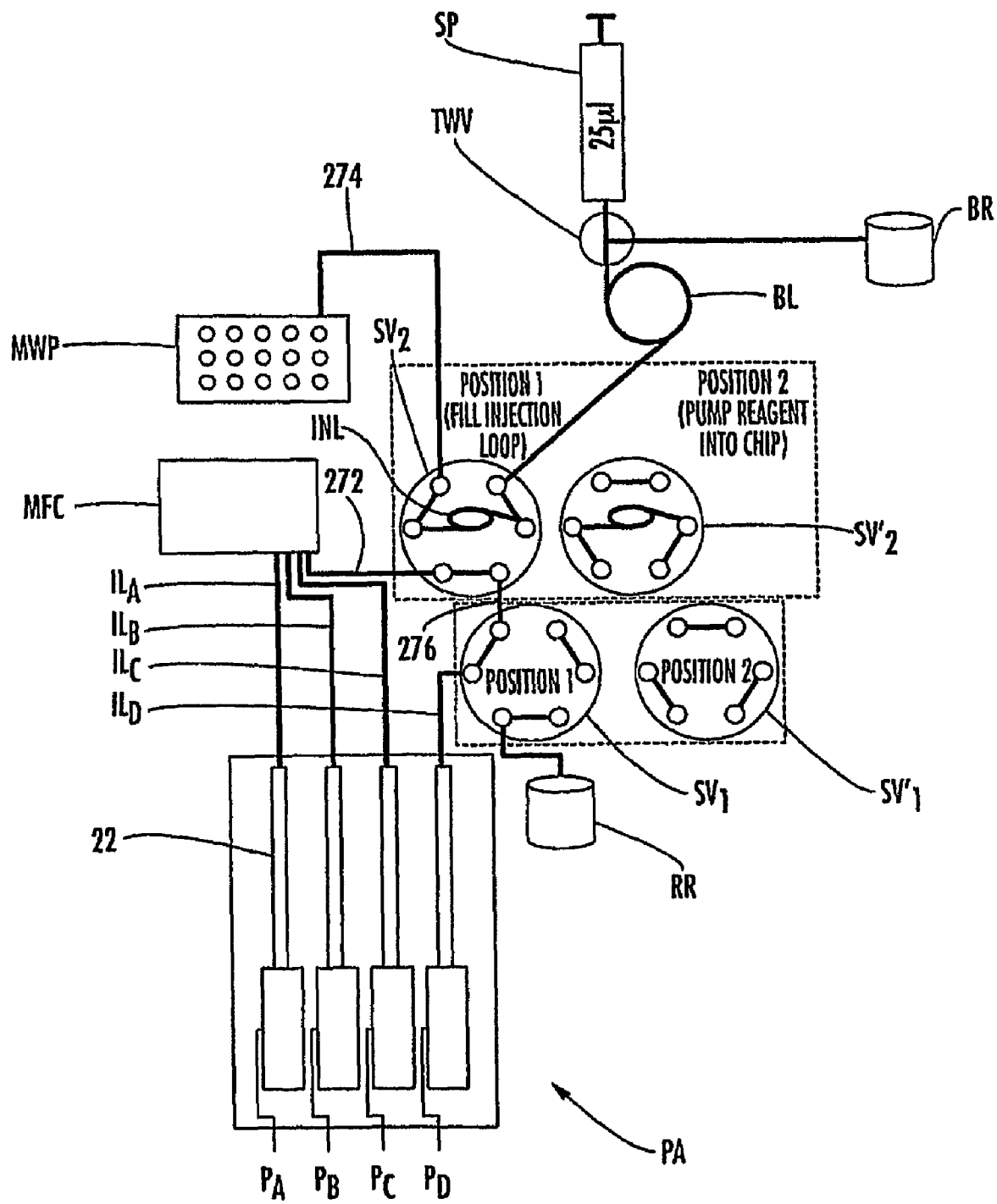

Referring now to FIGS. 22A-22C, non-limiting examples of liquid handling systems are illustrated. These systems can be implemented with pump assembly PA in accordance with any of the embodiments of sample processing apparatus SPA disclosed herein. The automation provided by these systems offers many advantages. First, the automation can allow unattended refill of reagents in pumps $P_A$-$P_D$, thus enabling the system to run unattended without operator intervention for days at a time. Second, the automation can allow automatic change of reagent in pumps $P_A$-$P_D$, and thus allow the system to test a series of reagents such as in screening pharmaceutical compounds, as well as the automatic reconfiguration of loaded reagents to automatically test the network of hypotheses for automated assay development and automatic hypothesis testing with intelligent systems. The automation also reduces the frequency that operators need to make and break fluidic interconnects. Thus, contamination and air bubbles in the system can be reduced, and the service life of the fluidic interconnects extended. These systems can incorporate an automated liquid handler that can be computer controlled via integrated computer software as part of any embodiment of the microfluidic systems disclosed herein. Managing the microfluidic system with a single software package enables real time decision-making and feedback control, thereby giving the system unprecedented flexibility and run time. This approach has not heretofore been practicable for displacement flows, because of the absence of displacement pumps that pump slowly enough for microfluidic systems as discussed hereinabove. An example of a suitable automated liquid handling system is the FAMOS™ micro autosampler available from LC Packings, Sunnyvale, Calif. This system provides for automated sample injection of any volume ranging from 50 nl up to 25 µl from 96- and 384-well plates. The device can include a sample tray that is equipped with Peltier cooling to avoid degradation of thermally labile samples.

Referring to FIG. 22A, addition of reagent to one or more of pumps $P_A$-$P_D$ can be achieved through inclusion of a switching valve SV located between one or more pumps $P_A$-$P_D$ and an external reagent reservoir RR (connection to pump $P_A$ as shown in FIG. 22A). An example of a suitable switching valve SV is a multi-port valve having a number of ports A-F available through which fluid can be selectively conducted. As appreciated by persons skilled in the art, a multi-port valve typically has a rotatable internal body containing internal passages. Through actuation of the internal body, either manually or via programmable control, each internal passage can be aligned with a pair of ports in order to selectively define one or more fluid flow paths through the valve. Switching valve SV can switch such that its associated pump $P_A$, $P_B$, $P_C$ or $P_D$ communicates alternately between microfluidic chip MFC (the first position schematically illustrated in FIG. 22A, where the switching valve is designated SV) and external reagent reservoir RR (the second position in FIG. 22A, where the switching valve is designated SV'). Pumps like syringe pumps contain a finite reservoir (e.g. the barrel of a gastight syringe may only contain 10 µl). When used in pumps $P_A$-$P_D$, the pumps can run out of reagent, and switching valve SV can switch such that the pump is in communication with external reagent reservoir RR, and then the pump can work in reverse, pumping reagent back into barrel 22 of the pump whereby the pump is reloaded with reagent. This permits extended runs of the system without human intervention. Refrigeration of external reagent reservoir RR permits extended storage of temperature-labile reagents.

Referring to FIG. 22B, switching valve SV can also be used in combination with one or more of pumps $P_A$-$P_D$ and an automated plate handler to perform automated addition of reagent or wash buffers from a multi-well plate MWP (e.g. a 96-well or 384-well plate). According to one embodiment, switching valve SV can be equipped with an injection loop having a volume of 1.0 microliter. Switching valve SV can include injection loop INL having fused silica lined PEEK® tubing. Multi-well plate MWP can be refrigerated to preserve temperature-labile reagents. This configuration enables serial addition of different reagents, for example, to screen inhibitors against an enzyme or to test multiple reagents for optimization of a biochemical reaction, or to provide wash buffers or rinsing fluids.

In this embodiment, switching valve SV again has two positions (SV and SV') and 6 or another number of ports as needed. Switching valve SV can permit the addition of only small amounts of reagent (sub-microliter) into a capillary 272 in between a pump $P_A$, $P_B$, $P_C$ or $P_D$ and microfluidic chip MFC, obviating the need to flush the pump $P_A$, $P_B$, $P_C$ or $P_D$ in between reagent changes. Reagents from multi-well plate MWP can be aspirated into a capillary 274 connected to switching valve SV. As appreciated by persons skilled in the art of automated liquid handling, the tip of capillary 274 can be carried on a motorized, programmable X-Y or X-Y-Z carriage or other robotic-type effector, permitting removal of reagent from any well in multi-well plate MWP. This capillary tip can be fitted with an independently actuated needle for piercing foil, plastic film or other types of septa used to seal the wells of multi-well plate MWP. Multi-well plate MWP can include 96 wells or another suitable number of wells. When injection loop INL is to be filled, the capillary 274 can be lowered into a well containing the fluid to be injected.

As shown in FIG. 22B, a syringe pump SP can be employed to implement the movement of reagents. Syringe pump SP can be provided as part of a suitable, commercially available automated liquid handling system as noted hereinabove. Syringe pump SP can be a larger liquid movement instrument (e.g., 25 μl) in comparison with pumps $P_A$-$P_D$, with coarser control and more rapid flow rates, thereby permitting rapid change of reagents and flushing of reagents from injection loop INL. Syringe pump SP can pull reagent from a selected well of multi-well plate MWP and into injection loop INL. Before stopping, syringe pump SP can pull sufficient volume from the selected well to fill capillary 274, injection loop INL, and excess to further flush injection loop INL with the fluid. While injection loop INL is being filled in position 1, one of pumps $P_A$, $P_B$, $P_C$ and $P_D$ can be used to push solvent through capillaries $I_A$, $I_B$, $I_C$ and $I_D$, respectively, for flushing capillaries $I_A$, $I_B$, $I_C$ and $I_D$ and microfluidic chip MFC. When switching valve SV is switched back to position SV' in position 2, injection loop INL becomes placed in line with pump $P_A$ allowing pump $P_A$ to push the fluid in injection loop INL into microfluidic chip MFC.

When switching valve SV switches to position 2, one of pumps $P_A$, $P_B$, $P_C$ and $P_D$ can be connected through injection loop INL to microfluidic chip MFC. One of pumps $P_A$, $P_B$, $P_C$ and $P_D$ can advance fluid from injection loop INL through a corresponding capillary $I_A$, $I_B$, $I_C$ and $I_D$ into microfluidic chip MFC. Simultaneously, the carriage can move capillary 274 to a well of multi-well plate MWP having a rinsing fluid. Syringe pump SP can then repeatedly pull fluid into and then expel fluid from capillary 274 to rinse it clean.

Furthermore, syringe pump SP can be placed in communication with a three-way valve TWV, an external buffer reservoir BR, and a buffer loop BL (if additional buffer volume is needed or desired) to enable syringe pump SP to flush injection loop INL with buffer. Three-way valve TWV can permit refilling of syringe pump SP from buffer reservoir BR, preventing contamination of syringe pump SP and associated lines with any fluid from injection loop INL and the alternate fluid connection with buffer loop BL.

Referring to FIG. 22B, when it is time to advance the next fluid in sequence into microfluidic chip MFC, one of pumps $P_A$, $P_B$, $P_C$ and $P_D$ can stop and switching valve SV can move to position 1. Syringe pump SP can then pull rinsing fluid through injection loop INL to flush it clean or it can push fluid from buffer reservoir BR to flush injection loop INL clean. Next, capillary 274 can be moved to the next well of multi-well plate MWP and the process repeated.

Referring to FIG. 22C, multiple combinations of switching valves and three-way valves can also be used in combination with one or more of pumps $P_A$-$P_D$ and an automated plate handler to realize more complex schemes, such as to permit addition of multiple reagents and refill of the buffer used as a hydraulic fluid in syringe pump that pumps through injection loop. For instance, one or more pairs of multi-port switching valves $SV_1$ and $SV_2$ can be interposed in the liquid circuit between microfluidic chip MFC and one or more corresponding pumps $P_A$-$P_D$. One of the ports of first switching valve $SV_1$ communicates with external reagent reservoir RR, and another of its ports communicates with pump $P_A$, $P_B$, $P_C$ or $P_D$ and its input line $IL_A$, $IL_B$, $IL_C$ or $IL_D$, and another port communicates with a port of second switching valve $SV_2$ via a transfer line 276. Another port of second switching valve $SV_2$ communicates with microfluidic chip MFC, thus providing fluidic communication with pump $P_A$, $P_B$, $P_C$ or $P_D$ and microfluidic chip MFC. Other ports of second switching valve $SV_2$ communicate with capillary 272 and buffer loop BL, respectively. Injection loop INL is connected to second switching valve $SV_2$.

In the present, exemplary configuration, first switching valve $SV_1$ has two primary positions (the first position designated $SV_1$ and the second position designated $SV'_1$) and second switching valve $SV_2$ likewise has two primary positions (the first position designated $SV_2$ and the second position designated $SV'_2$). When both switching valves $SV_1$ and $SV_2$ are in their respective first positions, their corresponding pump of pump assembly (pump $P_D$ in the illustrated embodiment) fluidly communicates with an input of microfluidic chip MFC. At its second position, first switching valve $SV'_1$ permits pump $P_D$ to draw additional reagent from reagent reservoir RR for refilling purposes. At its first position, second switching valve $SV_2$ can fill injection loop INL with a reagent selected from multi-well plate MWP, or flush injection loop INL with buffer from the system comprising syringe pump SP, three-way valve TWV, external buffer reservoir BR, and buffer loop BL, as described hereinabove. At its second position, second switching valve $SV'_2$ brings injection loop INL into fluid communication between pump assembly PA and microfluidic chip MFC, allowing the selected reagent residing in injection loop INL to be supplied to microfluidic chip MFC under the fine, precise control of the associated pump of pump assembly PA (pump $P_D$ in the illustration).

As described hereinabove, each component of the systems illustrated in FIGS. 22A-22C can be individually thermally insulated, or the entire system can be disposed in a thermally insulated or regulated enclosure.

Carry-over can occur as different fluids are added into a microfluidic chip, such as microfluidic chip MFC shown in FIGS. 22A-22C. Carry-over can become greater as the volumetric flow rate through the microfluidic chip decreases, and can become extremely problematic at the very low flow rates desired for microfluidic systems, such as 30 nl/min. This is because the volumes displaced through the system are small relative to the volumes contained in the system. For example, the internal volume (sometimes referred to as "dead space") of the smallest commercially available switching valve is 28 nl—Model CN2 switching valve from Valco Instrument Company of Houston, Tex., U.S.A. Thus, any void volumes or sources of contamination, which would be insignificant for faster flows that displace larger volumes per unit time, are now significant and, frequently, debilitating.

Figure 23:
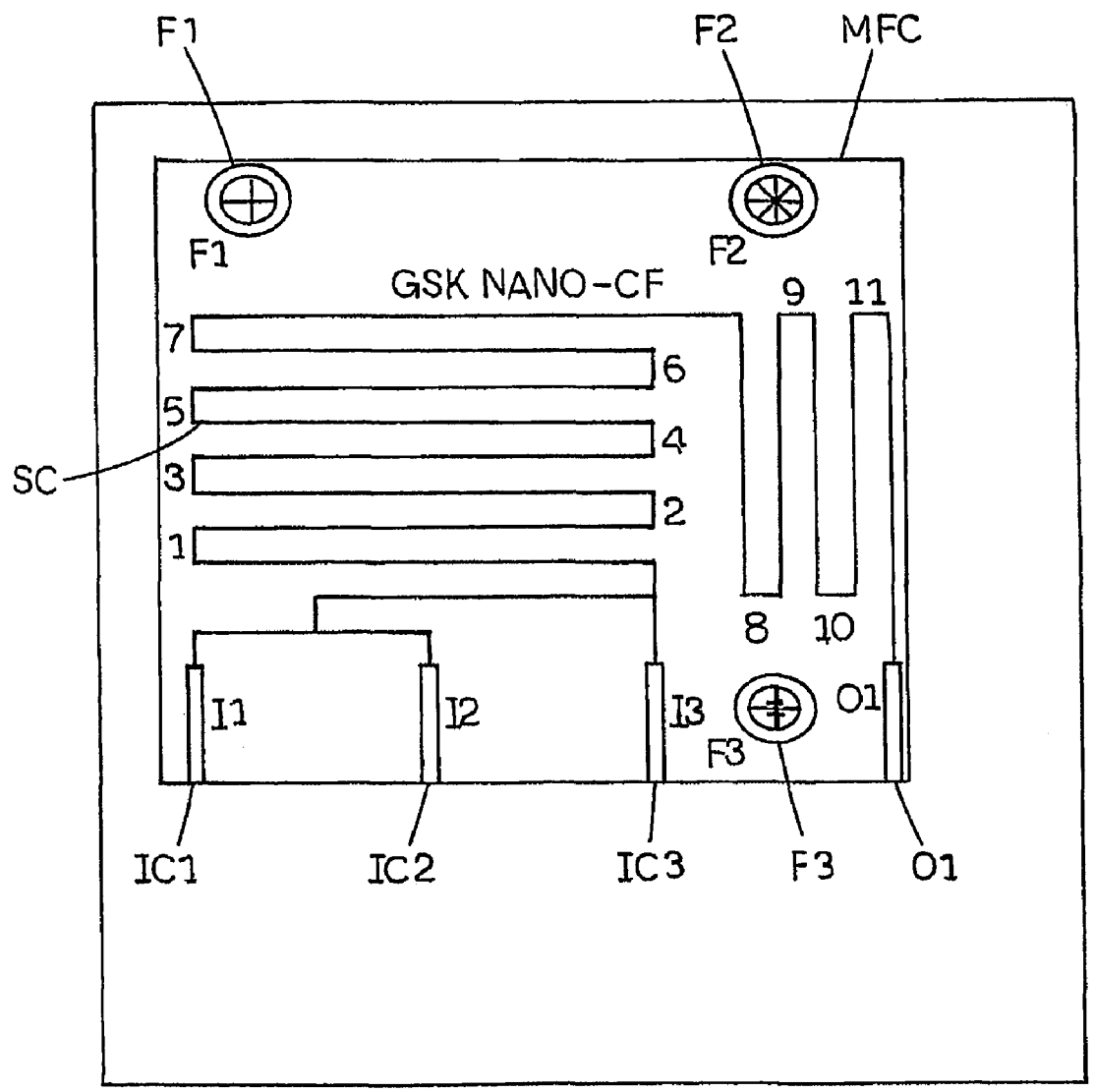
FIG. 23 is another microfluidic chip that can be used according to one embodiment.

To illustrate this carryover, experiments were conducted in which concentration gradients of fluorescent compounds were run against non-fluorescent buffer in a microfluidic chip MFC shown in FIG. 23 and described in detail in Example 5.

Carry-over in this exemplary system is believed to be generated by several factors: (1) large dead volumes in the switching valve SV (about 28 nl for the valves used), (2) large void or "unswept" volumes—outpockets from which contaminants enter or exit primarily by diffusion, and (3) moving parts which become "painted" by contaminating chemicals which only diffuse away very slowly. Thus, carry-over can be greatly reduced by removing moving parts, dead volumes, and void volumes from the fluidic system.

Carry-over can be eliminated or substantially reduced by utilizing the system described below including: (a) an on/off fluid freeze valve that has minimal dead volume, zero void volume, and no moving parts and, (b) an injection loop connected to the rest of the microfluidic system with interconnects having minimal dead volume and minimum void volume. According to one embodiment of a fluid freeze valve, the fluid freeze valve can change a capillary to an "off" state by lowering the temperature of fluid in the capillary such that the fluid reaches a solid or nearly solid state for stopping or substantially reducing the fluid flow through the capillary. Additionally, the system can increase the temperature of the frozen or nearly frozen fluid to return the capillary to an "on" state such that the fluid returns to a liquid state for allowing fluid flow through the capillary.

FIGS. 24A-24C illustrate different views of a fluid freeze valve, generally designated FFVS, applied to a fluid-carrying capillary IL. Referring specifically to FIG. 24A, a top perspective view of fluid freeze valve FFVS is illustrated. Fluid freeze valve FFVS can include a movable top plate MTP and a thermo-electric cooler TEC (such as the Peltier Temperature Controller available from Stable Micro Systems Ltd. of London, England). Movable top plate MTP can be rotatably movable with respect to thermoelectric cooler TEC such that capillary IL can be positioned between movable top plate MTP and thermoelectric cooler TEC. FIG. 24B illustrates a side cross-sectional view of movable top plate MTP, thermo-electric cooler TEC, and capillary IL wherein thermo-electric cooler TEC is not energized such that fluid F can flow through lumen L of capillary IL in the "on" state. Movable top plate MTP can be made of a material having low thermal mass, low thermal conductivity, and does not absorb water. Movable top plate MTP can form an airtight seal around thermo-electric cooler TEC, or the assembly can be placed in an air-tight, low humidity chamber, such that water from the atmosphere does not condense onto thermoelectric cooler TEC, thereby adding thermal mass. FIG. 24C illustrates a side cross-sectional view of movable top plate MTP, thermoelectric cooler TEC, and capillary IL wherein thermoelectric cooler TEC is energized for reducing the temperature of capillary IL such that fluid F reaches a solid or nearly solid state to stop fluid flow through lumen L of capillary IL in the "off" state. Thermo-electric cooler TEC can also apply heat to capillary IL such that fluid F in a frozen or nearly frozen state can rapidly thaw, thereby returning the fluid freeze valve FFVS to the "on" state.

Figure 25A:
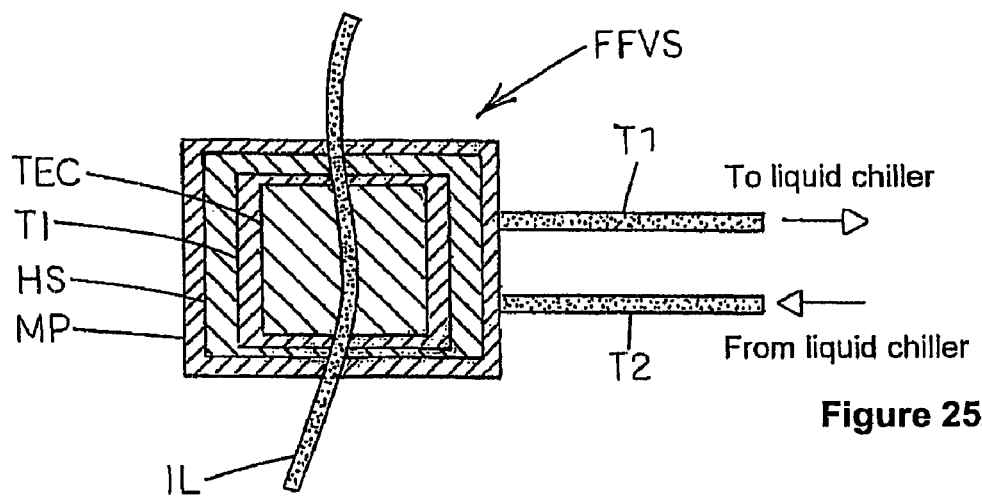
FIGS. 25A-25C are top, front and side views of another fluid freeze valve applied to a fluid-carrying capillary.
Figure 25B:
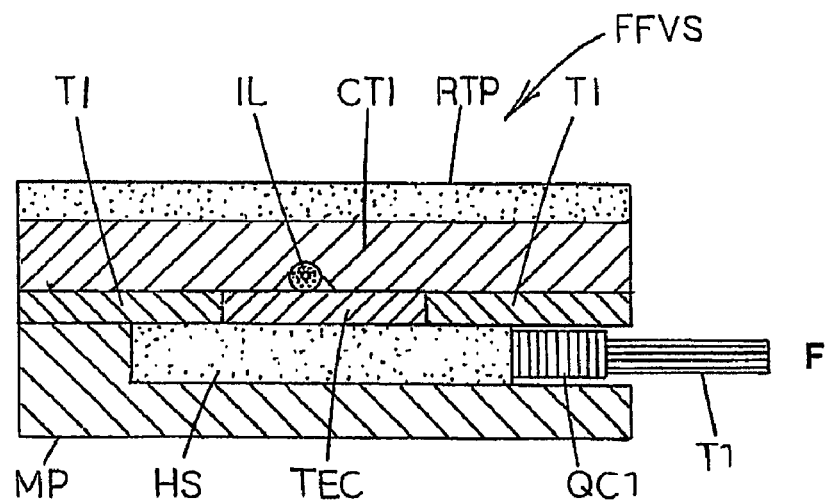
Figure 25C:
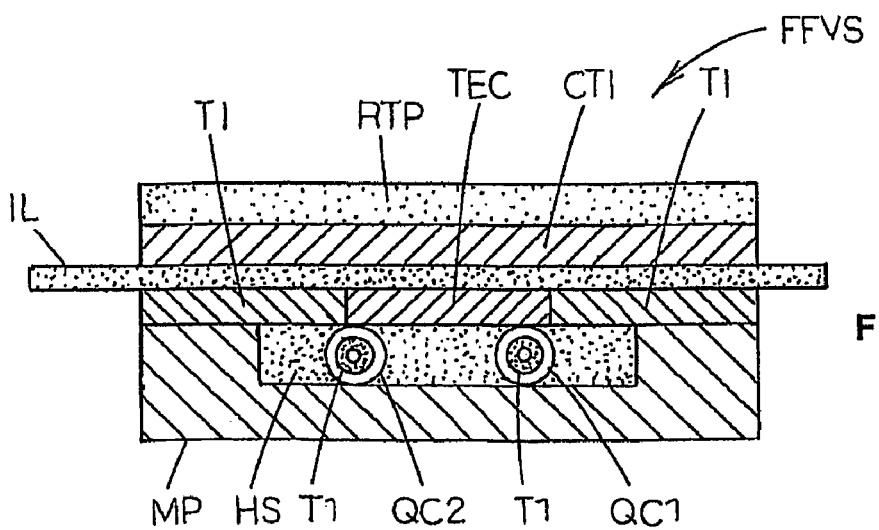

FIGS. 25A, 25B, and 25C illustrates a top, front and side view, respectively, of another fluid freeze valve, generally designated FFVS, applied to a fluid-carrying capillary IL. Fluid freeze valve FFVS can include a thermo-electric cooler TEC for application to a capillary IL. Thermo-electric cooler TEC can be attached to a heat sink HS containing a circulating water heat exchanger for removing heat from thermoelectric cooler TEC. Heat sink HS can also include tubes T1 and T2 for delivering and returning fluid to a liquid chiller (not shown). Tubes T1 and T2 can be connected to heat sink HS via quick-connects QC1 and QC2, respectively. The assembly can be mounted into a mounting plate MP for mounting to external supports.

Referring to FIG. 25A, fluid freeze valve FFVS can include an insulated housing surrounding thermoelectric cooler TEC comprising a movable top plate RTP lined on its internal surface with a conformal thermal insulation CTI that both pushes capillary IL against the surface of thermoelectric cooler TEC and thermally isolates capillary IL and thermoelectric cooler TEC from oscillations in ambient temperature. Similarly, the sides of thermo-electric cooler TEC can be surrounded by thermal insulation TI to further thermally isolate capillary IL and thermo-electric cooler TEC. Insulation can be important when a freeze valve is used to control low flow rates, such as of the nanoliter/minute scale. This can be important because water increases with volume when it freezes. For example, a thermoelectric cooler (such as thermoelectric cooler TEC shown in FIG. 25) of about 2 centimeters across can freeze about 2 centimeters of fluid in a capillary. If the capillary has an internal diameter of 50 micrometers, two centimeters of this capillary confines about 20 nanoliters. A length of 1 millimeter encloses about 2.0 nanoliters. Water increases volume about 9% when it freezes. If the edges of the frozen volume of fluid move 1 millimeter due to oscillations of ambient temperature that can affect either the temperature of the capillary or the temperature of thermo-electric cooler TEC, then the fluid adjacent to the frozen plug of fluid will change volume by about 0.18 nanoliters. For example, for flows of about 15 nanoliters/minute, such a 1 mm thaw over 1 minute represents a variation of more than 1%. Note that a capillary IL having a larger internal diameter can have a larger volume per unit length, so in the case where the fluid thaws over a fixed length, then a capillary having a larger diameter may introduce more noise to the flow.

Fluid freeze valves (such as fluid freeze valves FFVS shown in FIGS. 24A-24C and 25A-25C) can be applied to the systems described herein for stopping flow in a capillary attached to a microfluidic chip. For example, a fluid freeze valve can be applied to a capillary connecting a microsyringe pump and a microfluidic chip, a capillary connecting a microsyringe pump and an outside reservoir, or a capillary connecting a microfluidic chip and an outside multi-well plate or reservoir. It is important that the connection between the capillary and the microfluidic chip have minimal dead volume and minimal void volume, or carry-over may be increased.

FIGS. 26A-26D illustrate top plan views of different stages in a sample process run by a microfluidic system, generally designated MS. Microfluidic system MS can include a microfluidic chip MFC having injection loop INL and a plurality of fluid freeze valves VS1, VS2, and VS3. Injection loop INL can comprise a microchannel etched in microfluidic chip MFC having dimensions of about 150 micrometers wide, 150 micrometers deep, and 2 centimeters long for yielding a volume of 450 nanoliter. Alternatively, microchannel can have other suitable dimensions for achieving a desired volume. Microfluidic chip MFC can include a first and second input channel CH1 and CH2 for fluidly connecting or communicating at a merge point ML for combining fluids advanced therein from microsyringe pumps MP1 and MP2, respectively. Injection loop INL can be fluidly connected at one end to capillary CP1 and at an opposing end to capillary CP2. Capillaries CP1 and CP2 can be made of fused silica with 150 micrometers outside diameter and 75 micrometers inside diameter, respectively, available from Polymicro Technologies LLC. of Phoenix, Ariz. Capillaries can be connected in accordance with embodiments disclosed in co-pending, commonly owned U.S. Provisional Application entitled MICROFLUIDIC CHIP APPARATUSES, SYSTEMS, AND METHODS HAVING FLUIDIC AND FIBER OPTIC INTERCONNECTIONS, U.S. Provisional Application No. 60/707,246, the content of which is incorporated herein in its entirety.

Referring to FIGS. 26A-26D, microfluidic system MS includes an aging loop AL or mixing channel communicating at one end to merge location ML. Merge location ML can also communicate with microsyringe pumps MP1 and MP2. Aging loop AL can also communicate at another end to a waste unit 2100 via a capillary CP3. According to one embodiment, injection loop INL can be filled, aging loop AL can be rinsed, and reactions can be run in microfluidic system MS through aging loop AL. Fluid freeze valve VS1 can be positioned on capillary CP3 for controlling fluid flow between aging loop AL and waste container 2100. Fluid freeze valves VS2 and VS3 can be positioned on capillaries CP1 and CP2, respectively, for controlling fluid flow between another waste unit 2102 and multi-well plate MWP, respectively. Microfluidic system MS can also include microsyringe pump MP3 connected to injection loop INL. Injection loop INL can be filled with different fluids from multi-well plate MWP for sequentially adding reagents in-line with pump MP3 as needed.

Figures 26A, 26B:
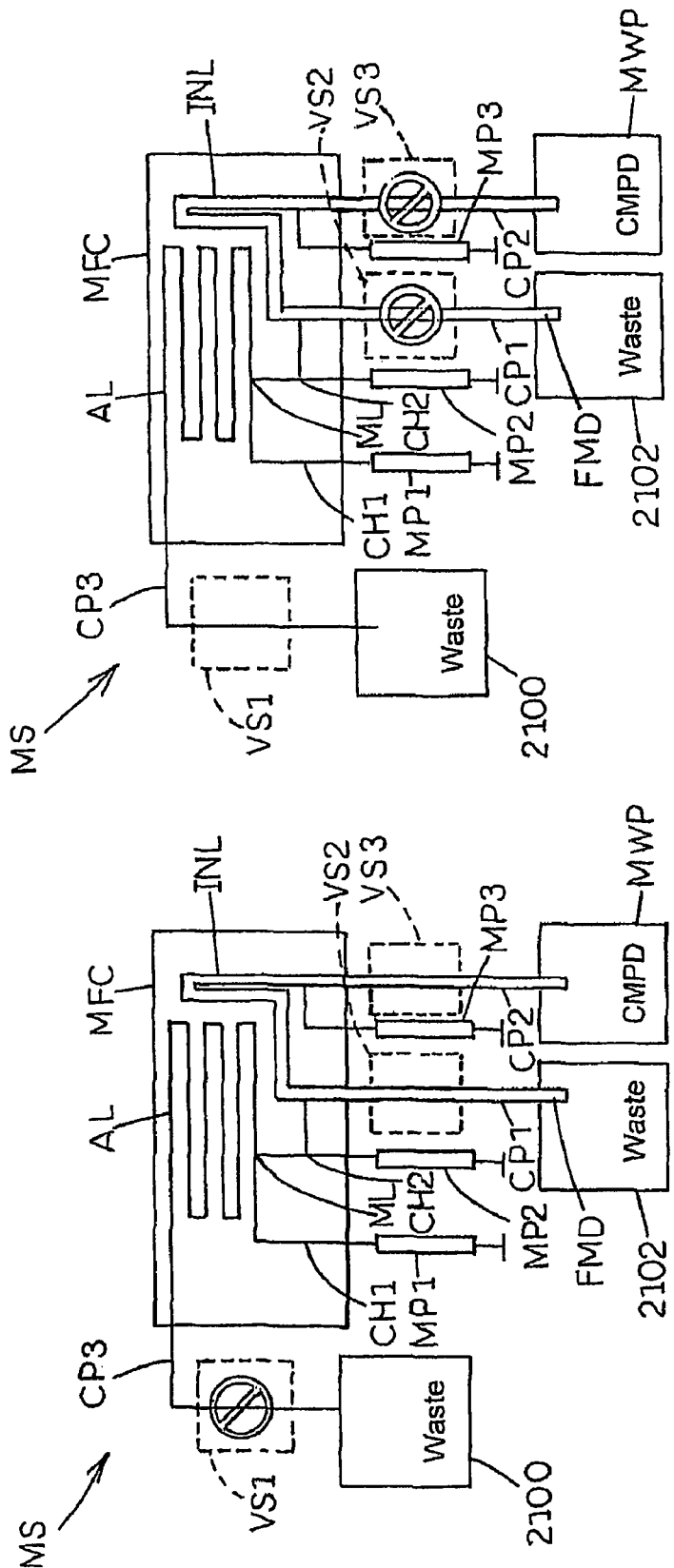
FIG. 26A is a top plan view of a microfluidic system with fluid freeze valves in a state for filling an injection loop with a fluid from one of the wells of a multi-well plate.
FIG. 26B is a top plan view of the microfluidic system shown in FIG. 26A with the fluid freeze valves in a state for running a gradient.

FIG. 26A illustrates the state of fluid freeze valves VS1, VS2, and VS3 of microfluidic system MS for filling injection loop INL with a fluid from one of the wells of multi-well plate MWP. Fluid freeze valve VS1 can be set to the "off" state for reducing the temperature of the fluid in capillary CP3. Fluid freeze valve VS1 can reduce the fluid temperature such that the flow of the fluid in capillary CP3 is stopped. Next, capillary CP2 can be lowered into a well of multi-well plate MWP having a desired fluid. Fluid freeze valves VS2 and VS3 are set to the "on" state to thaw, if necessary, the fluids in capillaries CP1 and CP2, respectively, for allowing fluids to flow through capillaries CP1 and CP2. Next, multi-well plate MWP can be pressurized, or its waste unit 2100 can be put under vacuum, for generating a pressure difference across injection loop INL to force fluid through injection loop INL. Microsyringe pumps MP1, MP2, and MP3 can be static during this stage and, due to the incompressibility of water, flow in capillaries attached to microsyringe pumps MP1, MP2, and MP3 is zero. Alternatively, additional freeze valves can valve the flow from microfluidic chip MFC and microsyringe pumps MP1, MP2, and MP3 to prevent the backflow from microfluidic chip MFC to microsyringe pumps MP1, MP2, and MP3.

FIG. 26B illustrates a stage following the stage shown in FIG. 26A wherein microfluidic system MS runs a gradient. Fluid freeze valve VS1 is set to the "on" state to open capillary CP3 such that fluid can flow from aging loop AL to waste unit 2100. Fluid freeze valves VS2 and VS3 are set to the "off" state to close capillaries CP1 and CP2, respectively, such that fluid does not flow through injection loop INL. Next, microsyringe pumps MP1, MP2, and MP3 can advance fluids through aging loop AL and other suitable microchannels of microfluidic chip MFC to achieve the desired function of the microfluidic chip MFC.

Figures 26C, 26D:
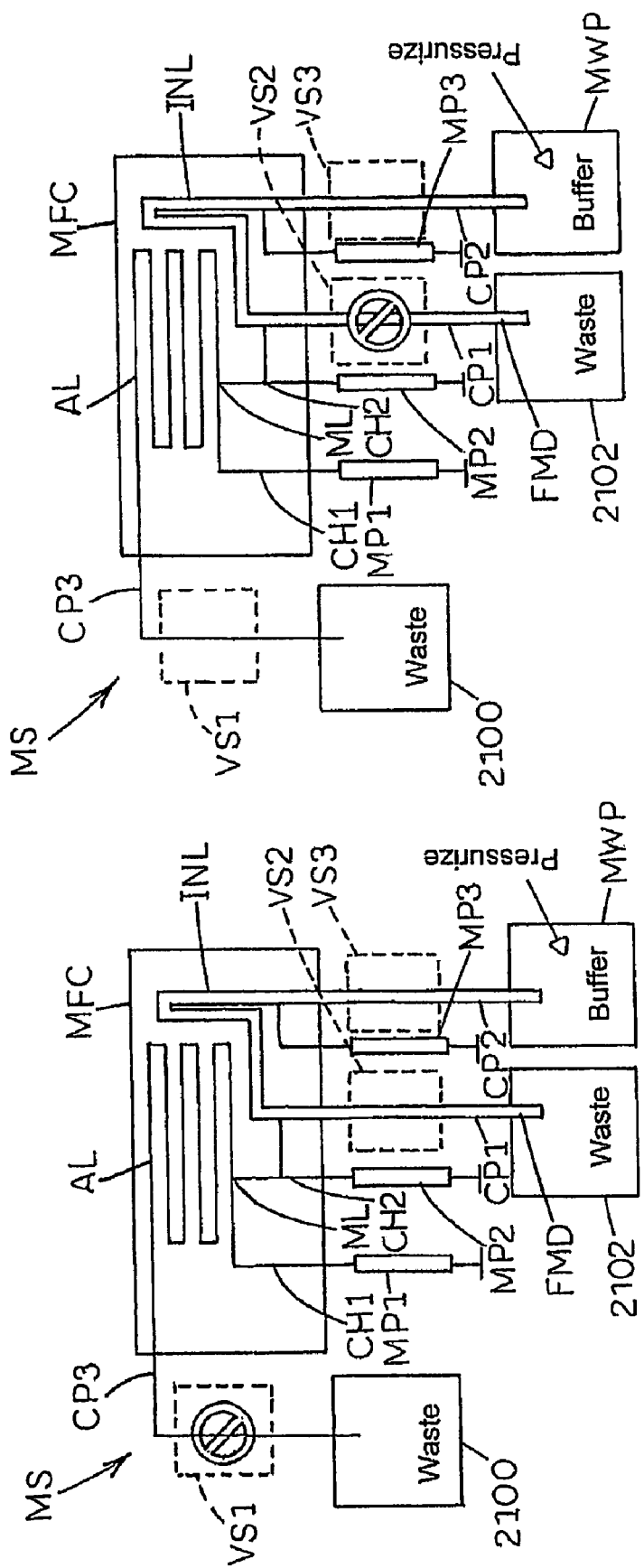
FIG. 26C is a top plan view of the microfluidic system shown in FIGS. 26A and 26B with the fluid freeze valves in a state for rinsing the injection loop.
FIG. 26D is a top plan view of the microfluidic system shown in FIGS. 26A, 26B, and 26C with the fluid freeze valves in a state for rinsing the aging loop.

FIG. 26C illustrates a stage following the stage shown in FIG. 26B wherein injection loop INL can be rinsed. Injection loop INL of microfluidic chip MFC can be rinsed by moving capillary CP2 to a well of multi-well plate MWP containing rinse fluid. Next, fluid freeze valve VS1 can be set "off" and microsyringe pumps MP1, MP2 and MP3 held in position for preventing fluids from flowing through aging loop AL. Fluid freeze valves VS2 and VS3 can be set "on" to allow fluid to flow through injection loop INL from a rinse-containing well of multi-well plate MWP to waste unit 2102. Multi-well plate MWP can then be pressurized for moving the rinse fluid from multi-well plate MWP and through injection loop INL and then into waste unit 2102. Microsyringe pump MP3 also can be advanced a short amount to purge the end of its line during this wash step.

FIG. 26D illustrates a stage following the stage shown in FIG. 26C wherein aging loop AL can be rinsed. Fluid freeze valve VS2 can be set "off" to prevent fluid from flowing into waste unit 2102. Fluid freeze valve VS1 can be set "on" for allowing fluid to flow from the rinse-containing well of multi-well plate MWP through aging loop AL and into waste unit 2100. Multi-well plate MWP can then be pressurized for moving the rinse fluid from multi-well plate MWP through aging loop AL and then into waste unit 2100. Microsyringe pumps MP1 and MP2 can also be advanced a short amount to purge the ends of their lines during this wash step. Next, the process can be repeated.

Figure 26E:
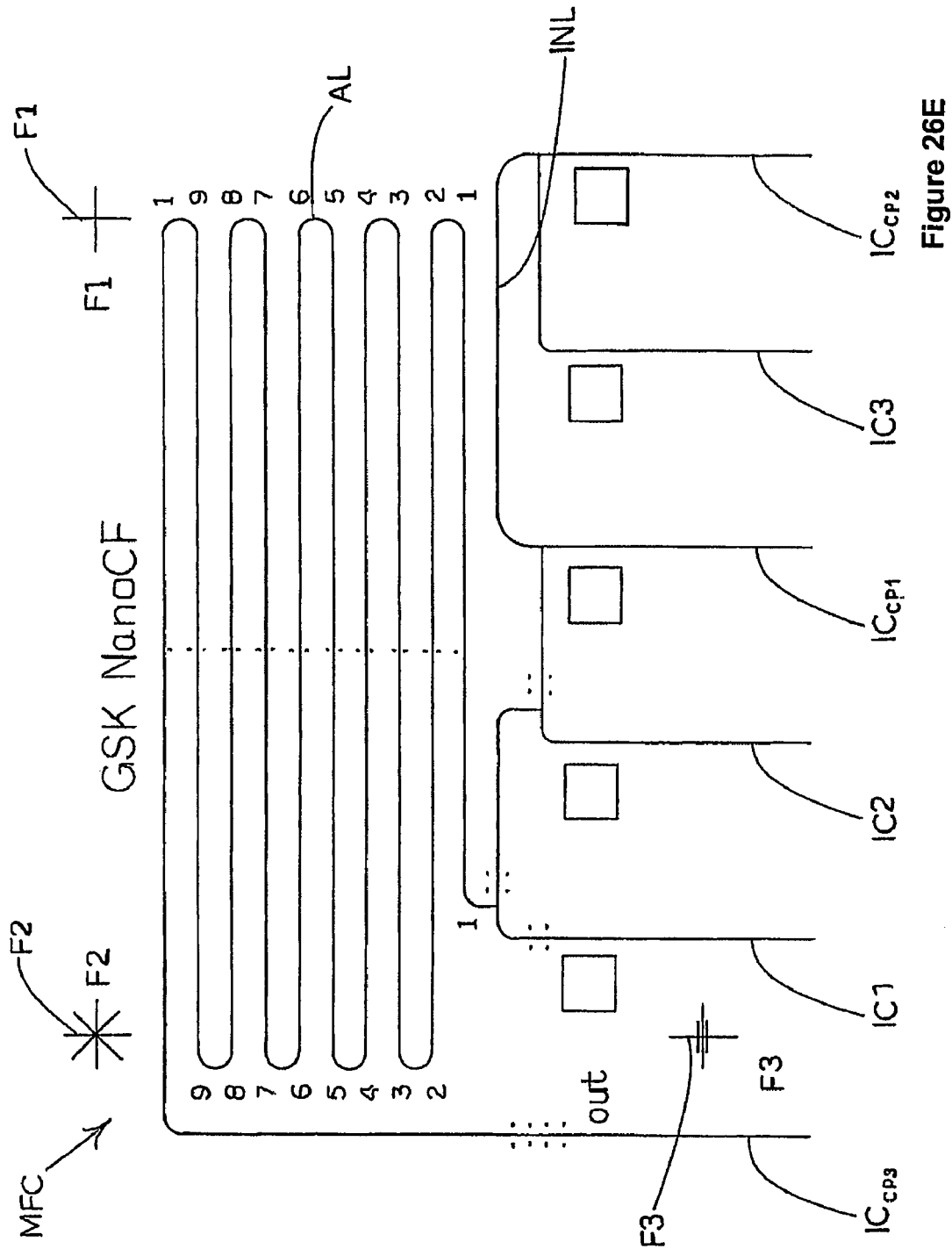
FIG. 26E is a top plan view of another exemplary microfluidic chip.

FIG. 26E is a top plan view of another exemplary microfluidic chip, generally designated MFC, having an injection loop INL; interconnect channels IC1, IC2, and IC3 for connecting to capillaries that connect to microsyringe pumps MP1, MP2, and MP3, respectively (shown in FIGS. 26A-26D); an interconnect channel $IC_{CP3}$ that can connect to output capillary CP3 (shown in FIGS. 26A-26D); interconnect channels $IC_{CP1}$ and $IC_{CP2}$ that can connect to capillaries CP1 and CP2, respectively (shown in FIGS. 26A-26D); an aging loop AL; and fiducial marks (F1, F2, and F3) for automated alignment.

The collective resistance to flow generated by capillaries CP1, CP2, and CP3 and injection loop INL, combined with the pressure difference from the inlet to outlet of microfluidic chip MFC, can determine the volumetric flow rate. Thus, higher pressures can be generated at the inlet (capillary CP2) to increase volumetric flow rates. Driving flow by application of a vacuum to capillary CP1 during fluid changes in injection loop INL or to capillary CP3 during washes of the aging loop can limit the pressure difference to 15 pounds per square inch (p.s.i.) due to bubble formation via out-gassing of dissolved gases and cavitation of the fluid due to boiling at zero absolute pressure. Driving flow by pressurizing the inlet can generate higher pressure difference. In either case, flow metering device FMD on capillary CP1 can be used to meter the flow through capillary CP1 and, thus, injection loop INL, and this measurement can be used to determine when to turn off the pressure or vacuum to stop flow through the injection loop INL. Conversely, the flow rate through injection loop INL can be calculated, and the application of pressure or vacuum can be timed to control the volume that flows through injection loop INL. Placement of flow metering device FMD after on-chip injection loop INL removes any carry-over associated with metering device FMD from injection loop INL while still permitting accurate measurement of flow rates through injection loop INL.

Larger internal diameters for capillaries CP1, CP2, and CP3 can be used to decrease resistance and thus increase flow rates. Larger capillary diameters can also increase the volume of capillaries CP1, CP2, and CP3 which results in unwanted fluid waste. Additionally, larger capillary internal diameters can make the system more prone to noise in the flow rate introduced by fluctuating freeze-thaw at the edges of the freeze-valve as discussed above. Thus, increasing the pressure difference can generate more rapid flows and prevent unwanted increases in capillary diameters and noise. For the dimensions given above for capillaries CP1 and CP2 and for injection loop INL, with capillaries approximately 60 cm long, pressures up to 125 p.s.i. can be used to generate flow rates of 50 microliters/minute that push a volume equal to that of injection loop INL and capillary CP2 through injection loop INL in about 3 seconds for permitting rapid fluid exchanges. Higher pressures can permit more rapid fluid exchanges.

Pressurizing an inlet can increase the pressure through microfluidic system MS. If the entire system can withstand the increased pressure, then the higher pressures convey several advantages. Bubbles can sometimes be accidentally introduced into a microfluidic system, and pressurizing the inlet facilitates the removal of these bubbles. A higher pressure compresses bubbles, making it easier to flush the bubbles out of injection loop INL. The higher pressure can also increase the gas-carrying capacity of the fluid, accelerating the rate at which bubbles dissolve into the fluid and, thereby, more quickly removing bubbles that will not flush out.

Figure 27A:
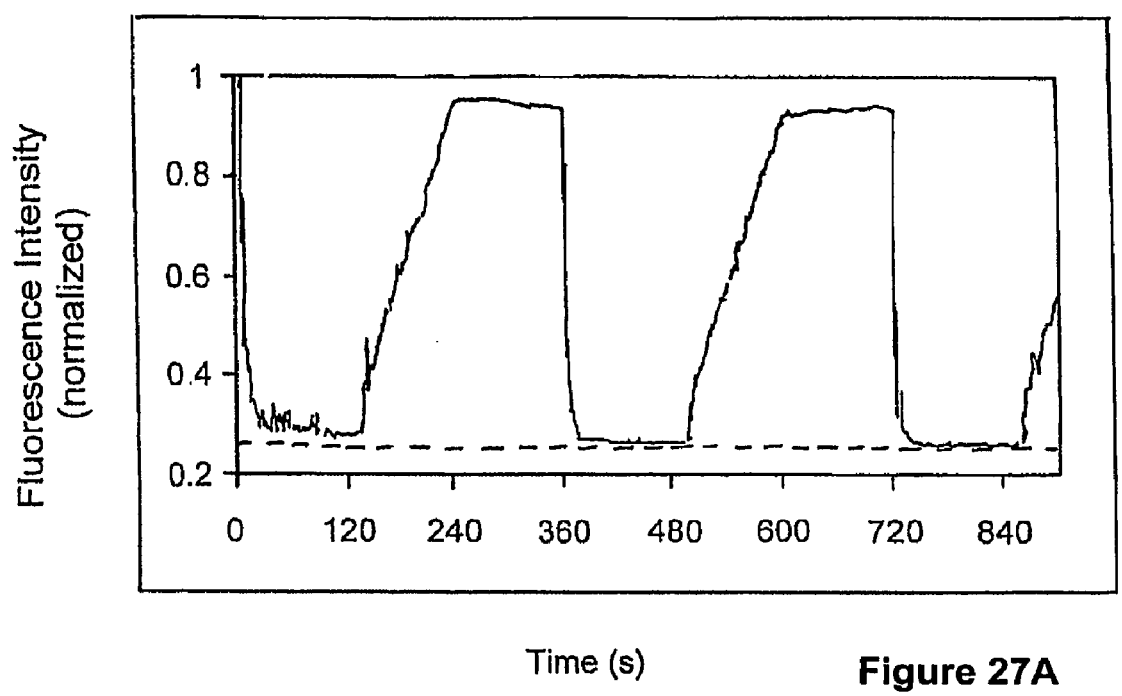
FIG. 27A is a graph showing the results of a carry-over experiment conducted with the microfluidic system shown in FIGS. 26A-26D.
Figure 27B:
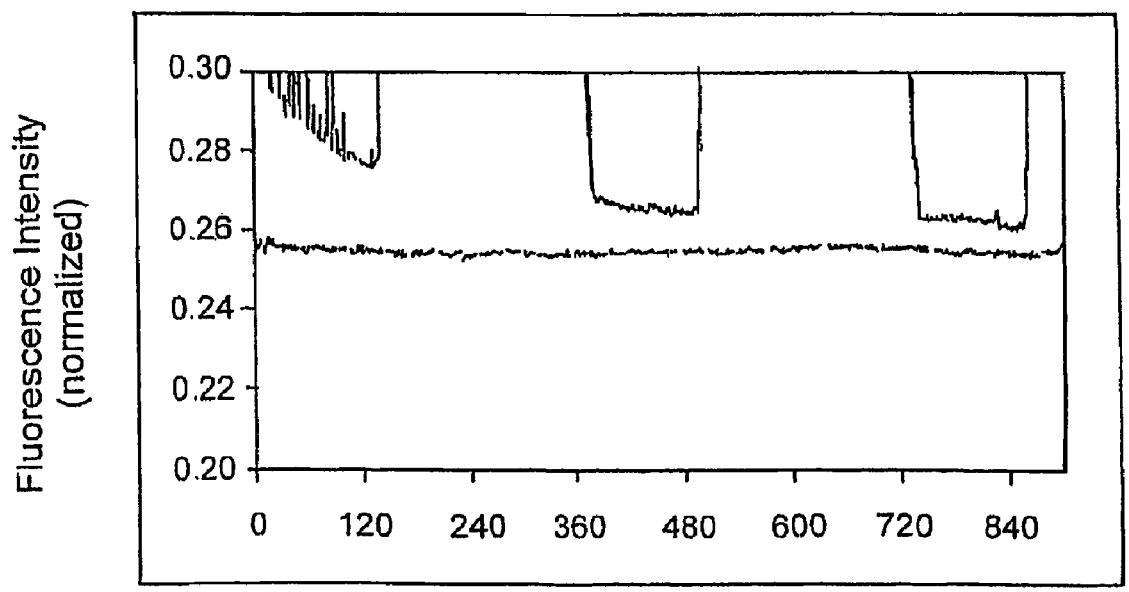
FIG. 27B is a graph showing a detail of the graph shown in FIG. 27A.
Figure 51A:
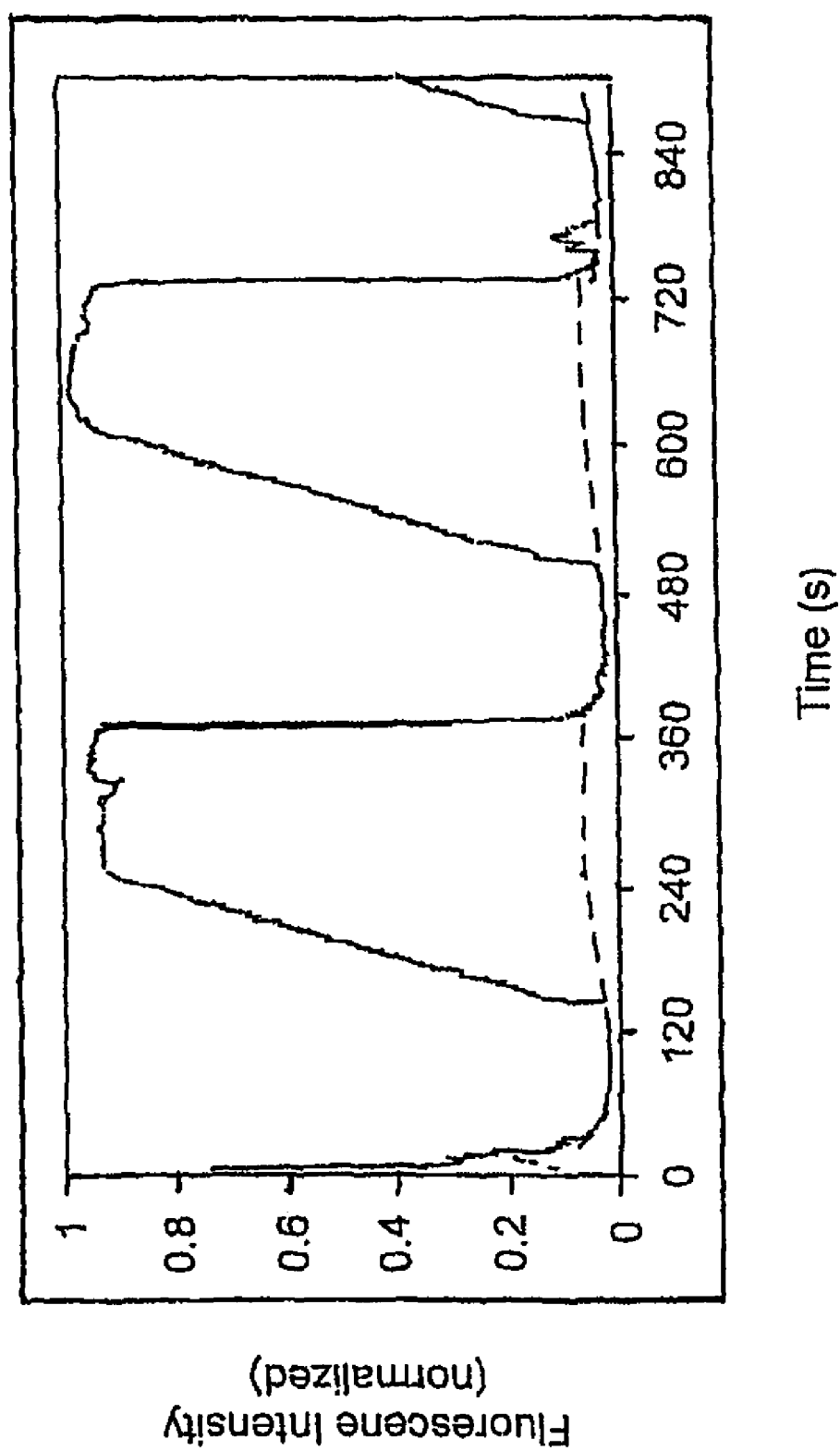
FIG. 51A is a graph showing the fluorescence measured according to one carry-over process.
Figure 51B:
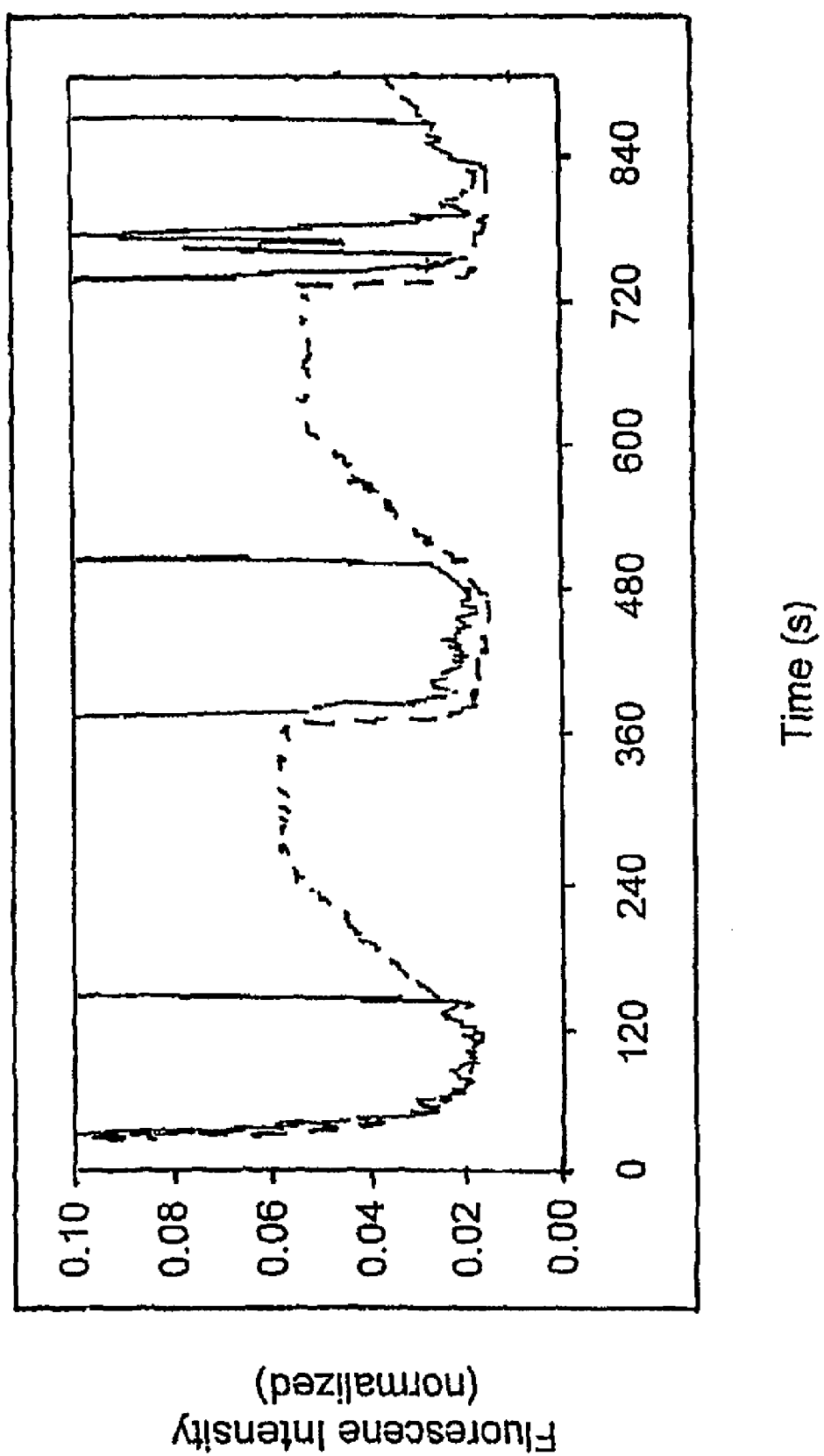
FIG. 51B is a graph showing that small gradients are visible in one carry-over process.

FIGS. 27A and 27B illustrate graphs showing the results of a carry-over experiment, similar to those presented in FIGS. 51A and 51B discussed herein below, but conducted with microfluidic system MS shown in FIGS. 26A-26D. FIG. 27B shows an enlarged Y-axis of FIG. 27A. Here, carry-over is now undetectable, that is, no gradient is visible in the "buffer-only" gradient (indicated by dashed lines).

Figure 28:
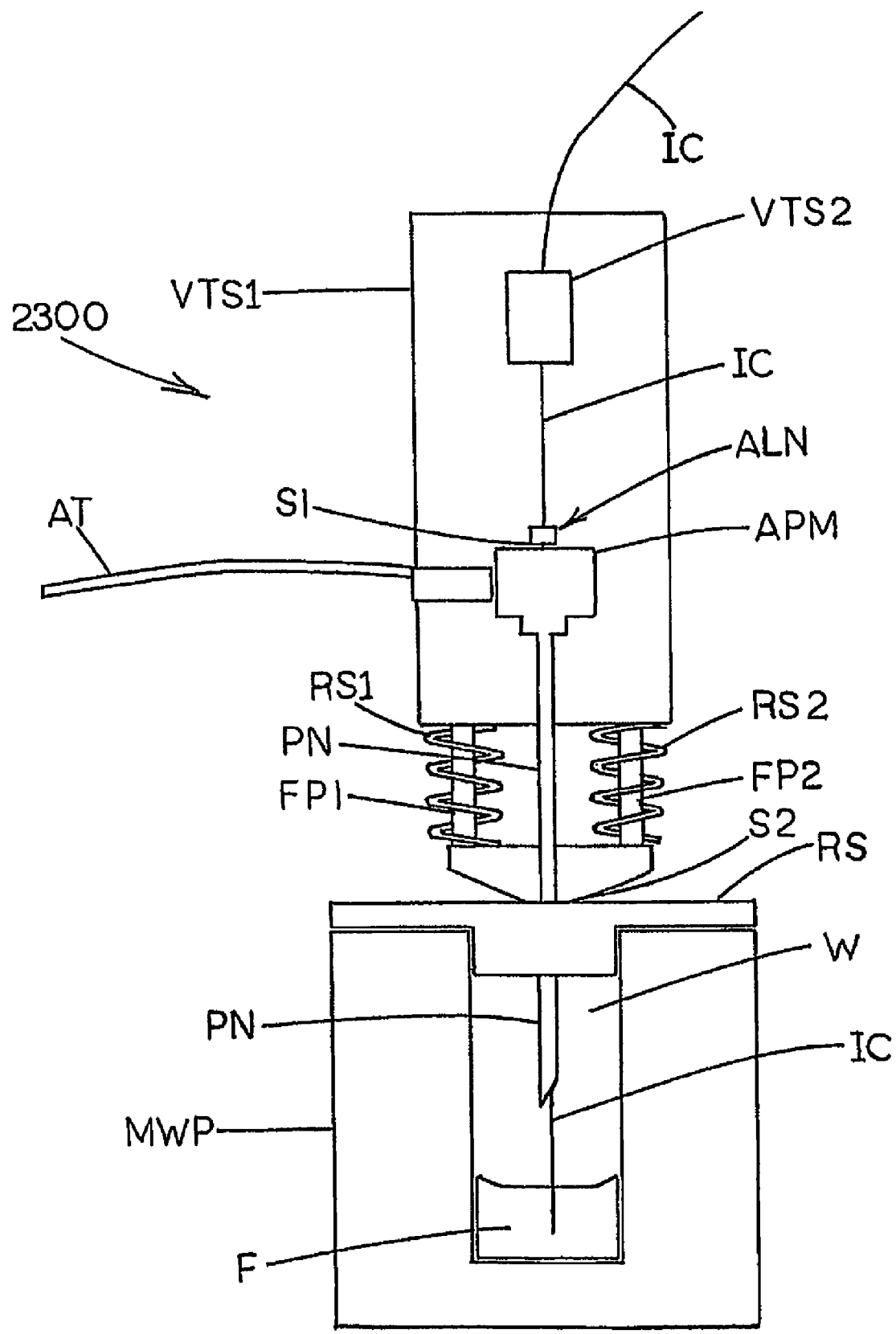
FIG. 28 is a side cross-sectional view of an automated liquid handling system for making a reversible, pressure-tight seal between a multi-well plate and an input capillary.
Figure 29A:
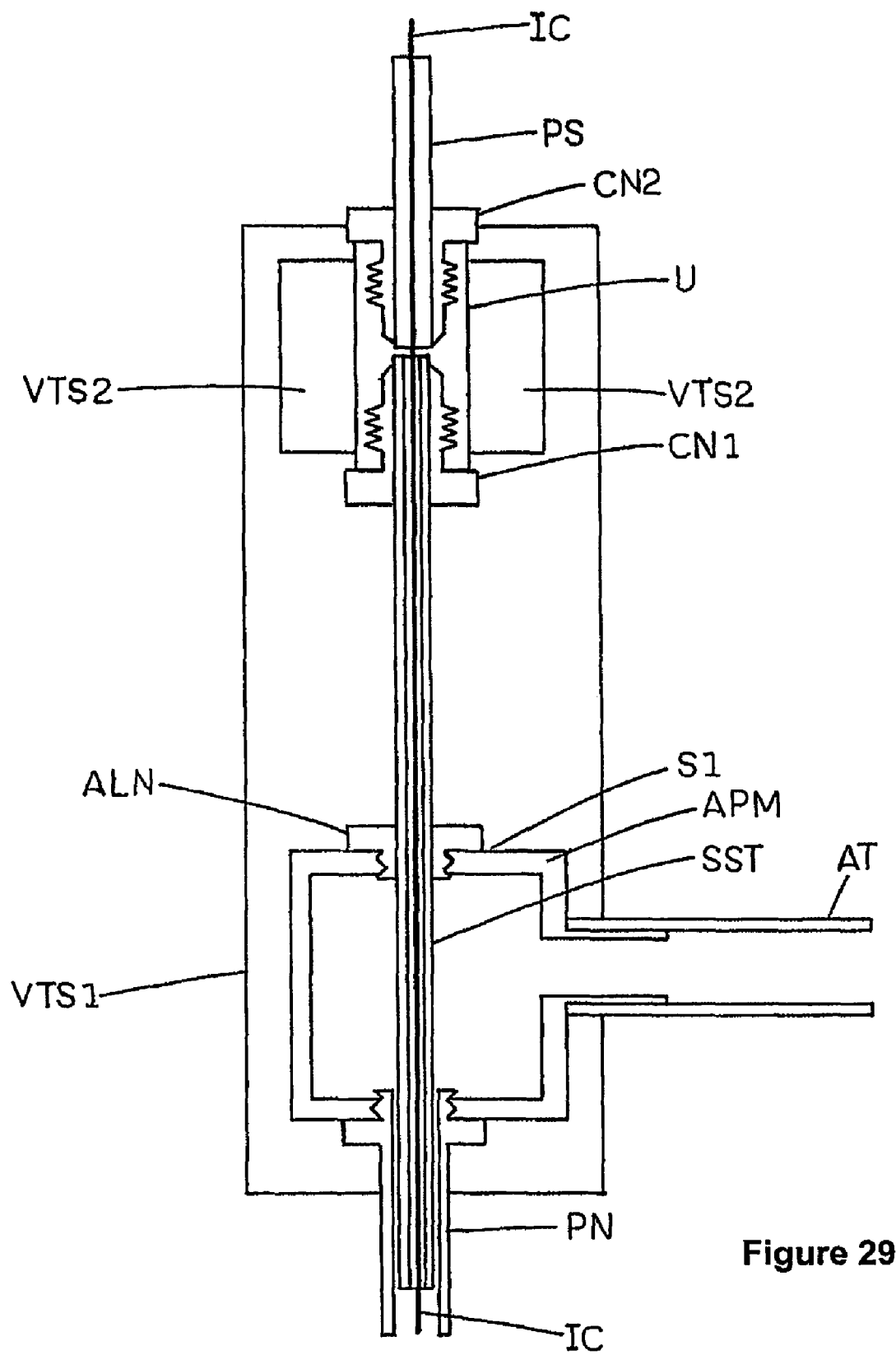
FIG. 29A is another side cross-sectional view of an automated liquid handling system for making a reversible, pressure-tight seal between a multi-well plate and an input capillary.
Figure 29B:
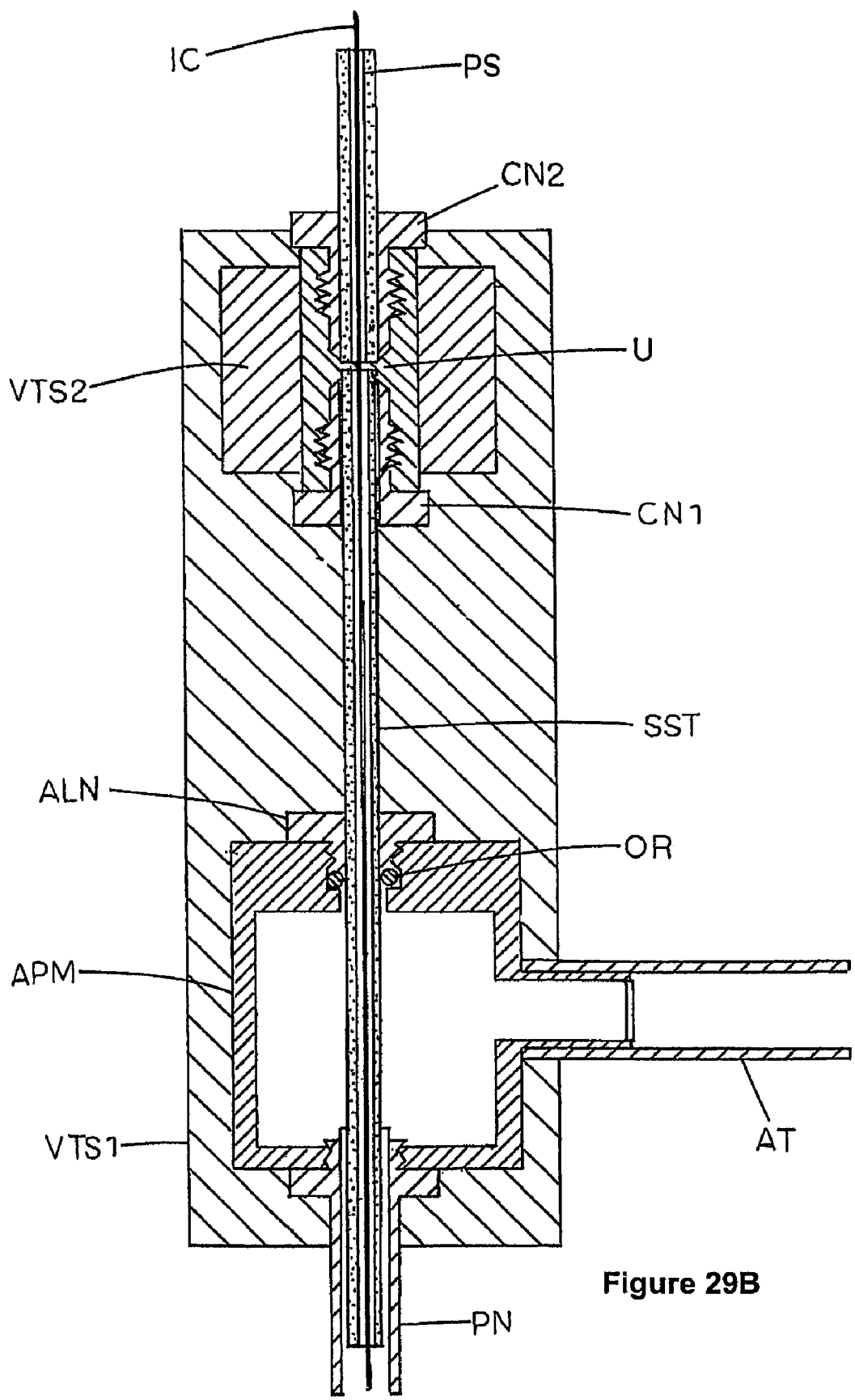
FIG. 29B is another side cross-sectional view of an automated liquid handling system for making a reversible, pressure-tight seal between a multi-well plate and an input capillary.

Pressure-tight fittings can be utilized to create a seal around a multi-well plate (such as multi-well plate MWP shown in FIGS. 26A-26D) for driving fluid through an injection loop (such as injection loop INL shown in FIGS. 26A-26D) and an aging loop (such as aging loop AL shown in FIGS. 26A-26D). FIGS. 28, 29A, and 29B illustrate side cross-sectional views of an automated liquid handling system, generally designated 2300, for making a reversible, pressure-tight seal between a multi-well plate MWP and an input capillary IC. Liquid handling system 2300 can be a modified FAMOS™ micro autosampler available from LC Packings, Sunnyvale, Calif. Multi-well plate MWP can include a well W containing a fluid F. Well W can be sealed with a rubber septum RS. Handling system 2300 can include a hollow piercing needle PN for piercing rubber septum RS. Input capillary IC can pass through the center of piercing needle PN into well W. Piercing needle PN can be connected to an air pressure manifold APM. Air pressure manifold APM can also be connected to an air tube AT that supplies pressurized air from an air compressor (not shown).

Referring again to FIG. 28, air pressure manifold APM can be mounted or otherwise attached to a first vertical translation stage VTS1. First vertical translation stage VTS1 can be motorized and controlled by a computer (not shown) of handling system 2300. The computer of handling system 2300 can direct first vertical translation stage VTS1 to move vertically to desired locations. Input capillary IC can be affixed to a second vertical translation stage VTS2. Second vertical translation stage VTS2 can be mounted onto first vertical translation stage VTS1. Thus, movement of second vertical translation stage VTS2 can move input capillary IC vertically with respect to piercing needle PN for allowing input capillary IC to retract into piercing needle PN to avoid damaging input capillary IC when piercing needle PN pierces septum RS. Vertical translation stages VTS1 and VTS2 and piercing needle PN can be positioned over well W for piercing rubber septum RS with a robotic arm (not shown).

Handling system 2300 can include pressure-tight seals at the following two locations: (1) a seal S1 can be positioned between input capillary IC and air pressure manifold APM for providing sealing as capillary IC moves within manifold APM; and (2) a seal S2 can be positioned between piercing needle PN and multi-well plate MWP. Seal S1 can be created by an air-lock nut ALN that can be a threaded screw through which a hole is drilled. The diameter of the hole in nut ALN can match the diameter of input capillary IC such that only a small gap remains for allowing capillary IC to slide through the air-lock nut ALN as second vertical translation stage VTS2 moves vertically. Seal S2 can be created by forcing needle PN into septum RS.

Referring to FIG. 28, handling system 2300 can include a spring loaded foot SLF mounted by two foot posts FP1 and FP2 with return springs RS1 and RS2, respectively; for preventing seal S2 from lifting up while piercing needle PN moves vertically. Foot posts FP1 and FP2 can be fixed to foot SLF and slide in and out of vertical translation stage VTS1, thus return springs RS1 and RS2 push multi-well plate MWP downward as piercing needle PN moves upward.

FIG. 29A illustrates a side cross-sectional view of air pressure manifold APM and vertical translation stages VTS1 and VTS2. According to one embodiment, input capillary IC can be made of fused silica having an outside diameter of 150 micrometers and an inside diameter of 75 micrometers. The end (not shown) of input capillary IC that extends into the fluid can have its polyimide jacket stripped to reduce the possibility of carryover of fluid in any gap that may form between the silica wall and its polymide jacket. Manifold APM can include an air-lock nut ALN and a stainless steel tubing SST providing mechanical rigidity to input capillary IC to form a seal S1 whereby stainless steel tube SST, with input capillary IC contained within, moves with respect to air pressure manifold APM. Stainless steel tubing SST can be rigidly mounted to second vertical translation stage VTS2 by fixing a union U to second vertical translation stage VTS2. Union U can be a MICROTIGHT® union available from Upchurch Scientific. A coned nut CN can be used to bind tubing SST to union U. Coned nut CN1 can be a NANOPORT® coned nut (PN F-126S) available from Upchurch Scientific. Another coned nut CN2 can affix capillary IC via plastic sleeve PS to union U and capillary IC for forming a pressure-tight seal. Plastic sleeve PS can be a MICROTIGHT® tubing sleeve (Part No. F-372) available from Upchurch Scientific. This configuration of sleeve PS, union U, tubing SST, and coned nuts CN1 and CN2 form a pressure-tight seal between capillary IC and the upper end of tubing SST for withstanding a pressure up to about 200 pounds per square inch. Capillary IC can range between an outside diameter of 90 and 360 micrometers. This assembly permits capillary IC to be inserted into the stainless steel tube with a pressure-tight seal being formed by tightening coned nut CN2. Furthermore, capillary IC can be changed by releasing coned nut CN2, threading another capillary IC through a sleeve PS and then through union U, and tightening coned nut CN2. This permits readily changing capillary IC and its associated microfluidic chip MFC with another.

Referring to FIG. 29A, air lock nut ALN can form a seal S1 between manifold APM and tubing SST. Air lock nut ALN can be formed by drilling a 1/32" hole through the center of a plastic screw. The diameter of the drilled hole can closely match the outer diameter of tubing SST. Grease can be used to lubricate any gap between the drilled hole and tubing SST. Tubing SST can also be small enough to pass into the inner bore of piercing needle PN. The gap between tubing SST and air-lock nut ALN can be sufficiently small that very little pressurized gas can pass. Tubing SST can be sufficiently rigid that it can be easily pushed through the tight gap in air-lock nut ALN. The gap between tubing SST and the inner bore of piercing needle PN can leave enough clearance for gas to flow freely from manifold APM through piercing needle PN into multi-well plate MWP, permitting rapid pressurization of a well in multi-well plate MWP.

Referring to FIG. 29A, the configuration shown can create a nearly pressure-tight seal whereby input capillary IC can move vertically with respect to piercing needle PN to create seal S1 between capillary IC and manifold APM. Alternatively, seal S1 can be formed as depicted in FIG. 29B. An o-ring OR compressed by air lock nut ALN forms the seal between air pressure manifold APM and stainless steel tube SST.

Figure 30:
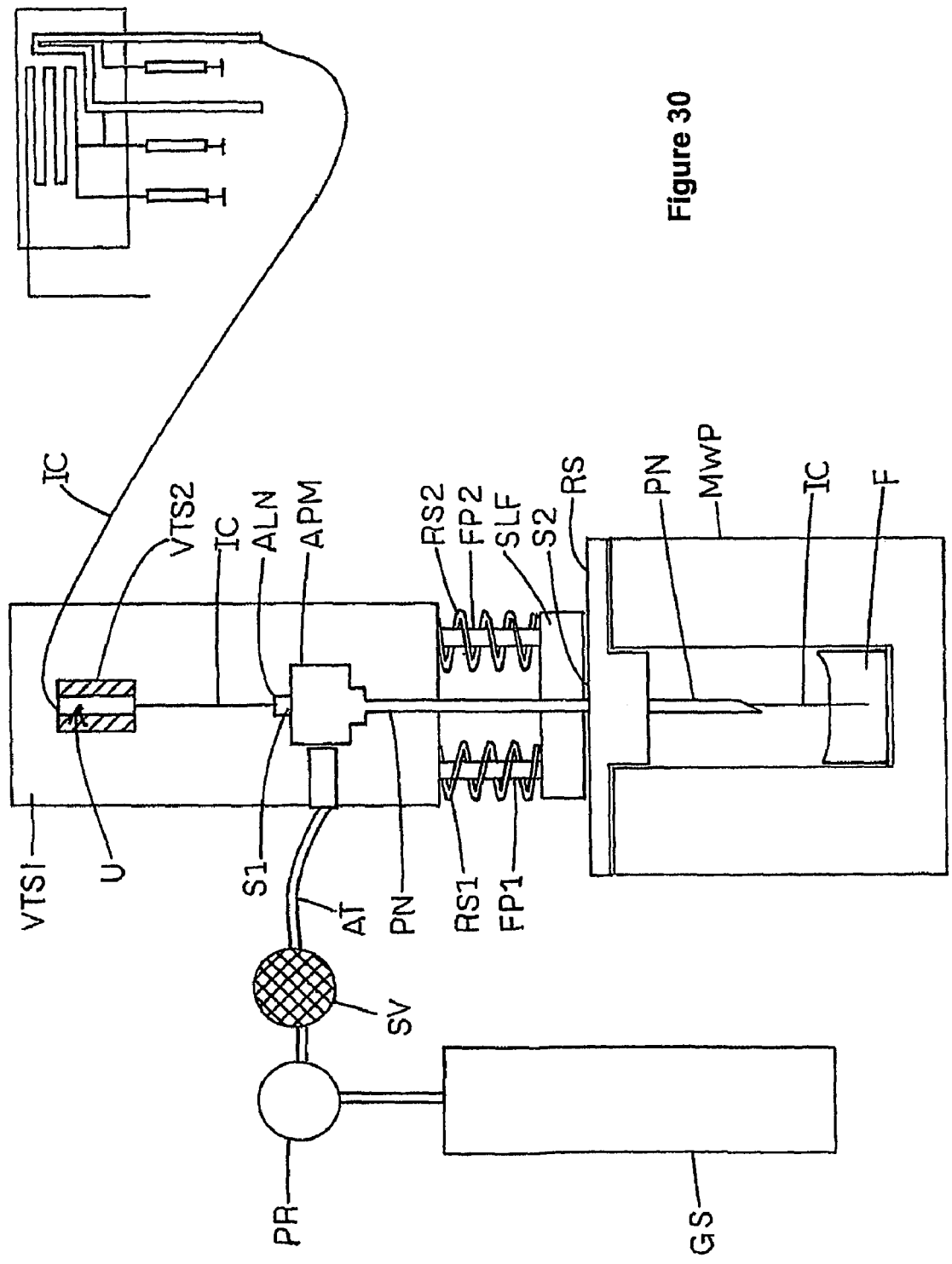
FIG. 30 is cross-sectional view of a configuration for forming a seal in the automated liquid handling system shown in FIG. 29.

FIGS. 30, 31A, 31B, and 31C illustrate cross-sectional views of different configurations for forming seals S1 and S2 shown in FIG. 28. Referring to FIG. 30, a cross-sectional view of a configuration for forming seal S2 is illustrated. Seal S2 can be formed when rubber septum RS is positioned to cover well W of multi-well plate MWP. According to one embodiment, foot SLF is a circular foot that presses uniformly onto septum RS such that seal S2 between septum RS and multi-well plate MWP can withstand the pressure. Seal S2 between septum RS and needle PN can be formed by the action of needle PN piercing septum RS. Thus, seal S2 can be formed by septum RS that is pushed by foot SLF.

Referring to FIG. 31A, a cross-sectional view of a configuration for forming a seal S3 between an elastomeric gasket EG and a multi-well plate MWP is illustrated. As opposed to the configuration shown in FIGS. 28-30, seal S can be formed without utilizing a rubber septum (such as rubber septum RS shown in FIGS. 28-30). Elastomeric gasket EG can be held against the top of multi-well plate MWP with a foot FO, foot posts FP1 and FP2, and return springs RS1 and RS2. Gasket EG can include a small hole at about its center through which a piercing needle PN can pass with no gap for forming seal S between the top of multi-well plate MWP and piercing needle PN via gasket EG. Thus, seal S between piercing needle PN and multi-well plate MWP can be formed by gasket EG that is depressed downward by foot FO. Optionally, a foil or thin plastic film can be used to seal multi-well plate MWP, for example, to prevent evaporation of water from the solutions in the wells of multi-well plate MWP. FIG. 31B illustrates a bottom view of foot FO, gasket EG, piercing needle PN, and capillary IC.

Alternatively, seal S2 can be formed as depicted in FIG. 31C. An o-ring OR compressed by foot lock nut FLN forms the seal between foot F and the piercing needle PN. A gasket EG forms the seal between foot FO and the top of multi-well plate MWP. Thus, seal S between piercing needle PN and multi-well plate MWP can be formed by o-ring OR, foot FO, and gasket EG that is depressed downward by foot FO. Again, a foil can be placed over the top of the wells W on multi-well plate MWP to prevent evaporation of samples during handling, and the piercing needle pierces this foil to permit access by input capillary IC.

Figure 32:
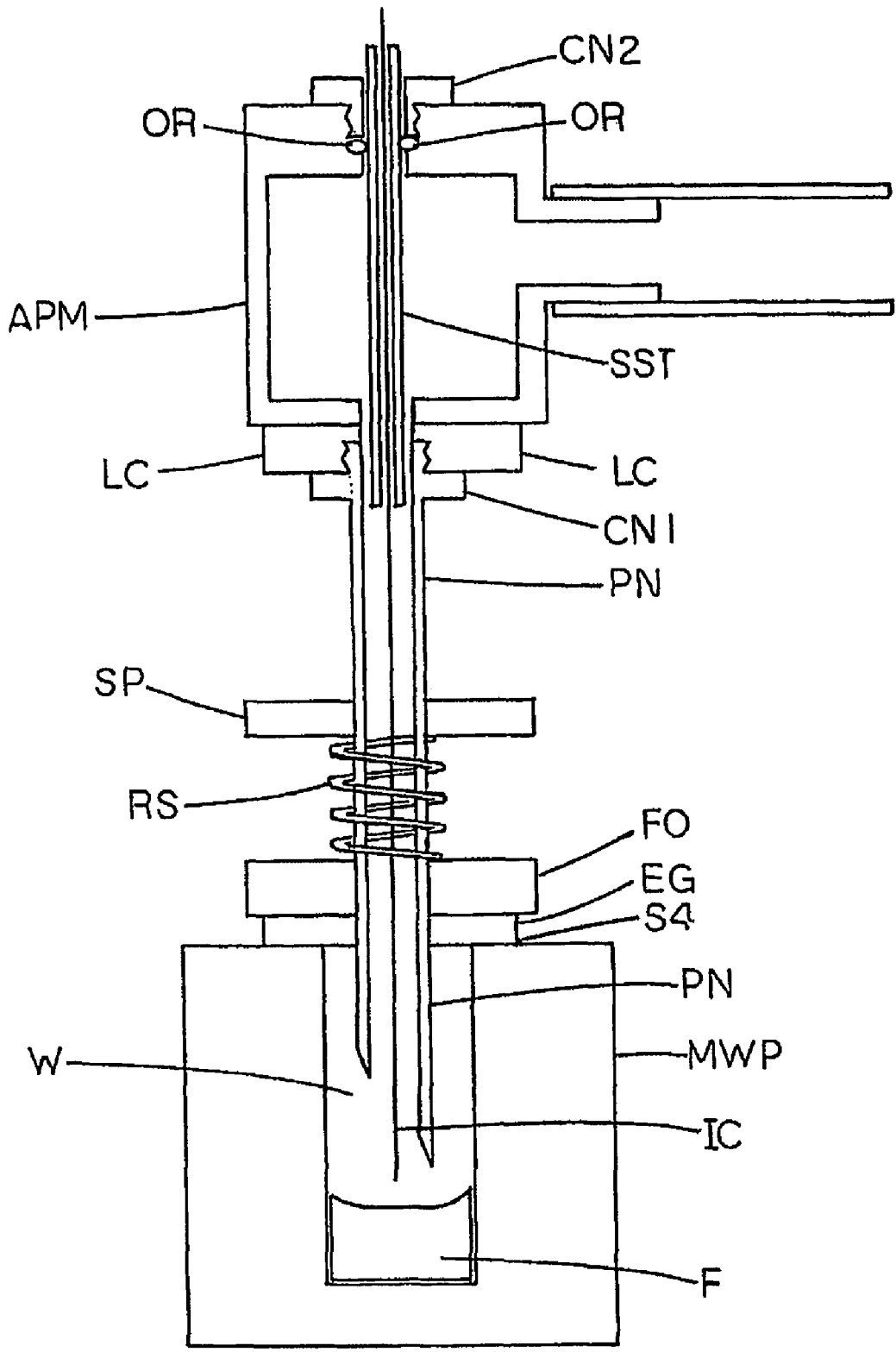
FIG. 32 is a cross-sectional view of an alternate configuration for forming a seal between an elastomeric gasket and a multi-well plate.

FIG. 32 illustrates a cross-sectional view of an alternate configuration for forming a seal S4 between an elastomeric gasket EG and a multi-well plate MWP. This configuration can provide sufficient force to always withstand the applied pressure. The configuration can include a foot FO and an elastomeric gasket EG. Elastomeric gasket EG can be suspended by a return spring RS affixed to a stop plate SP that is bonded to a piercing needle PN for allowing foot FO to automatically level as it touches the top of multi-well plate MWP. A vertical translation stage (such as second vertical translation stage VTS2 shown in FIG. 31A) can push piercing needle PN downward. As the vertical translation stage pushes piercing needle PN downward, foot FO pushes upward on return spring RS which pushes against a stop plate SP bonded to piercing needle PN. Thus, the force of foot FO being pushed against multiwell plate MWP is transmitted to piercing needle PN which is mounted to a through-hole load cell LS. Load cell LC can be a load cell (PN LC8100-200-10) available from Omega Engineering Inc. of Stamford, Conn., U.S.A. Alternatively, foot FO can be directly bonded to piercing needle PN such that the force on the foot is directly transmitted to load cell LC. The internal electrical resistance of load cell LC varies with load on the cell. This resistance can be measured by applying an excitation voltage and then measuring the resultant electrical current with a current-measuring device, such as model DP25B from Omega Engineering Inc. A computer (not shown) can monitor the signal from the load cell to measure the force on foot FO, and use this as a feedback signal to indicate that the vertical translation stage can stop when a pre-determined force is reached. An o-ring OR can be used to compressively seal cone nut CN2 against air pressure module APM. According to one embodiment, well W can be one of 384 circular wells in multi-well plate MWP and the diameter of the opening of well W can be about 0.15 inches. Therefore, the area of the opening of well W in this embodiment is about 0.0177 inches, so a pressure of 200 pounds per square inch can be contained with a holding force of about 3.5 pounds.

Referring again to FIG. 30, the configuration can include an off-board compressed gas supply GS, or a suitable compressed gas cylinder or air compressor as known to those of ordinary skill in the art. Pressure can be controlled by a pressure regulator PR that can feed an electrically-actuated switch valve SV. Switching valve SV can be connected to a 24-Volt power supply.

According to some exemplary experiments, flows have been generated of 75 microliters per minute through the injection loop with pressures of 125 pounds per square inch in the multi-well plate. As described herein, the flow rate through the microfluidic chip is determined by the combined resistance to flow in the capillaries and microchannels. The total volume of flow through the system, which determines the degree of rinsing of the injection loop and the aging loop is then controlled by either modulating the pressure, modulating the total time that pressure is applied, or both. It is also possible to measure the flow through the outlet capillary (capillary CP1 in FIG. 26B) using a flow measuring device (flow measuring device FMD in FIG. 26B) capable of measuring flows of ~100 nanoliter/min, such as the SLG1430 available from Sensirion, Inc. of Zurich, Switzerland. Thus, the electrically-actuated switching valve can be switched off when the desired volume has flown through the injection loop.

As described above, flow through the on-chip injection loop can be driven by a vacuum at the output rather than a pressure at the input. While this limits the pressure difference to 15 pounds per square inch, it obviates the need for all of the special pressure-tight seals described above. The only pressure-tight seal needed is the seal between the outlet capillary and the vacuum container, and this seal need not be interrupted at any time during use of the microfluidic chip. The vacuum need only be vented and reapplied, which can be easily implemented with electrically-actuated switching valves in communication with the vacuum container.

Figures 33A, 33B:
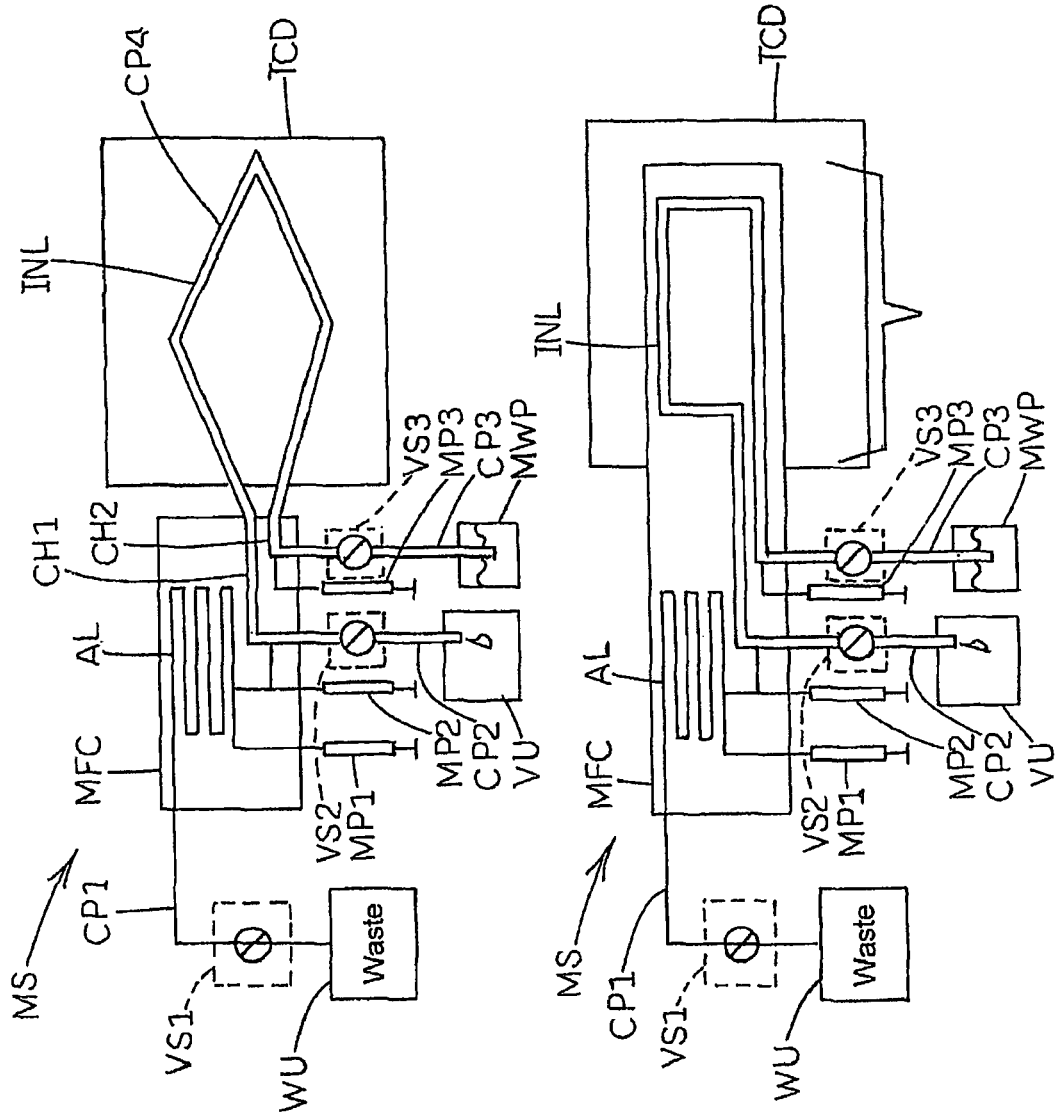
FIG. 33A is a schematic view of a microfluidic system for maintaining fluids in an injection loop and aging loop at different temperatures.
FIG. 33B is a schematic view of another microfluidic system for maintaining fluids in an injection loop and aging loop at different temperatures.

In some instances, fluid in an injection loop (such as injection loop INL shown in FIGS. 26A-26D) should be maintained at a temperature different than that of an aging loop (such as aging loop AL shown in FIGS. 26A-26D). For example, a biochemical assay should be run at 37° Celsius in the aging loop while the fluid in the injection loop should be stored at 4° Celsius until the fluid enters the aging loop. FIGS. 33A and 33B illustrate schematic views of different microfluidic systems, generally designated MS, for maintaining fluids in an injection loop INL and aging loop AL at different temperatures. Microfluidic system MS can include a microfluidic chip MFC, a waste unit WU, a vacuum unit VU, a multi-well plate MWP, microsyringe pumps MP1, MP2, and MP3, and an injection loop INL. Waste unit WU can be connected to aging loop AL via a capillary CP1. Vacuum unit VU and multi-well plate MWP can be connected to injection loop INL via capillaries CP2 and CP3, respectively. Microfluidic system MS can also include fluid freeze valves VS1, VS2, and VS3 connected to capillaries CP1, CP2, and CP3, respectively.

Referring specifically to FIG. 33A, injection loop INL can comprise channels CH1 and CH2 in microfluidic chip MFC and a capillary CP4. Channels CH1 and CH2 and capillary CP4 can form injection loop INL and fluidly connect microsyringe MP3 and multi-well plate MWP at one end of injection loop INL to vacuum unit VU, aging loop AL, waste unit WU, and microsyringe pumps MP1 and MP2 at an opposing end of injection loop INL. Microfluidic system MS can also include a temperature control device TCD (such as a Peltier thermoelectric device) connected to a portion of capillary CP4 for cooling the fluid in that portion of capillary CP4. Temperature control device TCD can maintain the fluid at a desired temperature such as a desired temperature lower than the fluid in aging loop AL. Capillaries can be connected to chips in accordance with embodiments disclosed in a co-pending, commonly owned U.S. Provisional Application entitled MICROFLUIDIC CHIP APPARATUSES, SYSTEMS, AND METHODS HAVING FLUIDIC AND FIBER OPTIC INTERCONNECTIONS, U.S. Provisional Application No. 60/707,2466, the content of which is incorporated herein in its entirety.

FIG. 33B illustrates a schematic diagram of microfluidic chip MFC having a portion containing injection loop INL that extends into temperature control device TCD. In this embodiment, injection loop INL is contained entirely on-chip and is located to a side portion of microfluidic chip MFC attached to temperature control unit TCU.

As previously discussed, noise in a fluid mix concentration or poor mixing of constituents can result in poor data quality in microfluidic systems. This poor data quality is typically observed as a random series of locally steep concentration gradients in the mixed fluids. Steep concentration gradients can be reduced via molecular diffusion and dispersion. In a microfluidic system, molecular diffusion and dispersion can occur as a fluid advances through a microscale channel. Diffusion and dispersion transport the fluid from regions of high concentration to regions of low concentration, occur whenever the concentration gradient is non-zero, and decrease the magnitude of the concentration gradient.

Diffusion in the axial direction of a microfluidic channel can be seemingly greater than expected from molecular diffusion. This is because microfluidic channels have a parabolic velocity profile that is typical for laminar flow in a tube—the axial velocity is maximal and the velocity at the wall is zero. Thus, a concentration gradient experiences dispersion arising from both molecular diffusion and from distortion of the gradient by the velocity profile, a phenomenon called Taylor-Aris dispersion. Although not intending to be bound by theory, the chemical, therefore, appears to have a different axial diffusion coefficient, D', provided by the following equation:

$$D' = D_c + \frac{r^2 V^2}{48 D_c}$$

wherein $D_c$ is the diffusion coefficient, r is the radius of the channel, and V is the average velocity.

Figure 34:
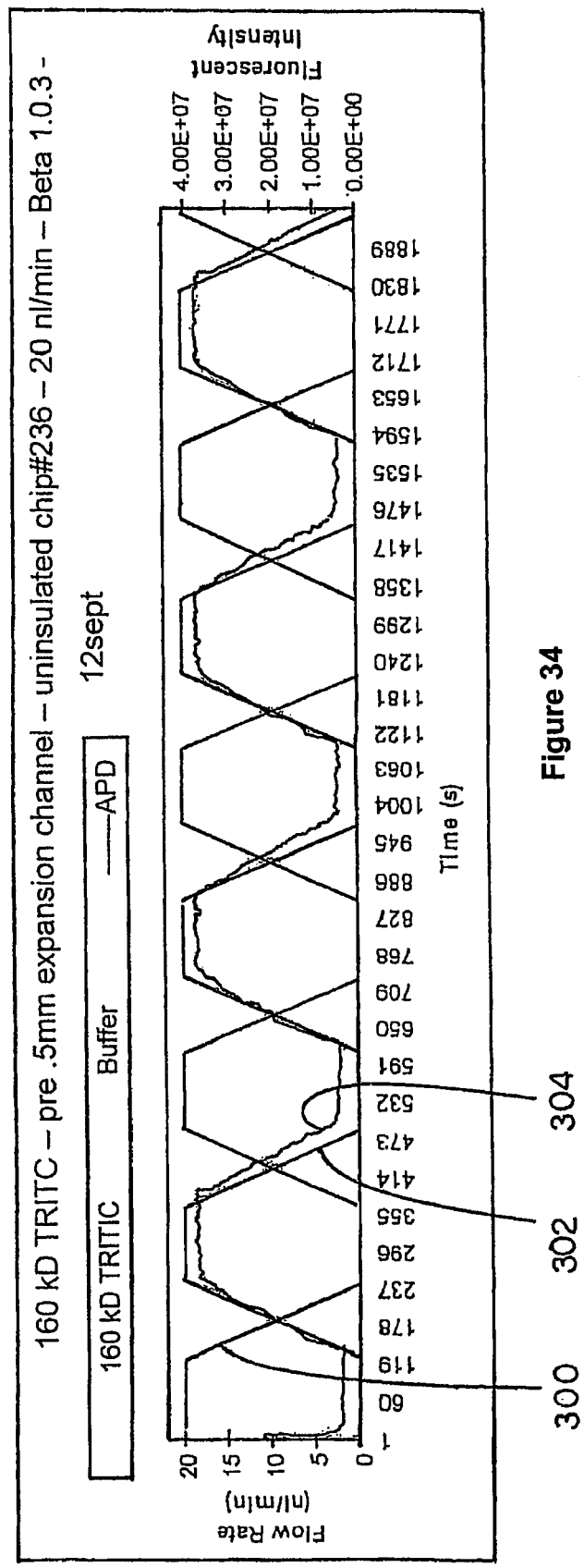
FIG. 34 is an exemplary graph showing the noise generated by a first and second pump advancing fluid in a microfluidic system such as the system shown in FIG. 8.

Regarding FIG. 34, a concentration gradient can be measured over time at one point in a microfluidic system producing a time-varying signal. Conversely, the concentration gradient can be measured along the length of the channel, producing a distance-varying signal. The two signals are coupled by the flow of the fluid containing the gradient along the length of the channel. The desired gradient is one that varies with defined frequency—temporal frequency and spatial frequency. Noise in a concentration gradient appears as an unintended or unexpected oscillation of the concentration. Therefore, a concentration gradient can be thought of as an oscillation in chemical concentration in which there are several contributing frequencies. Noise is the contribution of external disturbances having a spectrum of temporal and spatial frequency. Frequently, noise has a higher frequency than the desired concentration gradient. When the concentration gradient is considered as a spatially varying signal, noise is, therefore, manifested as locally steep concentration gradients superposed on the desired, concentration gradient.

Figure 35:
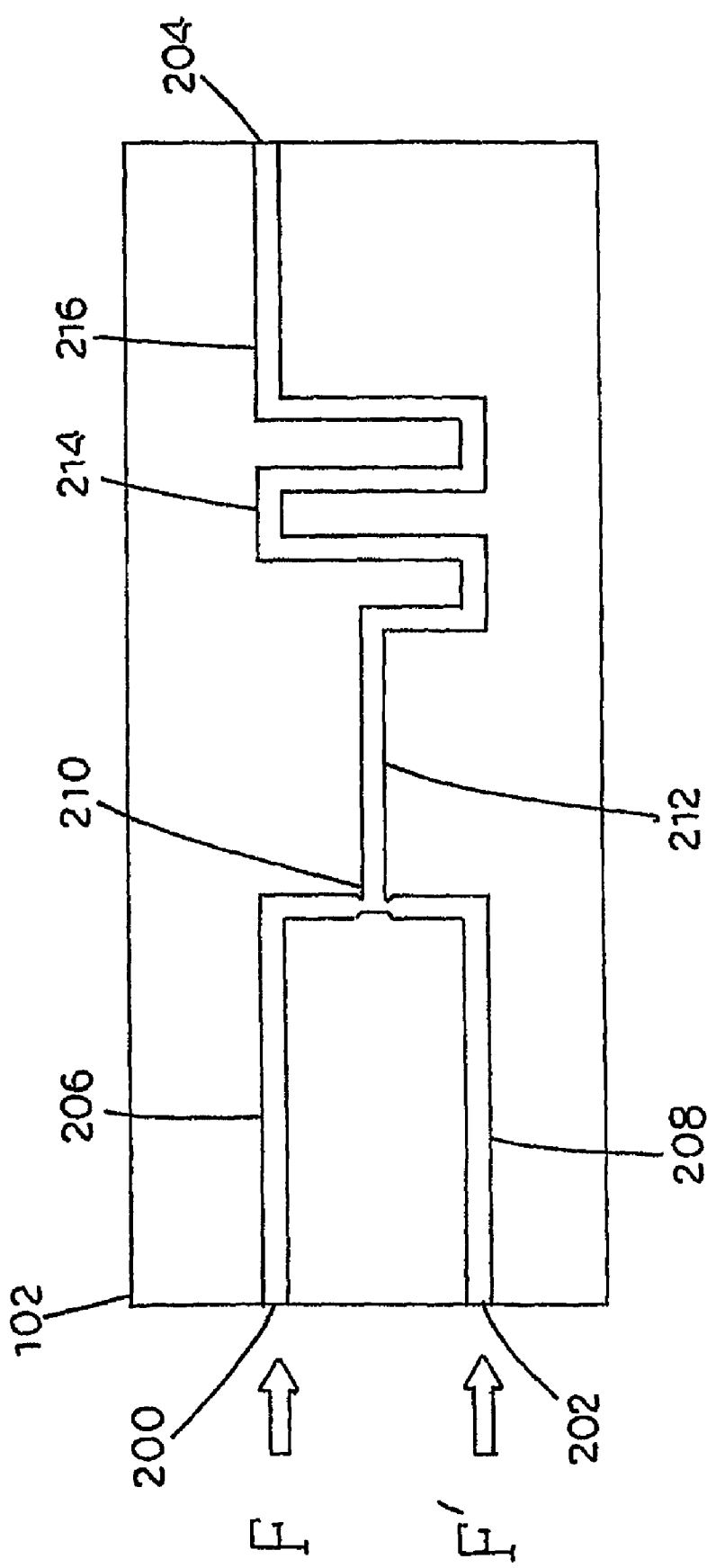
FIG. 35 is a schematic diagram of the channel and mixing region layout of a microfluidic chip.

Specific channel geometries, referred to herein as controlled dispersion elements, can facilitate diffusion and dispersion that more strongly dissipate these steeper concentration gradients—the higher spatial frequency components contributed by noise—while having only small effects on the shallower gradients—the lower spatial frequency components of the desired gradient. It is, therefore, possible to use the geometries to filter out noise associated with mechanical instabilities. For example, the "racetrack" effect caused by a fluid advancing through a curved channel can provide increased dispersion. Additionally, for example, controlled dispersion elements such as channel expanders and reducers can provide increased dispersion. An expander is a channel section where the cross-sectional area of the channel increases in the direction of fluid flow. A reducer is a channel section where the cross-sectional area of the channel decreases in the direction of fluid flow. An expander can be followed downstream by a reducer to form an expansion channel, as described in more detail below. Additionally, outpockets of channels can increase dispersion by creating local regions where the fluid is nearly stagnant. As fluid of differing concentration flows past these outpockets, diffusion between slower moving fluid in the outpocket and the passing fluid near the center of the channel causes dispersion of concentration gradients. For example, consider the case in which fluid of low concentration moves down the channel and fills the outpockets. If a fluid of higher concentration next moves down the channel, then diffusion into the low concentration fluid in the outpocket can decrease the concentration nearer the center of the channel, decreasing the magnitude of the concentration at the center. Again, if a fluid of lower concentration now follows, diffusion out of the outpockets will elevate the concentration nearer the channel center. The total result is that oscillation in axial concentration gradients are reduced, with higher spatial frequencies being affected more strongly. These specific channel geometries can be formed at sections of a microfluidic chip, such as chip 102 shown in FIG. 35, where it is desired to reduce steep concentration gradients. The incorporation of controlled dispersion elements such as, for example, serpentine and expansion channels into microfluidic chips, such as chip 102, for reducing fluid flow noise is described hereinbelow.

Figure 36:
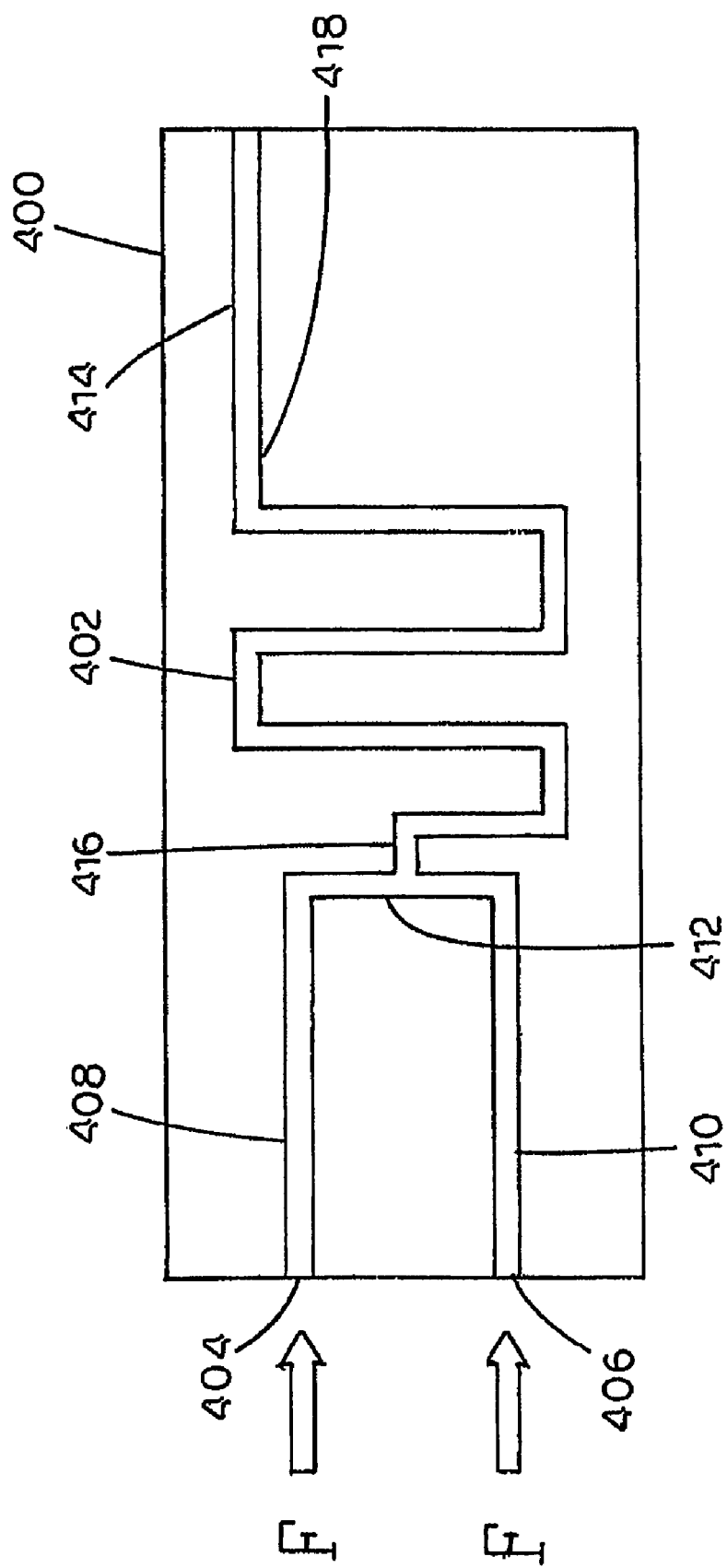
FIG. 36 is a schematic diagram of the layout of a microfluidic chip including a serpentine channel for reducing noise in a concentration gradient.

A controlled dispersion element in the form of a channel including one or more curved sections, such as a serpentine channel, can be used for diffusing and dispersing locally steep concentration gradients to dissipate noise in a fluid mix concentration. As stated above, the rate of dispersion can be increased by the "racetrack" effect, which can occur as a fluid advances through a curved channel section. FIG. 36 illustrates a schematic diagram of the layout of a microfluidic chip 400 including a serpentine channel 402 for reducing noise in a concentration gradient. Microfluidic chip 400 can include in some embodiments at least two inputs 404 and 406 connected to pumps, such as pumps $PA_1$ and $PA_2$ shown in FIG. 12, for advancing fluids F through chip 400. Separate, and different if desired, fluids F can be advanced by the pumps through premixing channels 408 and 410 and combined downstream at a fluid mixing region 412. Pumps $PA_1$ and $PA_2$ can be controlled by a pump controller, such as computer 108, to combine fluids F at mixing region 412 and vary the concentration gradient of the fluids over time. Chip 400 can also include a detection channel 414 downstream from serpentine channel 402 for subjecting the mixed fluids to analysis by detection equipment.

Serpentine channel 402 can be positioned immediately downstream from mixing region 412 to disperse noise in the concentration gradient immediately after mixing. In this embodiment, serpentine channel 402 has a length of 10 centimeters and a cross-sectional area of 500 square micrometers. Alternatively, serpentine channel can have a length between approximately 0.1 and approximately 500 centimeters and a cross-sectional area between approximately 10 and 100,000 square micrometers. Serpentine channel 402 can disperse the noise generated by any type of mechanical instability, such as the noise in the fluid flow originating upstream from serpentine channel 402. Channels that are longer and have more turns can more completely decrease noise in a concentration gradient, with the noise decreasing continuously along the length of the channel.

Figure 37:
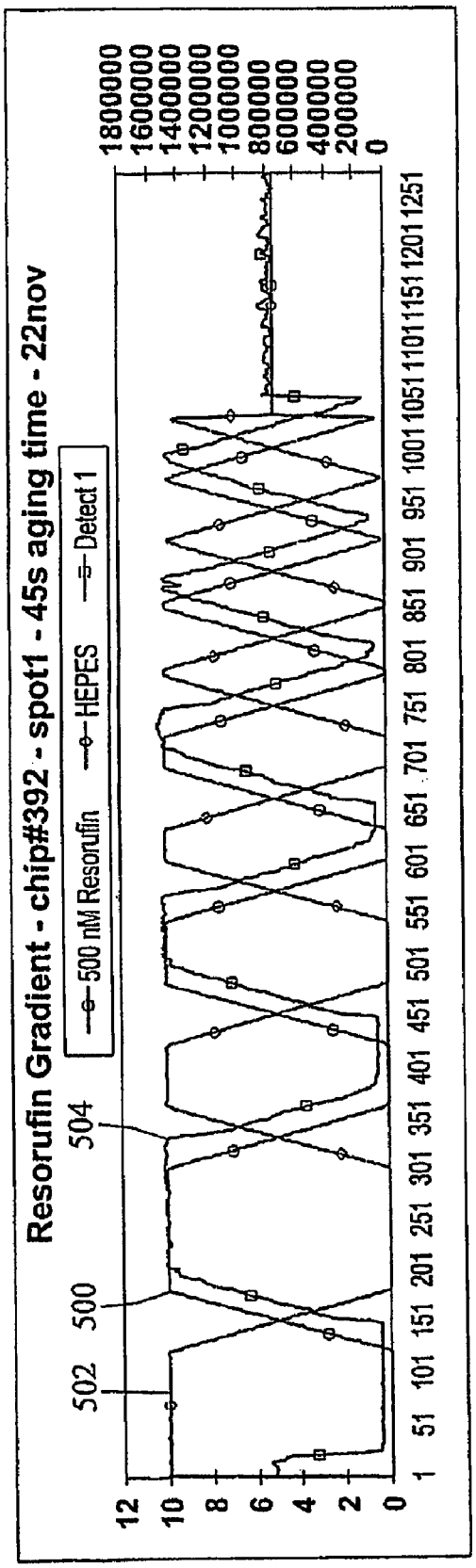
FIG. 37 is an exemplary graph of the results of running variable concentration gradients in the microfluidic chip shown in FIG. 8.
Figure 38:
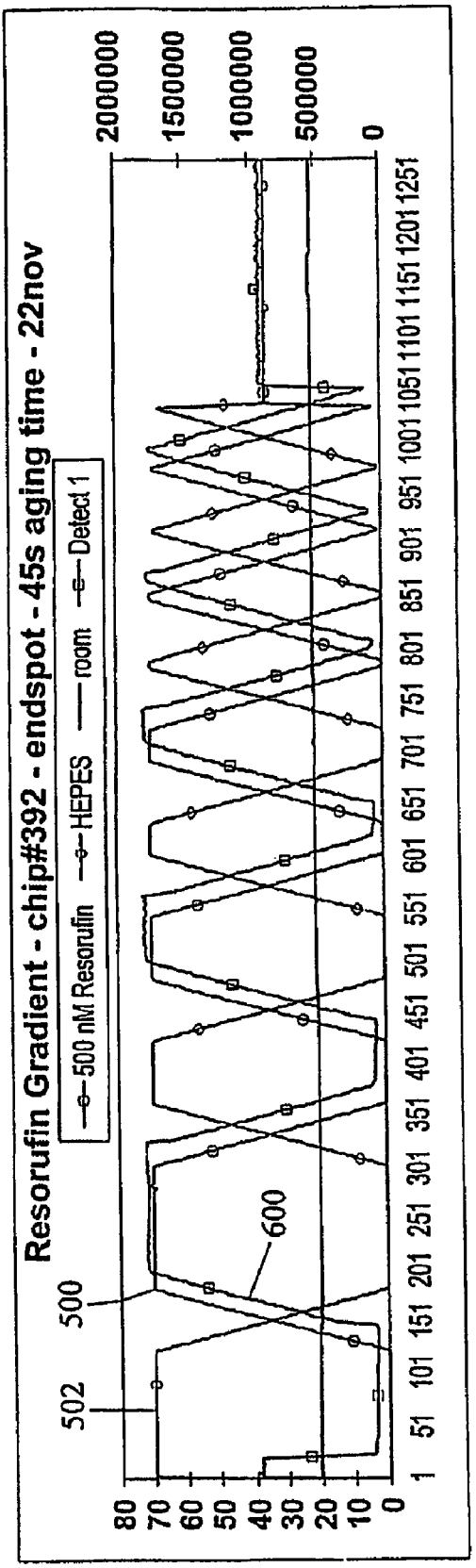
FIG. 38 is another exemplary graph of the results of running variable concentration gradients in the microfluidic chip shown in FIG. 8.

FIGS. 37 and 38 illustrate exemplary graphs of the results of running variable concentration gradients in chip 400 (shown in FIG. 36). In this example, pumps, such as pumps $PA_1$ and $PA_2$ shown in FIG. 12, advance fluorescent resorufin and a buffer, respectively, through channels 408 and 410, respectively. Graph lines 500 and 502 represent varying flow velocity profiles of fluids advanced in first and second premixing channels 408 and 410, respectively. Graph line 504 (shown in FIG. 37) represents the measurements collected just after mixing region 412 (shown in FIG. 36) at a point indicated by reference numeral 416. Referring now to FIG. 38, graph line 600 represents the measurements collected downstream from serpentine channel 402 (shown in FIG. 36) at a point indicated by reference numeral 418. By comparing the graphs shown in FIGS. 37 and 38, it can be seen that the data measured before serpentine channel 402 (shown at point 416 in FIG. 36) is noisier than the data measured after serpentine channel 402 (shown at point 418 in FIG. 36). The data measured after serpentine channel 402 is less noisy because some of the fluctuations in the concentration gradient were averaged out by dispersion through serpentine channel 402. In one embodiment, serpentine channel 402 can be connected to mixing region 412 by a connector channel having a length less than approximately 20 centimeters.

As stated above, noise in the concentration of fluid mixtures can also be reduced by a variety of controlled dispersion elements, including for example, expansion channels. When fluid flows through an expansion channel, noise in the fluid flow is reduced by dispersion. Dispersion can be increased by increasing the cross-sectional area of the expansion channel with respect to the channels connecting to the expansion channel, as described above in the equation for Taylor-Aris dispersion. A portion of a channel having an expansion or contraction of the cross-sectional area in the direction of fluid flow can increase dispersion.

Expansion channels can be shaped and sized for introducing a desired amount of dispersion over a predetermined spatial frequency. For example, an expansion channel acts as a low-pass filter and can be shaped and sized to possess selected cut-off frequency and decay. A channel possessing an expansion channel filter will filter only the region of the gradient that is in the filter and, thus, only the desired spatial frequency.

Figure 39A:
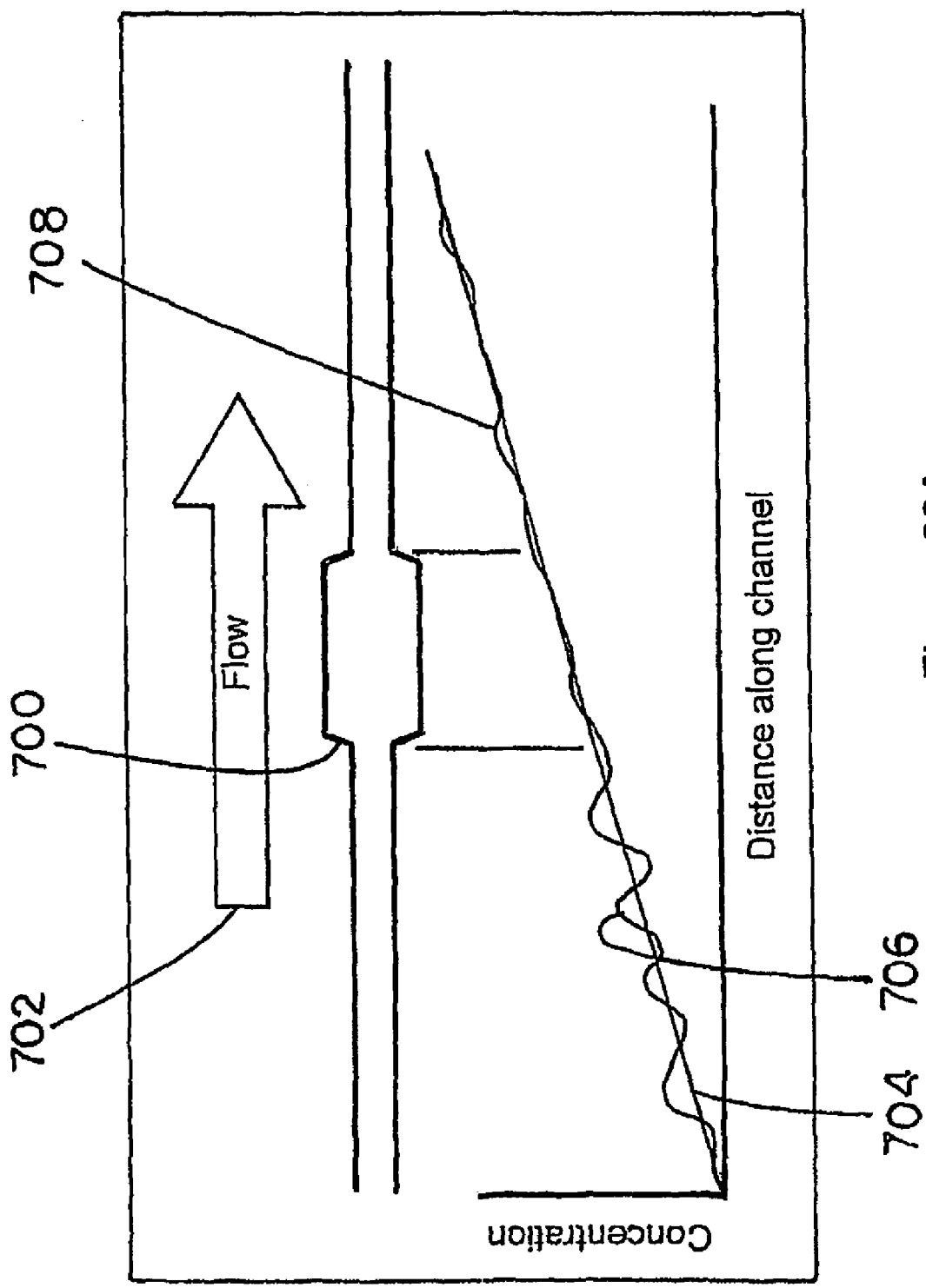
FIG. 39A is a schematic diagram of an expansion channel and a corresponding graph showing the concentration gradient of a fluid as the fluid advances along the length of the expansion channel.

FIG. 39A illustrates a schematic diagram of an expansion channel 700 and a corresponding graph showing the concentration gradient of a fluid as the fluid advances along the length of the expansion channel. The fluid flows in a direction indicated by reference numeral 702. Graph line 704 represents a desired zero-noise gradient generated by upstream pumps, such as pumps $PA_1$ and $PA_2$ shown in FIG. 12. The zero-noise gradient has a lower spatial frequency than the filter and, thus, is only slightly affected by the filter. Graph line 706 indicates the actual gradient of the fluid as it flows through channel 700. Features with spatial frequencies approximately equal to and exceeding that of the filter are filtered out (by diffusion and dispersion), so the concentration gradient, indicated by reference numeral 708, downstream from the filter has reduced noise from higher spatial frequencies. Thus, an expansion channel can act like a low-pass filter placed into the channel to filter noise in the chemical concentration gradient, much like a low-pass filter inserted into an electrical circuit to filter out noise in the electrical signal, and similarly the expansion channel can be designed to remove specific frequencies of noise. Increasing the diameter of the expansion filter increases the strength of the filter and decreases the cutoff frequency. Increasing the length of the filter increases the strength and decreases the cutoff frequency. Channel 700 can include tapered ends to eliminate nearly stagnant flows in the corners of channel 700. The tapered ends influence the frequency roll-off of the filter.

Figure 39B:
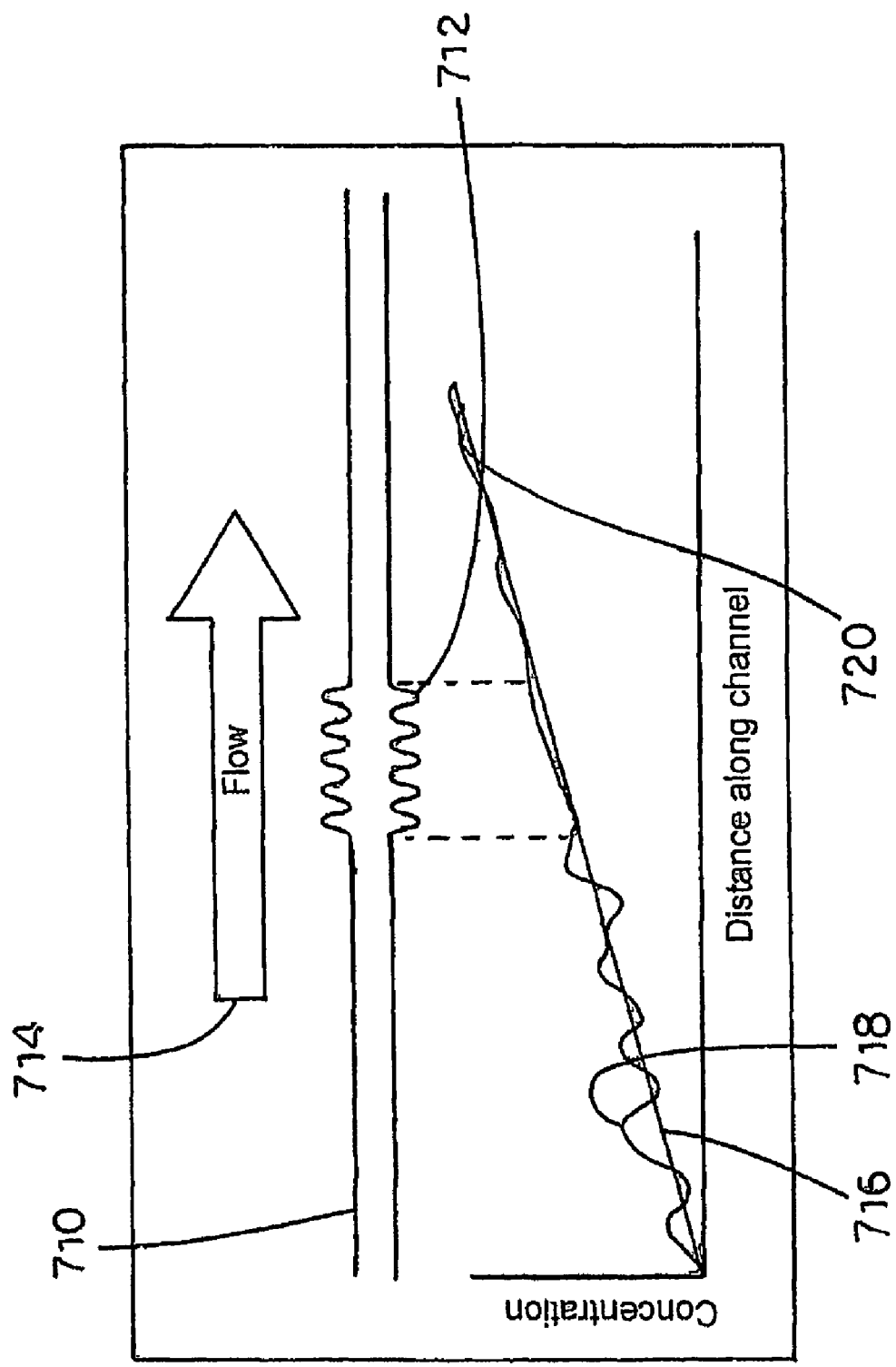
FIG. 39B is a schematic diagram of a plurality of outpockets and a corresponding graph showing the concentration gradient of a fluid as the fluid advances along the length of the expansion channel.

A similar filtering effect can be introduced by placing small outpockets along the wall of the microfluidic channel. Outpockets can be considered as small expansion channels placed in series. FIG. 39B illustrates a schematic diagram of a channel 710 having plurality of outpockets 712 and a corresponding graph showing the concentration gradient of a fluid as the fluid advances along the length of the expansion channel. The fluid flows in a direction indicated by reference numeral 714. Graph line 716 represents a desired zero-noise gradient generated by upstream pumps, such as pumps $PA_1$ and $PA_2$ shown in FIG. 12. The zero-noise gradient has a lower spatial frequency than the filter and, thus, is only slightly affected by the filter. Graph line 718 indicates the actual gradient of the fluid as it flows through channel 710. Features with spatial frequencies approaching that of the filter can be filtered out (by, for example, diffusion and dispersion), such that the concentration gradient, indicated by reference numeral 720, downstream from the filter has reduced noise from higher spatial frequencies. Increasing the distance outpockets 712 extend from the axis can increase the strength of the filter and decrease the cutoff frequency. Increasing the number of outpockets 712 can increase the strength and decrease the cutoff frequency.

Figure 40:
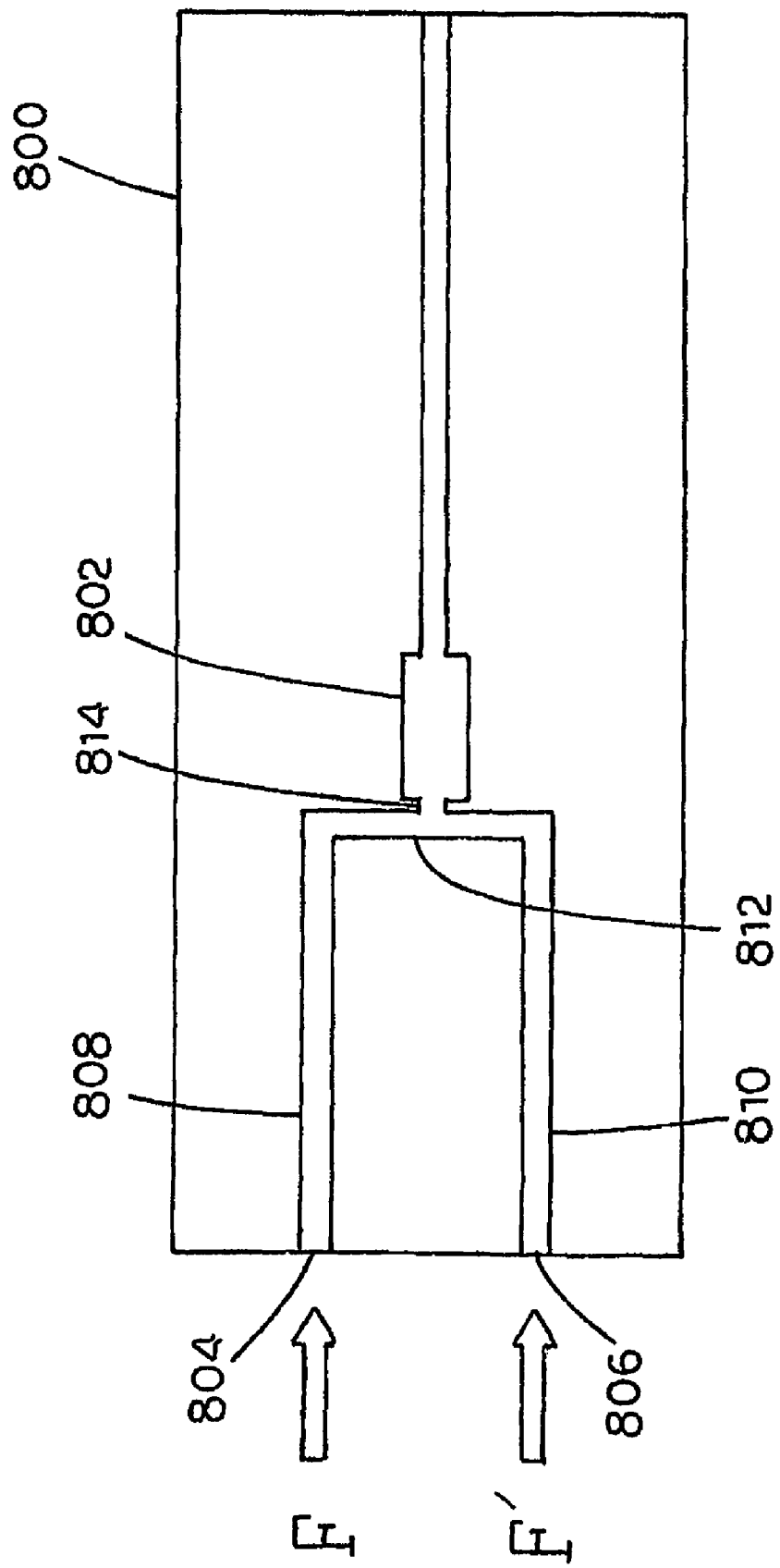
FIG. 40 is a schematic diagram of the layout of a microfluidic chip including an expansion channel for reducing noise in a concentration gradient.

FIG. 40 illustrates a schematic diagram of the layout of a microfluidic chip 800 including an expansion channel 802 for reducing noise in a concentration gradient. Microfluidic chip 800 can include two inputs 804 and 806 connected to pumps, such as pumps $PA_1$ and $PA_2$ shown in FIG. 12, for advancing fluids F and F', respectively, through chip 800. Separate, and different if desired, fluids F and F' can be advanced by pumps 104 and 106, respectively, through premixing channels 808 and 810, respectively, and combined downstream at a fluid mixing region 812. Mixing region 812 can have a cross-sectional area between approximately 10 and 100,000 square micrometers. Pumps $PA_1$ and $PA_2$ can be controlled by a pump controller, such as computer PC shown in FIG. 12, to combine the different fluids at mixing region 812 and vary the concentration gradient of the fluids over time. A connector channel 814 connects mixing region 812 to expansion channel 802. Expansion channel 802 can have a length between approximately 0.005 and 10 millimeters and a cross-sectional area between approximately 2 and 1,000 times the cross-sectional area of the connector channel 814. Microfluidic chip 800 can also include a connector channel 814 for connecting mixing region 812 to expansion channel 802. Connector channel 814 can have a length less than approximately 40 millimeters. The fluids are optionally laterally mixed before entering the expansion channel 802, wherein lateral is defined as being perpendicular to the streamlines of the fluid flow. The placement of expansion channel 802 downstream of mixing region 812 can take into consideration the time required for lateral mixing via diffusion of components in the different fluids entering from premixing channels 808 and 810. Thus, at a given volumetric flow rate and cross-sectional area of connector channel 814, the fluid travels, for example, 20 millimeters before it is well-mixed, then expansion channel 802 should not be placed nearer than 20 millimeters to mixing region 812, i.e. connector channel 812 should be at least 20 millimeters long. Alternatively, connector channel 814 can include geometries to laterally mix the fluids by, for example, chaotic advection, or connector channel 814 can include mechanical mixers, such as magnetic beads driven laterally across connector channel 814 by an oscillating magnetic field.

Figure 41:
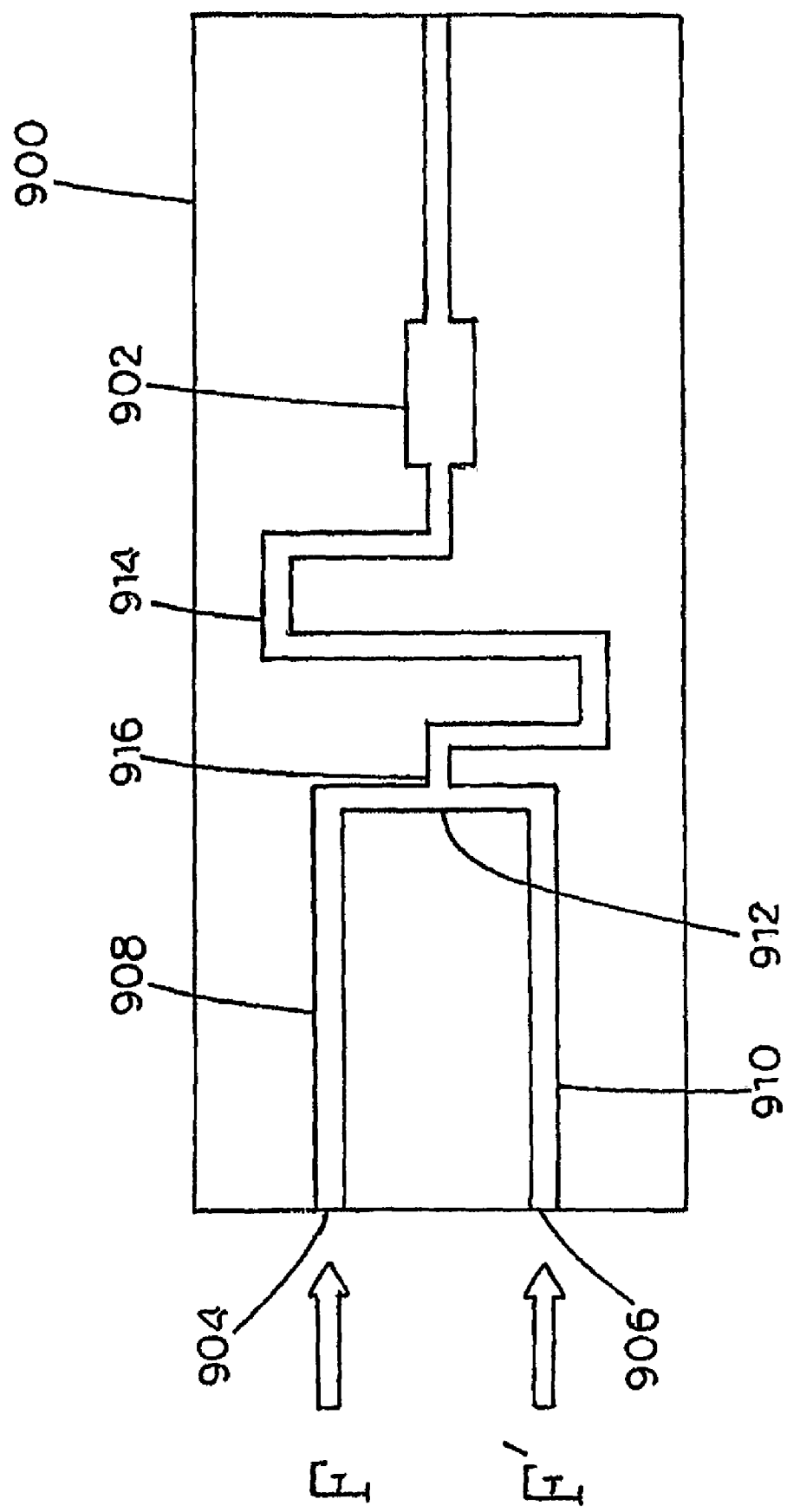
FIG. 41 is another schematic diagram of the layout of a microfluidic chip including an expansion channel for reducing noise in a concentration gradient.

FIG. 41 illustrates another schematic diagram of the layout of a microfluidic chip 900 including an expansion channel 902 for reducing noise in a concentration gradient. Microfluidic chip 900 can include inputs 904 and 906 for connection to pumps, such as pumps $PA_1$ and $PA_2$ shown in FIG. 12, for advancing fluids F and F', respectively, through chip 900. Separate, and different if desired, fluids F and F' can be advanced by pumps $PA_1$ and $PA_2$, respectively, through premixing channels 908 and 910, respectively, for advancing different fluids to a mixing region 912. Expansion channel 902 can be positioned immediately downstream from a serpentine channel 914 to disperse pump noise in the concentration gradient. Serpentine channel 914 can be positioned upstream from expansion channel 902 and immediately downstream from mixing region 912 to act as a connector channel to laterally mix fluids F and F'. Thus, a serpentine channel 914 can be used to provide sufficient channel length, bit still fit in a compact geometry on a microfluidic chip 102, to fully laterally mix the different fluids before the fluids enter expansion channel 902. Microfluidic chip 900 can also include a connector channel 916 for connecting mixing region 912 to serpentine channel 914.

Expansion channels, such as expansion channels 802 and 902 of FIGS. 40 and 41, respectively, can include certain features for achieving specific functions. For example, the expansion channels including abrupt changes in cross-sectional area tend to collect bubbles in the corners. The expansion channels can be tapered (i.e., the depth or width of the expansion channel at its ends can be changed in a gradual, continuous way) to overcome this problem. Additionally, abrupt changes in cross-sectional area introduce larger degrees of dispersion. This can cause an expansion channel to affect lower spatial frequencies more strongly—producing a more gradual roll-off of the frequency response of the expansion channel; conversely, a tapered expansion may have less dispersion and produce a sharper roll-off of the frequency response. Further, for example, the expansion channels can also be made narrow and deep for increasing the rate of mix via lateral diffusion in the expansion channel while retaining the function of being a filter.

Figure 42A:
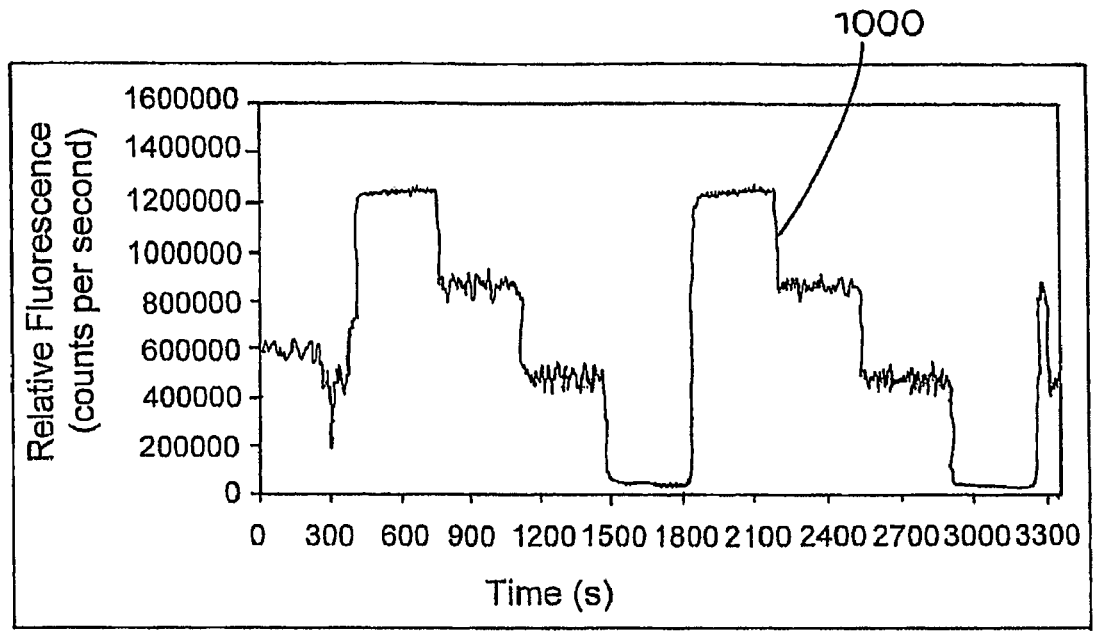
FIG. 42A is an exemplary graph showing noise generated by a first and second pump providing varying flow velocity profiles for fluids advanced by pumps in a chip such as the microfluidic chip shown in FIG. 8.
Figure 42B:
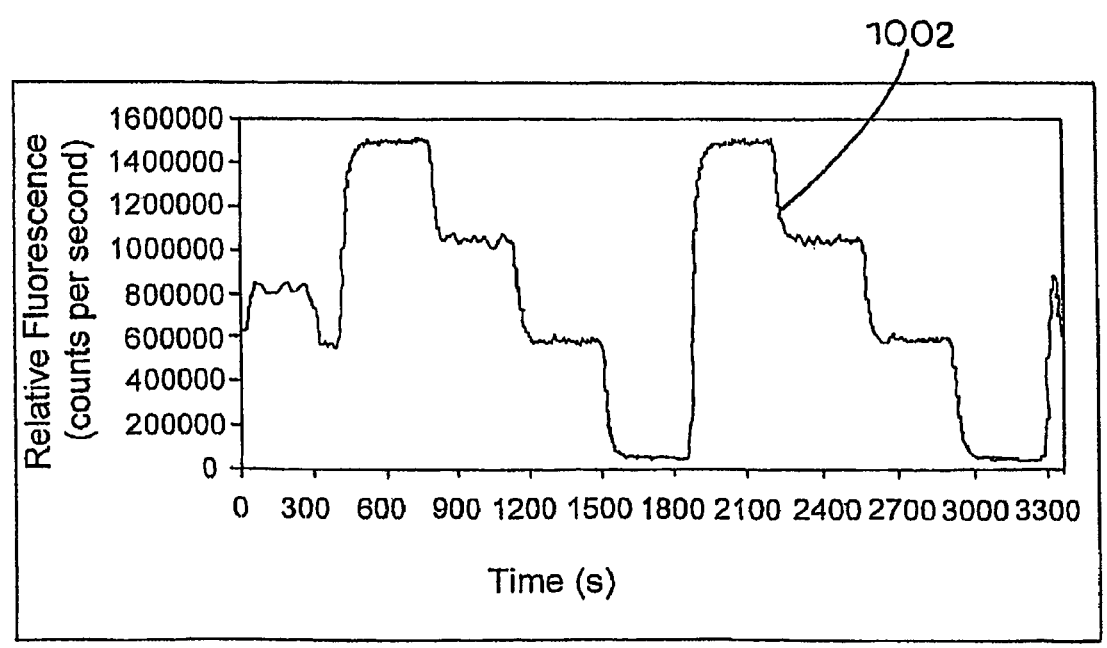
FIG. 42B is an exemplary graph showing the fluorescent signal measured immediately downstream from an expansion channel.

FIG. 42A illustrates an exemplary graph showing noise generated by pumps, such as first and second pumps $PA_1$ and $PA_2$ shown in FIG. 12, providing varying flow velocity profiles for fluids advanced by pumps in chip 800 (shown in FIG. 40) in a manner similar to that depicted in FIG. 34. Expansion channel 802 (shown in FIG. 40) measured 500 μm long by 300 μm wide by 100 μm deep. The fluid channel upstream and downstream of expansion channel 802 measured 25 μm wide by 15 μm deep. The combined volumetric flow rates of pumps $PA_1$ and $PA_2$ was 20 nl/min. The velocities of the pumps, and the resulting concentrations of fluorescent molecule are stepped through four steps (0:100, 33:67, 67:33, and 100:0). The flows are held constant at each step to better reveal the noise in the concentration gradient. Graph line 1000 represents the fluorescent signal measured by detection equipment immediately upstream from expansion channel 802. FIG. 42B illustrates an exemplary graph showing the fluorescent signal measured immediately downstream from expansion channel 802. As shown by graph line 1002, noise remains after flow through expansion channel 802; however, the noise is much less than that shown by graph line 1000 in FIG. 42A.

Figure 43:
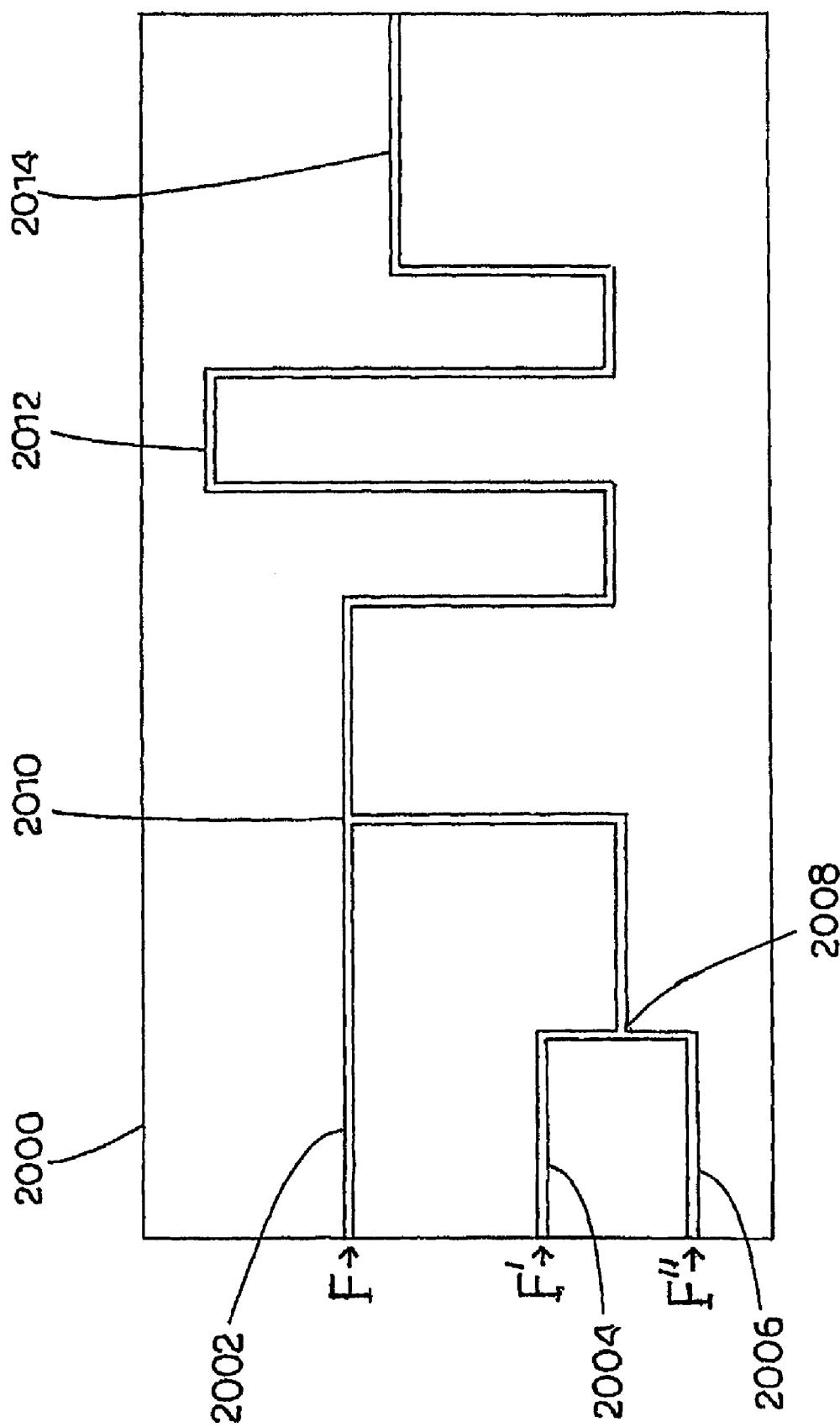
FIG. 43 is a schematic diagram of an exemplary embodiment of a microfluidic chip including channels for introducing three fluids.

Dispersion of different components in a mixing and reacting flow can lead to unexpected systematic errors in measurements of the reaction. Referring to FIG. 43, a schematic diagram of an exemplary embodiment of a microfluidic chip, generally designated 2000, including channels 2002, 2004, and 2006 for introducing fluids F, F", and F"', respectively. Fluids F' and F" mix at a first junction 2008. The flows of fluids F' and F" are controlled to produce linear concentration gradients useful in the methods of the presently disclosed subject matter described hereinabove in detail, and such as depicted in FIG. 34, with the combined volumetric flow rates of flows F' and F" equaling a constant. The mixed fluids F' and F" can then be mixed with fluid F at a second junction 2010. Here the flow rates of fluid F, F', and F" are constant, and the gradient generated at first junction 2008 persists.

In one instance, the concentration gradient generated at junction 2008 can have an analyte with a higher diffusivity than other components in the fluids. For example, the analyte is a low molecular weight inhibitor of an enzymatic reaction, with the enzyme being introduced in fluid F. The higher diffusivity of the inhibitor can cause it to disperse more rapidly than the enzyme. The result of this differential dispersion of components of the reaction is that the concentration of the inhibitor in a parcel of fluid traveling down aging loop 2012 varies over time. The concentrations of various components, including products of reactions, can be measured at detection point 2014.

Figure 44A:
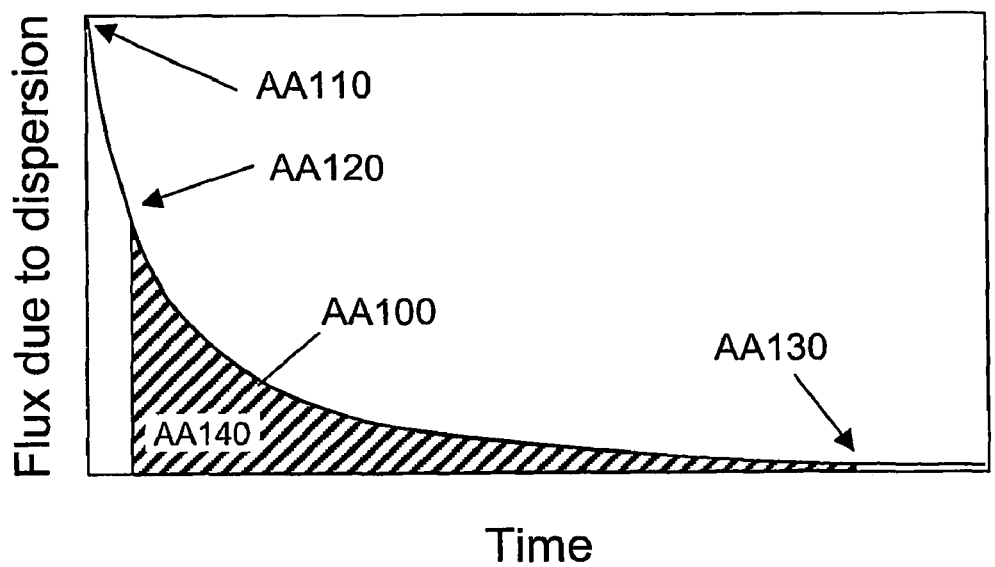
FIG. 44A is a graph showing flux (moles transported axially per unit time) due to dispersion of a concentration gradient of inhibitor over time in a fluid flowing down a microchannel of a microfluidic chip.

Referring to FIG. 44A, a plot of flux (moles transported axially per unit time) due to dispersion of a concentration gradient of inhibitor over time in a fluid flowing down a microchannel, such as those in microfluidic chip 2000 in FIG. 43, is shown. The plot, generally designated AA100, shows the flux of an inhibitor due to a concentration gradient generated by the mixing of fluids F' and F" at mixing point 2008. Point AA110 designates the point on curve AA100 immediately after mixing point 2008; point AA120 designates the point on curve AA100 corresponding to mixing point 2010; and point AA130 designates the point on curve AA100 corresponding to detection point 2014. The concentration gradient after mixing point 2008 is initially steep, so the flux at AA110 is initially large. Flux of the inhibitor makes the gradient less steep, so as the mixed fluids flow down the microchannel the flux decreases. The total change in concentration of the inhibitor due to dispersive flux as the fluid flows between mixing point 2010 and detection point 2014 is, therefore, proportional to the area designated AA140 under the curve AA100 between points AA120 and AA180.

This change in the concentration of the inhibitor over time can complicate many analyses. For example, in many analyses of enzyme behavior, the concentrations of components of the reaction are assumed to be constant throughout the reaction. The differential dispersion of the inhibitor, or any other low molecular weight species, such as a substrate, violates the assumption of constant concentration, and introduces errors into subsequent analyses. Differential dispersion of components can be greatly reduced by introducing dispersion into the gradient formed at junction 2008 but before it combines with fluid F at junction 2010. This can be accomplished through the incorporation of controlled dispersion elements, as exemplified in FIG. 45.

Figure 45:
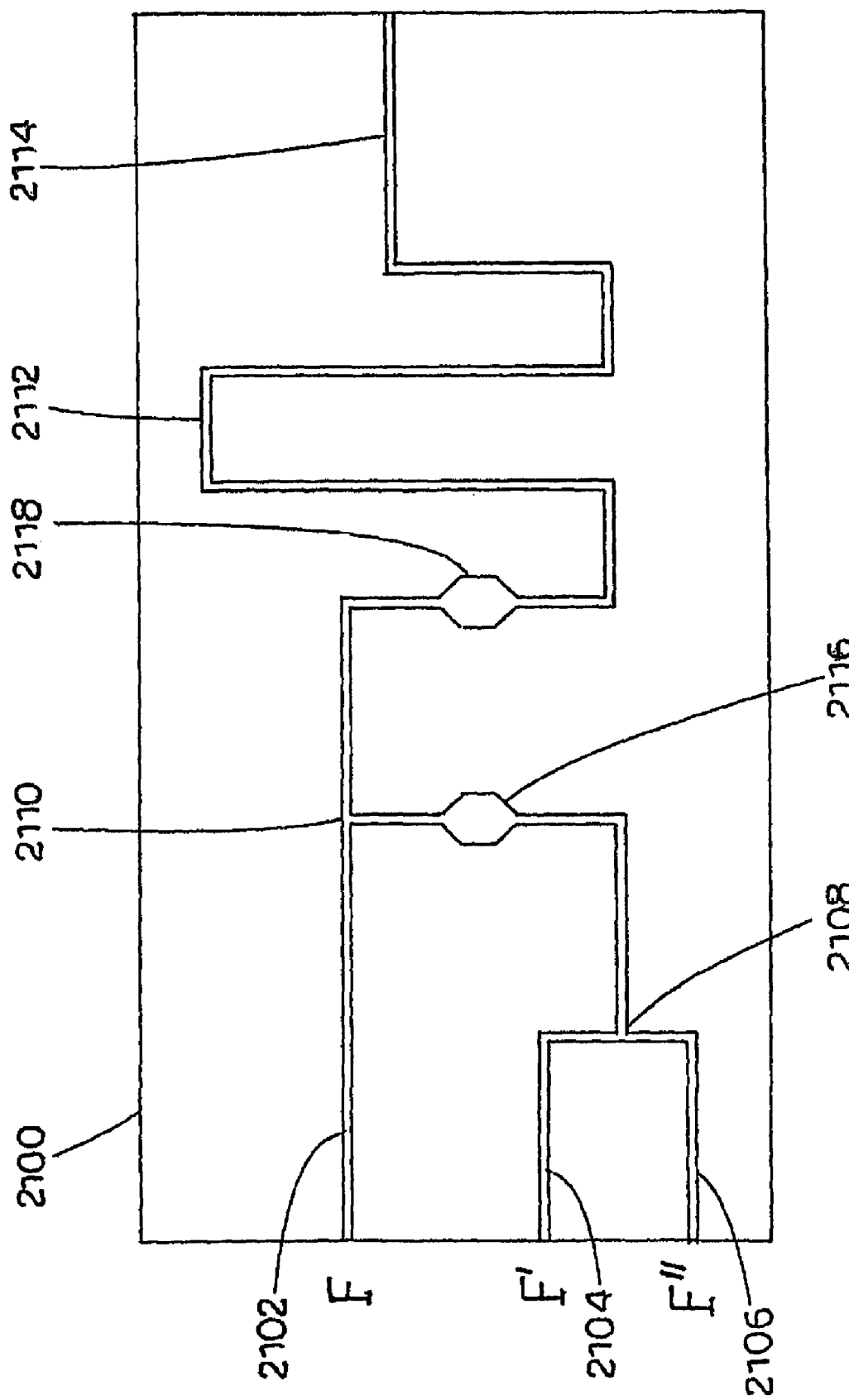
FIG. 45 is a schematic diagram of another exemplary embodiment of a microfluidic chip including channels for introducing three fluids.

Referring to FIG. 45, a schematic diagram of an exemplary embodiment of a microfluidic chip, generally designated 2100, including channels 2102, 2104, and 2106 for introducing fluids F, F", and F"', respectively. Microfluidic chip 2100 also includes a first mixing junction 2108, a second mixing junction 2110, a serpentine channel 2112, and output channel 2114 similar to microfluidic chip 2000 shown in FIG. 43. In addition, microfluidic chip 2100 can include expansion channels 2116 and 2118. Expansion channel 2116 is positioned between junctions 2108 and 2110. When a concentration gradient is created, dispersion occurs more rapidly at first, with dispersion slowing as the concentration gradient diminishes. The decrease in dispersion is exponential, approaching zero as the concentration gradient approaches zero. Placing controlled dispersion elements such as expansion channel 2116 between junctions 2108 and 2110 allows the rapid phase of dispersion to occur before, for example, the low molecular weight inhibitor mixes with the enzyme at junction 2110. The effect is that the remaining dispersion of the inhibitor is now much smaller and more closely matches the dispersion of the higher molecular weight enzyme. Further, expansion channel 2116 also serves to filter noise in the concentration gradient formed at mixing junction 2108. Expansion channel 2118 can optionally be placed downstream of junction 2110 to filter noise from the gradient introduced at junction 2110.

Figure 44B:
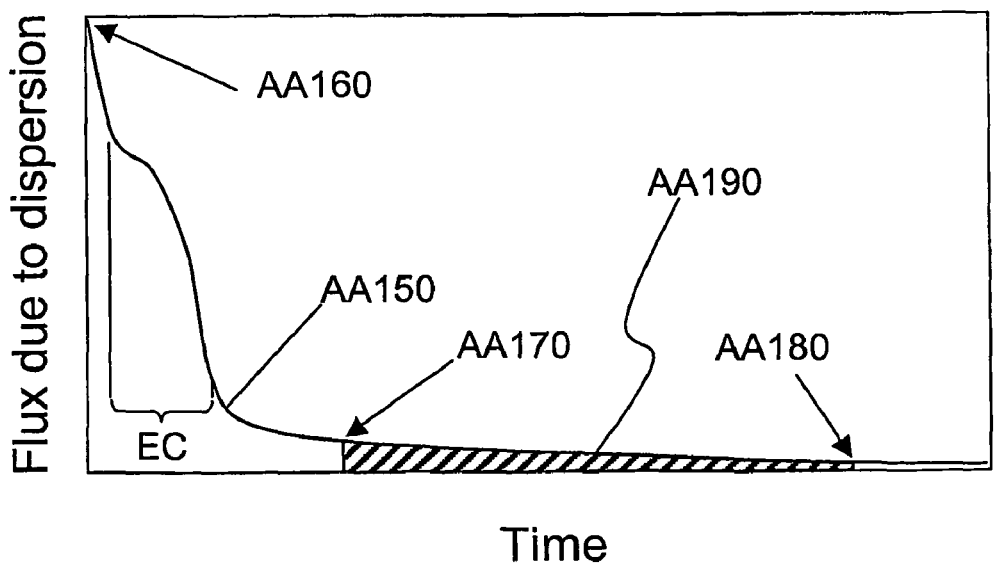
FIG. 44B is a graph showing flux due to dispersion of a concentration gradient of an inhibitor over time in a fluid flowing down a microchannel of a microfluidic chip.

Referring to FIG. 44B, a plot of flux, due to dispersion, of an inhibitor over time in a fluid flowing down a microchannel, such as those in microfluidic chip 2100 in FIG. 45, is shown. The plot, generally designated AA150, shows the flux of an inhibitor due to a concentration gradient generated by the mixing of fluids F' and F" at mixing point 2108. Point AA160 designates the point on curve AA150 immediately after mixing point 2108; point AA170 designates the point on curve AA150 corresponding to mixing point 2110; and point AA180 designates the point on curve AA150 corresponding to detection point 2114. The concentration gradient after mixing point 2108 is initially steep, so the flux at AA110 is initially large. Unlike FIG. 44A, the flux stays high as the flow enters the expansion channel 2116 and rapidly declines on exiting the expansion channel 2116, as designated by the region of curve AA150 delineated as EC. The flux that occurs in the expansion channel 2116 therefore greatly dissipates the concentration gradient and causes the flux to be much smaller on entering mixing point 2110, corresponding to point AA170 on curve AA150. The total change in concentration of the inhibitor due to dispersive flux as the fluid flows between mixing point 2110 and detection point 2114 is, therefore, proportional to the area designated AA190 under the curve AA150 between points AA170 and AA180. The area AA190 is much smaller than the area AA140 in FIG. 44A, demonstrating that the change in concentration of the inhibitor is much smaller between mixing point 2110 and detection point 2114 in microfluidic chip 2100 than between mixing point 2010 and detection point 2014 in microfluidic chip 2000. The result is that, due to expansion channel 2118, the change in concentration of the inhibitor experienced by an enzyme molecule in the combined flow of fluids F, F', and F" after mixing point 2110 in microfluidic chip 2100 is much smaller than after mixing point 2010 in microfluidic chip 2000.

Figure 46A:
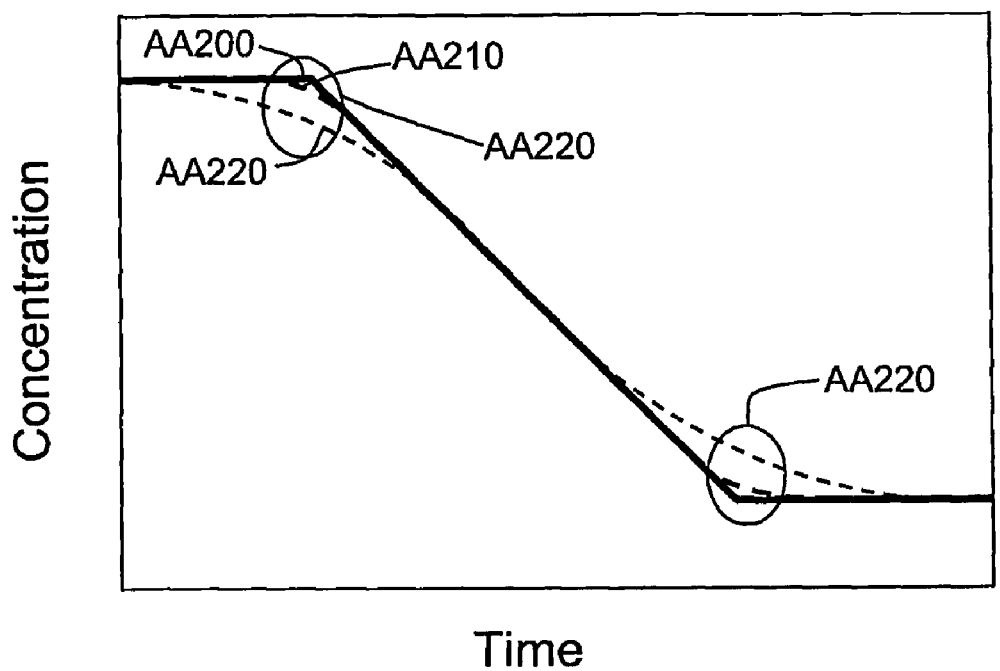
FIGS. 46A and 46B are graphs showing a chemical concentration gradient observed at several points in a microfluidic channel, such as in microfluidic chip.
Figure 46B:
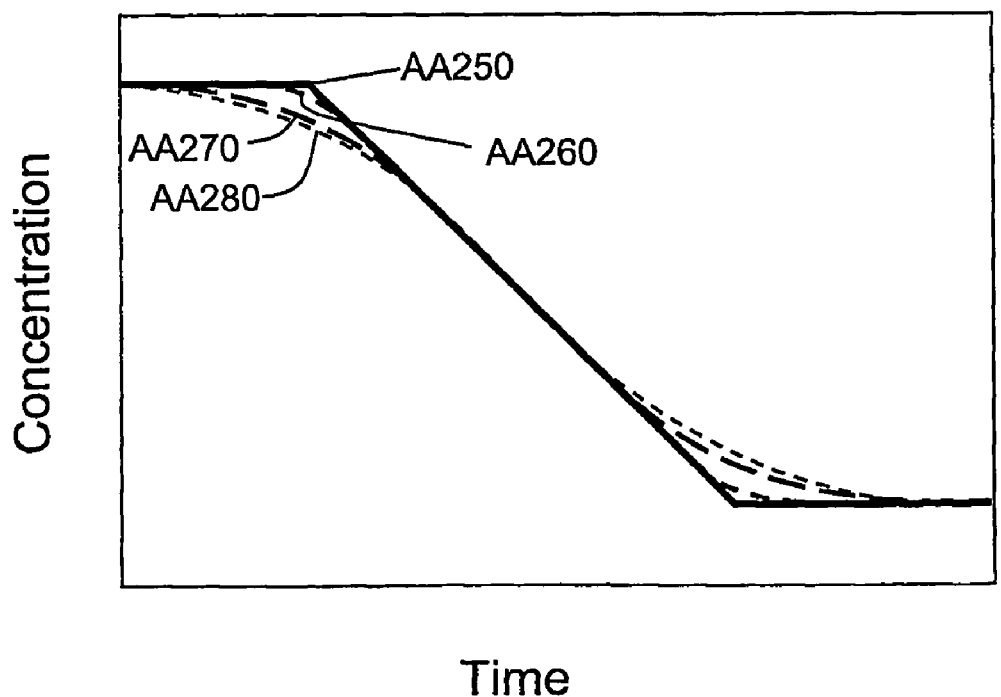

Another way to present these concepts is in FIGS. 46A and 46B, which are graphs of a chemical concentration gradient observed at several points in a microfluidic channel such as in microfluidic chip 2100 in FIG. 45 and in microfluidic chip 2000 in FIG. 43, respectively. Both present linear concentration gradients generated over time in a microfluidic ship, such as demonstrated in FIG. 34.

Referring now to FIG. 46A, for example, a gradient such as presented in plot AA200 can be generated at the first mixing point 2008 in microfluidic chip 2000 such that after undergoing dispersion in transit to second mixing point 2010 the gradient appears as in plot AA210. On transit to detection point 2014, additional and greater dispersion occurs such that the gradient appears as in plot AA220. The difference in the concentrations of plots AA210 and AA220 represents the time varying concentration experienced by an enzyme at that point in the gradient on transit from mixing point 2010 to detection point 2014. The largest differences appear at transitions in the gradient, such as those regions marked as AA230.

The purpose of a controlled dispersion element, such as the expansion channel 2116 in microfluidic chip 2100 in FIG. 45 is to reduce this difference in concentration from the final mixing point to the detection point. Referring now to FIG. 46B, plot AA250 represents the shape of the gradient immediately after mixing as it flows through mixing point 2108. Plot AA250 is identical to plot AA200 in FIG. 46A. Plot AA260 represents the shape of the gradient after it has undergone a small amount of dispersion immediately upstream of expansion channel 2116. Plot AA270 represents the shape of the gradient at mixing point 2110 after the gradient has undergone dispersion in expansion channel 2116. Plot AA280 represents the gradient at detection point 2114. Dispersion of the gradient in the expansion channel 2216 prior to mixing point 2110 greatly reduces the difference in concentration from the final mixing point to the detection point.

Adsorption of a molecule to the wall of a microfluidic channel can sometimes present a problem in microfluidic and other miniaturized systems in which the ratio of surface area to volume is many orders of magnitude larger than is found in more conventional approaches, such as for example, dispensing and mixing of solutions in microtiter plates. Adsorption of molecules in microfluidic systems and other miniaturized devices can be a major obstacle to miniaturization as the adsorption can affect molecule concentrations within fluids, thereby negatively impacting data collected from the microfluidic systems or other miniaturized devices. Adsorption driven changes in concentration can be especially problematic for microfluidic systems used to generate concentration gradients.

In some embodiments, the presently disclosed subject matter provides apparatuses and methods for using the same that can decrease the interference of adsorption to concentration dependent measurements, such as in biochemistry reactions including $IC_{50}$ determinations, by altering the geometry of a microfluidic channel. Although adsorption may not be eliminated, the change in concentration caused by adsorption can be minimized. In general terms, the effects of adsorption on measurements can be minimized by reducing the ratio of channel surface area to fluid volume within the channel (S/V), which also increases diffusion distances. However, as a high surface area to volume ratio can be an unavoidable consequence of the miniaturization of microfluidics, the geometries provided by some embodiments of the presently disclosed subject matter to minimize adsorption consequences are most unexpected by persons in the field of microfluidics. The presently disclosed subject matter provides for, in some embodiments, using large channel diameters in regions of the microfluidic chip most affected by adsorption of reaction components, that is, in regions where a reaction proceeds and/or where measurements are taken. In some embodiments of the presently disclosed subject matter, and with reference to the microfluidic chip embodiment shown in FIG. 8, large channel diameters at detection point DP can be provided to reduce adsorption effects, as a substitute for or in combination with aging loop AL (also referred to as a serpentine analysis channel).

Figure 53:
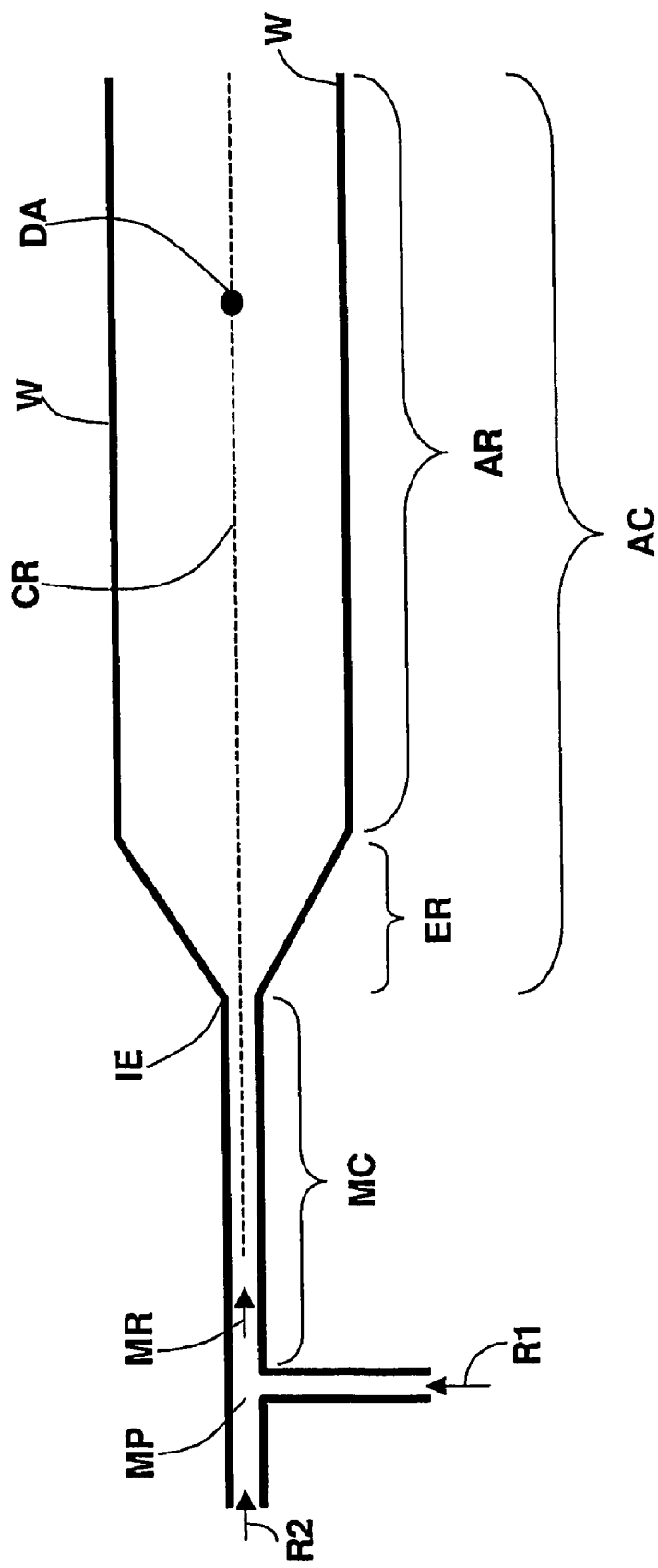
FIG. 53 is a schematic top view of an embodiment of an analysis channel disclosed herein and upstream fluidly communicating microscale channels.

Turning now to FIG. 53, an embodiment of a novel analysis channel of the presently disclosed subject matter is illustrated in a top view. FIG. 53 shows the direction of flow by arrows R1 and R2 of two fluid reagent streams, which can combine at a merge region or mixing point MP. After combining into a merged fluid stream, the reagents within the stream can flow in a direction indicated by arrow MR down a mixing channel MC that can be narrow to permit rapid diffusional mixing of the reagent streams, thereby creating a merged fluid reagent stream. The fluid stream of reagents can then pass into an analysis channel AC, at an inlet or inlet end IE that can have a channel diameter and a cross-sectional area equivalent to that of mixing channel MC. The merged fluid stream can then flow through an expansion region ER that can have a cross-sectional area that can gradually increase and where the surface area to volume ratio can thereby gradually decrease. The merged fluid stream can then continue into an analysis region AR of analysis channel AC with an enlarged cross-sectional area and a reduced surface area to volume ratio. A reaction can be initiated by mixing of the reagent streams at the mixing point MP. However, due to continuity of flow, the flow velocity slows dramatically in analysis region AR of analysis channel AC, and the majority of transit time between mixing point MP and a detection area DA is spent in the larger diameter analysis region AR. Measurements can be made inside this channel, such as with confocal optics, to achieve measurements at detection area DA, which can be located at a center axis CR of analysis region AR of analysis channel AC. Center analysis region CR can be a region equidistant from any channel wall W of analysis channel AC. Thus, the fluid at center analysis region CR of detection area DA can be effectively "insulated" from adsorption at channel walls W. That is, the amount of any reagents removed at channel wall W can be too small, due to the greatly decreased surface area, and the diffusion distance to channel wall W can be too long, due to the greatly increased diffusion distance from center analysis region CR to channel wall W, to greatly affect the concentration at centerline CL. The confocal optics, for example, can reject signal from nearer channel wall W of analysis region AR, permitting measurements to be made at center analysis region CR where the concentration is least affected by adsorption at channel wall W.

A consequence of increasing analysis channel AC cross-section by increasing channel diameter is that the ratio of channel surface area to fluid volume (S/V) within the channel is decreased, relative to a narrower channel. For example, to measure a reaction 3 minutes after mixing, with a volumetric flow rate of 30 nL/min, the reaction should be measured at a point in the channel such that a microfluidic channel section spanning from mixing point MP to detection area DA encloses 90 nL. For an analysis channel with a square cross-section and a diameter of 25 μm, this point is about 144 mm downstream from mix point MP. This channel has a surface area of $1.44 \times 10^{-5}$ square meters, yielding a surface to volume ratio S/V equal to $1.6 \times 10^5$ $m^{-1}$. For a channel with a diameter of 250 μm, the measurement is made 1.44 mm downstream from mix point MP. This wider channel has a surface area of $1.44 \times 10^{-6}$ square meters, yielding a S/V equal to $1.6 \times 10^4$ $m^{-1}$, which is $\frac{1}{10}^{th}$ the S/V of the narrower channel. This alone can decrease ten-fold the removal of compound per unit volume by adsorption.

This geometry change can also decrease the radial diffusive flux of compound. Flow in these small channels is at low Reynolds number, so diffusion from a point in the fluid is the only mechanism by which compound concentration changes radially in a microfluidic channel. Increasing the radius of the channel, thereby decreasing the radial diffusive flux, therefore, means that the concentration of compound at center analysis region CR of analysis region AR can be less affected by adsorption than in the smaller upstream channels.

Thus, increasing the cross-sectional area of analysis region AR of analysis channel AC can both decrease the amount of adsorption at the wall per unit volume and decrease the rate of flux of compound from center analysis region CR to any of channel walls W. Both together mean that the concentration at center analysis region CR can decrease more slowly due to adsorption of compound.

Further, in all embodiments, the surface area of all channels exposed to compounds, not just analysis channel AC, can preferably be kept minimal, especially those channels through which concentration gradients flow. This can be accomplished by making channels as short as practicable. Additionally, when the volume contained by a channel must be defined (e.g. where the channel must contain a volume of 50 nL), it is best to use larger diameters/shorter lengths wherever possible to reduce S/V.

Another benefit of increasing analysis channel AC cross-section by increasing channel diameter is that the length of the channel down which the fluid flows can be reduced. In the example given earlier, a channel with 25 μm diameter needed to be 144 mm long to enclose 90 nl whereas the channel with 250 μm diameter needed to be only 1.44 mm long. This shorter channel can be much easier to fabricate and has a much smaller footprint on a microfluidic chip.

Still another benefit of increasing analysis channel AC cross-section is that it will behave like an expansion channel, which filters noise out of chemical concentration gradients, as disclosed in co-pending, commonly owned U.S. Provisional Application entitled MICROFLUIDIC SYSTEMS, DEVICES AND METHODS FOR REDUCING NOISE GENERATED BY MECHANICAL INSTABILITIES, U.S. Provisional Application No. 60/707,245, herein incorporated by reference in its entirety. The result is that signal to noise is larger in an analysis channel AC with larger cross-section.

FIG. 54A presents a cross-sectional side view of a portion of a microfluidic chip MFC comprising mixing channel MC and analysis channel AC depicted in FIG. 53. Microfluidic chip MFC shown in FIG. 54A can be constructed by machining channels into a bottom substrate BS and enclosing channels by bonding a top substrate TS to bottom substrate BS or otherwise forming channels within microfluidic chip MC with bottom substrate BS and top substrate TS being integral. In FIG. 54A, only the flow of merged reagent fluid stream having a flow direction indicated by arrow MR after mixing point MP is shown. Flow in a microfluidic channel can be at low Reynolds number, so the streamline of fluid that flows along center analysis region CR of the narrower mixing channel MC can travel at the mid-depth along entire mixing channel MC, becoming center analysis region CR of analysis region AR of analysis channel AC. Detection area DA can reside along center analysis region CR at a point sufficiently far downstream of mixing channel MC to permit the reaction to proceed to a desired degree.

Analysis channel AC can approximate a circular cross-section as closely as possible to produce the smallest ratio of surface area to volume, and also to produce the largest diffusion distance from centerline center analysis region CR to a channel wall W. However, microfluidic channels may not be circular in cross-section due to preferred manufacturing techniques. Rather, they can be more likely square in cross-section, with the exact shape depending on the technique used to form the channels. For such channels, a cross-section of analysis channel AC, particularly within analysis region AR, can have an aspect ratio as close to one as possible or, more precisely stated, the distance from center analysis region CR to channel wall W can be as nearly constant in all radial directions as possible.

FIG. 54B shows two different cross-sectional views along analysis channel AC as viewed along cutlines A-A and B-B. Both cross-sectional views illustrate an aspect ratio approximating one. That is, for cross-section A-A, height $H_1$ of mixing channel MC is approximately equal to width $W_1$ of mixing channel MC, such that $H_1/W_1$ approximately equals one. Comparably, for cross-section B-B, height $H_2$ of mixing channel MC is approximately equal to width $W_2$ of mixing channel MC, such that $H_2/W_2$ approximately equals one.

FIG. 54B further shows that the cross-sectional area ($H_2 \times W_2$) of analysis region AR at cutline B-B, which is located at detection area DA of analysis region AR, is significantly larger than the cross-sectional area ($H_1 \times W_1$) of input end IE at cutline A-A. In some embodiments of the presently disclosed subject matter, the cross-sectional area at detection area DA can be at least twice the value of the cross-sectional area value at input end IE and further upstream, such as in mixing channel MC. Further, in some embodiments, the cross-sectional area at detection area DA can be between about two times and about ten times the value of the cross-sectional area value at input end IE. As shown in cutline B-B of FIG. 54B, detection area DA can be positioned along center analysis region CR approximately equidistant from each of walls W to provide maximal distance from walls W, and thereby minimize effects of molecule adsorption to walls W. It is clear from FIG. 54B that the larger cross-sectional area at cutline B-B can provide both greater distance from walls W and smaller S/V than the smaller cross-sectional area at cutline A-A, both of which can reduce adsorption effects on data analysis, as discussed herein. Although detection area DA is shown in the figures as a circle having a distinct diameter, the depiction in the drawings is not intended as a limitation to the size, shape, and/or location of detection area DA within the enlarged cross-sectional area of analysis region AR. Rather, detection area DA can be as large as necessary and shaped as necessary (e.g. circular, elongated oval or rectangle, etc.) to acquire the desired data, while minimizing size as much as possible to avoid deleterious adsorption effects on the data. Determination of the optimal balance of size, shape and location while minimizing adsorption effects is within the capabilities of one of ordinary skill in the art without requiring undue experimentation.

Additional details and features of analysis channel AC are disclosed in co-pending, commonly owned U.S. Provisional Application entitled METHODS AND APPARATUSES FOR REDUCING EFFECTS OF MOLECULE ADSORPTION WITHIN MICROFLUIDIC CHANNELS, U.S. Provisional Application No. 60/707,366, herein incorporated by reference in its entirety.

In some embodiments, the presently disclosed subject matter provides apparatuses and methods for making and using the same that can decrease the interference of adsorption to concentration dependent measurements, such as in biochemistry reactions (including $IC_{50}$ determinations), by reducing adsorption of molecules to microfluidic channel walls. In some embodiments, the presently disclosed subject matter provides microfluidic chips comprising channels and chambers with treated surfaces exhibiting reduced adsorption of molecules to channel walls, such as for example hydrophilic surfaces, and methods of preparing and using the same. In some embodiments, methods of preparing hydrophilic surfaces by treating hydrocarbon-based plastics, such as for example polycarbonate, with fluorine gas mixtures are provided. In some exemplary embodiments, the methods comprise contacting a mixture of fluorine gas and an inert gas with the surface to be treated, then flushing the surface with air. This treatment results in plastic surfaces of increased hydrophilicity (increased surface energy). Hydrophobic solutes, in particular known and potential drug compounds, in solutions in contact with these treated hydrophilic plastic surfaces are less likely to be adsorbed onto the more hydrophilic surfaces. Plastics comprising the treated surfaces are useful in providing many improved drug discovery and biochemical research devices for handling, storing, and testing solutions containing low concentrations of hydrophobic solutes.

Additional details and features of hydrophilic surfaces in microfluidic systems and methods of making and using the same are disclosed in co-pending, commonly owned U.S. Provisional Application entitled PLASTIC SURFACES AND APPARATUSES FOR REDUCED ADSORPTION OF SOLUTES AND METHODS OF PREPARING THE SAME, U.S. Provisional Application No. 60/707,288.

Further, in some embodiments of the presently disclosed subject matter, microfluidic systems are provided comprising an analysis channel with an enlarged cross-sectional area and a reduced surface area to volume ratio and further comprising channels and chambers with hydrophilic surfaces.

EXAMPLES

The following Examples have been included to illustrate representative modes of the presently disclosed subject matter. In light of the present disclosure and the general level of skill in the art, those of skill will appreciate that the following Examples are intended to be exemplary only and that numerous changes, modifications, and alterations can be employed without departing from the spirit and scope of the presently disclosed subject matter.

Example 1

Oxalate Vs. $NAD^+$ on Microtiter Plates

The inhibition mechanism of oxalate with respect to the substrate $NAD^+$ yields an uncompetitive profile as deduced from conventional orthogonal analysis (see Lien L V, Ecsedi G, Keleti T. (1979) *Acta Biochim Biophys Acad Sci Hung.* (1-2); 11-17).

Figure 47:
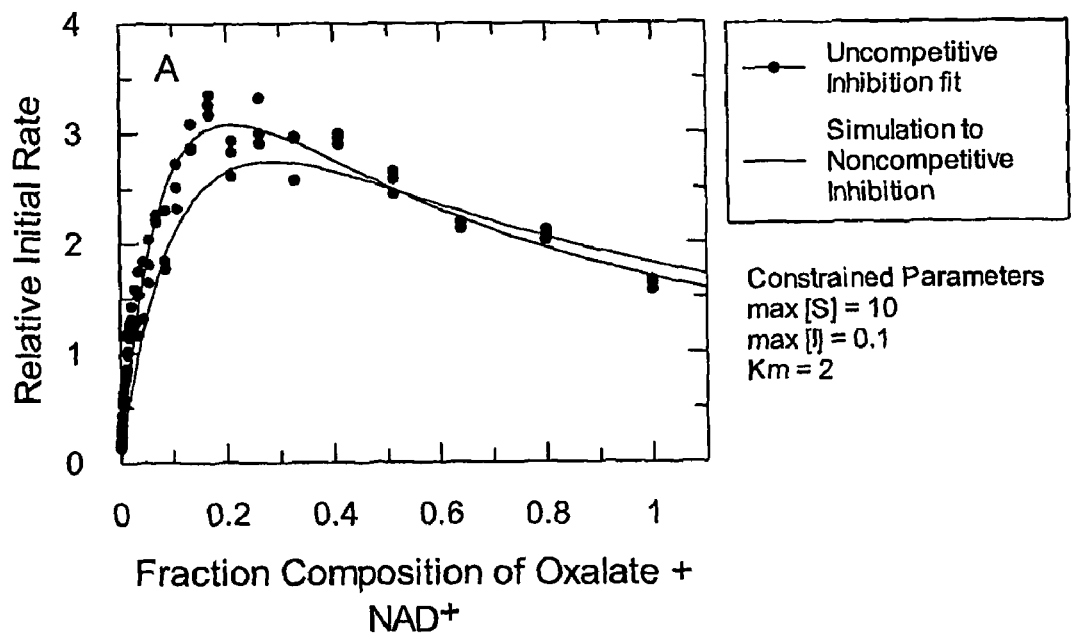
FIG. 47 is a graph of data showing mechanism of inhibition of oxalate with respect to $NAD^+$ against rabbit muscle lactate dehydrogenase using a continuous variation method on a microtiter plate.

Determination of the mechanism of inhibition by the inhibitor oxalate with respect to the substrate $NAD^+$ against the enzyme rabbit muscle lactate dehydrogenase (LDH)

using a microtiter plate to generate individual step concentration gradients was attempted. FIG. 47 is a graph showing the results of the experiment.

As FIG. 47 demonstrates, using known methods with microtiter plate step concentration gradients generates limited data, making a determination of mechanism of inhibition very difficult. FIG. 47 graphs both simulation curves for uncompetitive and noncompetitive inhibition. As can be seen, the limited data and the similarity of the uncompetitive and noncompetitive curves makes it difficult to determine the mechanism of inhibition with confidence. It is ambiguously suggested in this example that oxalate is an uncompetitive inhibitor against NAD⁺. However, the simulation of noncompetitive inhibition with reasonable $K_{is}$ and $K_{ii}$ values also presented in FIG. 47 suggests the possibility of erroneously fitting the dataset to an inaccurate kinetic model.

Example 2

Oxalate Vs. Lactate on Microtiter Plates

Figure 48:
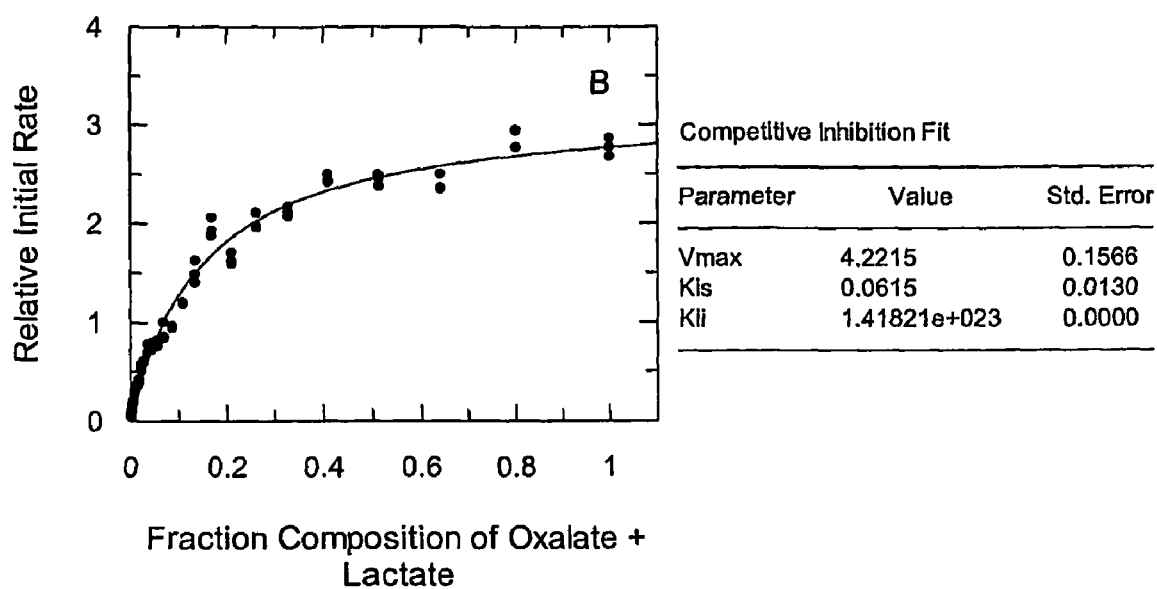
FIG. 48 is a graph showing mechanism of inhibition of oxalate with respect to lactate against rabbit muscle lactate dehydrogenase using a continuous variation method on a microtiter plate.

An attempt to determine the mechanism of inhibition by the inhibitor oxalate with respect to the substrate lactate against the enzyme rabbit muscle LDH using a microtiter plate to generate individual step concentration gradients was attempted. FIG. 48 is a graph showing the results of this experiment.

FIG. 48 appears to indicate the oxalate is a competitive inhibitor against lactate as a substrate, as reported previously (see Lien L V et al. (1979) *Acta Biochim Biophys Acad Sci Hung*. Vol. 1-2, pp. 11-17. Amongst the three aforementioned inhibition mechanisms, this is the only model that yields a hyperbolic profile, and as such is the only one that can be used to confidently deduce mechanism. However, again, the limited data prevents determination of the mechanism of inhibition with certainty.

Examples 3 and 4

The results from Examples 1 and 2 demonstrate that data from microtiter plates is too coarse to determine the mechanism of inhibition of an inhibitor with certainty. Although a competitive mechanism of inhibition can be presumed with some systems, distinguishing noncompetitive from uncompetitive inhibition is not possible unless the variance in the data is kept very small. In contrast, as demonstrated below, the novel methods disclosed herein utilizing a continuous variation of the ratio, B, produces high-resolution data, permitting determination of potency and discrimination of inhibitor mechanisms, including discriminating noncompetitive from uncompetitive inhibition mechanisms.

A fluorescence-coupled enzyme assay was developed using a microfluidics system described herein for creating a continuously variable concentration gradient to monitor the reduction of NAD⁺ by the enzyme LDH to give a fluorescent end product. This system was then adapted to measure potency and determine mechanism of inhibition by various inhibitors of LDH.

One of the products of the reaction in the assay, NADH, is coupled to *Thermus thermophilus* NADH oxidase to generate $H_2O_2$, which in turn is coupled to horseradish peroxidase which reacts with NADH and amplex red (Molecular Probes, Inc., Eugene, Oreg., U.S.A.) to give the fluorescent product resorufin. Catalase-coated agarose beads were used as a scrubbing system to minimize any extraneous source of $H_2O_2$. In addition, as a general rule, the experimental design for the assay solutions was configured so as to minimize any variability of the non-variable reagents. A protocol for titration of LDH with NAD⁺ is shown in Table 1. A simple modification of the protocol in Table 1 is made for determining the mechanism of inhibition and potency of the inhibitors. Specifically, the inhibitor at the desired maximum 2× concentration is added to solution 2.

TABLE 1

Protocol for NAD⁺ titration - *P. falciparum* LDH reaction
Assay base buffer: 50 mM HEPES, pH 7.6; 0.1% pluronic acid F68
Make assay buffer A in the above base buffer containing:
30 µM FAD (flavin adenine dinucleotide)
200 nM *thermus thermophilus* NADH oxidase
50 U/mL catalase-coated agarose beads beads

| Stock Component | Concentration (2x) | µL of stock |
|---|---|---|
| Solution 1 - 300 µL | | |
| buffer A | — | 298.8 |
| 1000 U/mL horseraddish peroxidase | 4 U/mL | 1.2 |
| Solution 2 - 100 µL | | |
| Solution 1 | — | 99 |
| 100 mM NAD⁺ | 1 mM | 1 |
| incubate for 30 min @ RT and spin solution in 0.2 µM filter to remove catalase beads | | |
| Solution 3 - 100 µL | | |
| buffer A | — | 84.7 |
| 2 M lactate | 200 mM | 10 |
| 1 mM amplex red (*add after 30 min. incubation period & before centrifugation) | 40 µM | 4 |
| 7.5 µM *P. falciparum* LDH | 100 nM | 1.3 |

Incubate all solutions for 30 min. and centrifuge in millipore 0.22 um filter tubes (UFC30GVNB; Millipore, Inc.) to remove catalase-coated agarose beads The protocol for generating the gradient on the microfluidics system is outlined in Table 2. The linear gradient is formed between pumps 1 and 2 (see for example, FIG. 34) with an isocratic flow from syringe 3. The pump numbers in Table 2 correspond to the solution numbers in Table 1. Two minute equilibration steps before and after the gradient are programmed to determine baseline signals for data processing.

TABLE 2

Pump gradient program for a typical protocol.

| | Total Flow Rate (%) 20 nL/min | | | | | |
|---|---|---|---|---|---|---|
| Interval Time | Pump 1 (%) | | Pump 2 (%) | | Pump 3 (%) | |
| (min) | Start | Finish | Start | Finish | Start | Finish |
| 2 | 50 | 50 | 0 | 0 | 50 | 50 |
| 2 | 50 | 0 | 0 | 50 | 50 | 50 |
| 2 | 0 | 0 | 50 | 50 | 50 | 50 |

The novel data analysis techniques described herein for determining the mechanism of inhibition of an inhibitor (or mechanism of activation of an activator) are applied to the data produced from the microfluidics system. The titration of the enzyme with a continuous linear variation of inhibitor and substrate from zero to a pre-determined finite concentration yields a characteristic rate profile that is defined by the specific type of interaction of the inhibitor and enzyme with respect to the substrate. The data is fitted to the novel mixed inhibition equation described herein above (Equation 4) using GraFit™ (Erithacus Software Limited, Surrey, United Kingdom):

$$v=V_{max}*S*B/K_m*(1+I*B/K_{is})+S*B*(1+I*B/K_{ii}),$$

where $V_{max}$ represents maximum velocity, S is the varied substrate concentration, I is the varied inhibitor concentration, $K_m$ is the Michaelis constant, B is the fraction composition of the gradient, $K_{is}$ the slope inhibition constant, and $K_{ii}$ is the intercept inhibition constant. In order to minimize the number of parameters for robust curve fitting, the non-linear fitting program was written to accept a constant value for $K_m$. In addition, the B term allows the user to enter finite S and I values for the maximum substrate and inhibitor concentrations, respectively. The floating parameters are $V_{max}$, $K_{is}$, and $K_{ii}$.

Most enzymes studied to date exhibit Michaelis-Menten saturation kinetics with their respective substrate(s) and yield a characteristic hyperbolic rate profile. The titration of LDH with a linear gradient of $NAD^+$ was performed on the microfluidics system described herein with the change in relative fluorescence intensity monitored under initial rate conditions. The data were fitted to the Michaelis-Menten equation and the $K_m$ value determined from the microfluidics system (54±2 µM) are shown to conform to that obtained on a microtiter plate.

The system was next tested with several different inhibitors of LDH to experimentally determine the potency and mechanism of action of the inhibitors using a continuously variable concentration gradient of the inhibitors created by the microfluidics system. Data from these experiments are provided below in Examples 3-5.

Example 3

GW409578X Vs. $NAD^+$ or Lactate Using Continuous Gradient

Figure 49A:
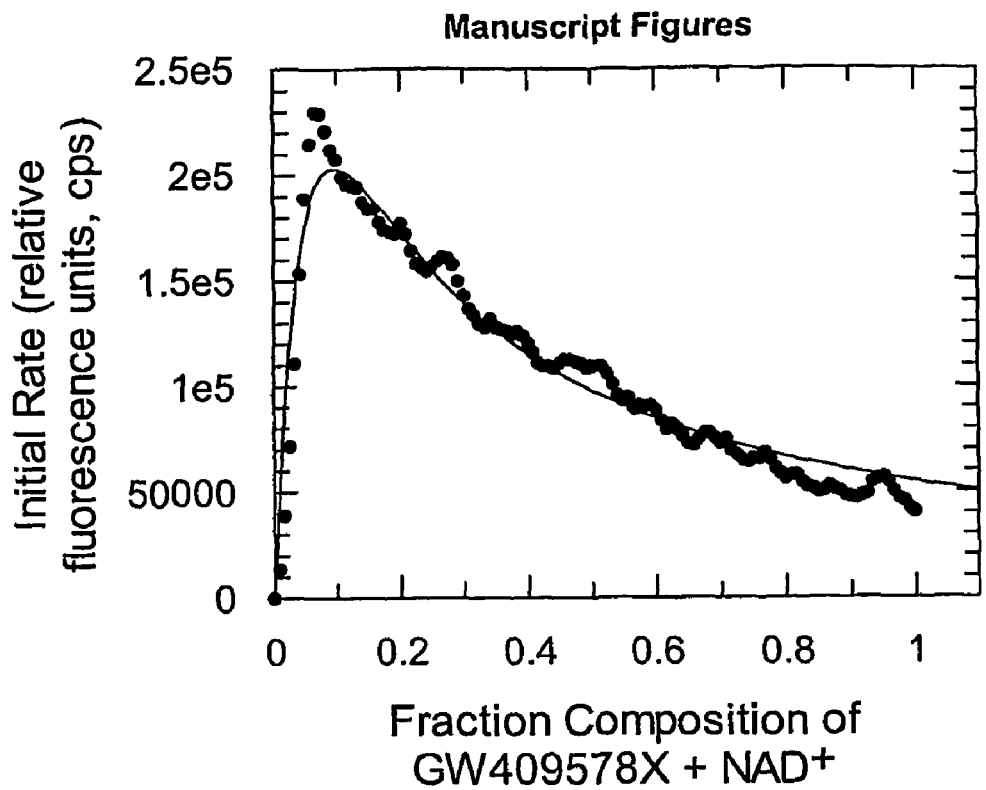
FIG. 49A is a graph that determines a classical kinetic mechanism of enzyme inhibition, showing the initial rate profile of the linear co-titration of LDH with GW409578X and $NAD^+$ indicating uncompetitive inhibition with a $K_{ii}$ value of $5.4\pm0.2$ µM and $K_{is}=9.2\times10^{14}$ (no slope inhibition component) and having the following values fixed: maximum $[NAD^+]=0.5$ mM, maximum [GW409578X]=0.05 mM, and $K_{NAD^+}=0.054$ mM.
Figure 49B:
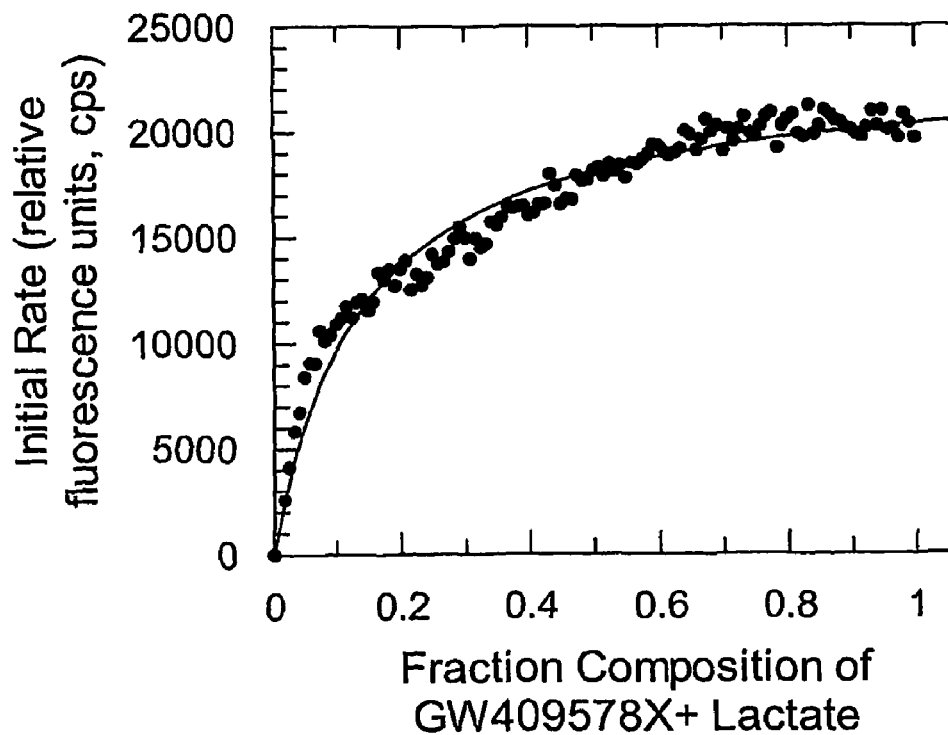
FIG. 49B is a graph that determines a classical kinetic mechanism of enzyme inhibition, showing the initial rate profile of the linear co-titration of LDH with GW409578X and lactate indicating competitive inhibition with a $K_{ii}$ value of $1\times10^{19}$ (no intercept inhibition component) and $K_{is}=8.2\pm0.4$ µM and having the following values fixed: maximum [lactate]=50 mM, maximum [GW409578X]=0.05 mM, and $K_{Lactate}=10$ mM.

A small molecule inhibitor (GW409578X) identified from a high-throughput screening campaign of a chemical library against LDH was interrogated against the substrates $NAD^+$ and lactate to validate the continuously variable concentration gradient method created by the microfluidics system and the ability to faithfully reproduce the kinetic mechanism of inhibition using the novel methods described herein. FIGS. 49A and 49B are graphs of data from these experiments showing the initial rate profile of the linear co-titration of LDH with the inhibitor GW409578X. The data graphed in FIG. 49A indicate uncompetitive inhibition of LDH by GW409578X with respect to $NAD^+$, with a $K_{ii}$ value of 5.4±0.2 µM and $K_{is}$ value of 9.2×10$^{14}$ (i.e., no slope inhibition component). The following values were fixed: maximum [$NAD^+$]=0.5 mM, maximum [GW409578X]=0.05 mM, and $K_{NAD^+}$=0.054 mM.

The data graphed in FIG. 49B indicate competitive inhibition of LDH by GW409578X with respect to lactate, with a $K_{ii}$ value of 1×10$^{19}$ (i.e., no intercept inhibition component) and $K_{is}$=8.2±0.4 µM. The following values were fixed: maximum [lactate]=50 mM, maximum [GW409578X]=0.05 mM, and $K_{Lactate}$=10 mM.

The diagnostic curves obtained for each experiment are mechanistically correct and yield accurate inhibition constants as compared with that determined via conventional analysis. It is also worth noting that the mechanism of inhibition determined for lactate vs. GW409578X using conventional analysis (a continuous 6×6 'grid' technique) yielded a K is value of 17+/−4 µM, which is a 24% standard error. Thus, the presently disclosed novel methods using a continuous concentration gradient provided more accurate data and used fewer reagents. The robustness of the novel methods described herein results in part from obtaining a large volume of high precision data throughout the duration of the continuous gradient.

Example 4

Oxalate Vs. $NAD^+$ Using Continuous Gradient

Figure 50:
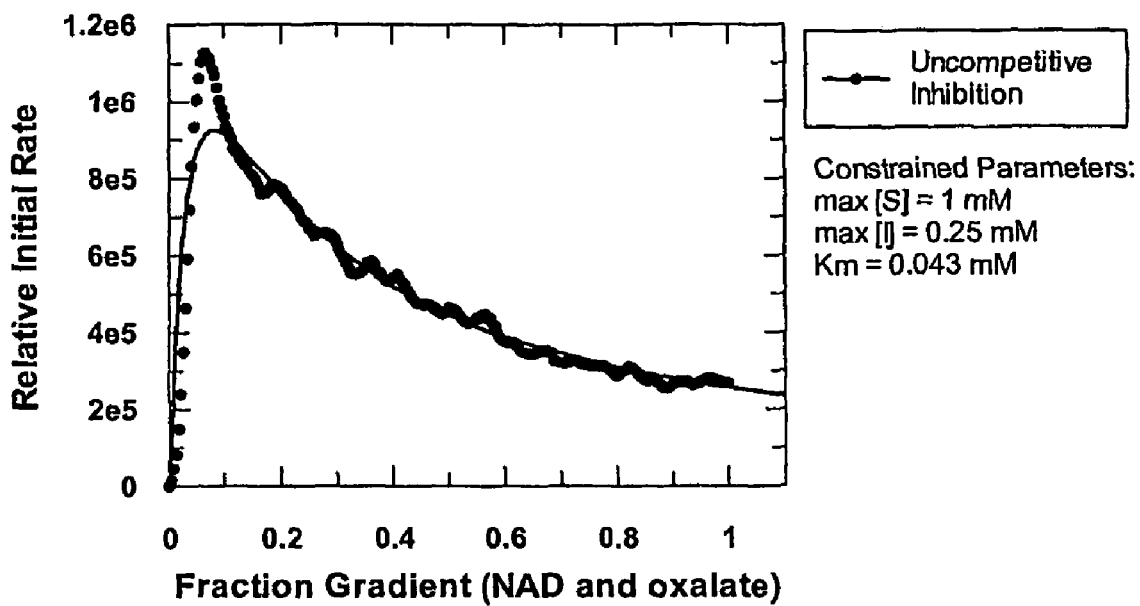
FIG. 50 is a graph showing application of a continuous variation method on a microfluidic system as described herein to determine mechanism of inhibition against *Plasmodium falciparum* lactate dehydrogenase (substrate=NAD⁺, inhibitor=oxalate)

A microfluidics device as described herein was used to create a continuously variable concentration gradient of the inhibitor oxalate with regard to the substrate $NAD^+$ against the enzyme *Plasmodium falciparum* LDH to experimentally determine the mechanism of inhibition. FIG. 50 is a graph showing the results from the experiment. Fit of the data to the newly developed Equation 4 and graphed in FIG. 50 clearly indicates a best fit to a model describing uncompetitive inhibition.

From this Example, in comparison with Examples 1 and 2, it can be seen that the presently disclosed subject matter provides for the capability of determining a mechanism of action and potency of an inhibitor of an enzyme with great accuracy, in contrast to known methods which require more reagents and provide less reliable data.

Example 5

Analysis and Reduction of Carryover in a Microfluidics System

To illustrate carryover and how it affects a microfluidics system, experiments were conducted in which concentration gradients of fluorescent compounds were run against non-fluorescent buffer in a microfluidic chip MFC shown in FIG. 23. FIG. 23 depicts another exemplary microfluidic chip MFC according to one embodiment, which can include input channels (IC1, IC2, and IC3), an output channel (O1), fiducial marks (F1, F2, and F3) for automated alignment, and a serpentine channel SC having 11 turns. Input channels IC1, IC2, and IC3 can be connected to pumps $P_A$, $P_B$, and $P_C$ via input lines $IL_A$, $IL_B$ and $IL_C$, respectively. In this embodiment, microfluidic chip MFC is about 22×21 millimeters.

For this experiment, the autosampling system depicted in FIG. 22B was used. The switching valve was a Model CN2 switching valve from Valco Instrument Company of Houston, Tex., U.S.A. Only three of the pumps were used, $P_B$, $P_C$, and $P_D$ connecting to input channels $IL_B$, $IL_C$ and $IL_D$, respectively, connecting to input channels $IC_3$, $IC_2$, and $IC_1$, respectively, on microfluidic chip MFC in FIG. 23. Initially, the entire system (all pumps $P_A$, $P_B$, and $P_C$, input lines $IL_A$, $IL_B$ and $IL_C$, capillary 272, microfluidic chip MFC, capillary 274, injection loop INL, buffer loop BL, three-way valve TWV, syringe pump SP, and buffer reservoir BR) was filled with non-fluorescent buffer (50 mM HEPES with 0.1% CHAPS, pH 7.0). One well of the multi-well plate (MWP) was filled with an aqueous solution of fluorescent dye (containing 0.5 µM resorufin (Molecular Probes, Eugene, Oreg.) in 50 mM HEPES with 0.1% CHAPS, pH 7.0). Another well contained only buffer (50 mM HEPES with 0.1% CHAPS, pH 7.0).

The switching valve SV was placed into Position 1 and capillary 274 was moved to the well containing the fluorescent solution. The injection loop INL was then filled with fluorescent solution by syringe pump SP, as described herein above. The switching valve SV was then changed to Position 2, placing the fluorescent solution-filled injection loop INL in line with pump $P_D$. The flow from microfluidic pumps $P_B$, $P_C$, and $P_D$ was as follows:

20-140 seconds: Pump $P_D$=0 nl/minute, Pump $P_C$=15 nl/minute 140-260 seconds: Pump $P_D$ increases linearly to 15 nl/minute, Pump $P_C$ decreases linearly to 0 nl/minute 260-380 seconds: Pump $P_D$=15 nl/minute, Pump $P_C$=0 nl/minute Pump $P_B$ flowed at a constant 10 nl/minute throughout.

Next, this flow was repeated, creating two gradients of fluorescent solution. Fluorescence was measured at the end of serpentine loop SL using a fluorescence detection system (such as sample processing apparatus SPA shown in FIG. 8). The fluorescence measured by the system is shown in FIGS. 51A and 51B which show the fluorescence intensity (normalized to peak fluorescence) for the concentration gradient of resorufin. The gradient of fluorescent compound is depicted by the solid line in FIG. 51A and FIG. 51B. FIG. 51B shows an expanded Y-axis.

After the gradient of fluorophores was run, the injection loop INL and capillary 274 were thoroughly rinsed by syringe pump SP. Capillary 272 and microfluidic chip MFC were flushed with buffer from all three microfluidic pumps $P_B$, $P_C$, and $P_D$. For all flushes, a volume minimally equivalent to 4 times the system volume were flushed through the respective portions of the system. All pumps stopped, and capillary 274 was moved to the buffer-only well on the multiwell plate (MWP), and the injection loop INL was filled with buffer. Gradients were then again run, identical to the ones above. Given the thorough flushing of the system, there should have been no fluorophore remaining anywhere in the system. Any fluorescence detected is, therefore, fluorescent compound carryover. The fluorescence measured by the system is shown in FIGS. 51A and 51B which show the fluorescence intensity (normalized to peak fluorescence) for the concentration gradient of resorufin. The gradient of fluorescent compound for this "buffer only" run is depicted by the dashed line in FIG. 51A and FIG. 51B. FIG. 51B shows an expanded Y-axis, and it is clear that fluorescence equal to about 6% of the previous signal is present, indicating a 6% carryover. The fact that the fluorescence returns to baseline in the regions where pump $P_C$ is flowing at 15 nl/minute and pump $P_D$ is flowing at 0 nl/minute indicates that the contaminating fluid is coming only from pump $P_D$ or the switching valve SV. Experiments with longer rinses produced smaller carry-over, but rinses of 30 minutes (minimally equaling 20 volumes) still had carry-over of about 4%. Thus, although very long rinses might reduce carry-over to acceptable levels, the duration of the rinses can be unacceptably long.

Figure 52:
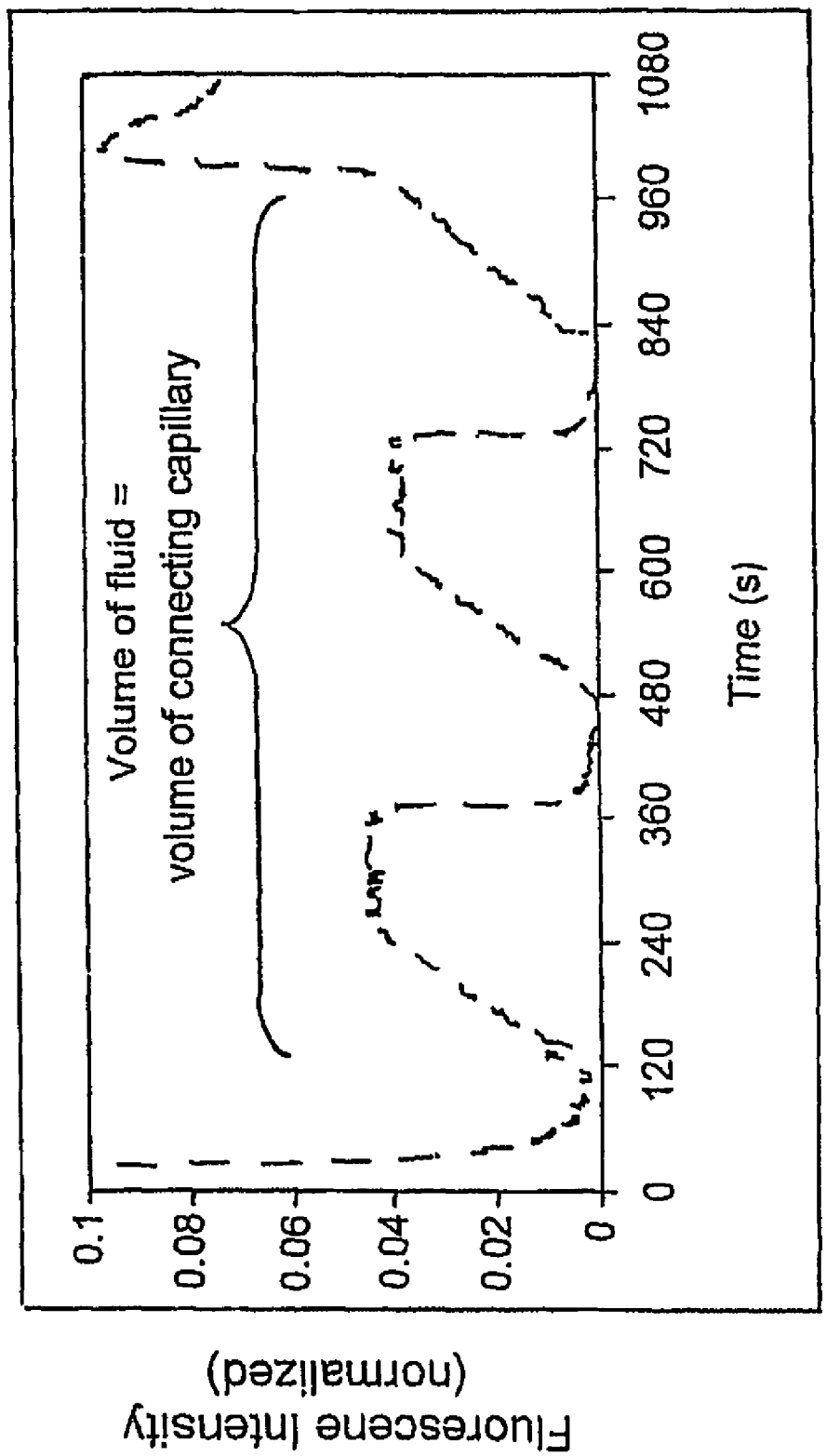
FIG. 52 is a graph showing a gradient of "buffer only"

FIG. 52 shows a graph of a similar gradient of "buffer only" generated by techniques to those similar above. Here, however, another problem with carryover, unique to running concentration gradients in this fashion, is shown. When the microfluidic pump $P_D$ has pushed a volume equivalent to the volume of capillary 272 through the microfluidic chip MFC, then a bolus of fluid enters the microfluidic chip MFC that had been sitting in the switching valve SV during the first portion of generating the gradient, i.e. during the first 120 seconds when pump $P_D$ is flowing at 0 nl/min. This demonstrates that a significant portion of the carryover comes from the switching valve SV. Apparently, while the fluid sits in the switching valve SV, it is contaminated by the valve, the result being that it has a much higher fluorescence, as evident by the large spike it generates when entering the chip; in this case rising to 10% of the original maximal fluorescence.

Carry-over in this system is believed to be generated by several factors: (1) large dead volumes in the switching valve SV (about 28 nl for the valves used), (2) large void or "unswept" volumes—outpockets from which contaminants enter or exit primarily by diffusion, and (3) moving parts which become "painted" by contaminating chemicals which only diffuse away very slowly. Thus, carry-over can be greatly reduced by removing moving parts, dead volumes, and void volumes from the fluidic system.

Carry-over can be reduced or eliminated through implementation of the measures discussed herein above. FIGS. 27A and 27B illustrate graphs showing the results of a carry-over experiment, similar to those presented in FIGS. 51A and 51B, but conducted with microfluidic system MS shown in FIGS. 26A-26D. Initially, injection loop INL was filled with buffer. FIG. 27B shows an enlarged Y-axis of FIG. 27A. Here, carry-over is now undetectable, that is, no gradient is visible in the "buffer-only" gradient (indicated by dashed lines).

It will be understood that various details of the subject matter disclosed herein may be changed without departing from the scope of the subject matter. Furthermore, the foregoing description is for the purpose of illustration only, and not for the purpose of limitation.

What is claimed is:

1. A method for determining one of a mechanism of inhibition, potency of an inhibitor, and both a mechanism of inhibition and potency of an inhibitor of a biological molecule, comprising:
   (a) contacting at least one inhibitor, a biological molecule, wherein the biological molecule comprises an enzyme, and at least one ligand for the biological molecule under conditions where concentrations of at least two of the at least one inhibitor, the biological molecule and the at least one ligand are simultaneously varied over a continuous concentration gradient;
   (b) measuring the enzymatic reaction over the continuous concentration gradient; and
   (c) determining an outcome of the contacting of the at least one inhibitor, the at least one ligand, and the biological molecule to determine one of the mechanism of inhibition, potency of the inhibitor, and both the mechanism of inhibition and potency of the inhibitor, wherein determining the outcome comprises determining the inhibition constant of the at least one inhibitor.

2. The method of claim 1, wherein the concentrations of the at least one inhibitor and the at least one ligand are simultaneously varied.

3. The method of claim 2, wherein the concentrations of the inhibitor and the at least one ligand are simultaneously varied such that a ratio of the concentrations is constant.

4. The method of claim 1, wherein the at least one inhibitor comprises two inhibitors, and wherein the two inhibitors both inhibit or are suspected to inhibit the biological molecule.

5. The method of claim 4, wherein the concentrations of the two inhibitors and the at least one ligand are simultaneously varied.

6. The method of claim 5, wherein the concentrations of the two inhibitors and the at least one ligand are simultaneously varied such that a ratio of the concentrations is constant.

7. The method of claim 4, wherein an interaction factor ($\alpha$) between the two inhibitors is determined.

8. The method of claim 7, wherein the determined interaction factor for the two inhibitors provides for determining whether the two inhibitors are synergistic, antagonistic or neutral with respect to each other.

9. The method of claim 1, wherein the at least one ligand comprises a substrate of the enzyme.

10. The method of claim 1, wherein the concentrations are simultaneously varied with discrete concentration gradients.

11. The method of claim 10, wherein each of the discrete concentrations are contained in discrete containers.

12. The method of claim 11, wherein the discrete containers are wells in a microtiter plate.

13. The method of claim 1, wherein the continuous concentration gradients are in a microfluidic chip.

14. The method of claim 1, wherein the determined inhibition constant is selected from the group consisting of an inhibition constant of the at least one inhibitor with the biological molecule, an inhibition constant of the at least one inhibitor with the biological molecule-ligand complex, and both the inhibition constant of the at least one inhibitor with the biological molecule and the inhibition constant of the at least one inhibitor with the biological molecule-ligand complex.

15. The method of claim 1, wherein the determined inhibition constant provides for determination of one of the mechanism of inhibition, potency of the inhibitor and both the mechanism of inhibition and potency of the inhibitor.

16. The method of claim 1, wherein the mechanism of inhibition determined for the inhibitor is selected from the group consisting of competitive, non-competitive, uncompetitive, and mixed.

17. The method of claim 1, wherein determining the potency of the inhibitor comprises determining the $IC_{50}$ of the inhibitor.

* * * * *